United States Patent
Capobianco et al.

(10) Patent No.: US 11,649,214 B2
(45) Date of Patent: May 16, 2023

(54) INHIBITORS OF THE NOTCH TRANSCRIPTIONAL ACTIVATION COMPLEX KINASE ("NACK") AND METHODS FOR USE OF THE SAME

(71) Applicant: UNIVERSITY OF MIAMI, Miami, FL (US)

(72) Inventors: Anthony J. Capobianco, Miami Beach, FL (US); Stephan C. Schürer, Coral Gables, FL (US); Xiaoxia Zhu, Palmetto Bay, FL (US); Tanya T. Kelley, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 18 days.

(21) Appl. No.: 16/967,652

(22) PCT Filed: Feb. 6, 2019

(86) PCT No.: PCT/US2019/016868
§ 371 (c)(1),
(2) Date: Aug. 5, 2020

(87) PCT Pub. No.: WO2019/157065
PCT Pub. Date: Aug. 15, 2019

(65) Prior Publication Data
US 2021/0171469 A1   Jun. 10, 2021

Related U.S. Application Data

(60) Provisional application No. 62/626,870, filed on Feb. 6, 2018.

(51) Int. Cl.
*C07D 231/54* (2006.01)
(52) U.S. Cl.
CPC .......... *C07D 231/54* (2013.01); *C12Y 207/00* (2013.01); *C12Y 306/01003* (2013.01)
(58) Field of Classification Search
CPC .................................................. C07D 231/54
USPC ........................................................ 514/406
See application file for complete search history.

(56) References Cited

FOREIGN PATENT DOCUMENTS

| WO | 2013/088256 A1 | 6/2013 |
| WO | 2016/077841 A1 | 5/2016 |
| WO | 2016/154255 A1 | 9/2016 |

OTHER PUBLICATIONS

Aster et al., Oncogenic forms of NOTCH1 lacking either the primary binding site for RBP-Jkappa or nuclear 1ocalization sequences retain the ability to associate with RBP-Jkappa and activate transcription, J. Biol. Chem., 272(17):11336-11343 (1997).

Astudillo et al., The small molecule IMR-1 inhibits the notch transcriptional activation complex to suppress tumorigenesis, Cancer Research, 76(12):3593-3603 (2016).
Berezovska et al., Aspartate mutations in presenilin and gamma-secretase inhibitors both impair notch1 proteolysis and nuclear translocation with relative preservation of notch1 signaling, J. Neurochem., 75(2):583-593 (2000).
Fischer et al., Anti-DLL4 inhibits growth and reduces tumor-initiating cell frequency in colorectal tumors with oncogenic KRAS mutations, Cancer Res., 71(5):1520-1525 (2011).
International Application No. PCT/US2019/016868, International Search Report and Written Opinion, dated Jun. 14, 2019.
International Preliminary Report on Patentability for corresponding International Application No. PCT/US2019/016868, dated Aug. 11, 2020.
Jeffries et al., Characterization of a high-molecular-weight Notch complex in the nucleus of Notch(ic)-transformed RKE cells and in a human T-cell leukemia cell line, Mol Cell Biol., 22(11):3927-3941 (2002).
Kloe et al., Small molecules that inhibit Notch signaling, Methods Mol. Biol., 1187:311-322 (2014).
Kovall et al., Crystal structure of the nuclear effector of Notch signaling, CSL, bound to DNA, EMBO J., 23(17):3441-3451 (2004).
Kovall, More complicated than it looks: assembly of Notch pathway transcription complexes, Oncogene, 27(38):5099-5109 (2008).
McGuffin et al., IntFOLD: an integrated server for modelling protein structures and functions from amino acid sequences, Nucleic Acids Res., 43(W1):W169-W173 (2015).
Moellering et al., Direct inhibition of the NOTCH transcription factor complex, Nature, 462:182-188 (2009).
Nam et al., Structural basis for cooperativity in recruitment of MAML coactivators to Notch transcription complexes, Cell, 124(5):973-983 (2006).
PubChem-CID-50848794, Create Date: (Feb. 22, 2011), 2 page.
PubChem-CID-50848832, Create Date: (Feb. 22, 2011), 2 page.
PubChem-CID-83829010, Create Date: (Oct. 20, 2014), 2 page.
Ranganathan et al., Notch signalling in solid tumours: a little bit of everything but not all the time, Nat. Rev. Cancer, 11(5):338-351 (2011).

(Continued)

*Primary Examiner* — Taofiq A Solola
(74) *Attorney, Agent, or Firm* — Marshall, Gerstein & Borun LLP

(57) ABSTRACT

Disclosed herein are Notch transcriptional activation complex kinase ("NACK") inhibitors, and methods for their use in treating or preventing diseases, such as cancer. The inhibitors described herein include compounds of Formula (Ia) and pharmaceutically acceptable salts thereof: wherein the substituents are as described.

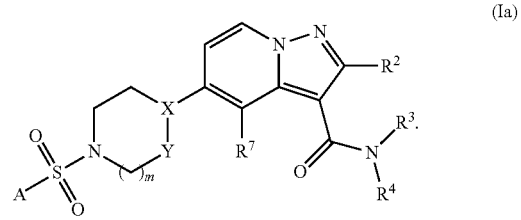

20 Claims, 26 Drawing Sheets
Specification includes a Sequence Listing.

(56) References Cited

OTHER PUBLICATIONS

Sharma et al., A monoclonal antibody against human Notch1 ligand-binding domain depletes subpopulation of putative breast cancer stem-like cells, Mol. Cancer Ther., 11(1):77-86 (2012).
Shih et al., Notch signaling, gamma-secretase inhibitors, and cancer therapy, Cancer Res., 67(5):1879-1882 (2007).
Takebe et al., Targeting notch signaling pathway in cancer: clinical development advances and challenges, Pharmacol. Ther., 141(2):140-149 (2014).
Tamura et al., Physical interaction between a novel domain of the receptor Notch and the transcription factor RBP-J kappa/Su(H), Curr. Biol., 5(12):1416-1423 (1995).
Taylor, Protein kinases: a diverse family of related proteins, Bioessays, 7(1):24-29 (1987).
Tiyanont et al., Insights into Notch3 activation and inhibition mediated by antibodies directed against its negative regulatory region, J. Mol. Biol., 425(17):3192-3204 (2013).
Wang et al., Notch signaling drives stemness and tumorigenicity of esophageal adenocarcinoma, Cancer Research, 74(21):6364-6374 (2014).
Weaver et al., NACK is an integral component of the Notch transcriptional activation complex and is critical for development and tumorigenesis, Cancer Research, 74(17):4741-4751 (2014).
Williams et al., Structural basis for the potent and selective binding of LDN-212854 to the BMP receptor kinase ALK2, Bone., 109:251-258 (2018).
Supplementary European Application No. 19750817.9, European Search Report and Opinion, dated Feb. 1, 2022.

FIG. 2A

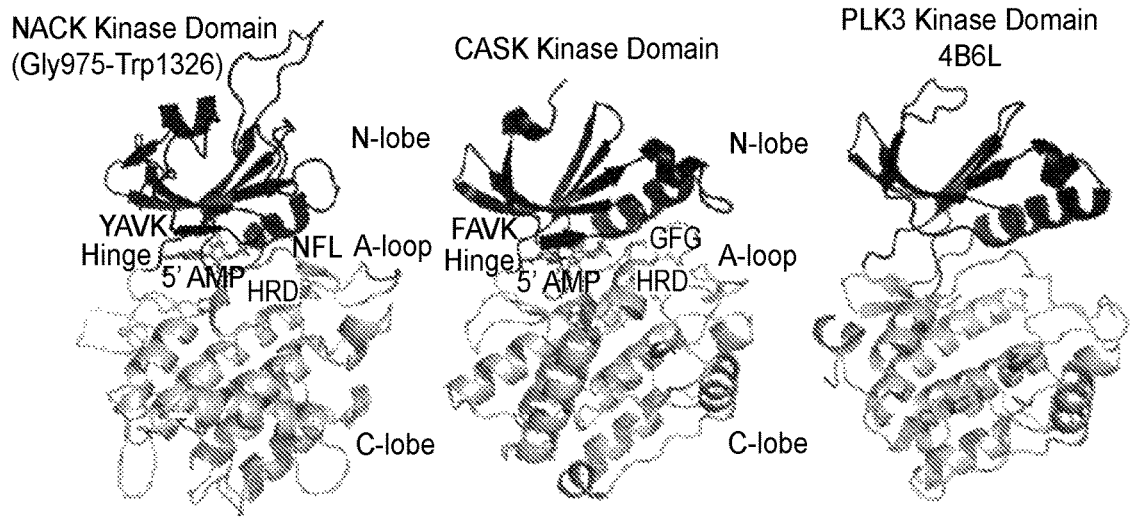

FIG. 2B

Comparisons of key motifs among NACK, CASK and PLK3

| Motifs Overlap | NACK (Human) | CASK (PDB: 3C0I) | PLK3 (PDB: 4B6L) |
|---|---|---|---|
| HRD motif (Catalytic residues) | HRD | HRD | HRD |
| | His1141 | His139 | His183 |
| | Arg1142 | Arg140 | Arg184 |
| | Asp1143 (H acceptor) | Asp141 | Asp185 |
| VAIK motif (Position α- and β- phosphate of ATP for phosphoryl transfer) | YAVK | FAVK | VAIK |
| | Tyr1019 | Phe38 | Val88 |
| | Ala1020 | Ala39 | Ala89 |
| | Val1021 | Val40 | Ile90 |
| | Lys1022 (ATP binding) | Lys41 | Lys91 |
| DFG motif (Metal binding) | NFL | GFG | DFG |
| | Asn1212 | Gly162 | Asp203 |
| | Phe1213 | Phe163 | Phe204 |
| | Leu1214 | Gly164 | Gly205 |

FIG. 3E
| NACK Residues | ATP Molecule | Interactions |
|---|---|---|
| Lys 1022 | Phosphate group | Salt bridge |
| Asn 1212 | Beta phosphate | H bond |
| His 1095 (backbone H) | Alpha phosphate O | H bond |
| Cys 999 | Gamma phosphate O | H bond |
| Asp 1048 (backbone O) | Adenine ring | H bond |
| Tyr 1006 | Gamma phosphate O | H bond |
FIG. 4A
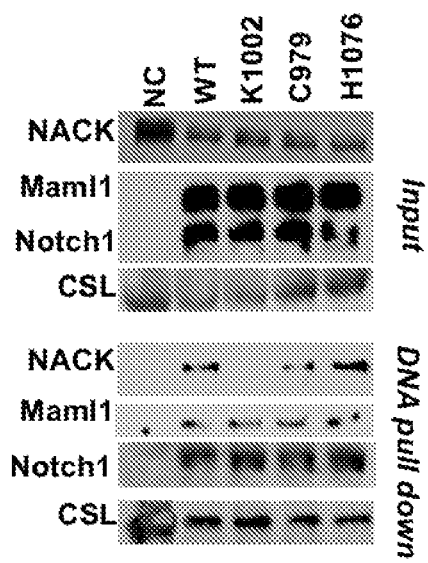
FIG. 4B
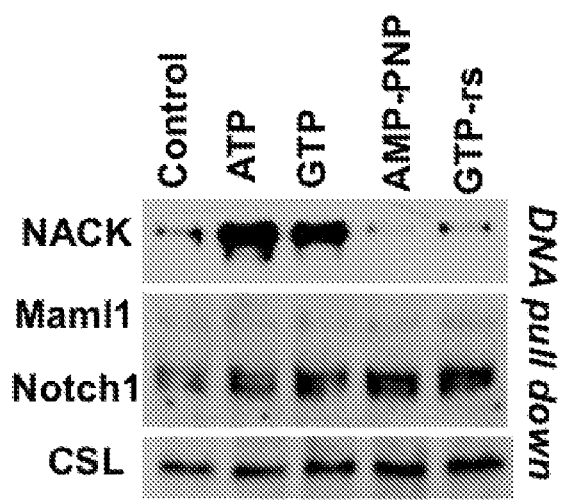
FIG. 4C
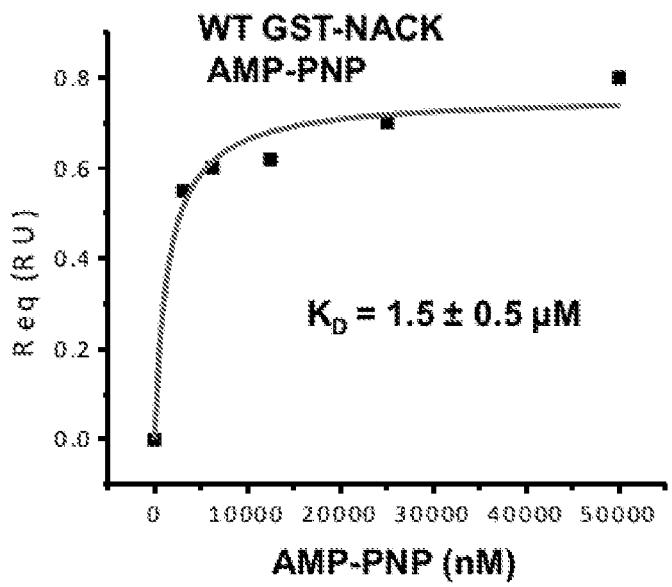

FIG. 10A
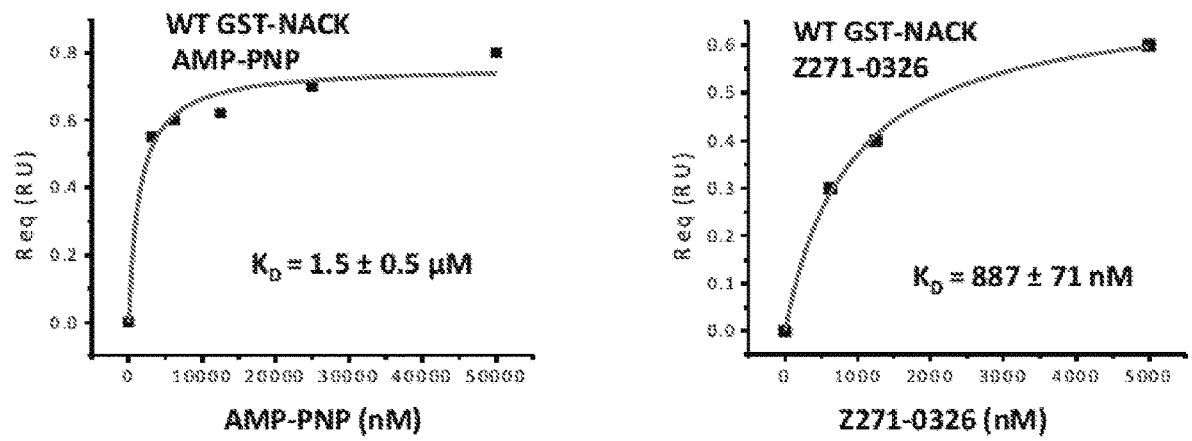
FIG. 10B
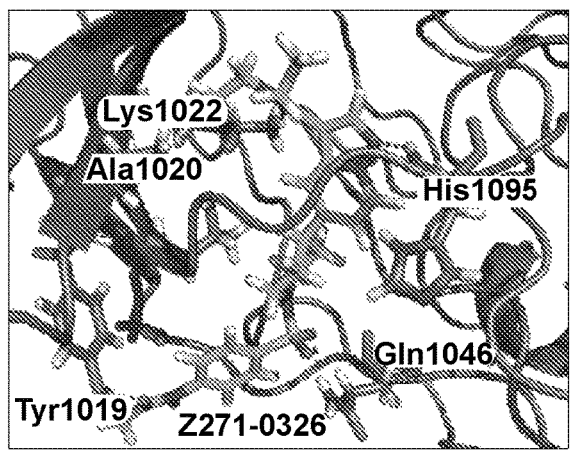
FIG. 10C
Important NACK residues responsible for Z271-0326 binding
| Residue | | Interaction |
|---|---|---|
| Lys 1022 | Side chain -$NH_3^+$ | H bond |
| His 1095 | Backbone -NH- | H bond |
| Gln 1046 | Side chain -$NH_2$ | H bond |
| Tyr 1019 | Side chain -OH | H bond |
| Ala 1020 | Side chain -$CH_3$ | Hydrophobic |

Mutation of putative Z271-0326 interacting residues renders NACK insensitive

FIG. 11E
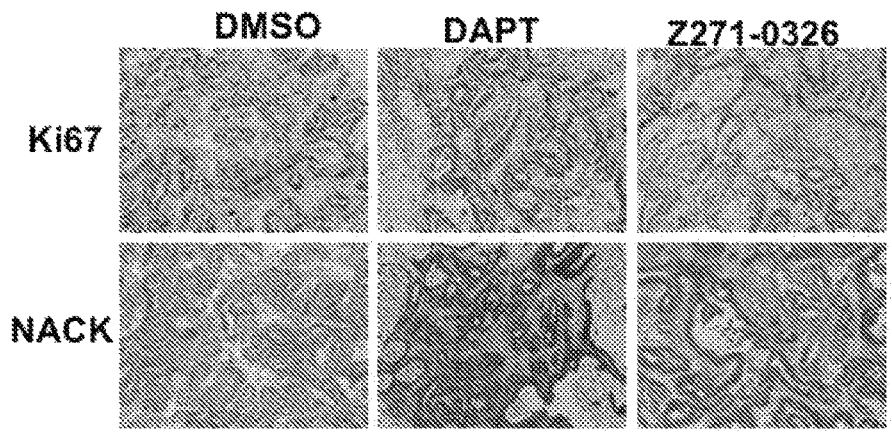
FIG. 12A
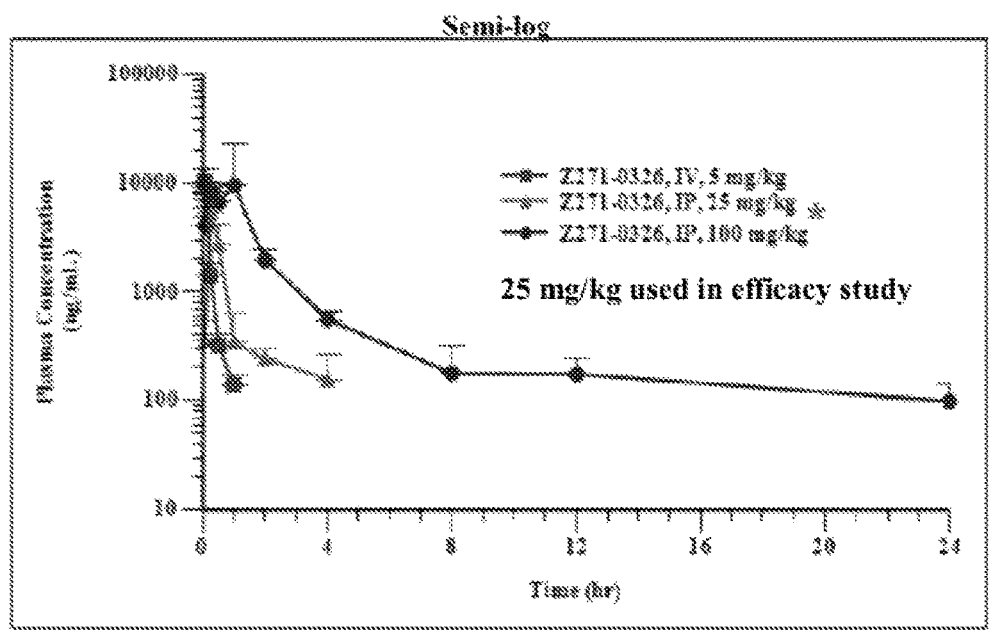
FIG. 12B
Pharmacokinetic parameters of Z271-0326 in plasma following a single intravenous (5 mg/kg) and intraperitoneal (25 and 100 mg/kg) administration to male C57 BL/6 mice
| Route | Dose (mg/kg) | $T_{max}$ (hr) | $C^0/C_{max}$ (ng/mL) | $AUC_{last}$ (hr*ng/mL) | $AUC_{inf}$ (hr*ng/mL) | $T_{1/2}$ (hr) | CL (mL/min/kg) | Vss (L/kg) |
|---|---|---|---|---|---|---|---|---|
| IV | 5 | - | 25078.74 | 2729.79 | 2769.49 | 0.23 | 30.09 | 0.21 |
| IP | 25 | 0.25 | 5344.40 | 2989.95 | 3592.35 | - | - | - |
| IP | 100 | 1.00 | 9481.07 | 19196.18 | 21767.19 | - | - | - |

SEQUENCE LISTING

<160> NUMBER OF SEQ ID NOS: 3

<210> SEQ ID NO 1
<211> LENGTH: 1406
<212> TYPE: PRT
<213> ORGANISM: Homo sapiens

<400> SEQUENCE: 1

```
Met His Gln Thr Leu Cys Leu Asn Pro Glu Ser Leu Lys Met Ser Ala
1               5                  10                  15

Cys Ser Asp Phe Val Glu His Ile Trp Lys Pro Gly Ser Cys Lys Asn
                20                  25                  30

Cys Phe Cys Leu Arg Ser Asp His Gln Leu Val Ala Gly Pro Pro Gln
            35                  40                  45

Pro Arg Ala Gly Ser Leu Pro Pro Pro Arg Leu Pro Pro Arg Pro
        50                  55                  60

Glu Asn Cys Arg Leu Glu Asp Glu Gly Val Asn Ser Ser Pro Tyr Ser
65                  70                  75                  80

Lys Pro Thr Ile Ala Val Lys Pro Thr Met Met Ser Ser Glu Ala Ser
                85                  90                  95

Asp Val Trp Thr Glu Ala Asn Leu Ser Ala Glu Val Ser Gln Val Ile
                100                 105                 110

Trp Arg Arg Ala Pro Gly Lys Leu Pro Leu Pro Lys Gln Glu Asp Ala
            115                 120                 125

Pro Val Val Tyr Leu Gly Ser Phe Arg Gly Val Gln Lys Pro Ala Gly
        130                 135                 140

Pro Ser Thr Ser Pro Asp Gly Asn Ser Arg Cys Pro Pro Ala Tyr Thr
145                 150                 155                 160

Met Val Gly Leu His Asn Leu Glu Pro Arg Gly Glu Arg Asn Ile Ala
                165                 170                 175

Phe His Pro Val Ser Phe Pro Glu Glu Lys Ala Val His Lys Glu Lys
            180                 185                 190

Pro Ser Phe Pro Tyr Gln Asp Arg Pro Ser Thr Gln Glu Ser Phe Arg
        195                 200                 205

Gln Lys Leu Ala Ala Phe Ala Gly Thr Thr Ser Gly Cys His Gln Gly
    210                 215                 220

Pro Gly Pro Leu Arg Glu Ser Leu Pro Ser Glu Asp Asp Ser Asp Gln
225                 230                 235                 240

Arg Cys Ser Pro Ser Gly Asp Ser Glu Gly Glu Tyr Cys Ser Ile
                245                 250                 255

Leu Asp Cys Cys Pro Gly Ser Pro Val Ala Lys Ala Ala Ser Gln Thr
            260                 265                 270

Ala Gly Ser Arg Gly Arg His Gly Gly Arg Asp Cys Ser Pro Thr Cys
        275                 280                 285

Trp Glu Gln Gly Lys Cys Ser Gly Pro Ala Glu Gln Glu Lys Arg Gly
    290                 295                 300

Pro Ser Phe Pro Lys Glu Cys Cys Ser Gln Gly Pro Thr Ala His Pro
305                 310                 315                 320

Ser Cys Leu Gly Pro Lys Lys Leu Ser Leu Thr Ser Glu Ala Ala Ile
                325                 330                 335
```

```
Ser Ser Asp Gly Leu Ser Cys Gly Ser Gly Ser Gly Ser Gly
        340                 345             350

Ala Ser Ser Pro Phe Val Pro His Leu Glu Ser Asp Tyr Cys Ser Leu
        355                 360             365

Met Lys Glu Pro Ala Pro Glu Lys Gln Gln Asp Pro Gly Cys Pro Gly
370                 375                 380

Val Thr Pro Ser Arg Cys Leu Gly Leu Thr Gly Glu Pro Gln Pro Pro
385                 390                 395                 400

Ala His Pro Arg Glu Ala Thr Gln Pro Glu Pro Ile Tyr Ala Glu Ser
            405                 410                 415

Thr Lys Arg Lys Lys Ala Ala Pro Val Pro Ser Lys Ser Gln Ala Lys
            420                 425                 430

Ile Glu His Ala Ala Ala Ala Gln Gly Gln Gly Gln Val Cys Thr Gly
            435                 440                 445

Asn Ala Trp Ala Gln Lys Ala Ala Ser Gly Trp Gly Arg Asp Ser Pro
450                 455                 460

Asp Pro Thr Pro Gln Val Ser Ala Thr Ile Thr Val Met Ala Ala His
465                 470                 475                 480

Pro Glu Glu Asp His Arg Thr Ile Tyr Leu Ser Ser Pro Asp Ser Ala
                485                 490                 495

Val Gly Val Gln Trp Pro Arg Gly Pro Val Ser Gln Asn Ser Glu Val
            500                 505                 510

Gly Glu Glu Glu Thr Ser Ala Gly Gln Gly Leu Ser Ser Arg Glu Ser
            515                 520                 525

His Ala His Ser Ala Ser Glu Ser Lys Pro Lys Glu Arg Pro Ala Ile
            530                 535                 540

Pro Pro Lys Leu Ser Lys Ser Ser Pro Val Gly Ser Pro Val Ser Pro
545                 550                 555                 560

Ser Ala Gly Gly Pro Pro Val Ser Pro Leu Ala Asp Leu Ser Asp Gly
                565                 570                 575

Ser Ser Gly Gly Ser Ser Ile Gly Pro Gln Pro Ser Gln Gly Pro
            580                 585                 590

Ala Asp Pro Ala Pro Ser Cys Arg Thr Asn Gly Val Ala Ile Ser Asp
            595                 600                 605

Pro Ser Arg Cys Pro Gln Pro Ala Ala Ser Ser Ala Ser Glu Gln Arg
610                 615                 620

Arg Pro Arg Phe Gln Ala Gly Thr Trp Ser Arg Gln Cys Arg Ile Glu
625                 630                 635                 640

Glu Glu Glu Glu Val Glu Gln Glu Leu Leu Ser His Ser Trp Gly Arg
                645                 650                 655

Glu Thr Lys Asn Gly Pro Thr Asp His Ser Asn Ser Thr Thr Trp His
            660                 665                 670

Arg Leu His Pro Thr Asp Gly Ser Gly Gln Asn Ser Lys Val Gly
            675                 680                 685

Thr Gly Met Ser Lys Ser Ala Ser Phe Ala Phe Glu Phe Pro Lys Asp
            690                 695                 700

Arg Ser Gly Ile Glu Thr Phe Ser Pro Pro Pro Pro Pro Lys Ser
705                 710                 715                 720

Arg His Leu Leu Lys Met Asn Lys Ser Ser Ser Asp Leu Glu Lys Val
                725                 730                 735

Ser Gln Gly Ser Ala Glu Ser Leu Ser Pro Ser Phe Arg Gly Val His
            740                 745                 750
```

```
Val Ser Phe Thr Thr Gly Ser Thr Asp Ser Leu Ala Ser Asp Ser Arg
            755                 760                 765

Thr Cys Ser Asp Gly Gly Pro Ser Ser Glu Leu Ala His Ser Pro Thr
770                 775                 780

Asn Ser Gly Lys Lys Leu Phe Ala Pro Val Pro Phe Pro Ser Gly Ser
785                 790                 795                 800

Thr Glu Asp Val Ser Pro Ser Gly Pro Gln Gln Pro Pro Pro Leu Pro
                805                 810                 815

Gln Lys Lys Ile Val Ser Arg Ala Ala Ser Ser Pro Asp Gly Phe Phe
            820                 825                 830

Trp Thr Gln Gly Ser Pro Lys Pro Gly Thr Ala Ser Pro Lys Leu Asn
        835                 840                 845

Leu Ser His Ser Glu Thr Asn Val His Asp Glu Ser His Phe Ser Tyr
        850                 855                 860

Ser Leu Ser Pro Gly Asn Arg His His Pro Val Phe Ser Ser Ser Asp
865                 870                 875                 880

Pro Leu Glu Lys Ala Phe Lys Gly Ser Gly His Trp Leu Pro Ala Ala
                885                 890                 895

Gly Leu Ala Gly Asn Arg Gly Gly Cys Gly Ser Pro Gly Leu Gln Cys
            900                 905                 910

Lys Gly Ala Pro Ser Ala Ser Ser Gln Leu Ser Val Ser Ser Gln
        915                 920                 925

Ala Ser Thr Gly Ser Thr Gln Leu Gln Leu His Gly Leu Leu Ser Asn
        930                 935                 940

Ile Ser Ser Lys Glu Gly Thr Tyr Ala Lys Leu Gly Gly Leu Tyr Thr
945                 950                 955                 960

Gln Ser Leu Ala Arg Leu Val Ala Lys Cys Glu Asp Leu Phe Met Gly
                965                 970                 975

Gly Gln Lys Lys Glu Leu His Phe Asn Glu Asn Asn Trp Ser Leu Phe
            980                 985                 990

Lys Leu Thr Cys Asn Lys Pro Cys Cys Asp Ser Gly Asp Ala Ile Tyr
        995                 1000                1005

Tyr Cys Ala Thr Cys Ser Glu Asp Pro Gly Ser Thr Tyr Ala Val
    1010                1015                1020

Lys Ile Cys Lys Ala Pro Glu Pro Lys Thr Val Ser Tyr Cys Ser
    1025                1030                1035

Pro Ser Val Pro Val His Phe Asn Ile Gln Gln Asp Cys Gly His
    1040                1045                1050

Phe Val Ala Ser Val Pro Ser Ser Met Leu Ser Ser Pro Asp Ala
    1055                1060                1065

Pro Lys Asp Pro Val Pro Ala Leu Pro Thr His Pro Pro Ala Gln
    1070                1075                1080

Glu Gln Asp Cys Val Val Val Ile Thr Arg Glu Val Pro His Gln
    1085                1090                1095

Thr Ala Ser Asp Phe Val Arg Asp Ser Ala Ala Ser His Gln Ala
    1100                1105                1110

Glu Pro Glu Ala Tyr Glu Arg Arg Val Cys Phe Leu Leu Leu Gln
    1115                1120                1125

Leu Cys Asn Gly Leu Glu His Leu Lys Glu His Gly Ile Ile His
    1130                1135                1140

Arg Asp Leu Cys Leu Glu Asn Leu Leu Leu Val His Cys Thr Leu
    1145                1150                1155

Gln Ala Gly Pro Gly Pro Ala Pro Ala Pro Ala Pro Ala Pro Ala
```

-continued

```
            1160                1165                1170
Pro Ala  Ala Ala Ala Pro  Pro Cys Ser Ser Ala  Ala Pro Pro Ala
    1175                 1180                1185

Gly Gly  Thr Leu Ser Pro  Ala Gly Pro Ala Ser  Pro Glu Gly
    1190                 1195                1200

Pro Arg  Glu Lys Gln Leu  Pro Arg Leu Ile Ile  Ser Asn Phe Leu
    1205                 1210                1215

Lys Ala  Lys Gln Lys Pro  Gly Gly Thr Pro Asn  Leu Gln Gln Lys
    1220                 1225                1230

Lys Ser  Gln Ala Arg Leu  Ala Pro Glu Ile Val  Ser Ala Ser Gln
    1235                 1240                1245

Tyr Arg  Lys Phe Asp Glu  Phe Gln Thr Gly Ile  Leu Ile Tyr Glu
    1250                 1255                1260

Leu Leu  His Gln Pro Asn  Pro Phe Glu Val Arg  Ala Gln Leu Arg
    1265                 1270                1275

Glu Arg  Asp Tyr Arg Gln  Glu Asp Leu Pro Pro  Leu Pro Ala Leu
    1280                 1285                1290

Ser Leu  Tyr Ser Pro Gly  Leu Gln Gln Leu Ala  His Leu Leu Leu
    1295                 1300                1305

Glu Ala  Asp Pro Ile Lys  Arg Ile Arg Ile Gly  Glu Ala Lys Arg
    1310                 1315                1320

Val Leu  Gln Cys Leu Leu  Trp Gly Pro Arg Arg  Glu Leu Val Gln
    1325                 1330                1335

Gln Pro  Gly Thr Ser Glu  Glu Ala Leu Cys Gly  Thr Leu His Asn
    1340                 1345                1350

Trp Ile  Asp Met Lys Arg  Ala Leu Met Met Met  Lys Phe Ala Glu
    1355                 1360                1365

Lys Ala  Val Asp Arg Arg  Gly Val Glu Leu Glu  Asp Trp Leu
    1370                 1375                1380

Cys Cys  Gln Tyr Leu Ala  Ser Ala Glu Pro Gly  Ala Leu Leu Gln
    1385                 1390                1395

Ser Leu  Lys Leu Leu Gln  Leu Leu
    1400                 1405

<210> SEQ ID NO 2
<211> LENGTH: 19
<212> TYPE: DNA
<213> ORGANISM: Artificial Sequence
<220> FEATURE:
<223> OTHER INFORMATION: Synthetic Primer

<400> SEQUENCE: 2
cgtgtctcct cctcccatt                                                    19

<210> SEQ ID NO 3
<211> LENGTH: 18
<212> TYPE: PRT
<213> ORGANISM: Artificial Sequence
<220> FEATURE:
<223> OTHER INFORMATION: Synthetic Primer

<400> SEQUENCE: 3

Gly Gly Gly Gly Gly Ala Thr Thr Cys Cys Gly Cys Thr Gly Thr Thr
1               5                   10                  15

Ala Thr
```

INHIBITORS OF THE NOTCH TRANSCRIPTIONAL ACTIVATION COMPLEX KINASE ("NACK") AND METHODS FOR USE OF THE SAME

CROSS-REFERENCE TO RELATED APPLICATIONS

This application is a U.S. National Stage of International Application No. PCT/US2019/016868, filed Feb. 6, 2019, which claims priority to U.S. Provisional Patent Application. No. 62/626,870, filed Feb. 6, 2018, the disclosures of which are hereby incorporated by reference in their entirety.

STATEMENT OF GOVERNMENT SUPPORT

This invention was made with government support under grant number 1R01CA169805-01, awarded by the National Cancer Institute National Institutes of Health. The Government has certain rights in the invention. The invention also was made with support under grant number 7BC01, awarded by the Bankhead-Coley Cancer Research Program.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 51617A Seqlisting.txt; Size: 13,024 bytes; Created: Aug. 4, 2020.

BACKGROUND

Field of the Invention

The present disclosure relates to inhibitors of the Notch activation complex kinase ("NACK"), and methods of using the inhibitors to treat and prevent diseases, such as cancer.

Description of Related Technology

The Notch pathway, a highly conserved cell signaling system present in most multicellular organisms, is widely used in development to govern cell fate specification, and to balance proliferative capacity and differentiation state. Notch drives a context-dependent cellular response by initiating and maintaining a transcriptional cascade. See Tamura et al. Curr Biol 5, 1416-23 (1995); Aster et al. J Biol Chem 272, 11336-43 (1997). Notch mediates this transcriptional response by directing the formation of a core Notch transcriptional activation complex ("NTC"), which is composed of the DNA binding protein CSL, the intracellular domain of Notch ("NICD") and the co-activator protein Mastermind ("MAML1"). Jeffries et al., Mol Cell Biol 22, 3927-41 (2002); Nam et al., Cell 124, 973-83 (2006); Kovall et al., EMBO J 23, 3441-51 (2004). Notch signaling activation is initiated by the binding of Notch ligands (Jagged and Delta-like) to the transmembrane Notch receptor through cell-to-cell contact. This event triggers the cleavage of the Notch receptor proteins to go through sequential cleavages, which result in the release of the active NICD from the plasma membrane and the translocation of NICD to the nucleus. See Ranganathan et al., Nat Rev Cancer 11, 338-351 (2011); Kovall, Oncogene 27, 5099-5109 (2008).

In the adult, the Notch pathway is restricted to small populations of progenitor and stem cells of regenerating tissues, such as the colon and brain. However, in many human cancers, the Notch pathway becomes reactivated. The deregulation of the Notch pathway underlies many aspects of cancer physiology, depending on cell type and context. Aberrant Notch activity has been demonstrated to play a role in the initiation and maintenance of the neoplastic phenotype, as well as playing a central role in cancer stem cells, which may underlie a role in metastasis and resistance to therapy. See Ranganathan et al., Nat Rev Cancer 11, 338-351 (2011).

Current compounds that regulate the Notch pathway include small molecule inhibitors that target the presenilin-dependent γ-secretase, an enzyme complex that is responsible for ligand-induced cleavage and activation of Notch, and monoclonal antibodies that target and disrupt Notch-DSL. See Takebe et al., Pharmacol Ther 141, 140-9 (2014); Shih et al., Cancer Res 67, 1879-82 (2007); Tiyanont et al., J Mol Biol 425, 3192-204 (2013); Sharma et al., Mol Cancer Ther 11, 77-86 (2012); Fischer et al, Cancer Res 71, 1520-5 (2011); Berezovska et al., J Neurochem 75, 583-93 (2000); De Kloe et al., Methods Mol Biol 1187, 311-22 (2014). Both of these approaches act at the top of the Notch signaling cascade to block ligand-dependent production of NICD. Moreover, γ-secretase is known to have many substrates in addition to the Notch pathway, which could contribute to off target effects. See Shih et al., Cancer Res 67, 1879-82 (2007).

Therefore, there is a need for inhibitors that directly target the Notch transcription complex (see Astudillo et al., Cancer Research 76, 3593-3603 (2016); Moellering et al., Nature 462, 182-8 (2009)), either by blocking the assembly of Notch transcriptional activation complex, or by inhibiting the activation of the Notch mediated transcription.

SUMMARY OF THE DISCLOSURE

In one aspect, the disclosure provides compounds of Formula (Ia), or pharmaceutically acceptable salts thereof:

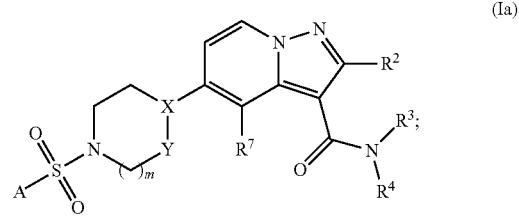

wherein A is $C_{1-4}$alkyl or

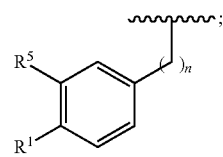

X is CH or N; Y is $CH_2$ or N, and when X is N, then Y is $CH_2$; m is 0 or 1, and when m is 1 then Y is $CH_2$; n is 0 or 1; $R^1$ is H, $C_{1-6}$alkyl, $C_{0-6}$alkyleneC(=O)$R^6$, halo, cyano, aryloxy, amino, $C_{0-3}$alkylene-amido, carbamyl, S-thiocarbamyl, or ureido; $R^2$ is H, halo, $C_{1-6}$alkyl, $C_{3-8}$cycloalkyl, or heteroaryl; each $R^3$ and $R^4$ independently is H, $C_{1-6}$ alkyl, or $C_{1-3}$aralkyl, or $R^3$ and $R^4$ and the nitrogen to which they are attached join together to form a 3-6 membered ring optionally comprising 1 to 3 additional heteroatoms selected from N, O, and S; $R^5$ is H, or $R^1$ and $R^5$ together with the atoms to which they are attached form a 5- or 6-membered heterocyclic ring comprising 1 to 3 ring heteroatoms selected from N, O, and S; $R^6$ is OH, $C_{1-6}$alkyl, or $OC_{1-6}$alkyl; and $R^7$ is H, halo or amino; with the proviso that the compound is not

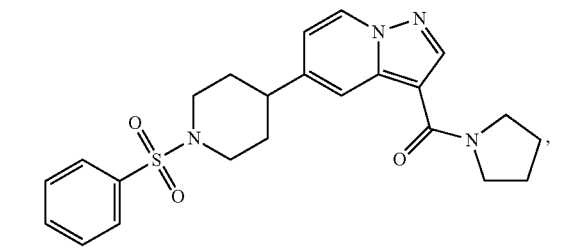

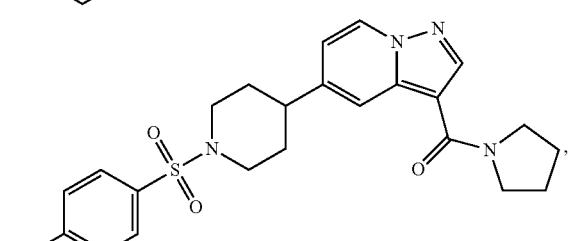

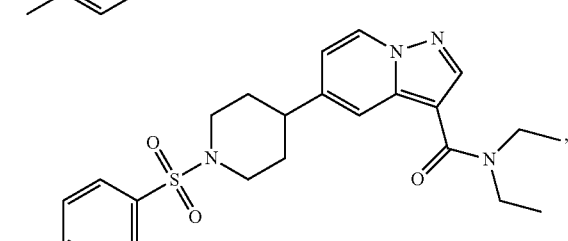

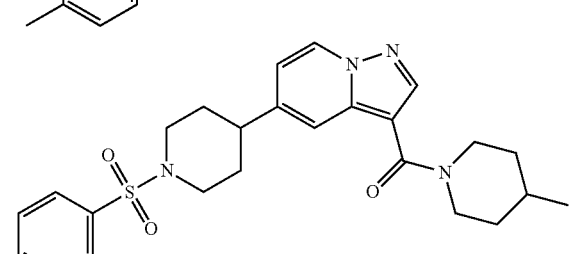

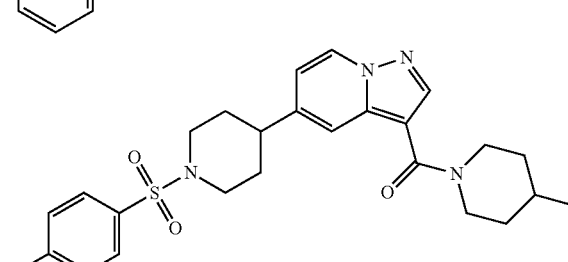

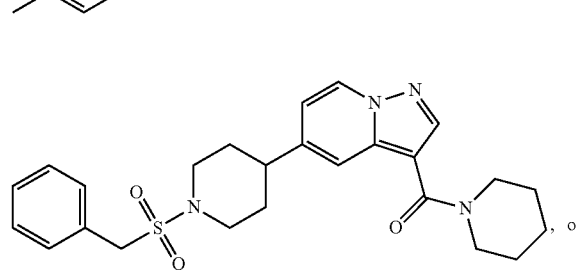, or

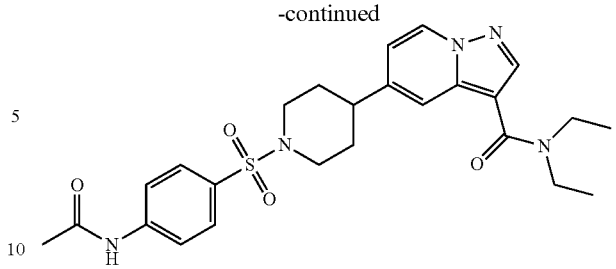

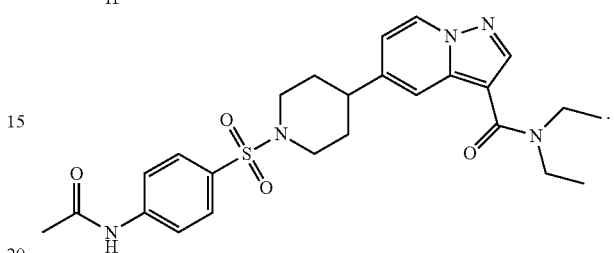

In some embodiments, A is methyl, ethyl, propyl, isopropyl, n-butyl, s-butyl, isobutyl, or t-butyl. In various embodiments, A is methyl. In some cases, A is

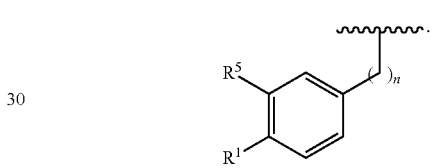

In various cases, n is 0. In some embodiments, n is 1. In various embodiments, $R^1$ and $R^5$ together with the atoms to which they are attached form a 5- or 6-membered heterocyclic ring comprising 1 to 3 ring heteroatoms selected from N, O, and S. In some cases, A is selected from the group consisting of

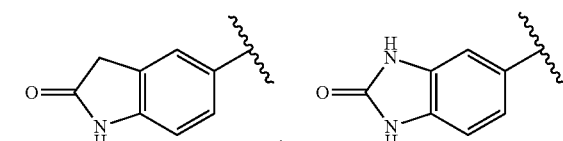

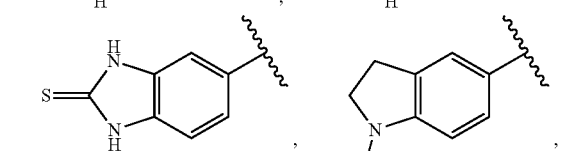

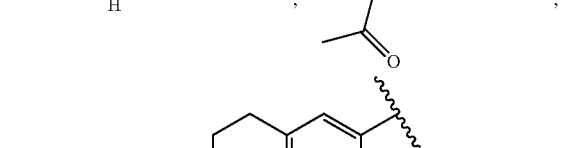

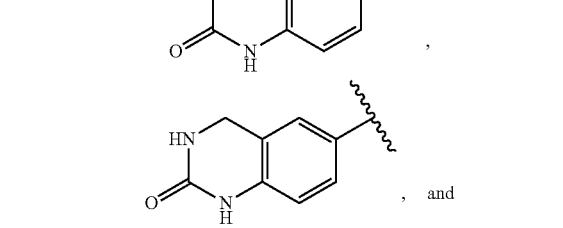, and

-continued

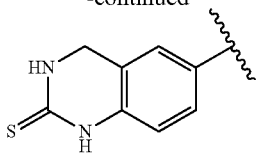

In various cases, $R^5$ is H. In some embodiments, $R^1$ is H. In various embodiments, $R^1$ is $C_{1-6}$alkyl. In some cases, $R^1$ is methyl, ethyl, fluoromethyl, or trifluoromethyl. In various cases, $R^1$ is $C_{0-6}$alkyleneC(=O)$R^6$. In some embodiments, $R^1$ is

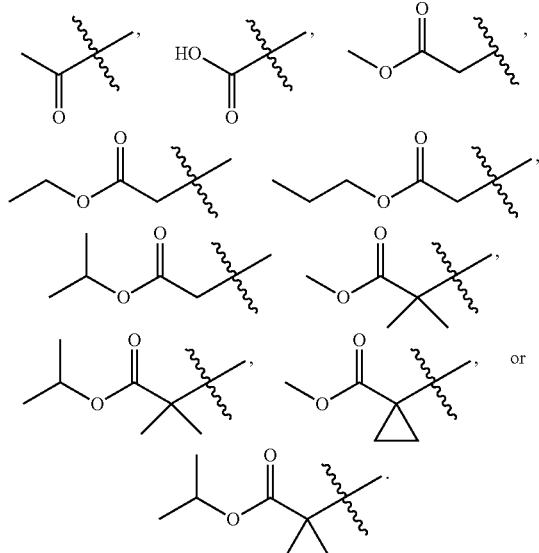

In various embodiments, $R^1$ is halo. In some cases, $R^1$ is F. In various cases, $R^1$ is cyano or aryloxy. In some embodiments, $R^1$ is CN or —OPh. In various embodiments, $R^1$ is amino. In some cases, $R^1$ is —NH$_2$, —N(CH$_3$)$_2$ or —NH$_2$Ph. In various cases, $R^1$ is $C_{0-3}$alkylene-amido, carbamyl, S-thiocarbamyl, or ureido. In some embodiments, $R^1$ is selected from the group consisting of

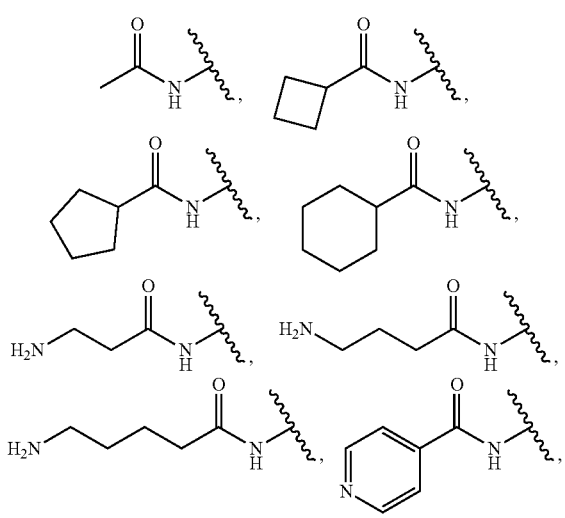

-continued

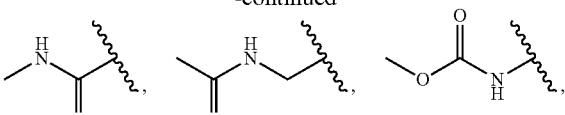
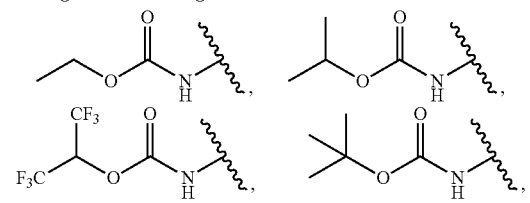
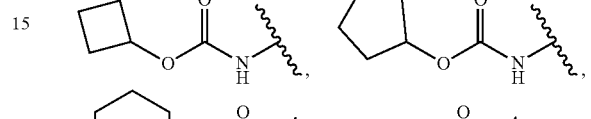
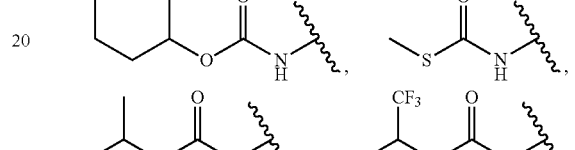
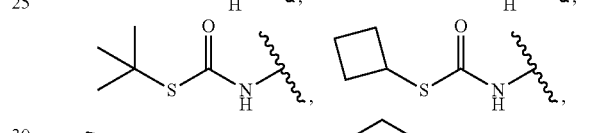
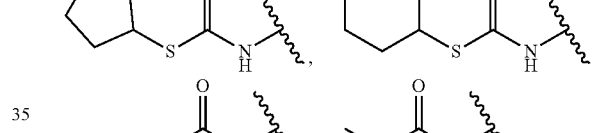
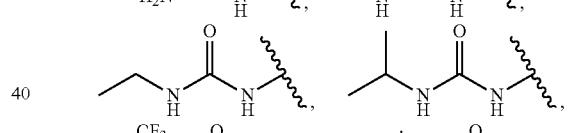
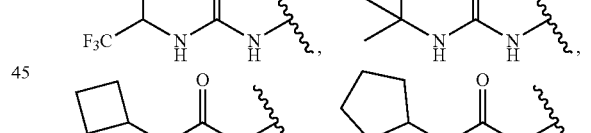
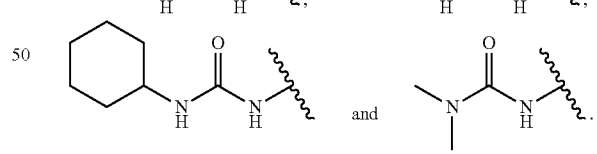

In various embodiments, A is selected from the group consisting of CH$_3$,

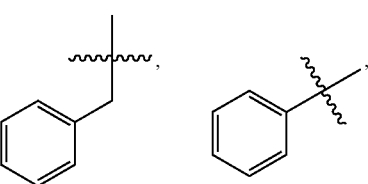

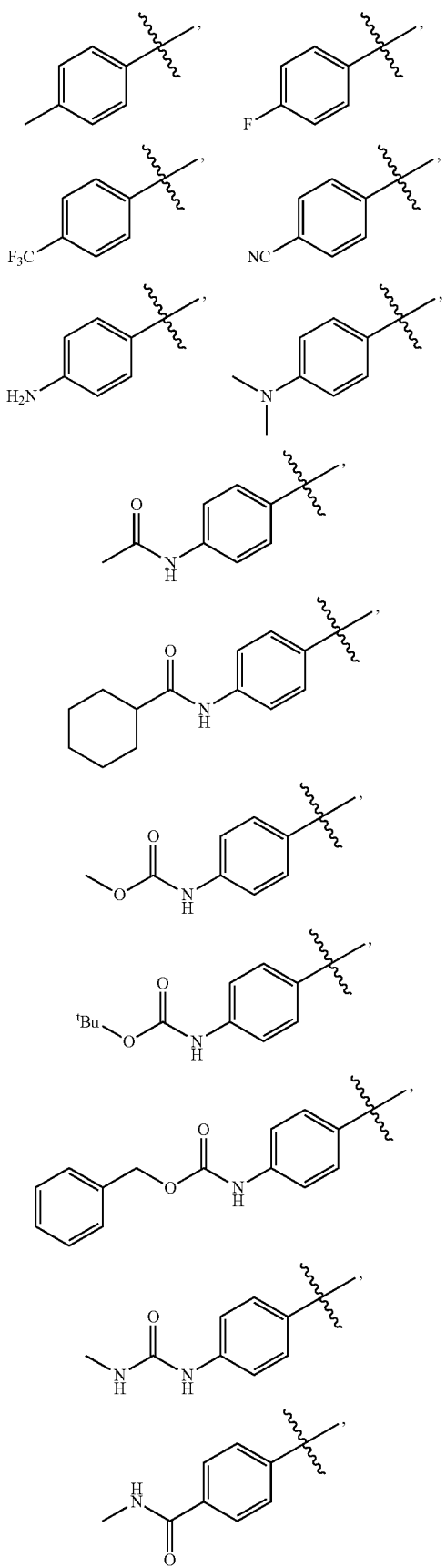

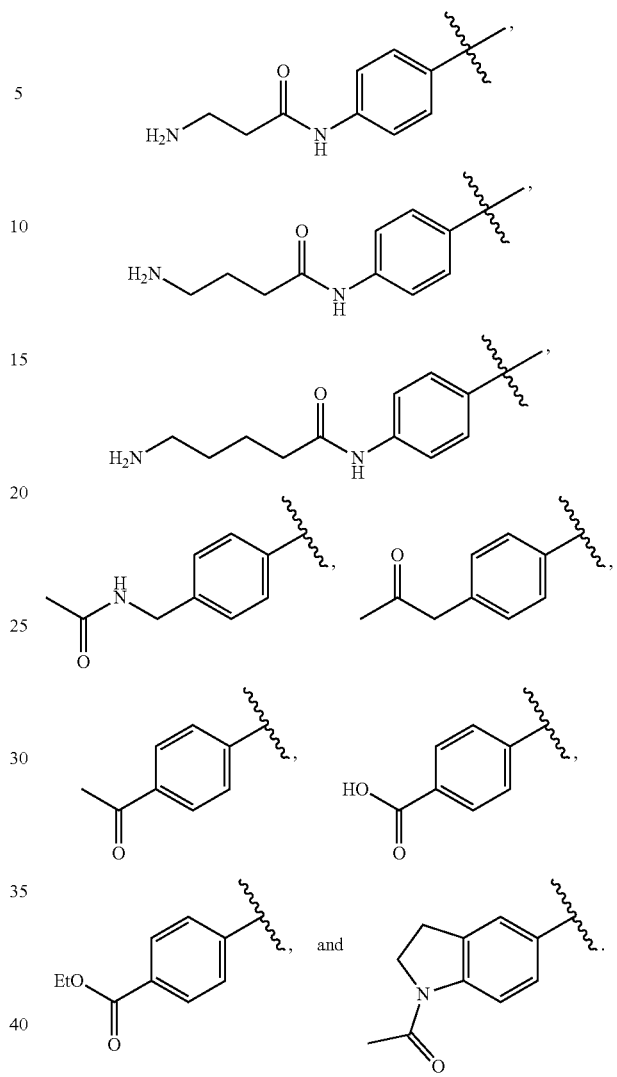

In some cases, X is CH. In various cases, X is N. In some embodiments, Y is $CH_2$. In various embodiments, Y is N. In some cases, m is 0. In various cases, m is 1.

In some embodiments, $R^2$ is H. In various embodiments, $R^2$ is Br or Cl. In some cases, $R^2$ is $CH_3$, $CF_3$, $CH_2OH$, or $CH_2OCH_3$. In various cases, $R^2$ is cyclopropyl, cyclobutyl, cyclopentyl, or cyclohexyl. In some embodiments, $R^2$ is 3-furanyl. In various embodiments, $R^2$ is selected from the group consisting of H, $CH_3$, $CF_3$, and cyclopropyl.

In some cases, each of $R^3$ and $R^4$ independently is H, $C_{1-6}$ alkyl, or $C_{1-3}$aralkyl. In various cases, each of $R^3$ and $R^4$ independently is H, $CH_3$, $CH_2CH_3$, $^tBu$, or $CH_2Ph$. In some embodiments,

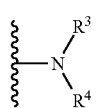

is selected from the group consisting of

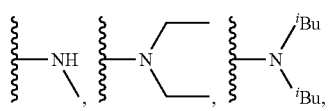

and

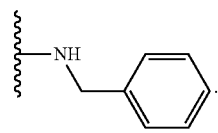 [SMILES: *NCc1ccccc1]

In various embodiments, $R^3$ and $R^4$ and the nitrogen to which they are attached join together to form a 5-6 membered ring. In some cases,

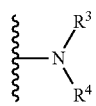

is selected from the group consisting of

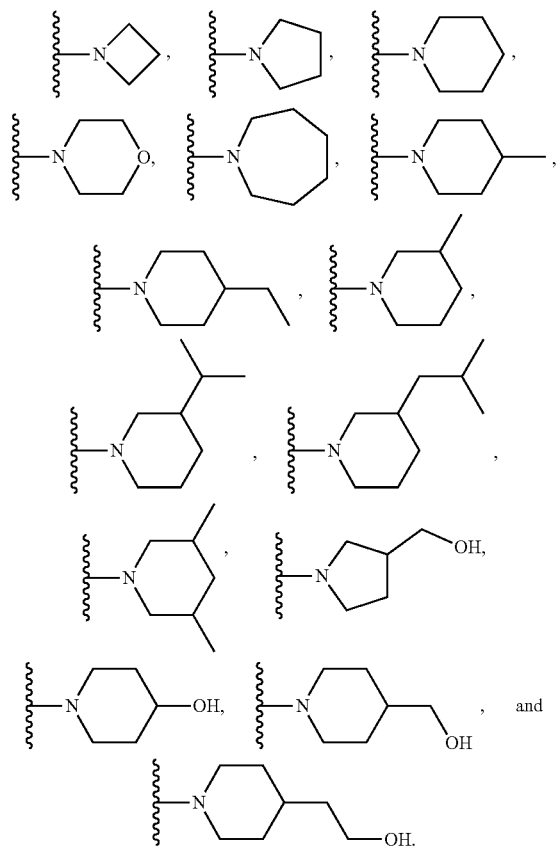

In various cases,

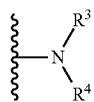

is selected from the group consisting of

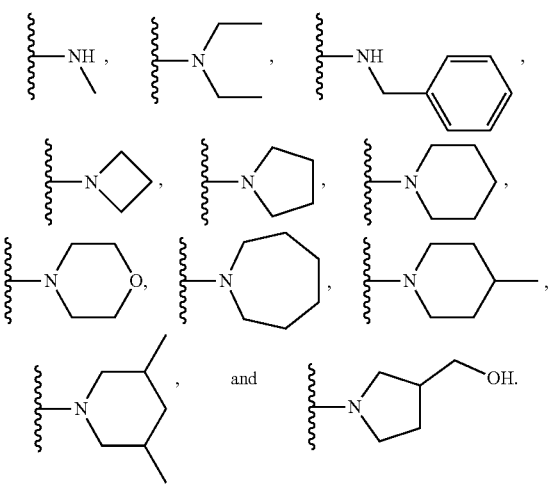

In some embodiments, $R^7$ is H. In various embodiments, $R^7$ is $NH_2$, Br, Cl, or F.

In some cases, provided herein is a compound listed in Table A, Table B, Table C, or a pharmaceutically acceptable salt of any of the foregoing.

In another aspect, the disclosure provides a pharmaceutical composition comprising a compound disclosed herein and a pharmaceutically acceptable carrier.

In yet another aspect, the disclosure provides a method of inhibiting the Notch activation complex kinase ("NACK") in a cell, comprising contacting the cell with a compound disclosed herein, or a pharmaceutically acceptable salt thereof, in an amount effective to inhibit NACK. In some embodiments, the compound or salt inhibits NACK recruitment to the Notch transcriptional complex ("NTC"). In various embodiments, the contacting comprises administering to a patient in need thereof. In various cases, the patient suffers from a disease associated with deregulation of the Notch transcriptional activation complex. In some embodiments, the disease is Tetralogy of Fallot ("TOF") or Alagille syndrome. In some cases, the disease is cancer. In some cases, the cancer is selected from the group consisting of T-cell acute lymphoblastic leukemia ("T-ALL"), B-cell acute lymphoblastic leukemia ("B-ALL"), breast cancer, medulloblastoma, colorectal cancer, non-small cell lung carcinoma ("NSCLC"), melanoma, cerebral autosomal-dominant ateriopathy with sub-cortical infarcts and leukoencephalophathy ("CADASIL"), chronic lymphocytic leukemia ("CLL"), hepatocellular carcinoma ("HOC"), myelomonocytic leukemia ("CMML"), pancreatic ductal adenocarcinoma ("PDAC"), head and neck squamous cell carcinoma ("HNSCC"), renal cell adenocarcinoma, and fibrosarcoma. In some cases, the disease is multiple sclerosis ("MS").

In yet another aspect, the disclosure provides a method of inhibiting kinase activity, ATPase activity, or both in a cell, comprising contacting the cell with a compound described herein, or a pharmaceutically acceptable salt thereof), in an amount effective to inhibit kinase and/or ATPase activity in the cell.

Further aspects and advantages will be apparent to those of ordinary skill in the art from a review of the following detailed description, taken in conjunction with the drawings. While the compounds and methods disclosed herein are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

FIG. 1 demonstrates that NACK is a novel therapeutic target in the Notch pathway.

FIG. 2 shows homology modeling and MD simulation of the kinase domain of NACK. FIG. 2A is a representation of the three-dimensional model for NACK kinase domain sequence using the IntFOLD method, compared with CASK kinase domain (PDB code: 3C0I) and PLK3 (PDB: 4B6L). The image was shown using PyMol. FIG. 2B shows comparisons between the key motifs of NACK, CASK and PLK3.

FIG. 3 shows a MD simulation of NACK coupled with ATP reveals the catalytic domain of NACK. FIG. 3E depicts the important NACK residues for ATP binding.

FIG. 4 demonstrates that NACK binds to the Notch transcription complex in an ATP-dependent manner. FIG. 4A shows NACK (K1002 or C979) mutations in mouse NACK blocks NACK recruitment to the Notch complex. FIG. 4B show that ATP and GTP hydrolysis is required for NACK recruitment. FIG. 4C shows the binding between NACK and ATP analog AMP-PNP using surface plasmon resonance (SPR).

FIG. 5 shows a cell-based assay to screen for inhibitors that selectively inhibit the viability of Notch/NACK dependent cell lines.

FIG. 6 shows in vitro biochemical assays to screen for the NACK inhibitors (iNACK) described herein.

FIG. 7 shows that the NACK inhibitors described herein block secondary sphere formation.

FIG. 8 shows that the NACK inhibitor Z271-0326 blocks Notch transcription complex binding to the Hes1 promoter.

FIG. 9. Demonstrates that the NACK inhibitor Z271-0326 induces cell apoptosis and senescence.

FIG. 10 shows surface plasmon resonance (SPR) analysis of Z271-0326 binding to NACK. FIG. 10A depicts surface plasmon resonance (SPR) analysis of Z271-0326 and AMP-PNP binding to GST tagged NACK protein (GST as control). FIG. 10B shows interactions between Z271-0326 and NACK. FIG. 10C shows the important residues responsible of Z271-0326 binding.

FIG. 11 demonstrates that Z271-0326 inhibits tumor growth of EAC47 PDX. FIG. 11E shows representative images of EAC47 PDX treated by DMSO, DAPT and Z271-0326 with Ki67 staining.

FIG. 12 shows the pharmacokinetic profile of Z271-0326 in a mouse.

DETAILED DESCRIPTION

Figure 1A:
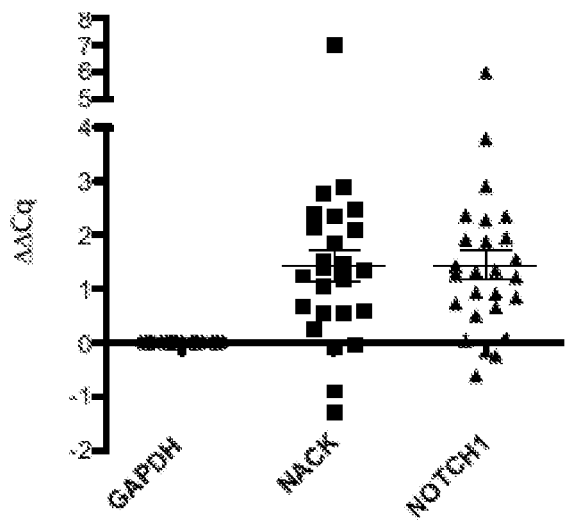
FIG. 1A shows the mRNA of clinical samples derived from surgically resected primary EAC (tumor tissue compared to its corresponding normal tissue), and demonstrates that mRNA levels of NACK and Notch1 are elevated in most of the tumor tissues compared to their corresponding normal tissues.

Provided herein are compounds that inhibit the Notch activation complex kinase ("NACK"), and methods of using the compounds to treat and prevent diseases associated with the Notch transcriptional activation complex ("NTC"), such as cancer. "Notch activation complex kinase" or "NACK" generally refers to a Notch-associated protein that functions as a co-activator of Notch transcriptional activity. NACK proteins can include a protein having a SEQ ID NO: 1; PEAK1 Related Kinase Activating Pseudokinase; Sugen Kinase 223; Pragmin, RND2 Effector Protein; SGK223; Tyrosine-Protein Kinase SgK223; Homolog Of Rat Pragma Of Rnd2; EC 2.7.10.2; PRAGMIN; and PEAK2.

The compounds and methods provided herein can complement existing strategies by providing rescue to resistance of the mAb or GSI therapies, resulting in therapeutic depth in the attack on an activated Notch pathway. By exploiting multiple targets within a particular cancer pathway, superior outcomes in individuals afflicted with the cancer can occur.

NACK acts as a Notch transcriptional co-activator, and an essential regulator of Notch-mediated tumorigenesis and development. See Weaver et al., Cancer Research 74, 4741-4751 (2014). NACK functions in an ATP dependent manner to bind to the Notch transcription complex and to activate Notch-mediated transcription. Because of NACK's prominent role in the Notch pathway, it can act as a suitable drug target.

Without being bound by any particular theory, the compounds described herein can interrupt recruitment of NACK to the Notch transcription complex, which inhibits Notch-mediated transcriptional cascade, and suppresses tumor growth in patients. In some cases, the compounds disclosed herein are specific inhibitors for Notch dependent cells, and therefore, do not inhibit or kill cells that are not dependent on Notch.

The Notch signaling pathway is a particularly attractive target for inhibitor development. Prior to ligand activation and cleavage, the Notch intracellular domain ("NICD") is bound to the cell membrane, and therefore, accessible to potential inhibitors. Further, the NTC is constantly being recycled, thus requiring constant reformation on chromatin for maintenance of the Notch transcriptional cascade driving the neoplastic phenotype. Therefore, ample opportunity exists for a small molecule to target the exposed interaction surfaces on the NTC components and prevent complex formation.

In various cases, the compounds of the disclosure can inhibit recruitment of NACK to the NTC by about 50%, 55%, 60%, 65%, 70%, 75%, 80%, 85%, 90%, 95%, 97%, or 99% or more of the positive control. In some embodiments, the compounds of the disclosure can inhibit recruitment by about 75%, 80%, 85%, 90%, 95%, 97%, or 99% or more of the positive control. For example, the compounds disclosed herein can inhibit recruitment by about 85%, 86%, 87%, 88%, 89%, 90%, 91%, 92%, 93%, 94%, 95%, 96%, 97%, 98%, or 99% or more of the positive control. Furthermore, the compounds disclosed herein can inhibit NACK with an $IC_{50}$ of about 5 µM or less, or about 4 µM or less, or about 3 µM or less, or about 2 µM or less, or about 1 µM or less, or about 0.6 µM or less, or about 0.5 µM or less, or about 0.4 µM or less, or about 0.3 µM or less, or about 0.2 µM or less, or about 0.1 µM or less, or about 0.05 µM or less. In some embodiments, the compounds of the disclosure can inhibit NACK with an $IC_{50}$ of about 1 µM or less, or about 0.6 µM or less, or about 0.5 µM or less, or about 0.4 µM or less, or about 0.3 µM or less, or about 0.2 µM or less, or about 0.1 µM or less, or about 0.05 µM or less. In some cases, the compounds of the disclosure can inhibit NACK with an $IC_{50}$ of about 0.5 µM or less, or about 0.4 µM or less, or about 0.3 µM or less, or about 0.2 µM or less, or about 0.1 µM or less, or about 0.05 µM or less. For example, the compounds of the disclosure can inhibit NACK with an $IC_{50}$ of about 0.2 µM or less, or about 0.19 µM or less, or about 0.18 µM or less, or about 0.17 µM or less, or about 0.16 µM or less, or about 0.15 µM or less, or about 0.14 µM or less, or about 0.13 µM or less, or about 0.12 µM or less, or about 0.11 µM or less, or about 0.10 µM or less, or about 0.09 µM or less, or about 0.08 µM or less, or about 0.07 µM or less, or about 0.06 µM or less, or about 0.05 µM or less. The compounds described herein can inhibit NACK by disrupting recruitment of NACK to the NTC.

The compounds of the disclosure have several advantageous properties and effects. The compounds can, for example: (1) selectively disrupt the recruitment of NACK to the NTC with $IC_{50}$s in the low micromolar range; (2) cause down regulation of Notch transcription activity; (3) block Notch transcription complex binding to the Hes1 promoter; (4) induce cell apoptosis and senescence; and/or (5) inhibit tumor growth.

Definitions

As used herein, "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), isobutyl (2,2-dimethylethyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "alkylene" refers to an alkyl group having a substituent. For example, the term "alkylene-aryl" refers to an alkyl group substituted with an aryl group. The term $C_n$ means the alkylene group has "n" carbon atoms. For example, $C_5$ alkylene refers to an alkylene group having a number of carbon atoms encompassing the entire range, as well as all subgroups, as previously described for "alkyl" groups. Unless otherwise indicated, the alkylene group itself can be unsubstituted or substituted.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_5$-$C_8$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated, share a carbon atom with another cycloalkyl or heterocycloalkyl group, or fused to another cycloalkyl group, a heterocycloalkyl group, an aryl group and/or a heteroaryl group. Cycloalkyl groups can be saturated or partially unsaturated ring systems optionally substituted with, for example, one to three groups, independently selected alkyl, alkylene-OH, $C(O)NH_2$, $NH_2$, oxo (=O), aryl, haloalkyl, halo, and OH.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group. Unless otherwise indicated, an aryl group can be fused to a cycloalkyl or heterocycloalkyl group.

As used herein, the term "aryloxy" refers to —O-aryl.

As used herein, the term "aralkyl" refers to an alkyl group that is substituted with an aryl moiety. The term $C_n$ indicates n carbon atoms of the alkyl group of the aralkyl.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, thiophenyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

As used herein, the term "halo" refers to a fluoro, chloro, bromo, or iodo group. The term "haloalkyl" refers to an alkyl group that is substituted with at least one halogen.

As used herein, the term "alkoxyl" refers to —OR, wherein 'R' is a radical.

As used herein, the term "amino" refers to a —$NH_2$ or —NH— group, wherein each hydrogen in each Formula can be replaced with an alkyl, cycloalkyl, aryl, heteroaryl, or heterocycloalkyl group.

As used herein, the term "amido" refers to an amino group that is substituted with a carbonyl moiety (e.g., —NRC(=O)— or —C(=O)NR—), wherein R is a substituent on the nitrogen (e.g., alkyl or H).

As used herein, the term "carbamyl" refers to the following functional group —NR(C=O)O— or —OC(=O)NR—, wherein R is a substituent on the nitrogen (e.g., alkyl or H).

As used herein, the term "S-thiocarbamyl" refers to the following functional group —SC(=O)NR— or —NRC(=O)S—, wherein R is a substituent on the nitrogen atom (e.g., H or alkyl).

As used herein, the term "ureido" refers to the following functional group —NR(C=O)NR—, wherein each R is a substituent on the nitrogen (e.g., alkyl or H).

A used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

As used herein, the term "therapeutically effective amount" means an amount of a compound or combination of therapeutically active compounds (e.g., an inhibitor described herein, or a combination of inhibitors) that ameliorates, attenuates or eliminates one or more symptoms of a particular disease or condition (e.g., cancer), or prevents or delays the onset of one of more symptoms of a particular disease or condition.

As used herein, the terms "patient" and "subject" may be used interchangeably and mean animals, such as dogs, cats, cows, horses, and sheep (i.e., non-human animals) and humans. Particular patients are mammals (e.g., humans). The term patient includes males and females.

As used herein, the term "pharmaceutically acceptable" means that the referenced substance, such as a compound of the present invention, or a formulation containing the compound, or a particular excipient, are safe and suitable for administration to a subject or patient. The term "pharmaceutically acceptable carrier" refers to a medium that does not interfere with the effectiveness of the biological activity of the active ingredient(s) and is not toxic to the host to which it is administered.

As used herein the terms "treating", "treat" or "treatment" and the like include preventative (e.g., prophylactic) and palliative treatment.

As used herein, the term "excipient" means any pharmaceutically acceptable additive, carrier, diluent, adjuvant, or other ingredient, other than the active pharmaceutical ingredient (API).

As used herein, the term "Notch transcriptional activation complex" ("NTC") refers to a complex of three proteins, the DNA binding protein CSL, the intracellular domain of Notch ("NICD") and the co-activator protein Mastermind ("MAML1"), which functions to activate transcription of target genes.

As used herein, the phrase "deregulation of the Notch transcriptional activation complex" or "deregulation of the NTC" refers to an abnormality in the regulatory ability of the NTC, resulting in reactivation of gene transcription.

Notch Transcriptional Activation Complex Kinase ("NACK") Inhibitors

Disclosed herein are compounds that can inhibit Notch activation complex kinase ("NACK").

In some embodiments, the disclosure provides a compound of Formula (Ia), or a pharmaceutically acceptable salt thereof:

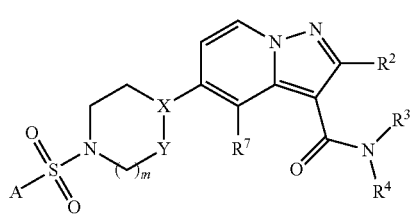

(Ia)

wherein:

A is $C_{1-4}$alkyl or

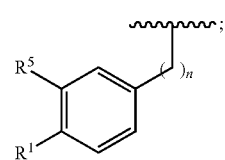

X is CH or N;

Y is $CH_2$ or N, and when X is N, then Y is $CH_2$;

m is 0 or 1, and when m is 1 then Y is $CH_2$;

n is 0 or 1;

$R^1$ is H, $C_{1-6}$alkyl, $C_{0-6}$alkyleneC(=O)$R^6$, halo, cyano, aryloxy, amino, $C_{0-3}$alkylene-amido, carbamyl, S-thiocarbamyl, or ureido;

$R^2$ is H, halo, $C_{1-6}$alkyl, $C_{3-8}$cycloalkyl, or heteroaryl;

each $R^3$ and $R^4$ independently is H, $C_{1-6}$ alkyl, or $C_{1-3}$aralkyl, or $R^3$ and $R^4$ and the nitrogen to which they are attached join together to form a 3-6 membered ring optionally comprising 1 to 3 additional heteroatoms selected from N, O, and S;

$R^5$ is H, or $R^1$ and $R^5$ together with the atoms to which they are attached form a 5- or 6-membered heterocyclic ring comprising 1 to 3 ring heteroatoms selected from N, O, and S;

$R^6$ is OH, $C_{1-6}$alkyl, or $OC_{1-6}$alkyl;

$R^7$ is H, halo or amino;

with the proviso that the compound is not

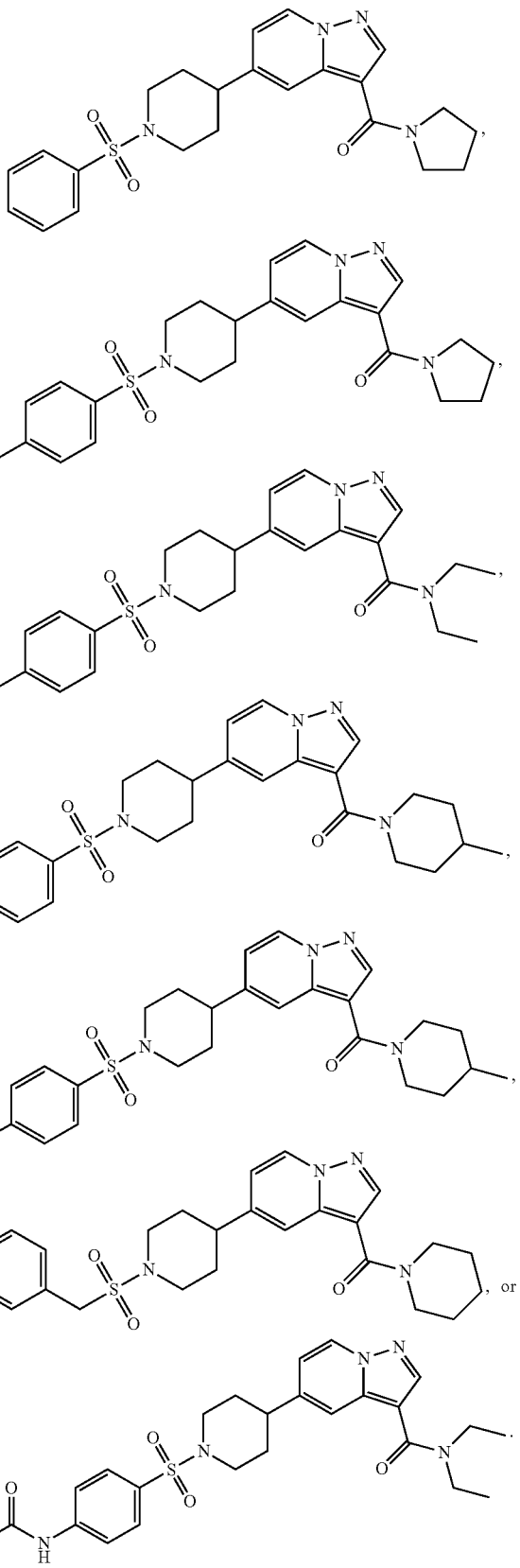

In some embodiments, the disclosure provides a compound of Formula (I), or a pharmaceutically acceptable salt thereof:

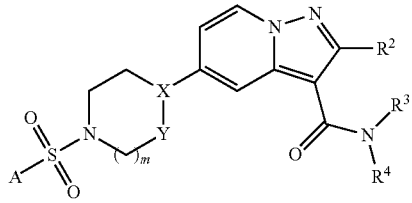
(I)

wherein A is $C_{1-4}$alkyl or

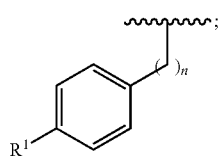

X is CH or N; Y is $CH_2$ or N, and when X is N, then Y is $CH_2$; m is 0 or 1, and when m is 1 then Y is $CH_2$; n is 0 or 1; $R^1$ is H, $C_{1-6}$alkyl, halo, cyano, aryloxy, amino, amido, carbamyl, or ureido; $R^2$ is H, halo, $C_{1-6}$alkyl, $C_{3-8}$cycloalkyl, or heteroaryl; and each $R^3$ and $R^4$ independently is H, $C_{1-6}$ alkyl, or $C_{1-3}$aralkyl, or $R^3$ and $R^4$ and the nitrogen to which they are attached join together to form a 5-6 membered ring; with the proviso that the compound is not

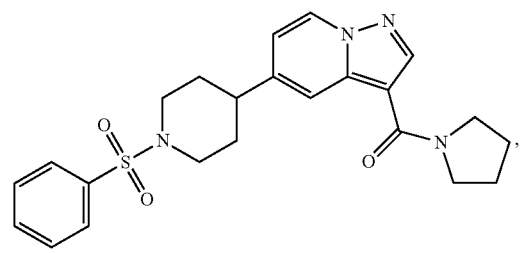

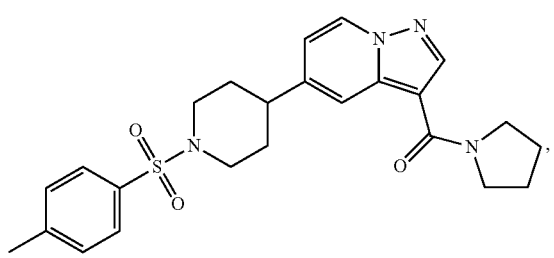

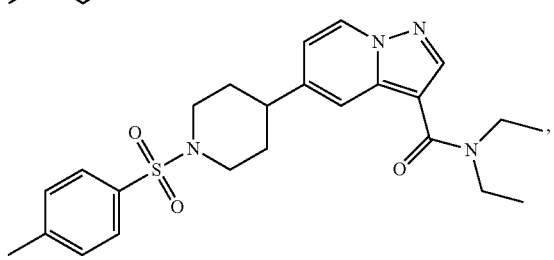

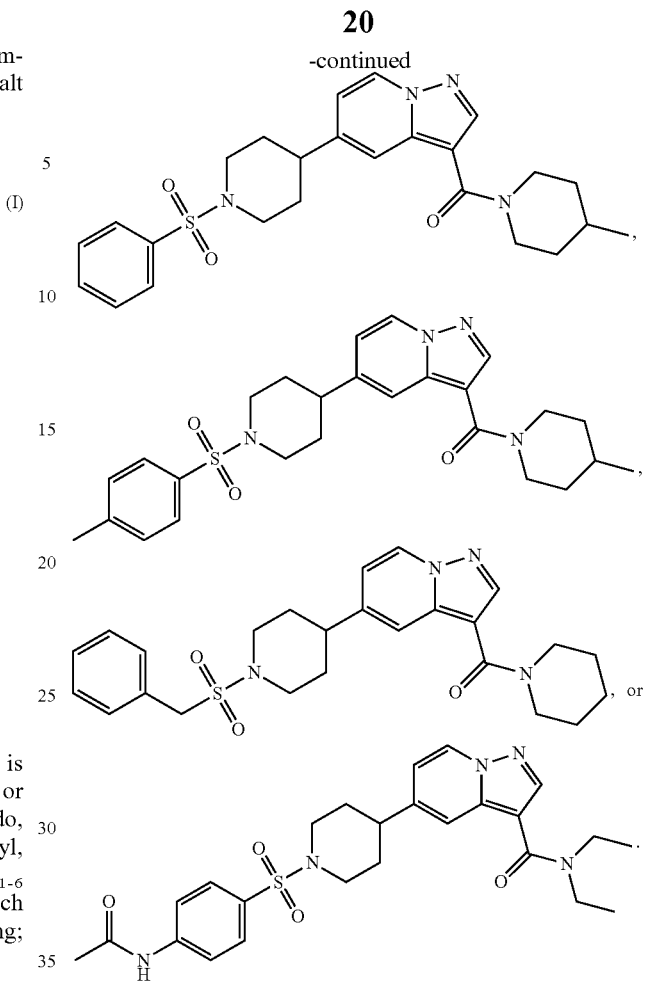

In some embodiments, A is $C_{1-4}$alkyl. Suitable A groups can include, for example, methyl, ethyl, propyl, isopropyl, n-butyl, s-butyl, isobutyl, or t-butyl. In some cases, A is methyl. In some embodiments, A is not $C_{1-4}$alkyl.

In some embodiments, A is

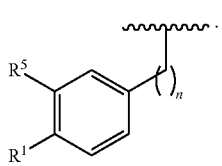

In some embodiments, n is 0. In various cases, n is 1. In some embodiments, $R^1$ and $R^5$ together with the atoms to which they are attached form a 5- or 6-membered heterocyclic ring comprising 1 to 3 ring heteroatoms selected from N, O, and S. In some cases, A is selected from the group consisting of

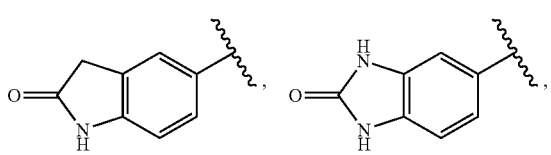

-continued

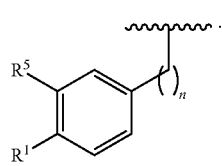

In some cases, A is

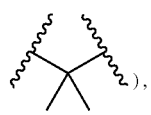 [SMILES: *C(*)(C)C]

and $R^5$ is H. In some cases, $R^1$ is H. In some embodiments, $R^1$ is $C_{1-6}$ alkyl. Suitable $R^1$ groups can include methyl, ethyl, propyl, isopropyl, n-butyl, s-butyl, isobutyl, t-butyl, pentyl, or hexyl. In some cases, $R^1$ is unsubstituted. For example, $R^1$ can be methyl or ethyl. In some cases, $R^1$ is substituted. For example, $R^1$ can be fluoromethyl or trifluoromethyl. In some embodiments, $R^1$ is $C_{0-6}$ alkyleneC(=O)$R^6$. In some cases, $R^1$ is $C_{1-3}$ alkyleneC(=O)$R^6$. In various embodiments, the alkylene group is unsubstituted. In some cases, the alkylene group is substituted with one or more alkyl groups (e.g., one or more methyl groups, such as

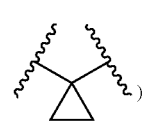 [SMILES: *C1(*)CC1]

or a spiro group (e.g.,

In some embodiments, $R^6$ is OH or OC$_{1-6}$alkyl (e.g., OMe, OEt, OPr, OiPr, 2-ethyl). In various embodiments, $R^6$ is $C_{1-6}$alkyl (e.g., methyl, ethyl, or propyl). Suitable $R^1$ groups can include

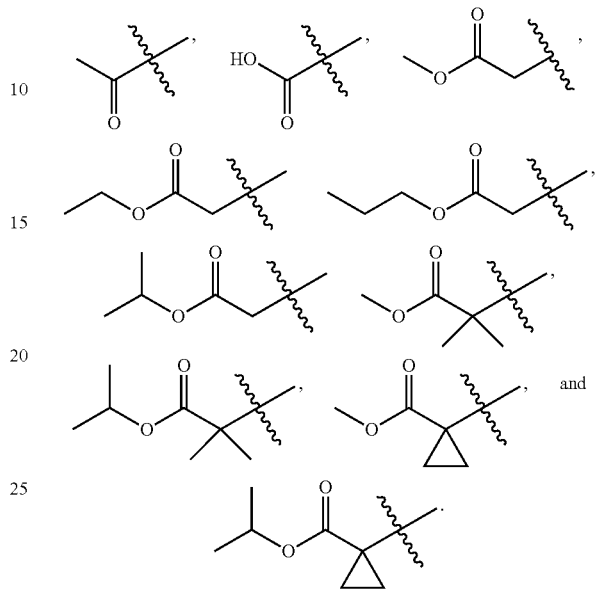

In some cases, $R^1$ is halo (e.g., F). In some embodiments, $R^1$ is cyano. In various embodiments, $R^1$ is aryloxy. For example, $R^1$ can be —CN or —OPh. In some cases, $R^1$ is amino (e.g., NH$_2$). In some embodiments, the amino is mono-substituted with a $C_{1-3}$alkyl group (e.g., methyl, ethyl, propyl). In various cases, the amino is di-substituted with the same or different $C_{1-3}$alkyl groups. For example, $R^1$ can be —NH$_2$, —N(CH$_3$)$_2$ or —NH$_2$Ph. In various cases, $R^1$ is $C_{0-3}$alkylene-amido. In some cases, $R^1$ is $C_0$alkylene-amido. In various cases, $R^1$ is $C_1$alkylene-amido. In some embodiments, the $C_{0-3}$alkylene-amido group terminates in a $C_{1-6}$alkyl group, a $C_{3-8}$cycloalkyl group, an amino group, or a heteroaryl group. Suitable $C_{0-3}$ alkylene-amido groups can include

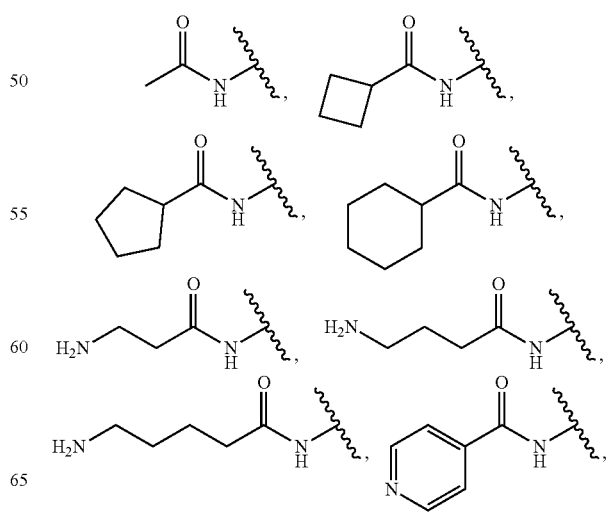

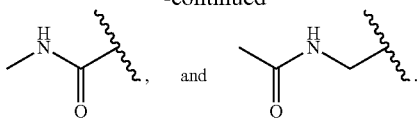

In some embodiments, R¹ is a carbamyl group. In some cases, the carbamyl group terminates in a $C_{1-6}$alkyl group or a $C_{3-8}$cycloalkyl group. In some embodiments, the alkyl group is substituted (e.g., with fluorine). Suitable carbamyl groups can include, for example,

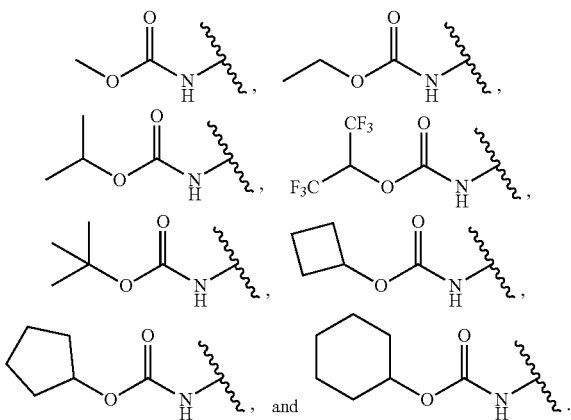

In some embodiments, R¹ is a S-thiocarbamyl group. In various embodiments, the S-thiocarbamyl group can terminate in a $C_{1-6}$alkyl group or a $C_{3-8}$cycloalkyl group. In some embodiments, the alkyl group is substituted (e.g., with fluorine). Suitable S-thiocarbamyl groups can include, for example,

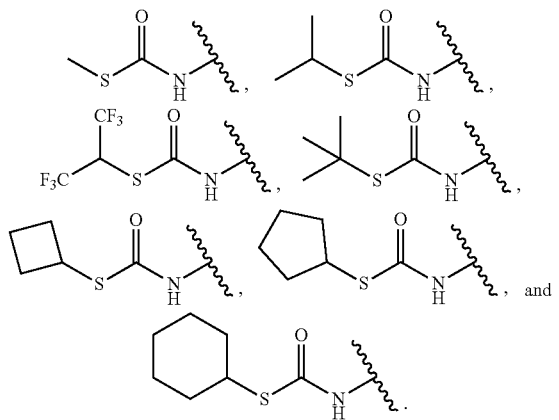

In some cases, R¹ is ureido group. In various cases, the ureido group can terminate in a $C_{1-6}$alkyl group or a $C_{3-8}$cycloalkyl group. In some embodiments, the alkyl group is substituted (e.g., with fluorine). Suitable ureido groups can include, for example,

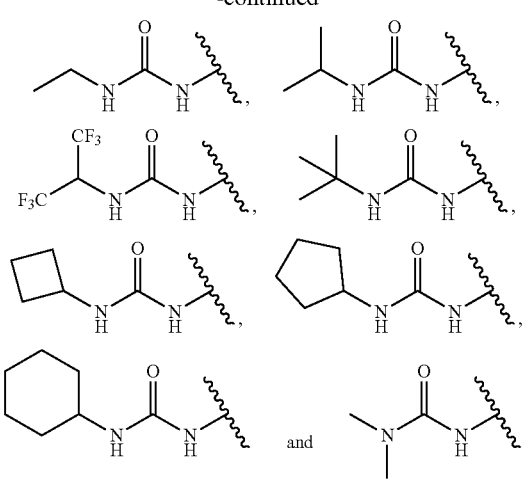

In various cases, R¹ is amido, carbamyl, or ureido.

In some cases, A is selected from the group consisting of $CH_3$,

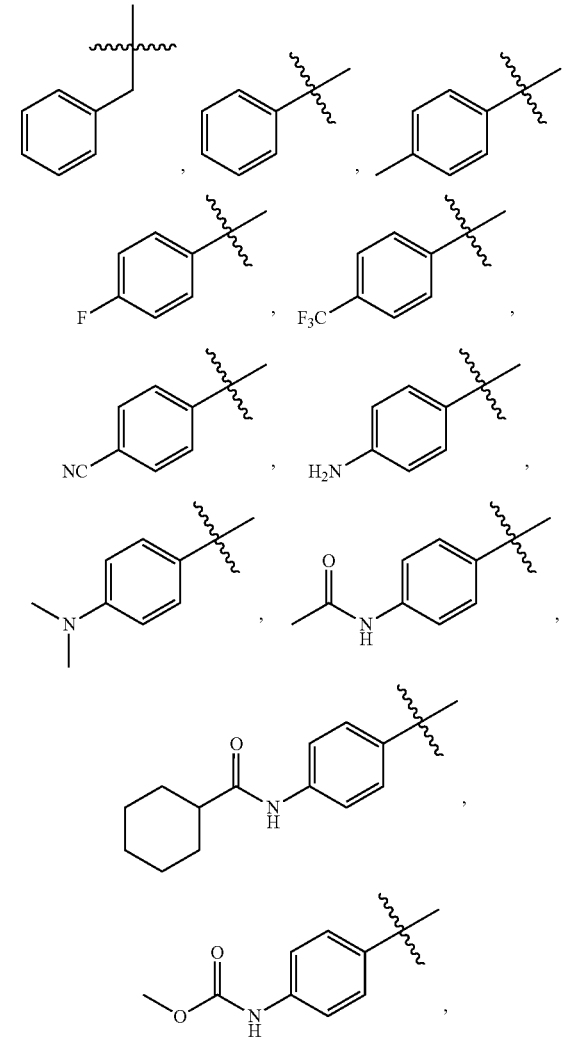

-continued

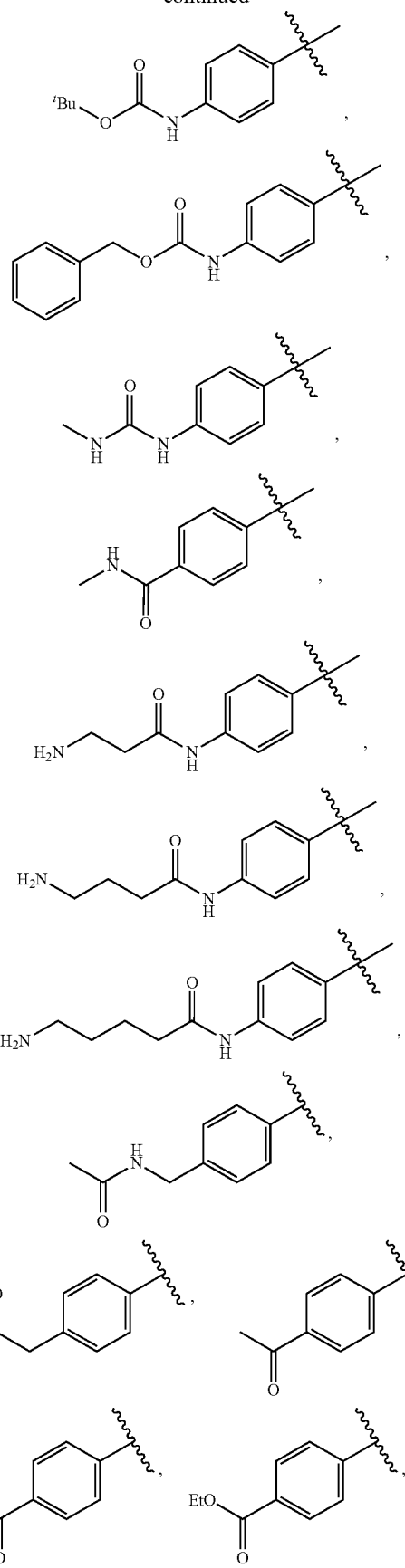

-continued

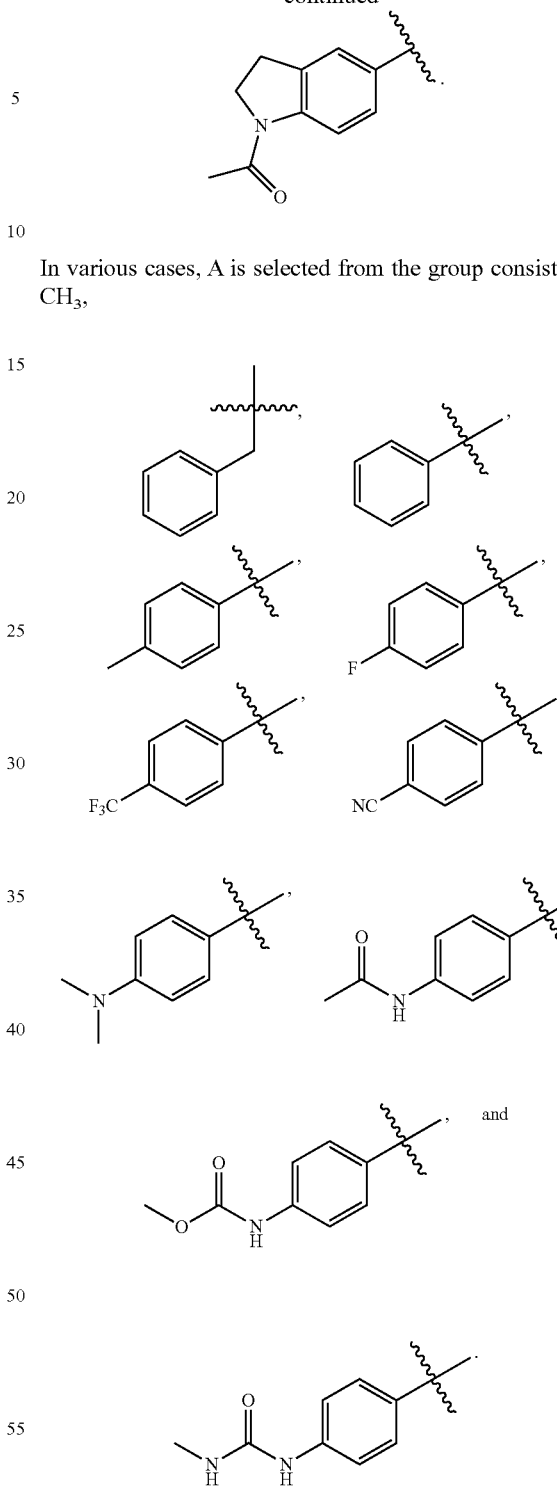

In various cases, A is selected from the group consisting of CH$_3$,

In some embodiments, X is CH. In various embodiments, X is N. In some cases, Y is CH$_2$. In various cases, Y is N. In some cases, m is 0. In various cases, m is 1. In some embodiments, X is CH, Y is CH$_2$, and m is 1. In various embodiments, X is CH, Y is CH$_2$, and m is 0. In some cases, X is N, Y is CH$_2$, and m is 1. In various cases, X is CH, Y is N, and m is 0. In some embodiments, the compound of Formula (Ia) has a structure of Formula (Ia'):

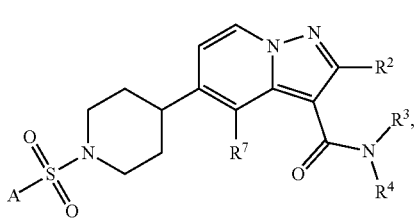

(Ia')

wherein the substituents are as previously defined.

In some embodiments, $R^2$ is H. In various embodiments, $R^2$ is halo. For example, $R^2$ can be Br or Cl. In some cases, $R^2$ is $C_{1-6}$ alkyl. Suitable $R^2$ groups can include methyl, ethyl, propyl, isopropyl, n-butyl, s-butyl, isobutyl, t-butyl, pentyl, or hexyl. In some cases, $R^2$ is unsubstituted. For example, $R^2$ can be methyl or ethyl. In some cases, $R^2$ is substituted. In various cases, $R^2$ can be substituted with a fluoro, hydroxyl, or alkoxyl group. For example, $R^2$ can be $CH_3$, $CF_3$, $CH_2OH$, or $CH_2OCH_3$. In some embodiments, $R^2$ is $C_{3-8}$cycloalkyl. In some cases, $R^2$ is cyclopropyl, cyclobutyl, cyclopentyl, or cyclohexyl. In various cases, $R^2$ is heteroaryl. In various embodiments, $R^2$ is selected from the group consisting of H, $CH_3$, $CF_3$, and cyclopropyl.

In some embodiments, $R^7$ is H. In various embodiments, $R^7$ is halo or amino. In some embodiments, $R^7$ is F, Cl, or Br. In some embodiments, $R^7$ is —$NH_2$. In some embodiments, each of $R^2$ and $R^7$ is H. In some cases, the compound of Formula (Ia) has a structure of Formula (Ia"):

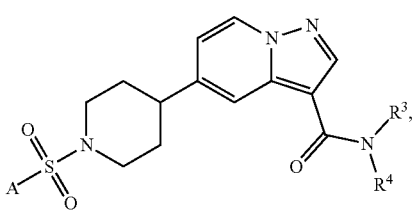

(Ia")

wherein the substituents are as previously defined.

In some embodiments, each of $R^3$ and $R^4$ independently is H, $C_{1-6}$ alkyl, or $C_{1-3}$aralkyl. Suitable alkyl groups include, for example, methyl, ethyl, propyl, isopropyl, n-butyl, s-butyl, isobutyl, t-butyl, pentyl, and hexyl. In some cases, each $R^3$ and $R^4$ independently is H, $CH_3$, $CH_2CH_3$, $^iBu$, or $CH_2Ph$. In various cases,

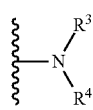

is selected from the group consisting of

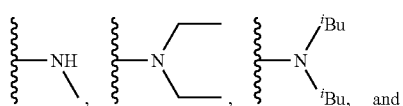

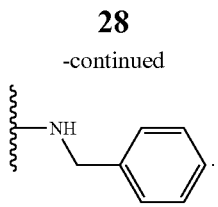

In some embodiments, $R^3$ and $R^4$ and the nitrogen to which they are attached join together to form a 3-6-membered ring. In some embodiments, $R^3$ and $R^4$ and the nitrogen to which they are attached join together to form a 4-membered ring. In some embodiments, $R^3$ and $R^4$ and the nitrogen to which they are attached join together to form a 5-6 membered ring. In various embodiments, the 5-6 membered ring is a pyrrolidine or piperidine ring. In some embodiments, the 3-6 membered ring comprises 1 to 3 additional heteroatoms selected from N, O, and S. In some cases,

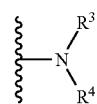

is selected from the group consisting of

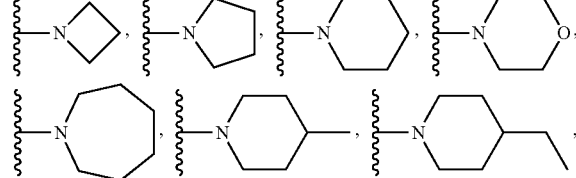

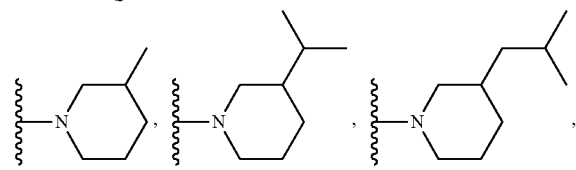

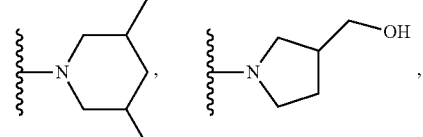

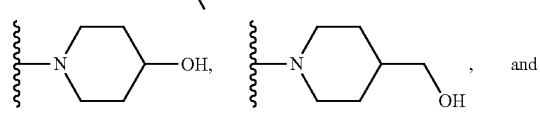

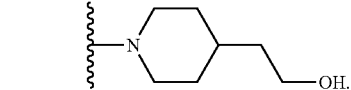

In various

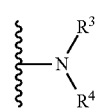

is selected from the group consisting of

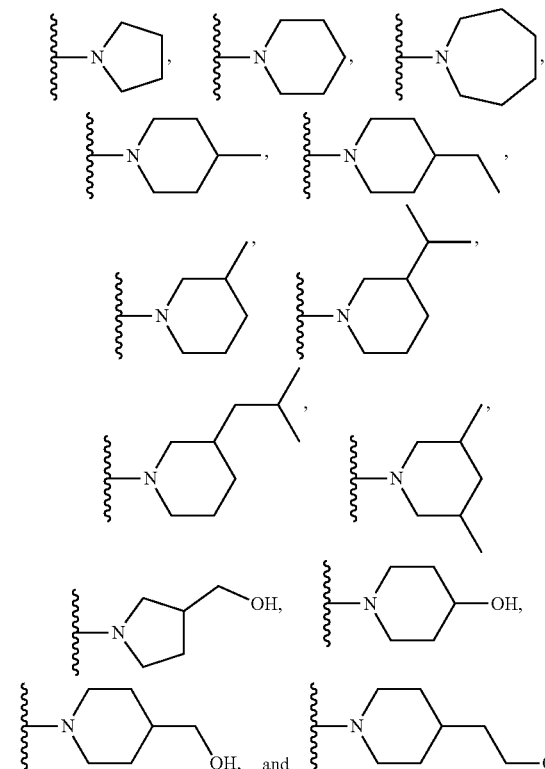

For example,

can be selected from the group consisting of

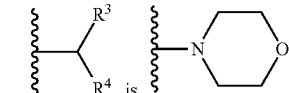

In some cases, $$\begin{matrix} R^3 \\ \text{\textit{\textasciitilde}}\!\!-\!\!\!\begin{matrix}\\ \\R^4\end{matrix} \text{ is } \text{\textit{\textasciitilde}}\!\!-\!\!N \!\!\!\begin{matrix}\square\end{matrix}\end{matrix}.$$

In some cases, $$\begin{matrix} R^3 \\ \text{\textit{\textasciitilde}}\!\!-\!\!\!\begin{matrix}\\ \\R^4\end{matrix} \text{ is } \text{\textit{\textasciitilde}}\!\!-\!\!N \!\!\!\begin{matrix}O\end{matrix}\end{matrix}.$$

Contemplated compounds of the disclosure include the compounds listed in Table A and pharmaceutically acceptable salts thereof:

TABLE A

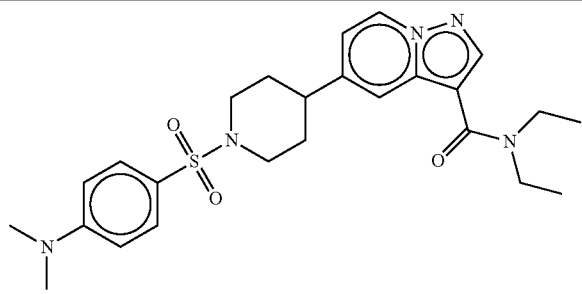

7B

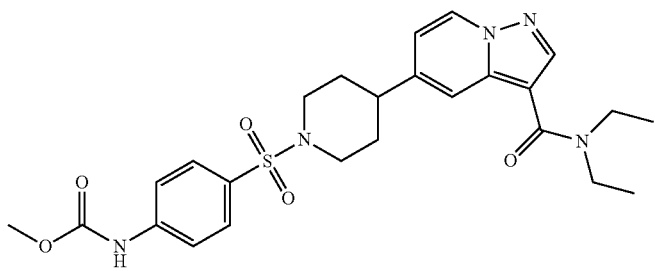 [SMILES: CCN(CC)C(=O)c1cnn2ccc(C3CCN(S(=O)(=O)c4ccc(NC(=O)OC)cc4)CC3)cc12]

7C

TABLE A-continued
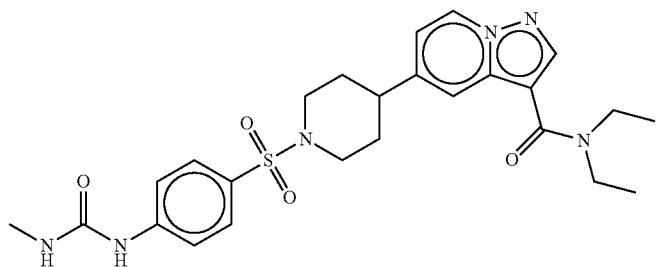 7D
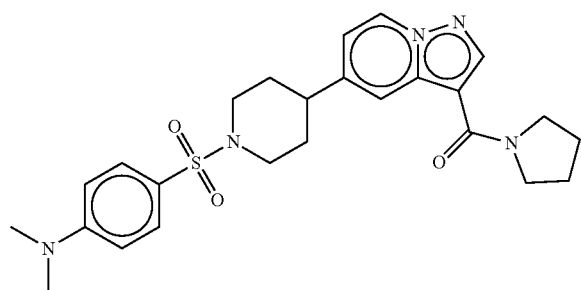 7F
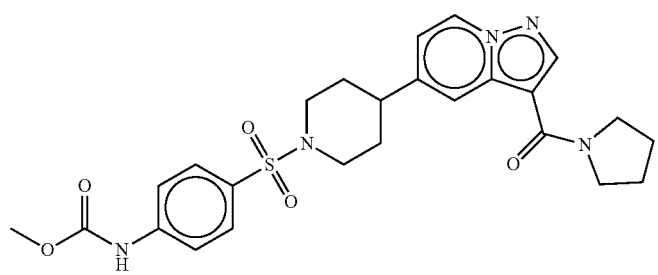 7G
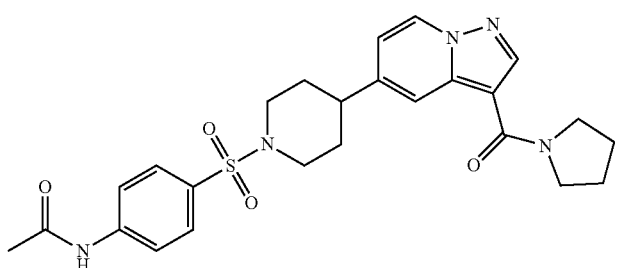 [SMILES: CC(=O)Nc1ccc(S(=O)(=O)N2CCC(c3ccn4ncc(C(=O)N5CCCC5)c4c3)CC2)cc1] 7H
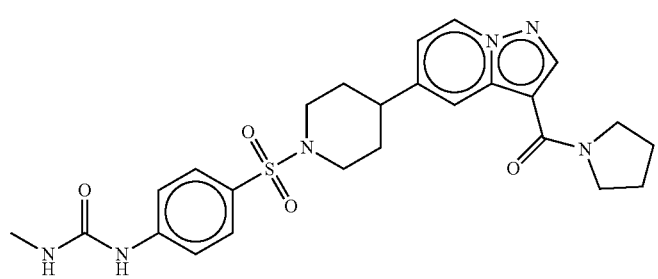 7I TABLE A-continued
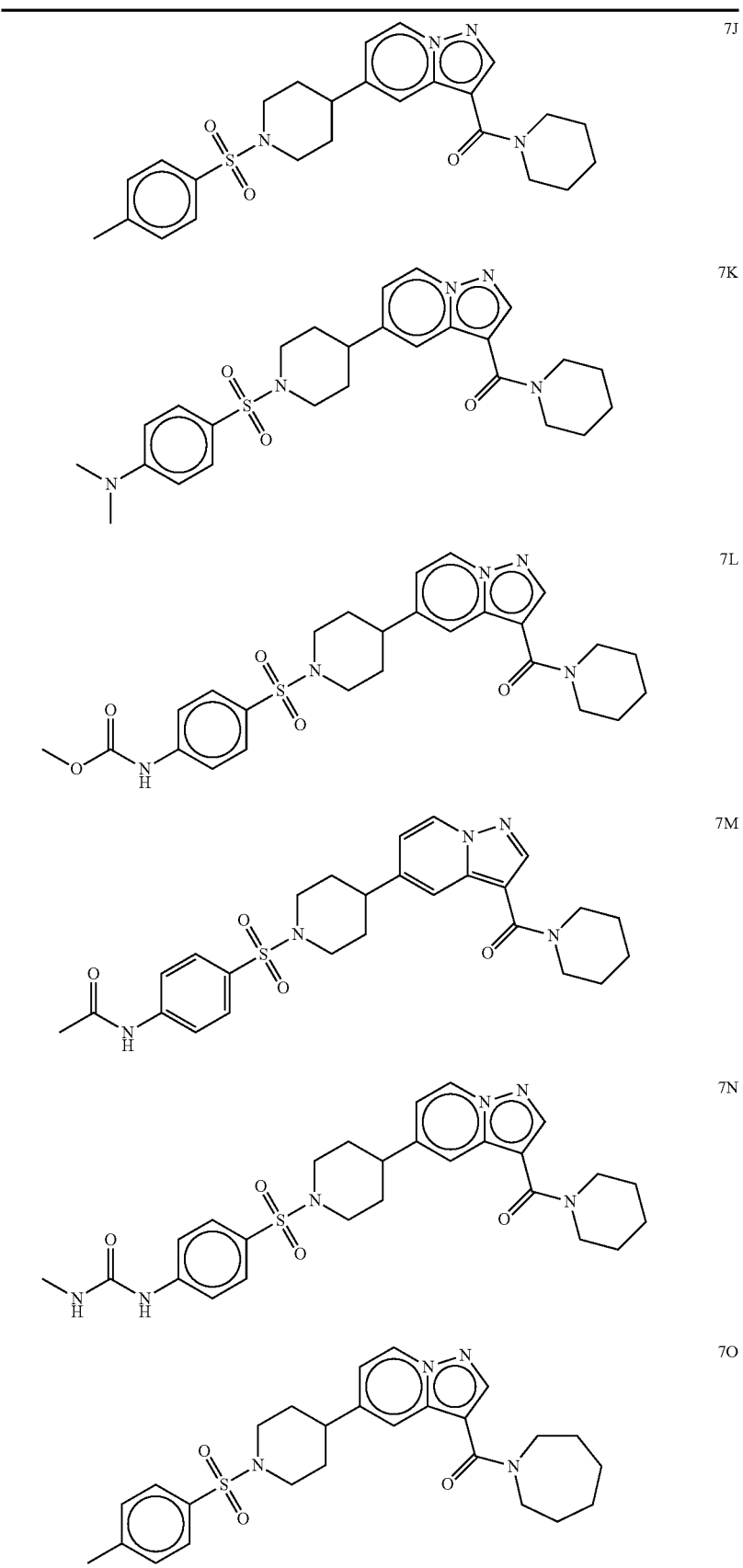
7J
7K
7L
7M
7N
7O TABLE A-continued
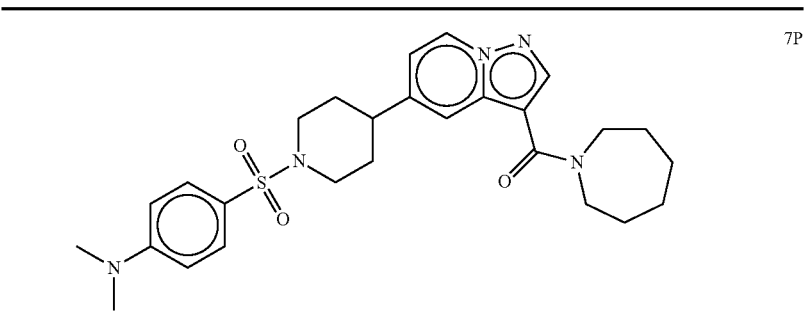
7P
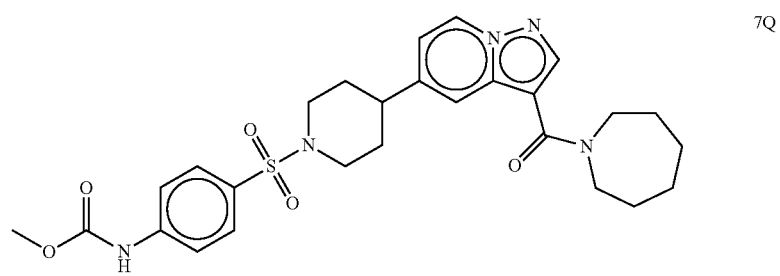
7Q
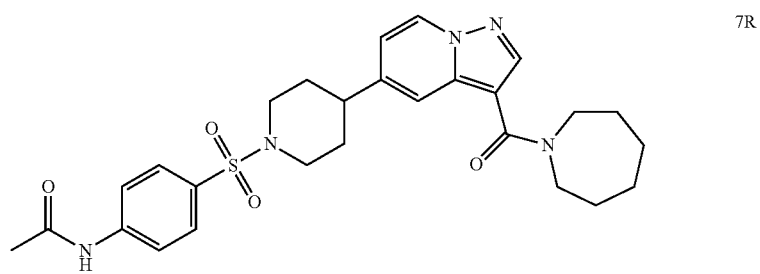
7R
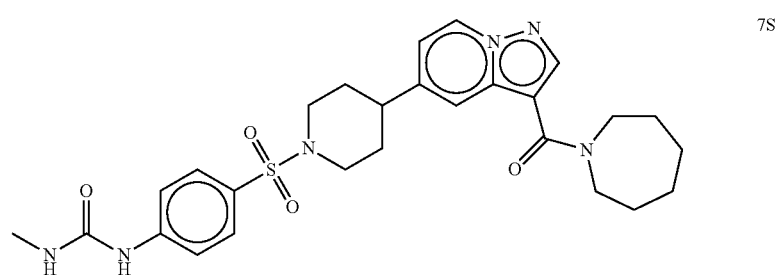
7S
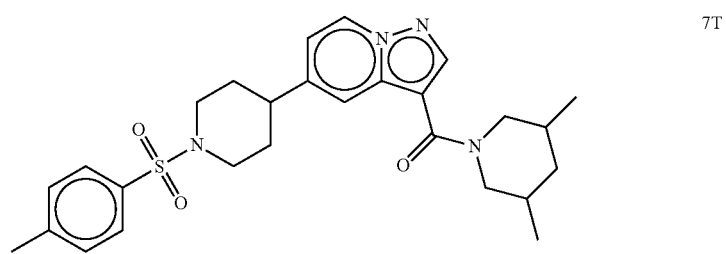
7T TABLE A-continued
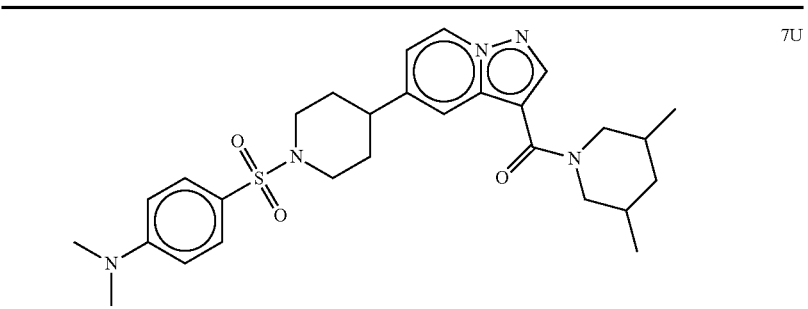
7U
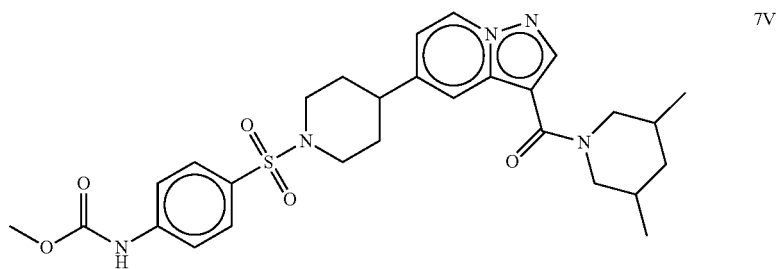
7V
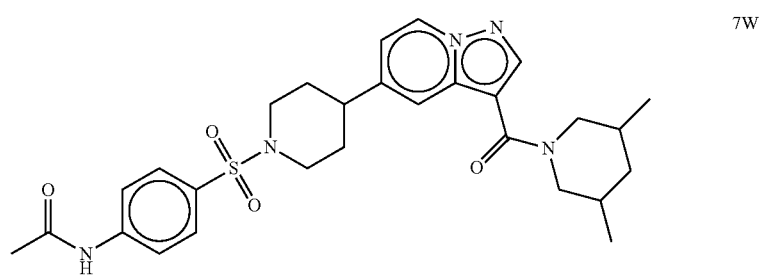
7W
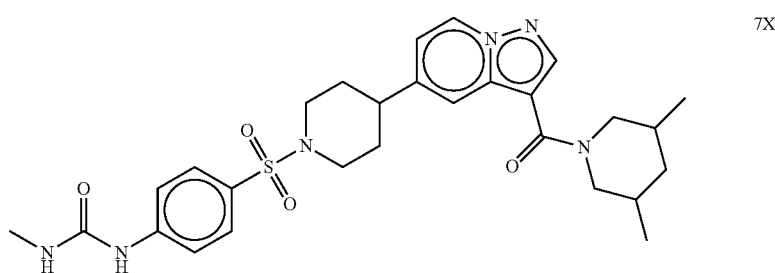
7X
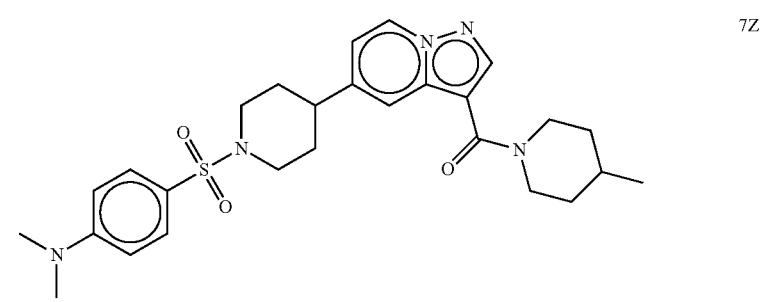
7Z TABLE A-continued
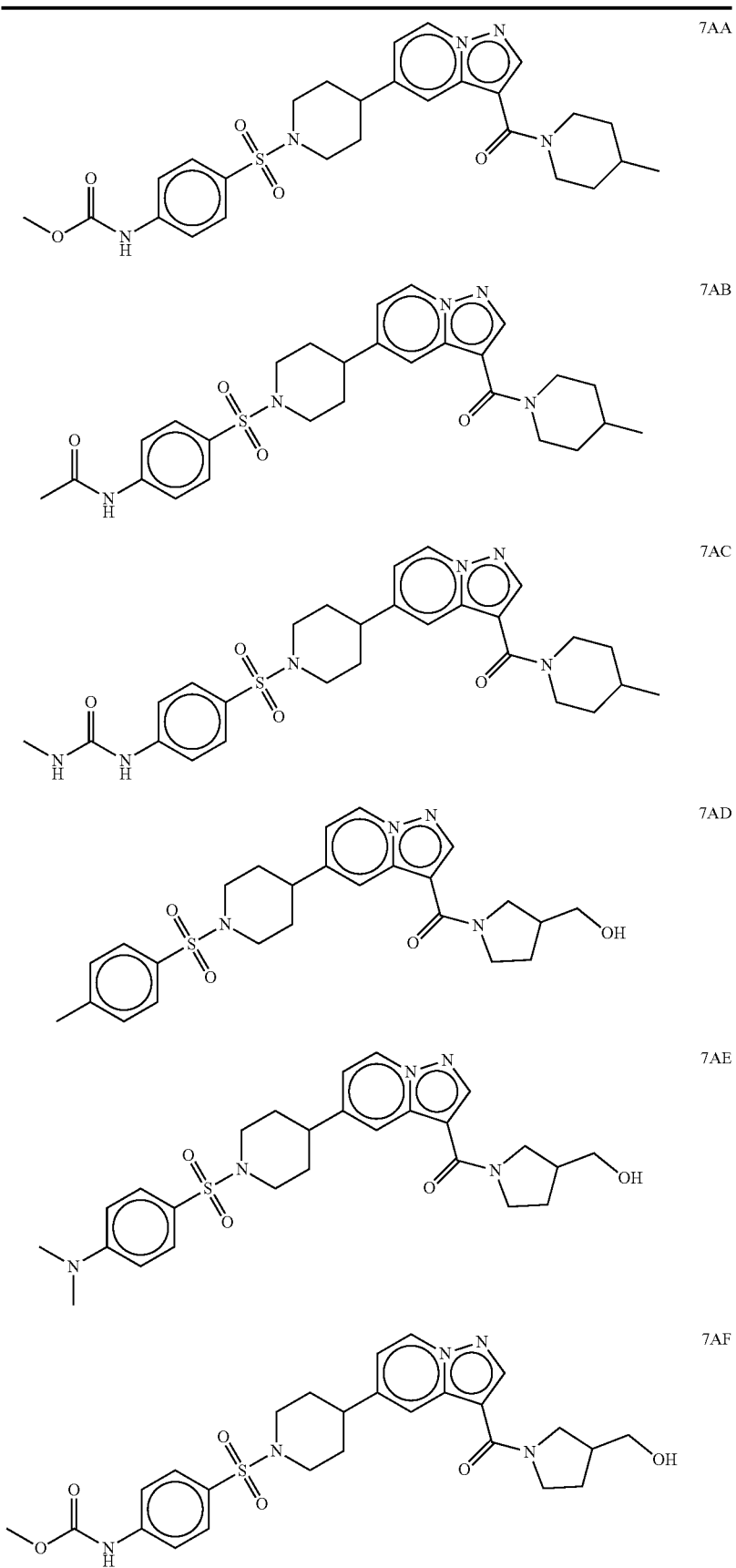

TABLE A-continued
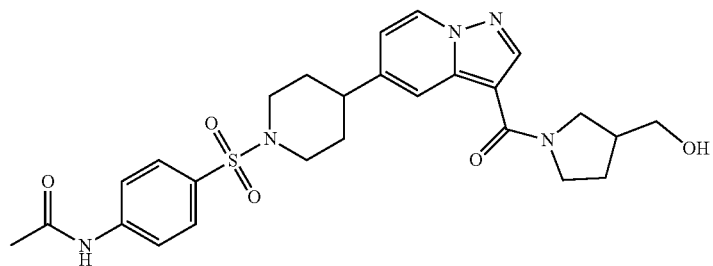
7AG
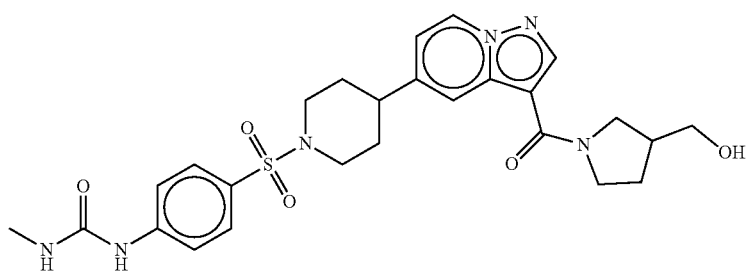
7AH
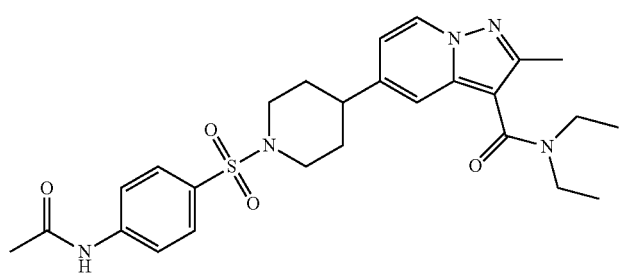 [SMILES: CCN(CC)C(=O)c1c(C)nn2ccc(C3CCN(S(=O)(=O)c4ccc(NC(C)=O)cc4)CC3)cc12]
7AI
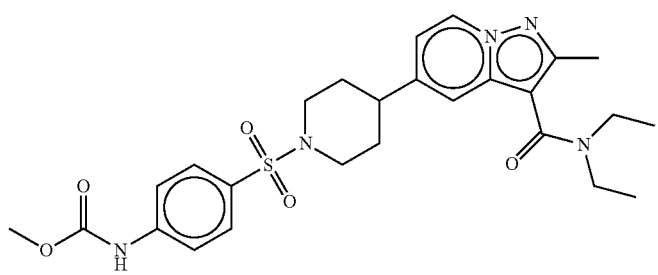
7AJ
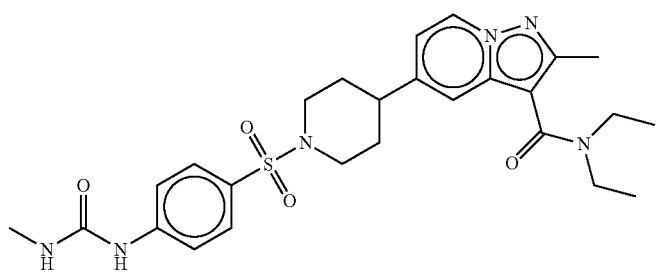
7AK TABLE A-continued
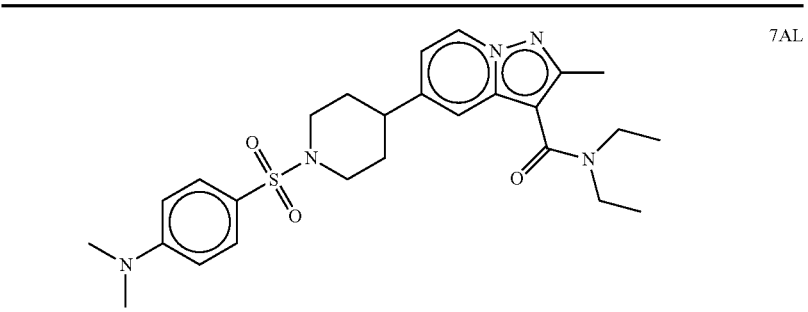
7AL
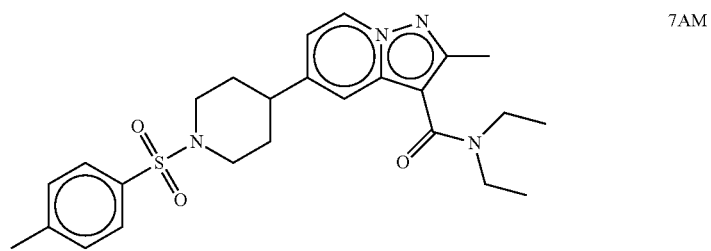
7AM
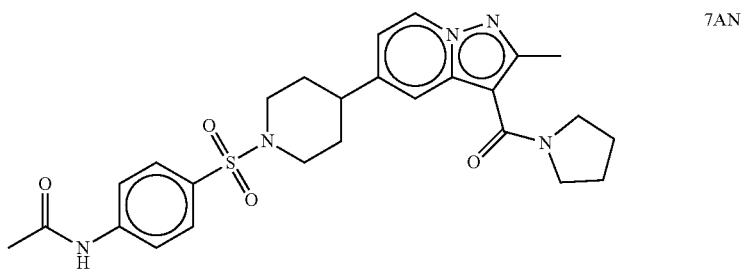
7AN
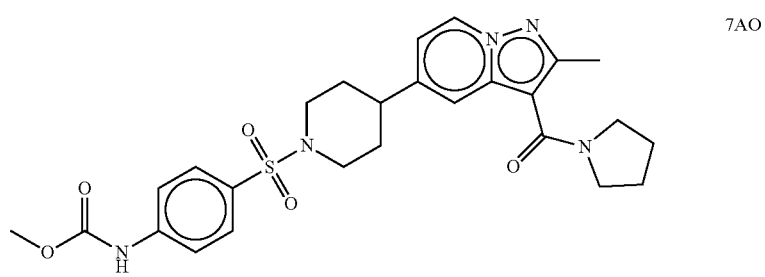
7AO
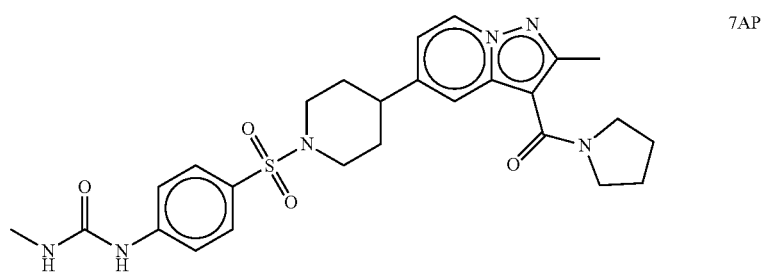
7AP TABLE A-continued
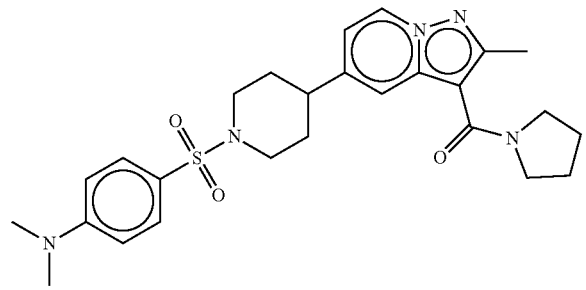
7AQ
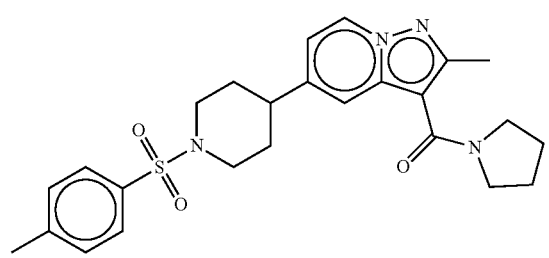
7AR
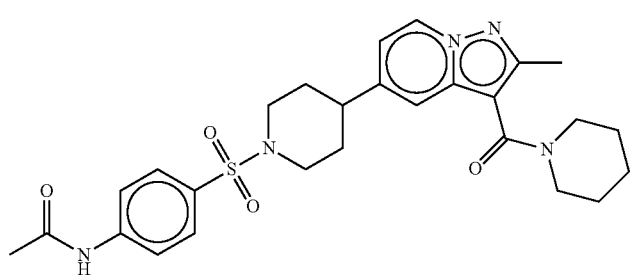
7AS
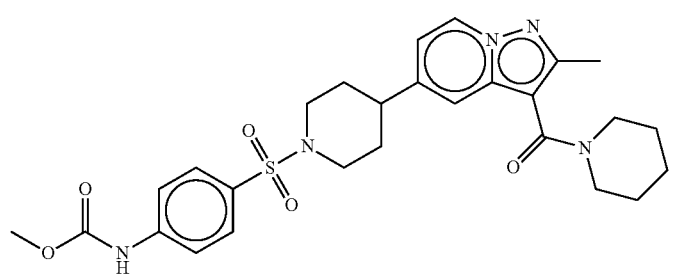
7AT
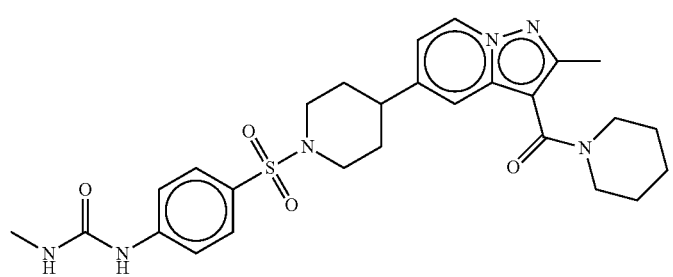
7AU TABLE A-continued
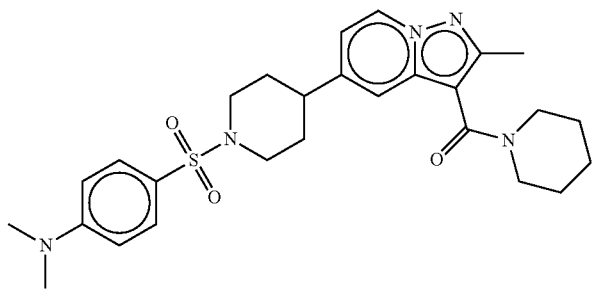
7AV
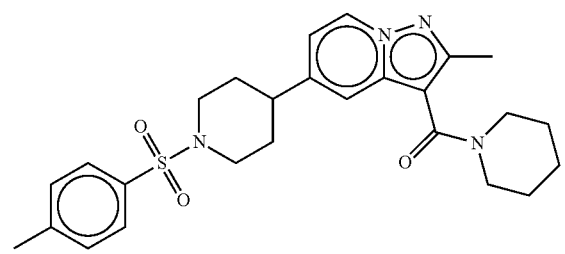
7AW
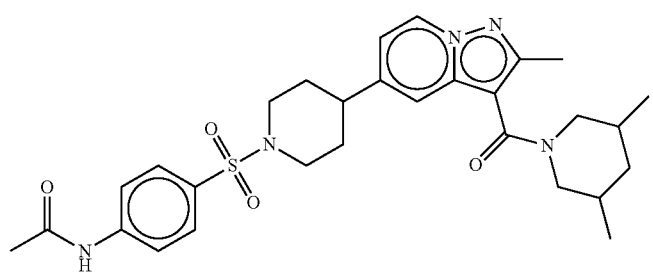
7AX
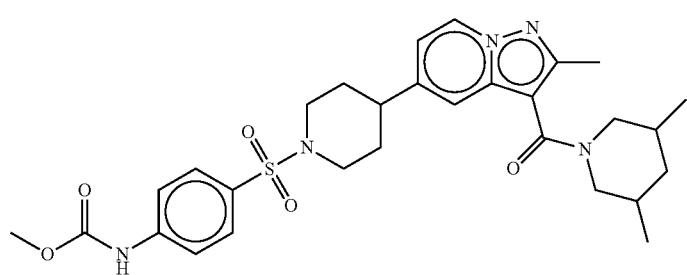
7AY
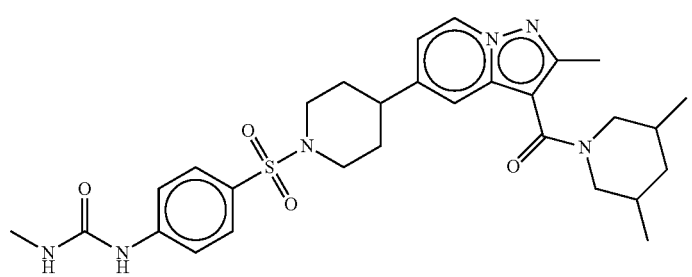
7AZ TABLE A-continued
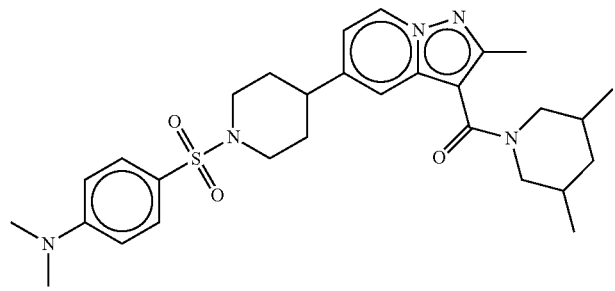
7BA
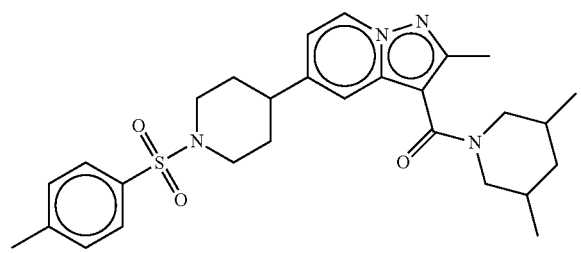
7BB
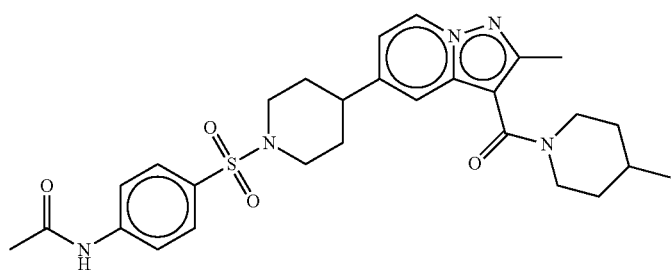
7BC
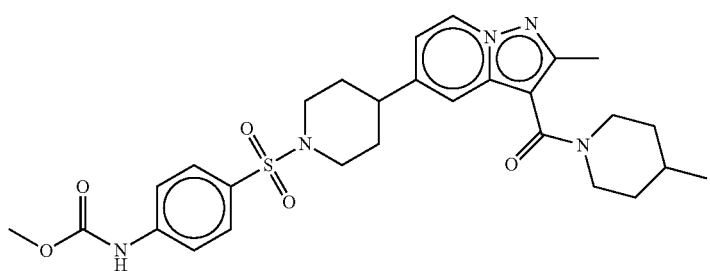
7BD
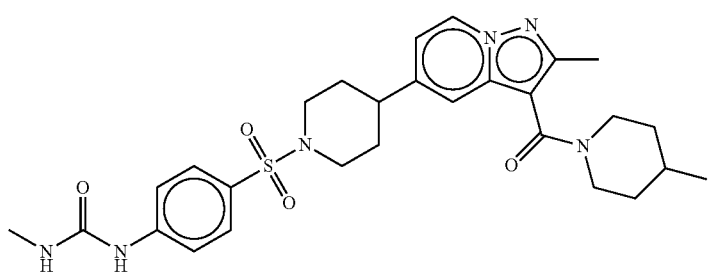
7BE TABLE A-continued
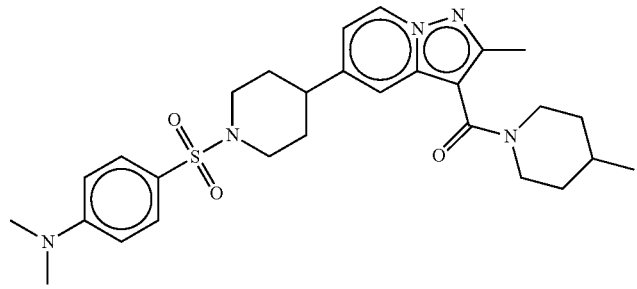
7BF
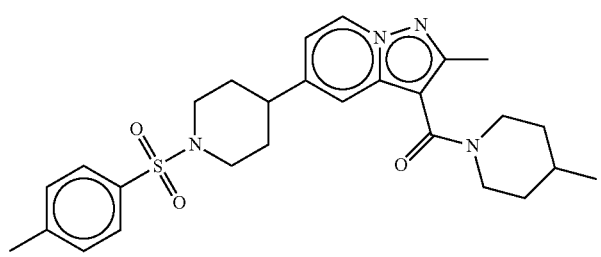
7BG
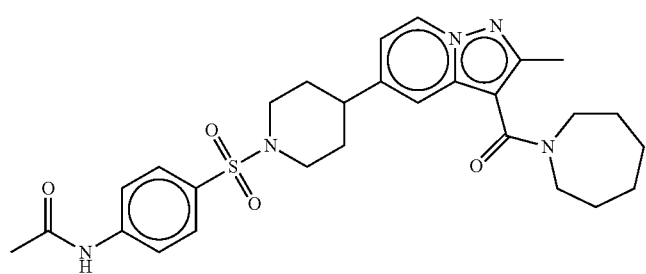
7BH
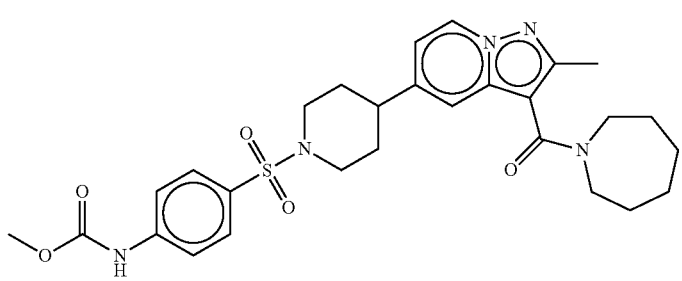
7BI
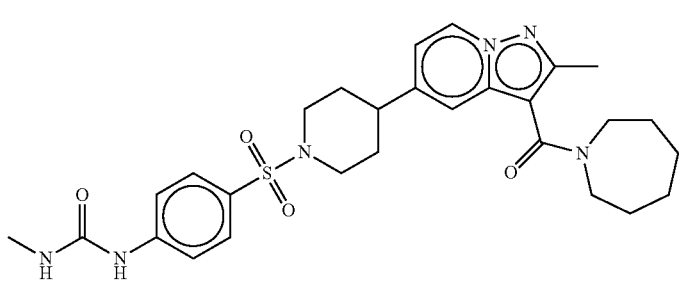
7BJ TABLE A-continued
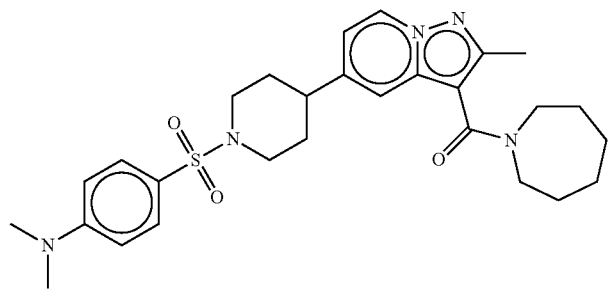
7BK
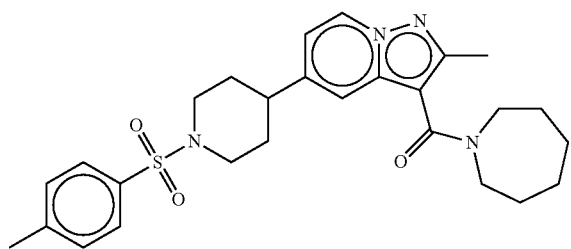
7BL
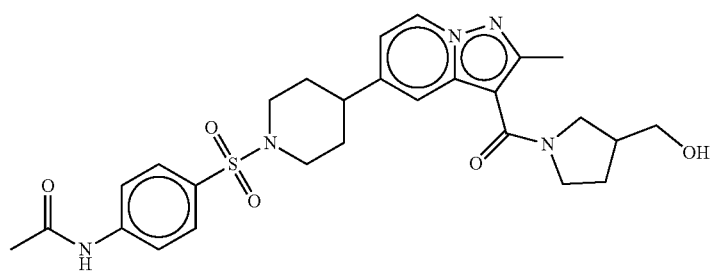
7BM
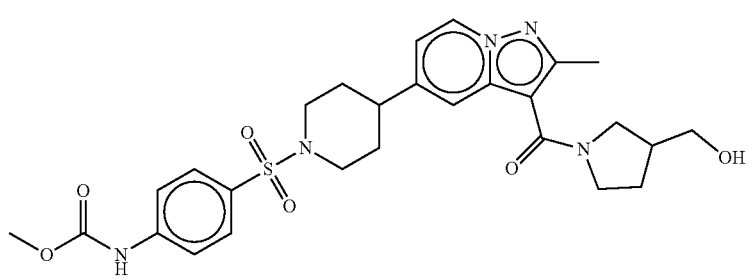
7BN
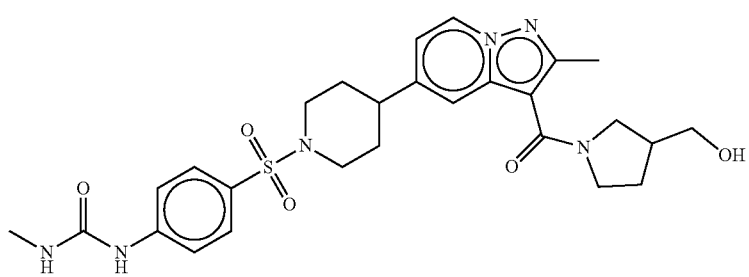
7BO TABLE A-continued
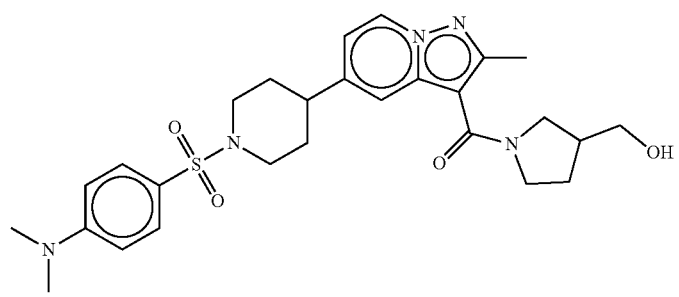
7BP
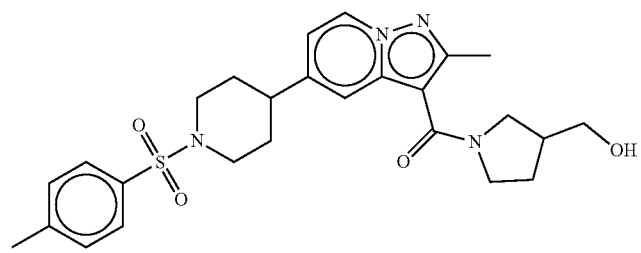
7BQ
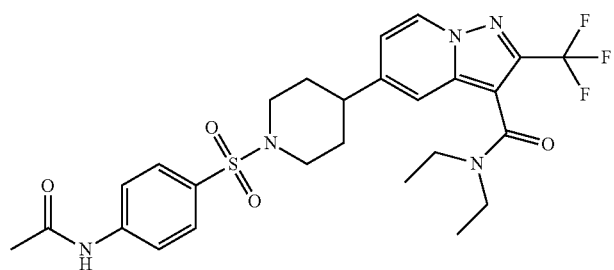 [SMILES: CCN(CC)C(=O)c1c(C(F)(F)F)nn2ccc(C3CCN(S(=O)(=O)c4ccc(NC(C)=O)cc4)CC3)cc12]
7BR
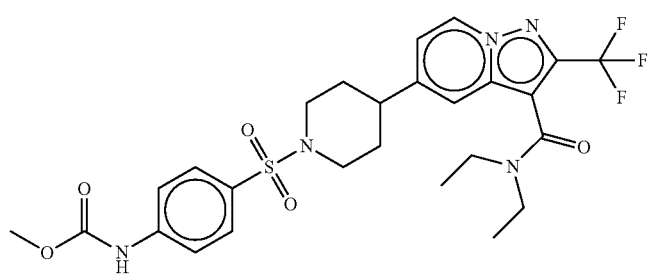
7BS
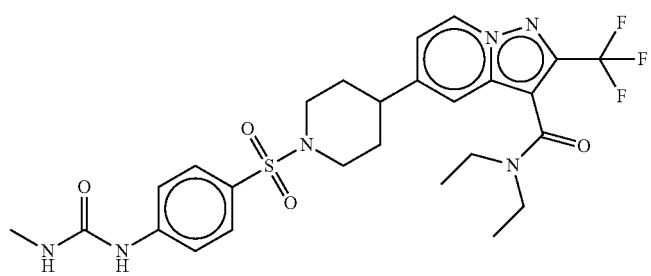
7BT TABLE A-continued
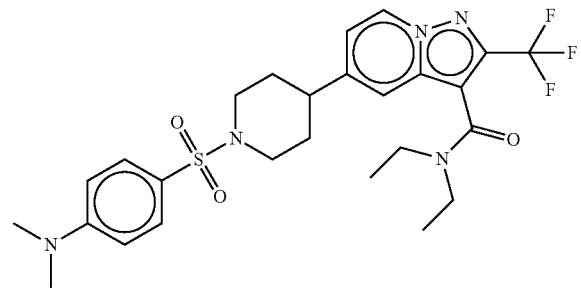
7BU
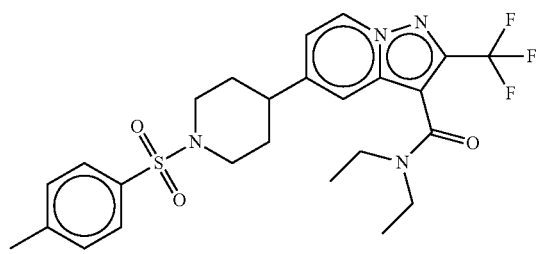
7BV
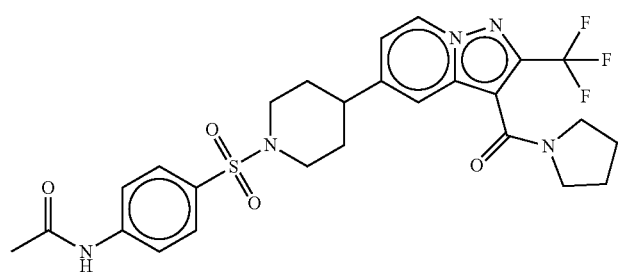
7BW
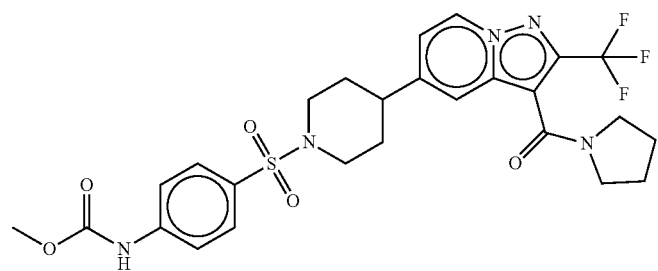
7BX
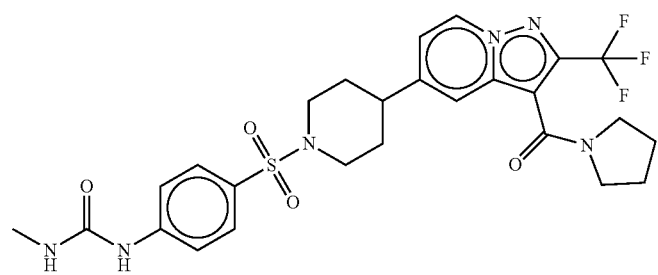
7BY TABLE A-continued
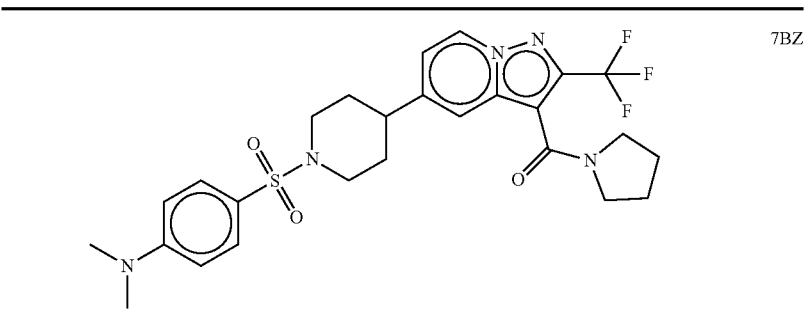
7BZ
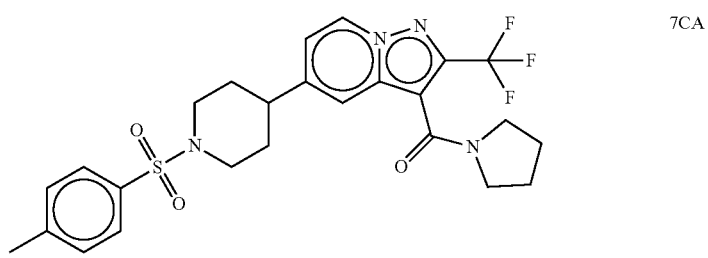
7CA
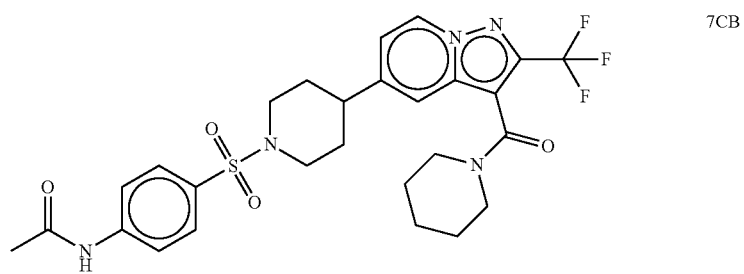
7CB
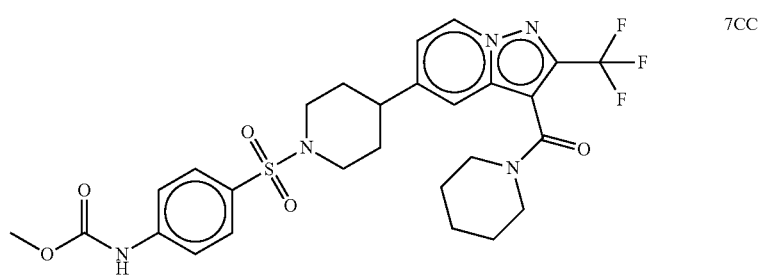
7CC
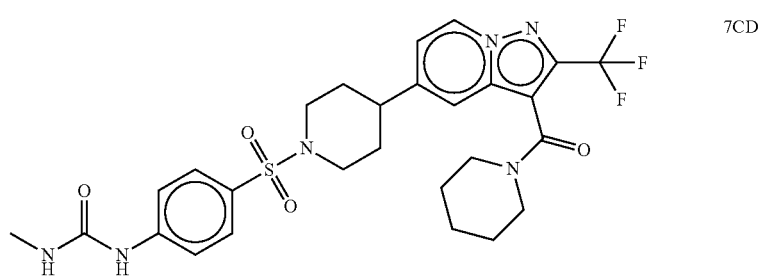
7CD TABLE A-continued
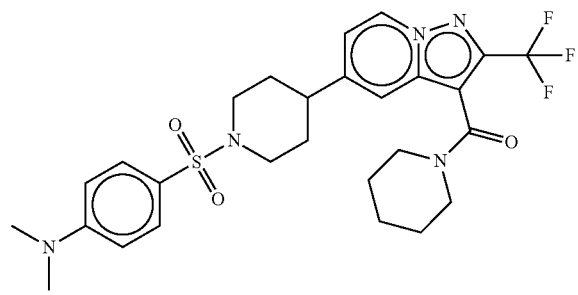
7CE
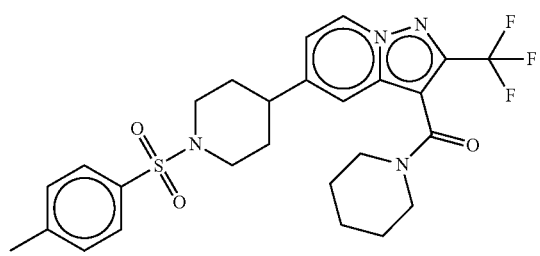
7CF
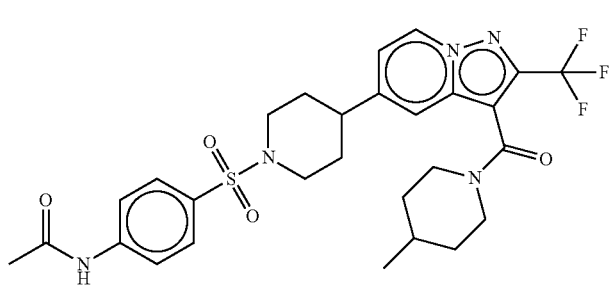
7CG
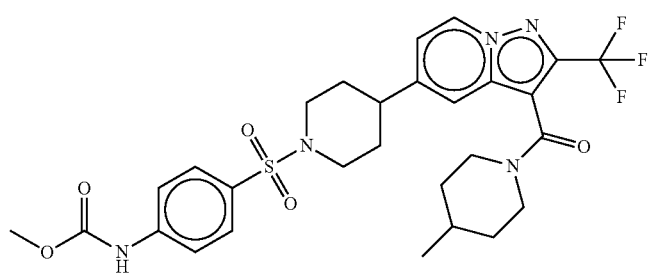
7CH
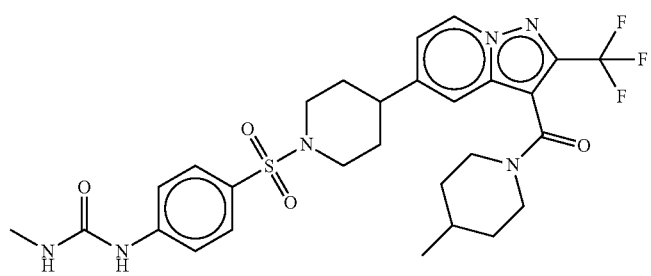
7CI TABLE A-continued
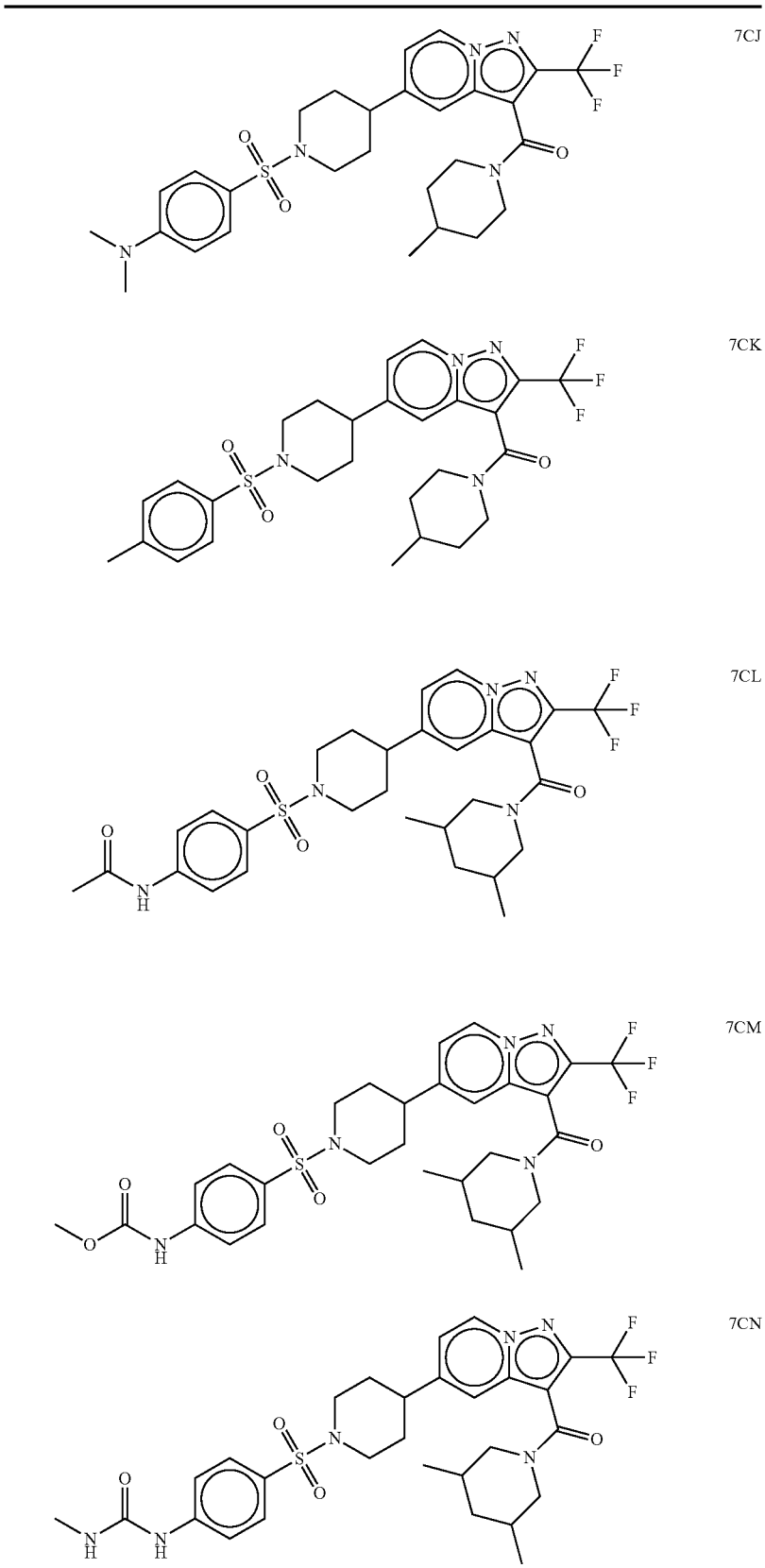

TABLE A-continued
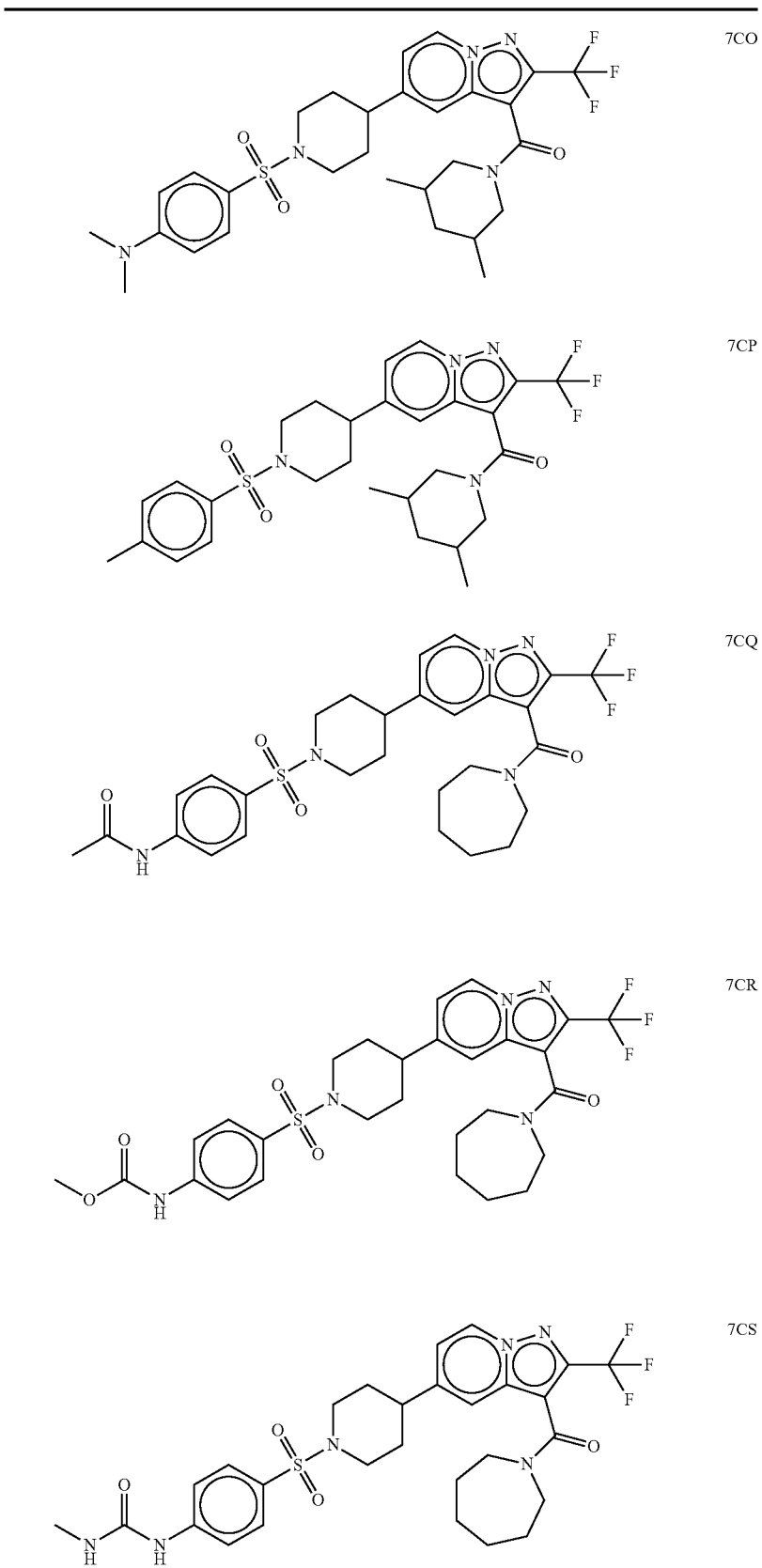
7CO
7CP
7CQ
7CR
7CS

TABLE A-continued
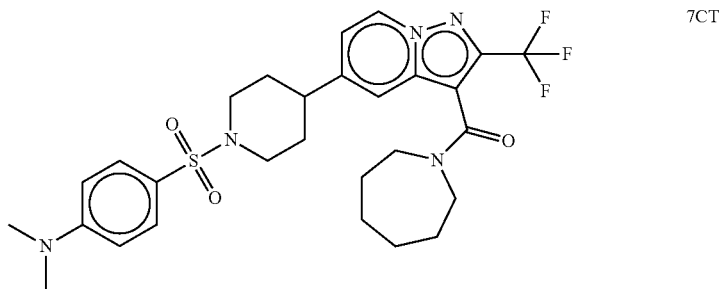
7CT
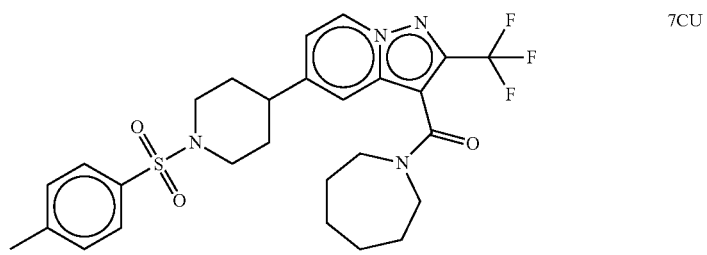
7CU
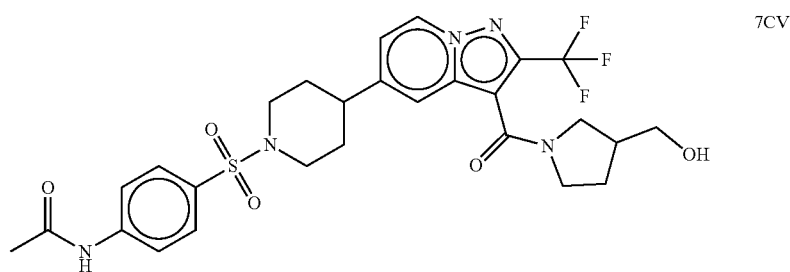
7CV
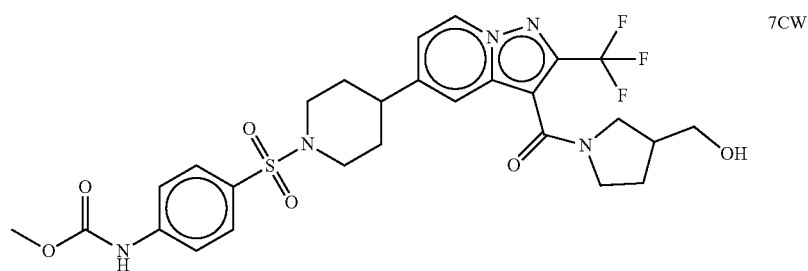
7CW
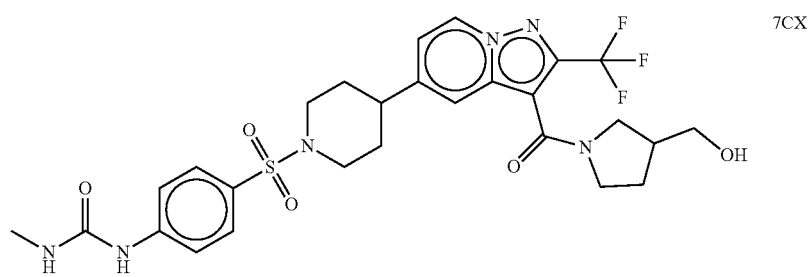
7CX TABLE A-continued
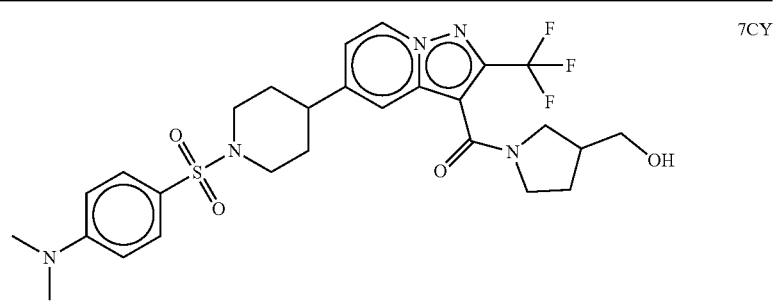
7CY
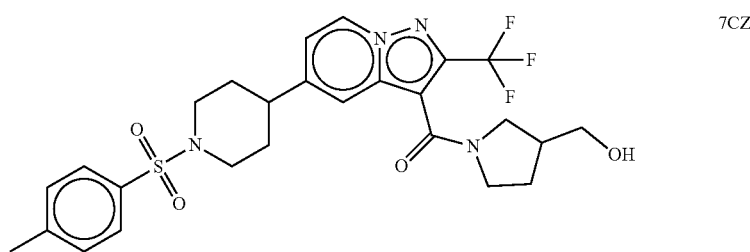
7CZ
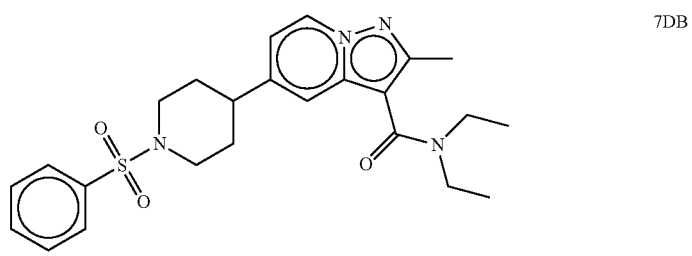
7DB
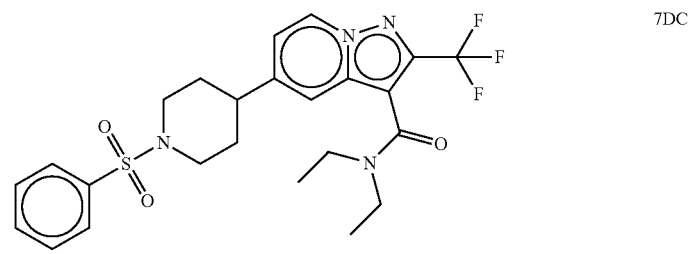
7DC
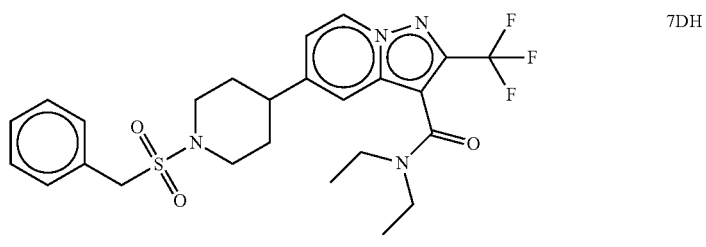
7DH
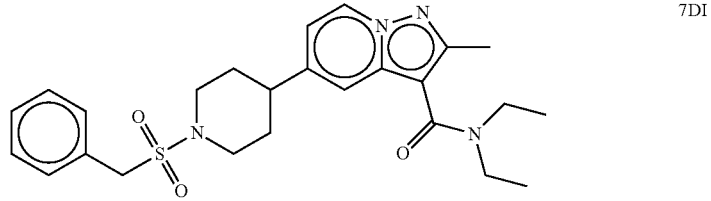
7DI TABLE A-continued
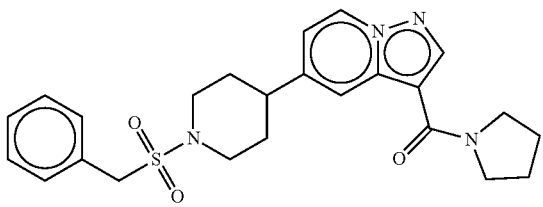
7DK
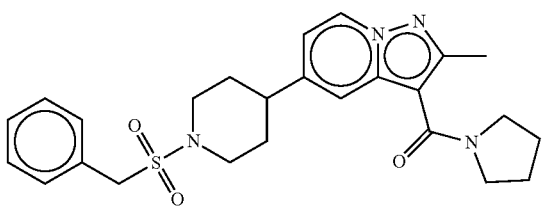
7DL
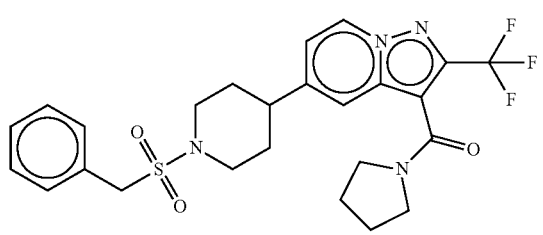
7DM
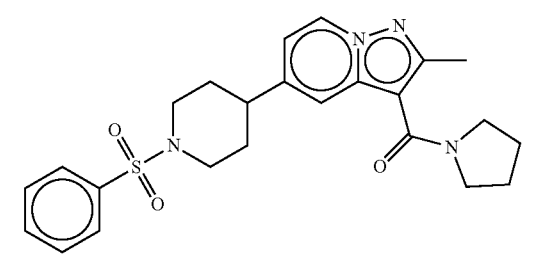
7DQ
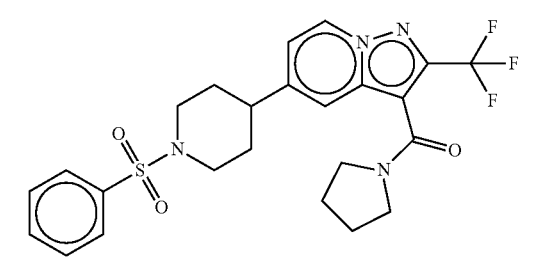
7DR
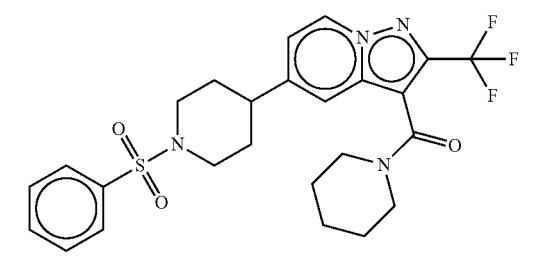
7DS TABLE A-continued

| | |
|---|---|
| (structure) | 7DT |
| (structure) | 7DU |
| (structure) | 7DY |
| (structure) | 7DZ |
| (structure) | 7EB |
| (structure) | 7EC |
| (structure) | 7ED |

TABLE A-continued
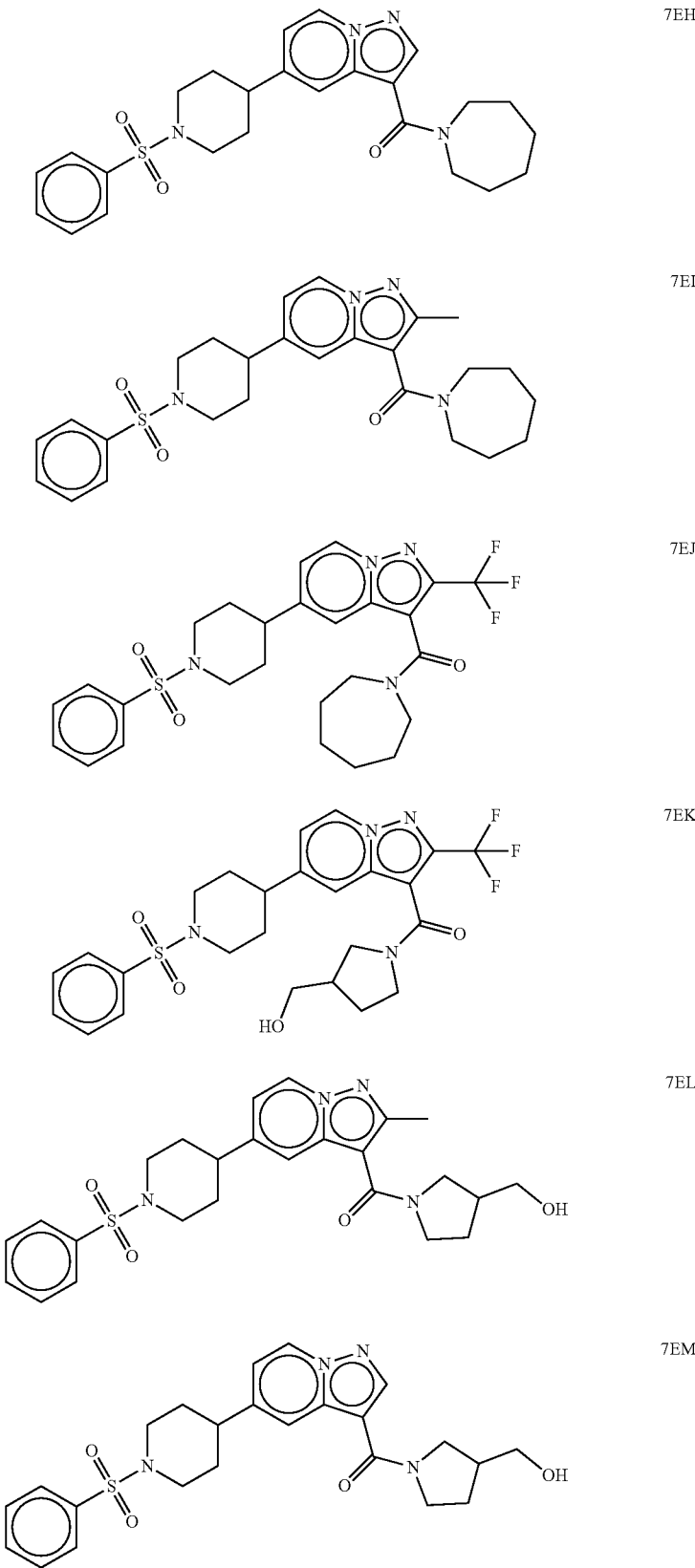
7EH
7EI
7EJ
7EK
7EL
7EM

TABLE A-continued
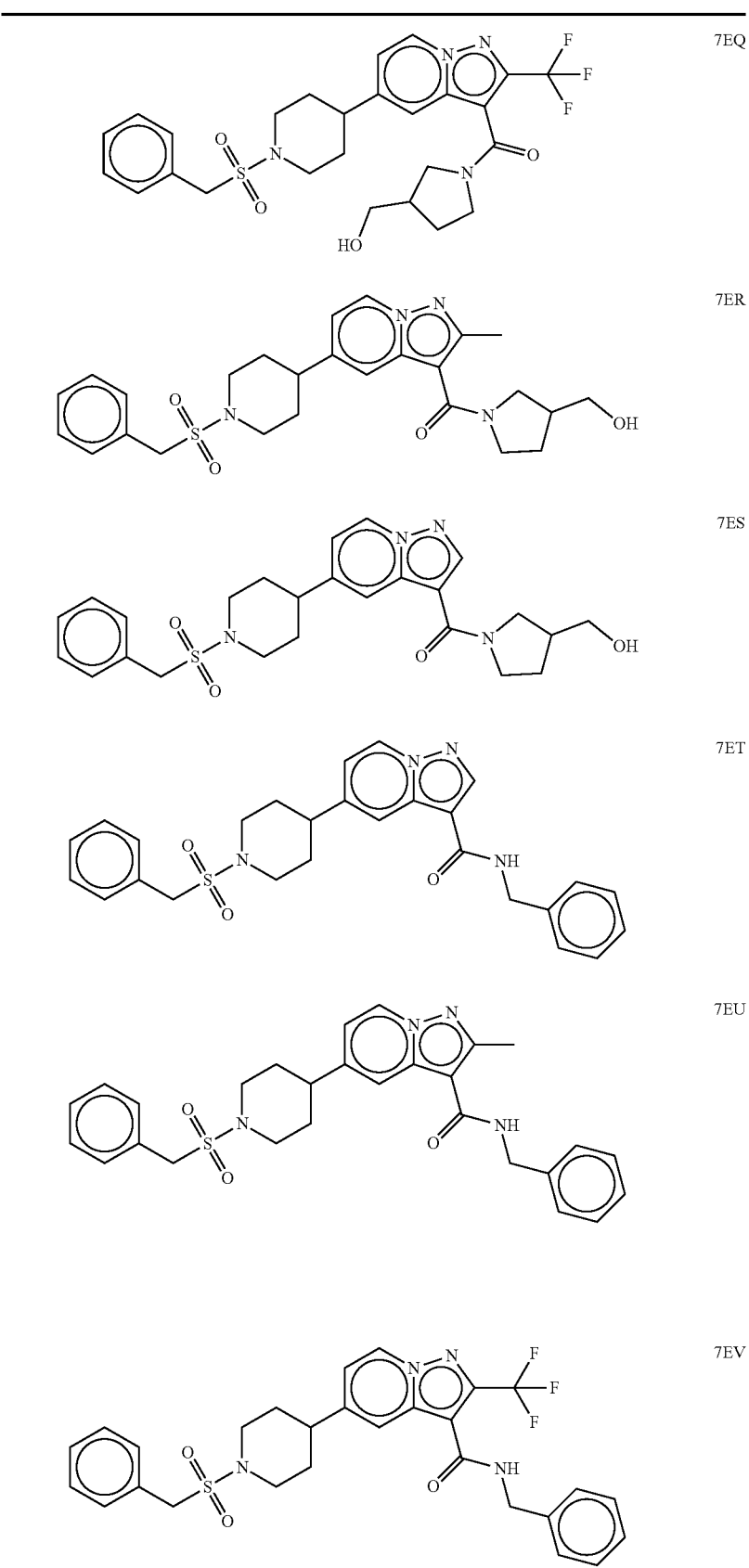

TABLE A-continued
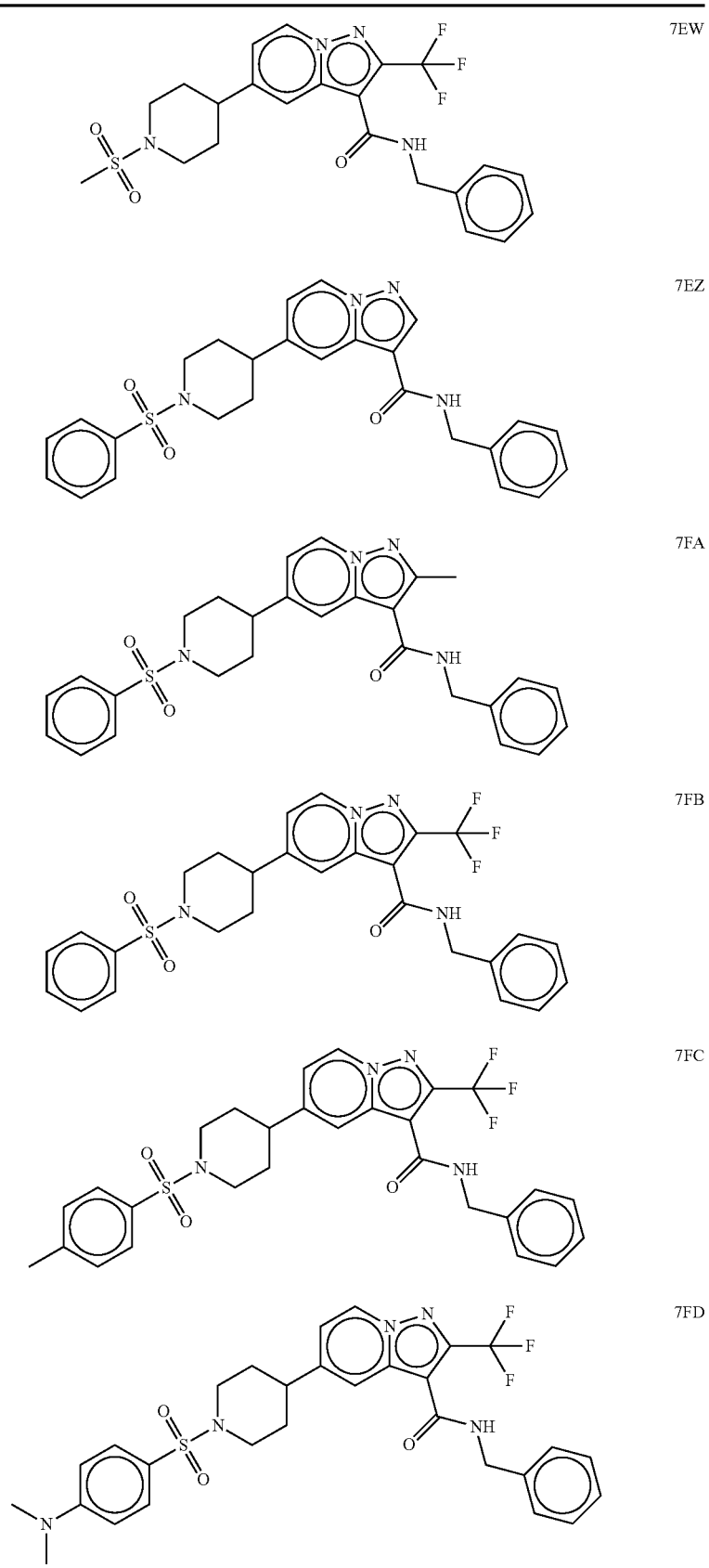
7EW
7EZ
7FA
7FB
7FC
7FD

TABLE A-continued
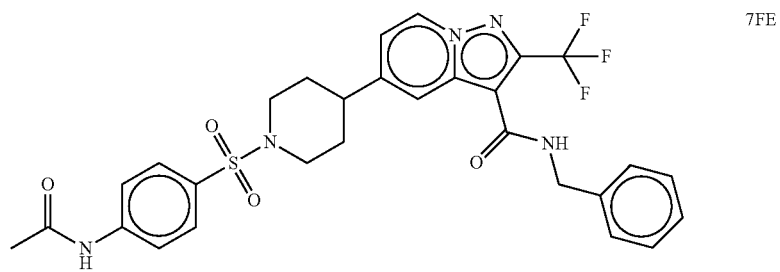 7FE
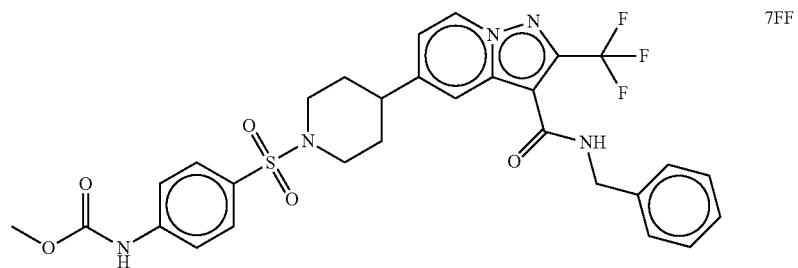 7FF
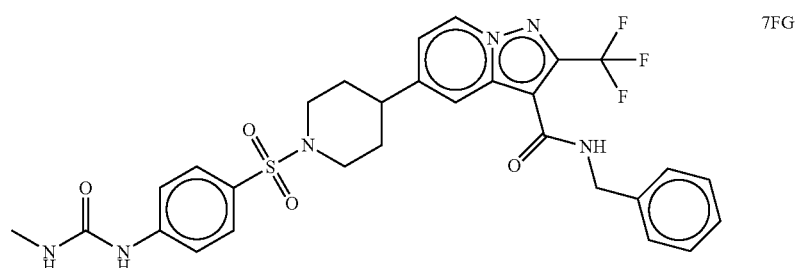 7FG
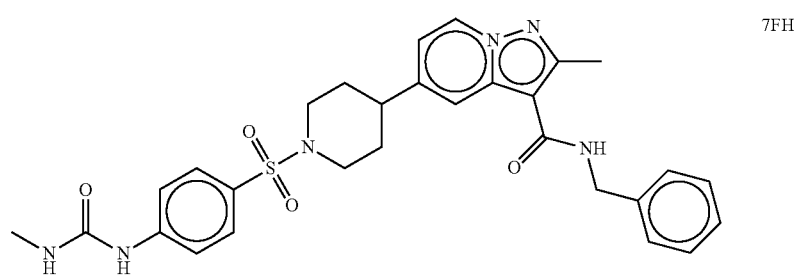 7FH
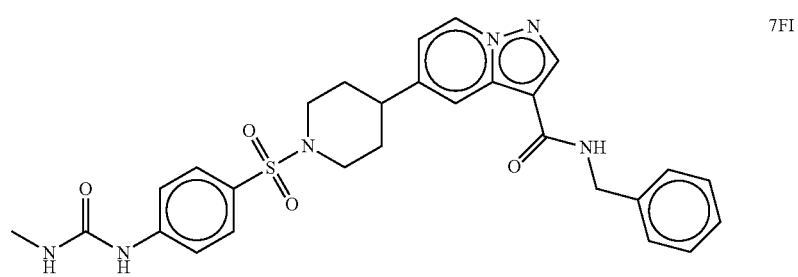 7FI
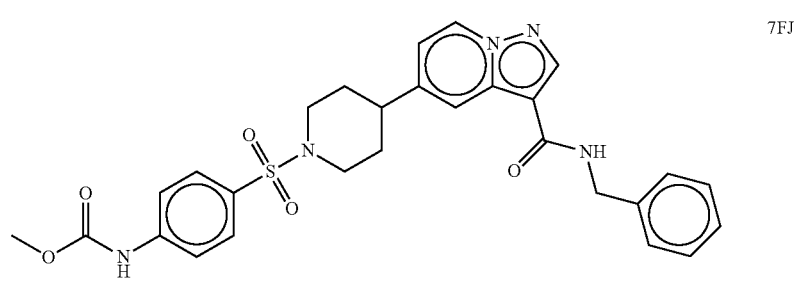 7FJ TABLE A-continued
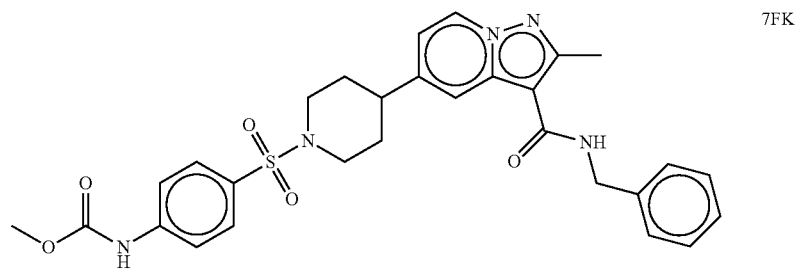
7FK
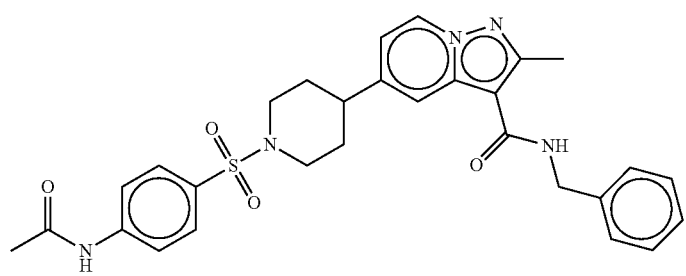
7FL
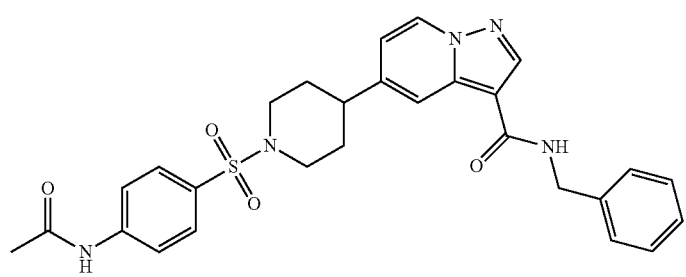 [SMILES: CC(=O)Nc1ccc(S(=O)(=O)N2CCC(c3ccn4ncc(C(=O)NCc5ccccc5)c4c3)CC2)cc1]
7FM
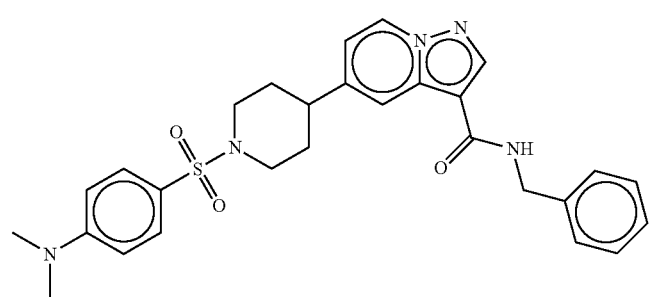
7FN
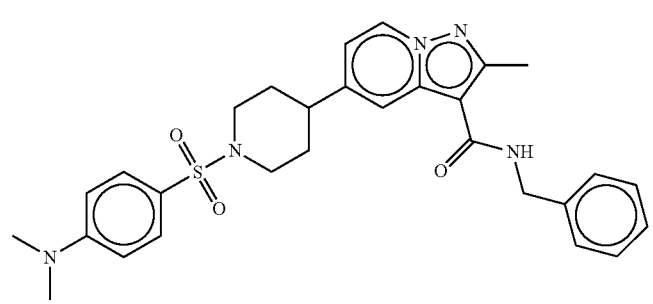
7FO TABLE A-continued
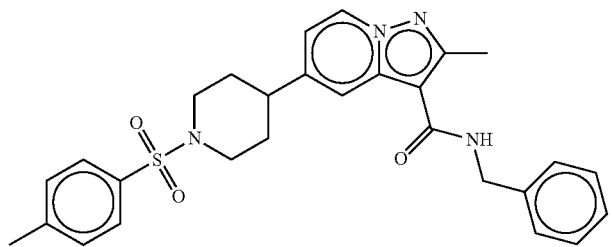
7FP
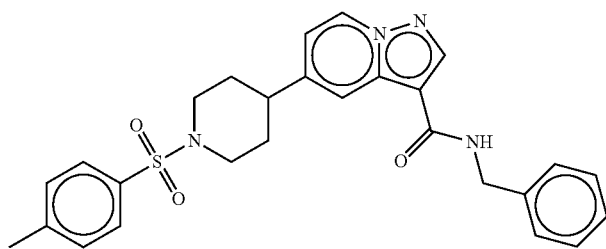
7FQ
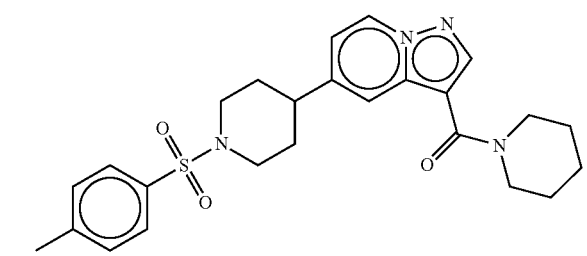
7FR
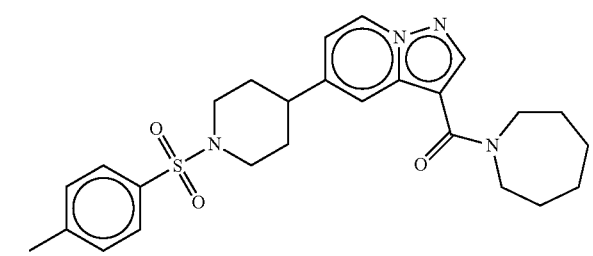
7FS
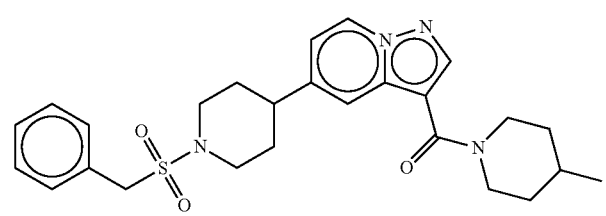
7FT
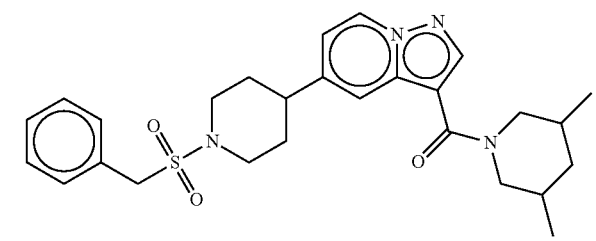
7FU TABLE A-continued
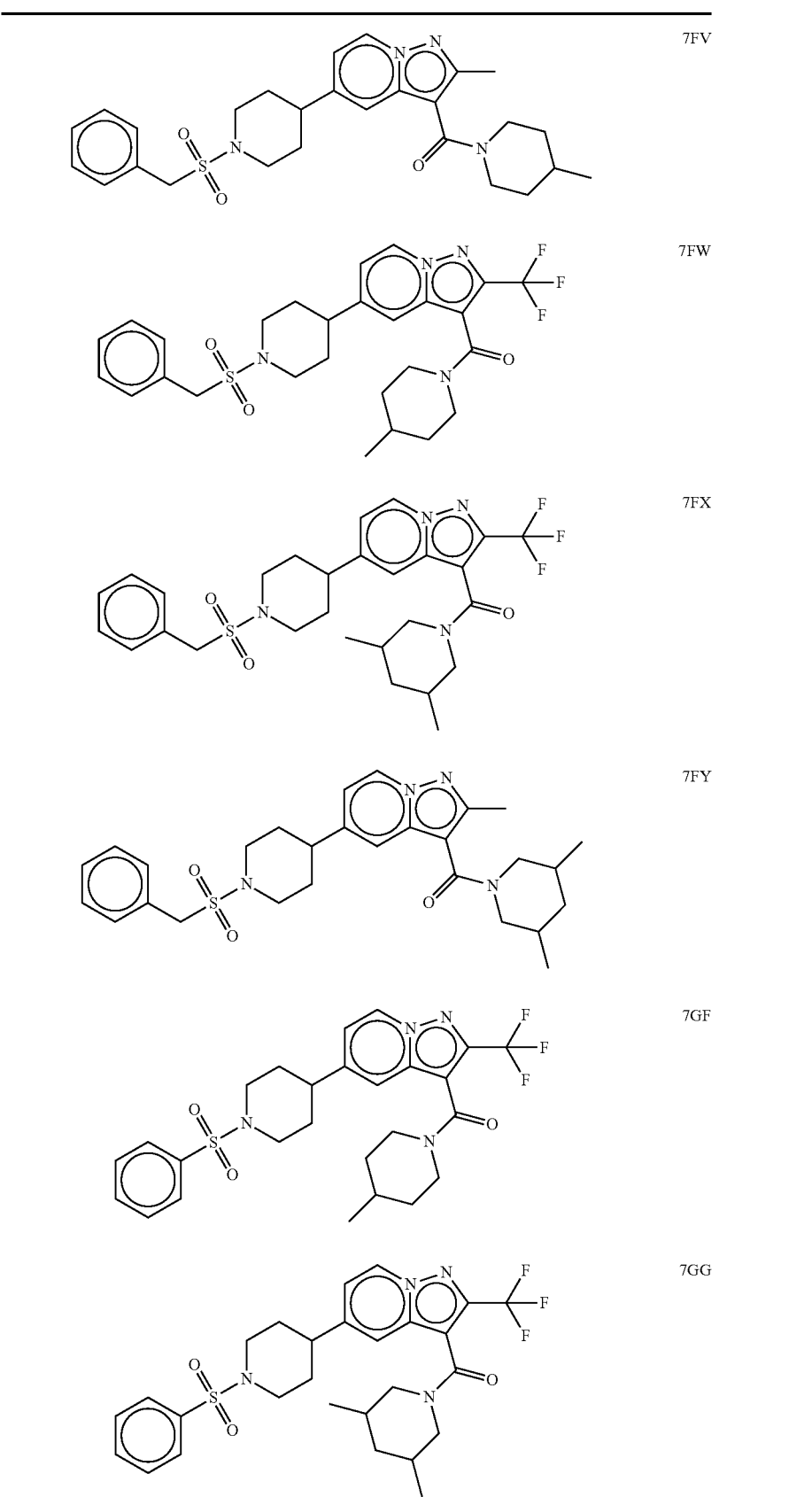

TABLE A-continued
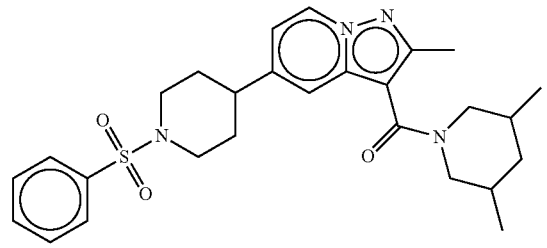
7GH
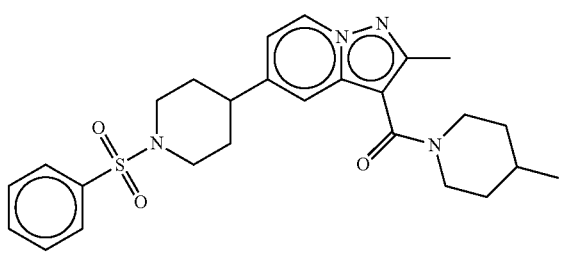
7GI
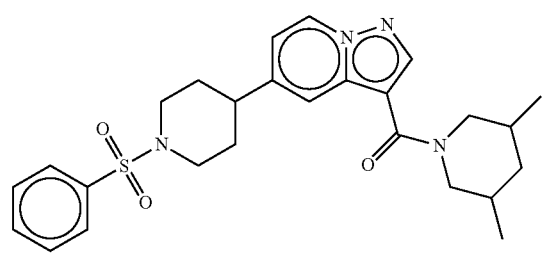
7GJ
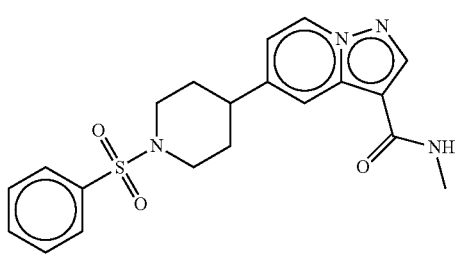
7GL
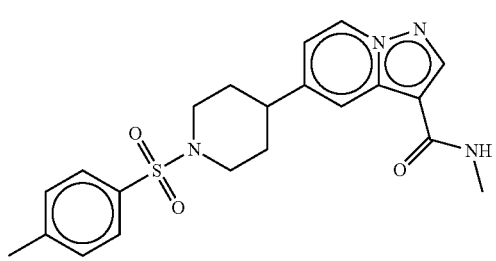
7GM
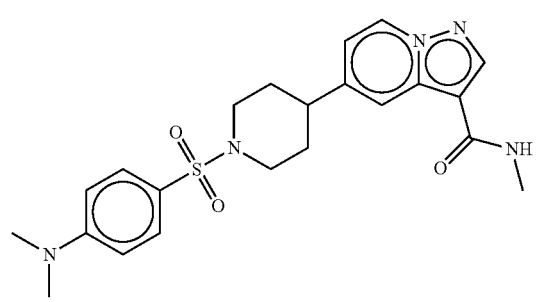
7GN TABLE A-continued
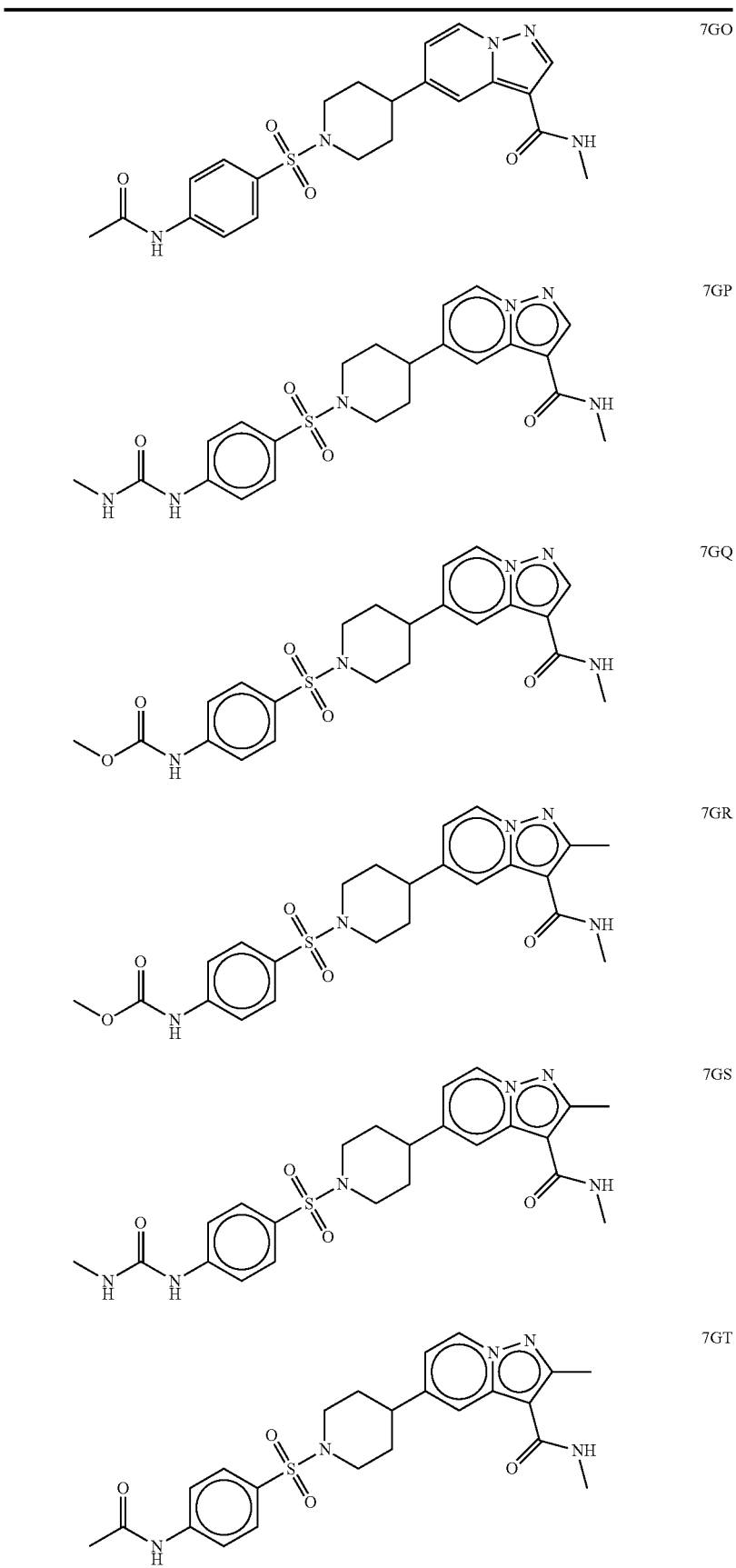

TABLE A-continued
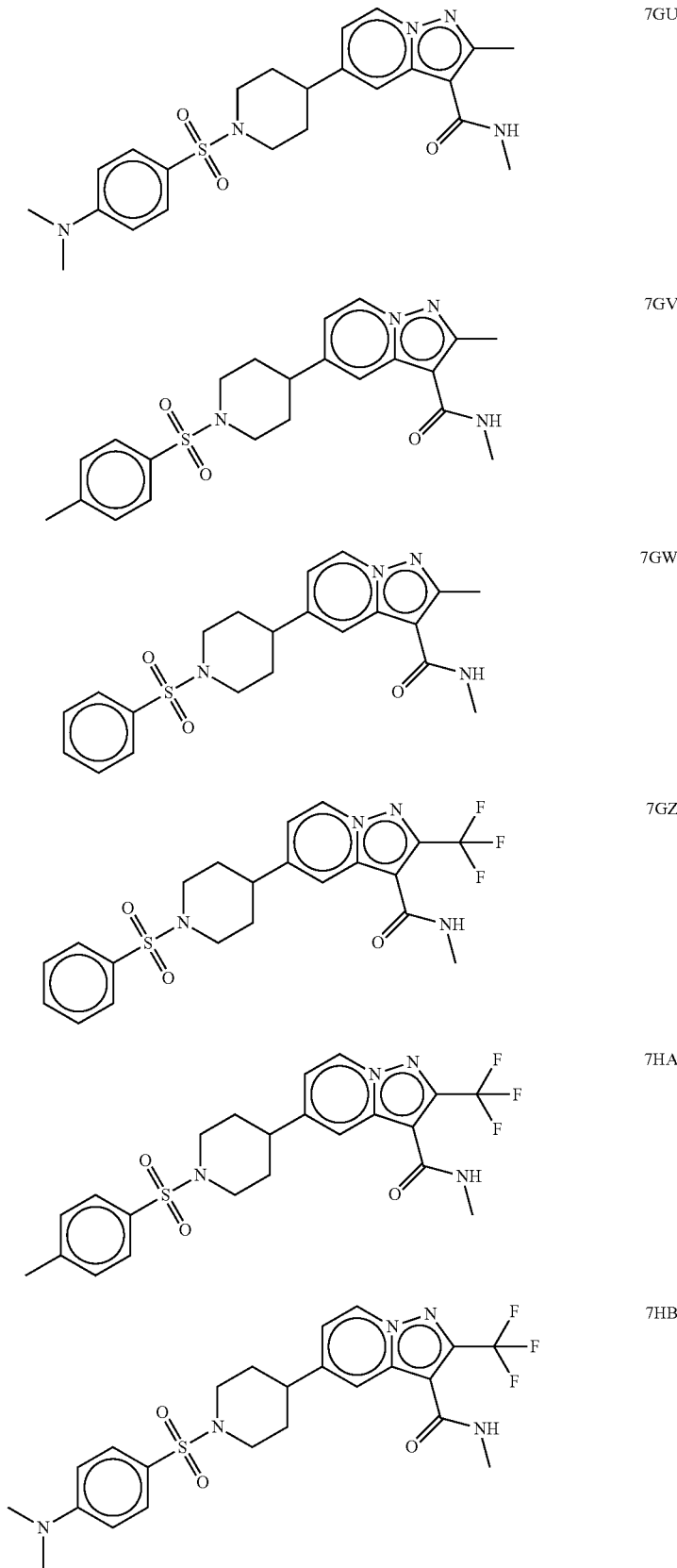
7GU
7GV
7GW
7GZ
7HA
7HB

TABLE A-continued
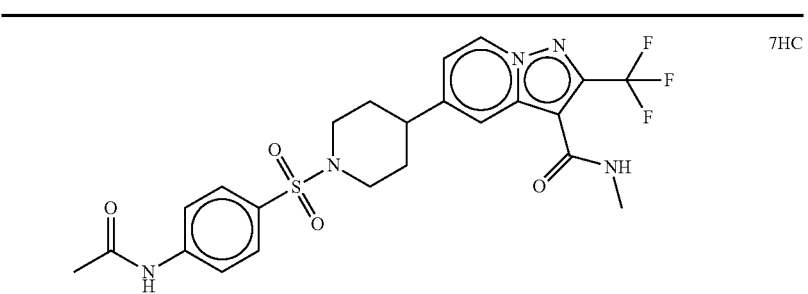
7HC
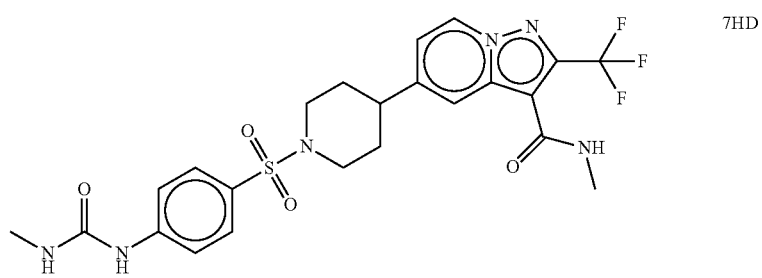
7HD
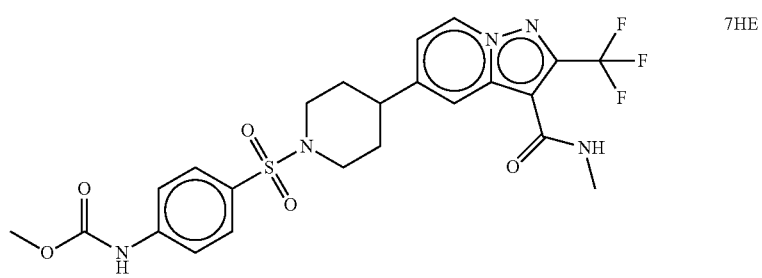
7HE
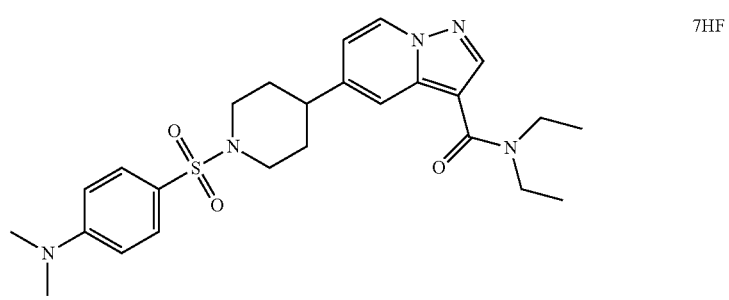
7HF
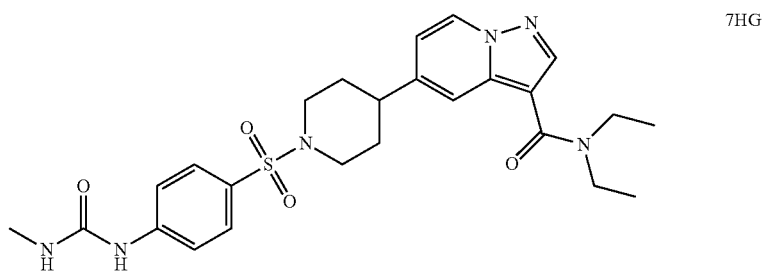
7HG TABLE A-continued
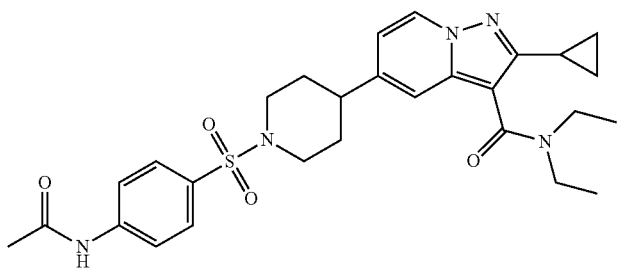 [SMILES: CCN(CC)C(=O)c1c(C2CC2)nn2ccc(C3CCN(S(=O)(=O)c4ccc(NC(C)=O)cc4)CC3)cc12]
7HH
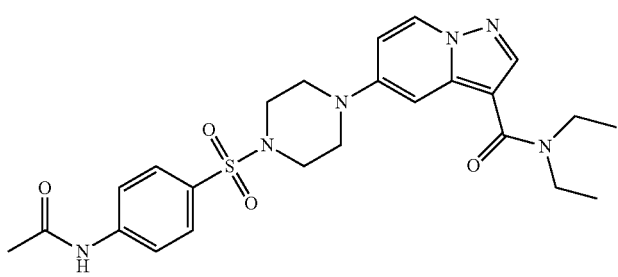 [SMILES: CCN(CC)C(=O)c1cnn2ccc(N3CCN(S(=O)(=O)c4ccc(NC(C)=O)cc4)CC3)cc12]
7HI
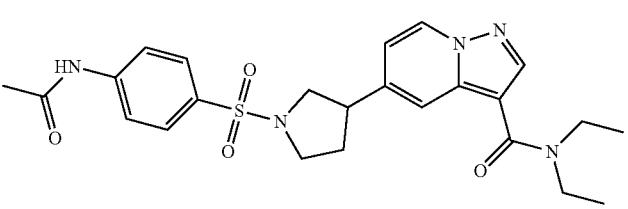 [SMILES: CCN(CC)C(=O)c1cnn2ccc(C3CCN(S(=O)(=O)c4ccc(NC(C)=O)cc4)C3)cc12]
7HJ
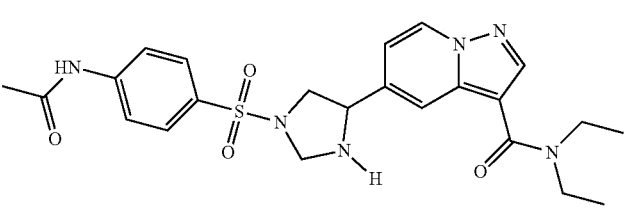 [SMILES: CCN(CC)C(=O)c1cnn2ccc(C3CN(S(=O)(=O)c4ccc(NC(C)=O)cc4)CN3)cc12]
7HK
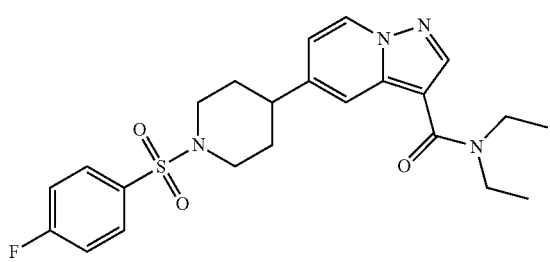 [SMILES: CCN(CC)C(=O)c1cnn2ccc(C3CCN(S(=O)(=O)c4ccc(F)cc4)CC3)cc12]
7HL Additional contemplated compounds of the disclosure include the compounds listed in Table B and pharmaceutically acceptable salts thereof:
TABLE B
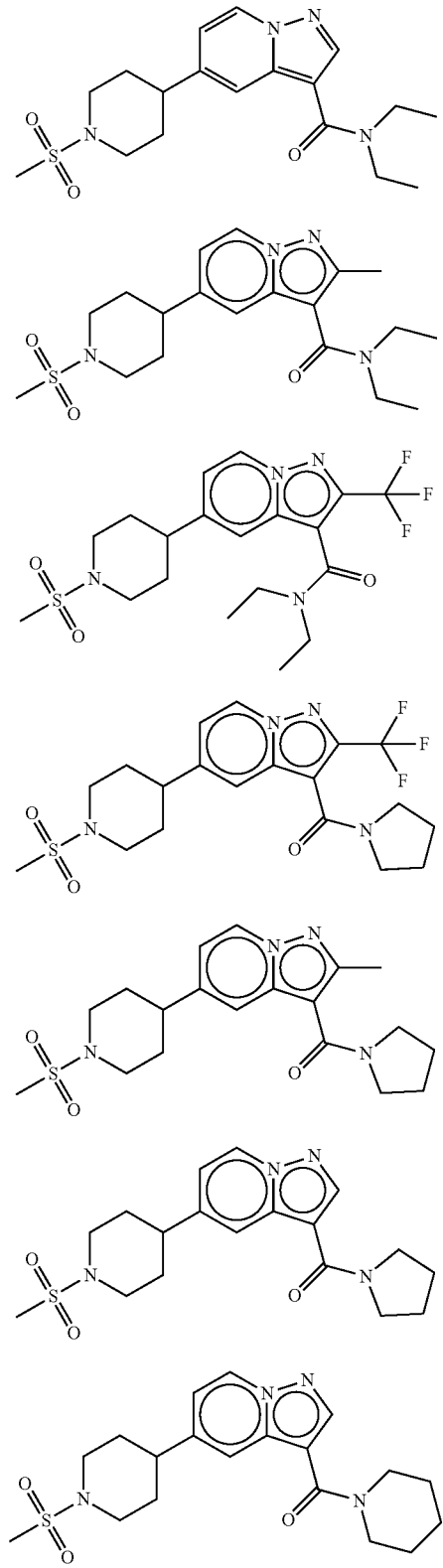
TABLE B-continued
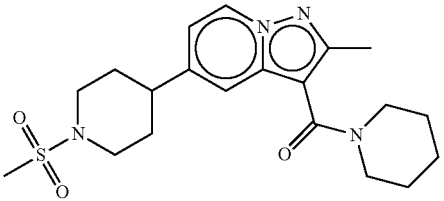
7DW
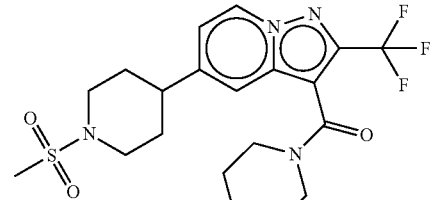
7DX
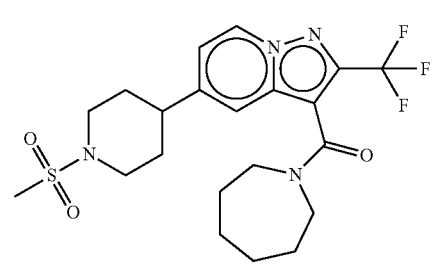
7EE
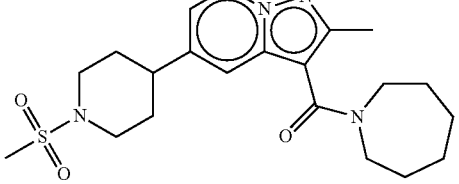
7EF
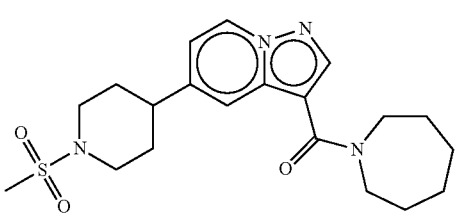
7EG
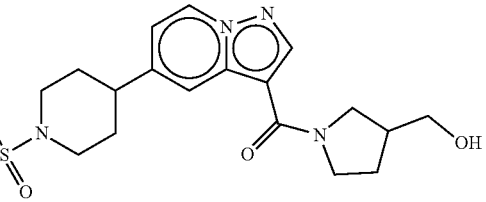
7EN
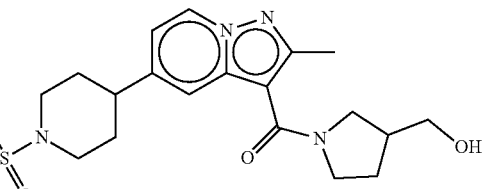
7EO TABLE B-continued
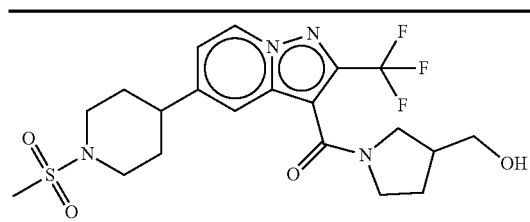 7EP
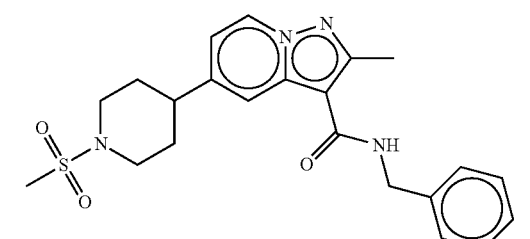 7EX
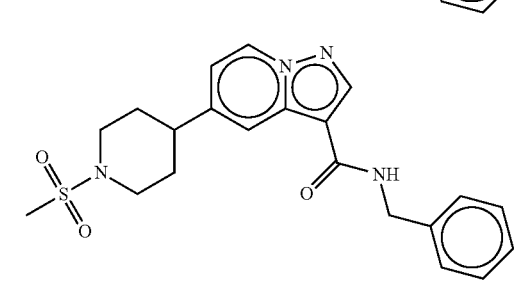 7EY
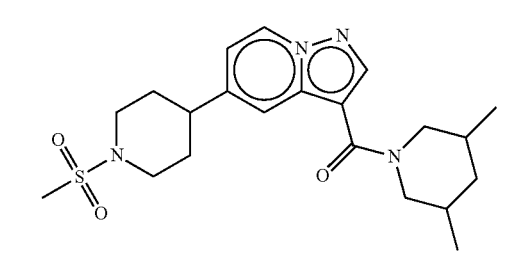 7FZ
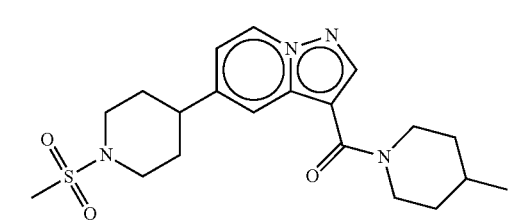 7GA
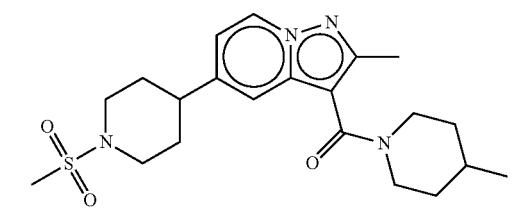 7GB
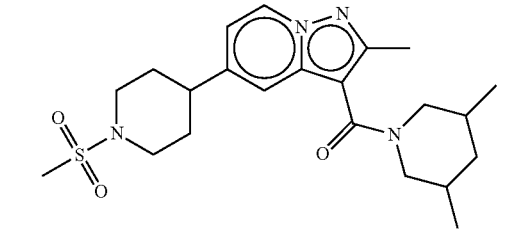 7GC
TABLE B-continued
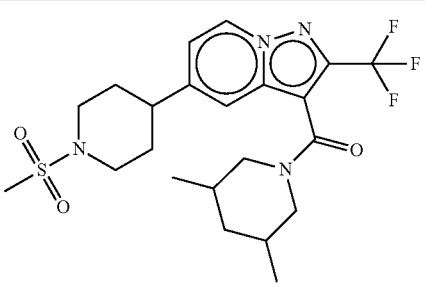 7GD
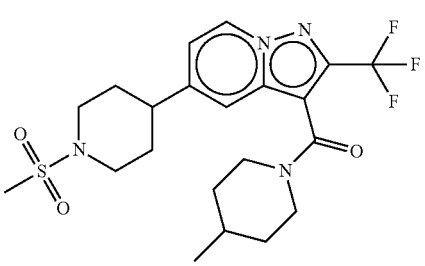 7GE
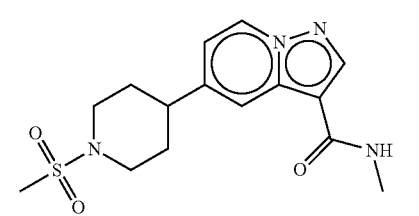 7GK
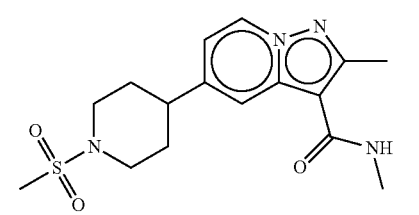 7GX
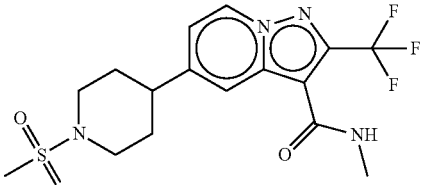 7GY
Additional contemplated compounds of the disclosure include the compounds listed in Table C and pharmaceutically acceptable salts thereof:

TABLE C
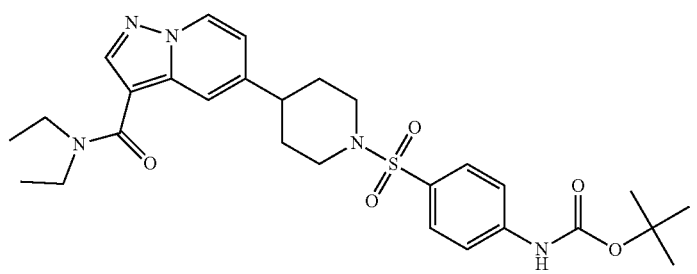 [SMILES: CCN(CC)C(=O)c1cnn2ccc(C3CCN(S(=O)(=O)c4ccc(NC(=O)OC(C)(C)C)cc4)CC3)cc12]
7HM
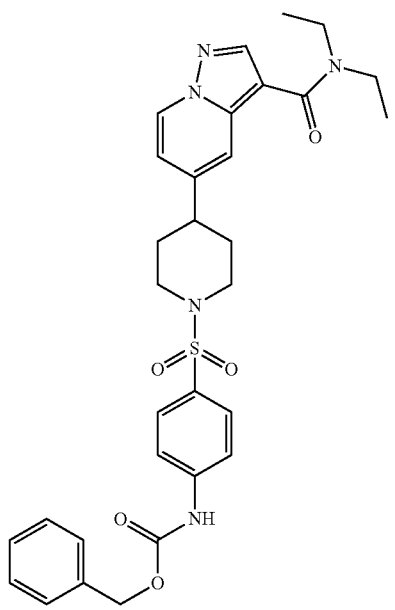 [SMILES: CCN(CC)C(=O)c1cnn2ccc(C3CCN(S(=O)(=O)c4ccc(NC(=O)OCc5ccccc5)cc4)CC3)cc12]
7HN
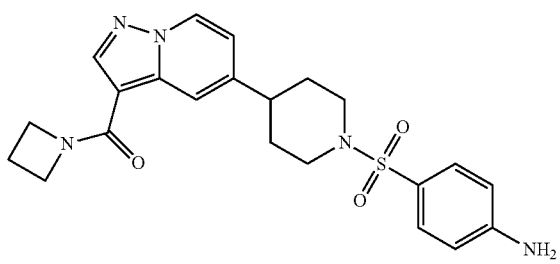 [SMILES: Nc1ccc(S(=O)(=O)N2CCC(c3ccn4ncc(C(=O)N5CCC5)c4c3)CC2)cc1]
7HO
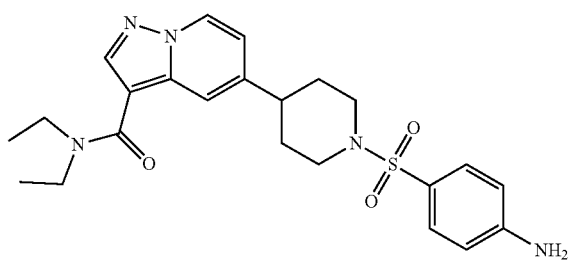 [SMILES: CCN(CC)C(=O)c1cnn2ccc(C3CCN(S(=O)(=O)c4ccc(N)cc4)CC3)cc12]
7HP

TABLE C-continued
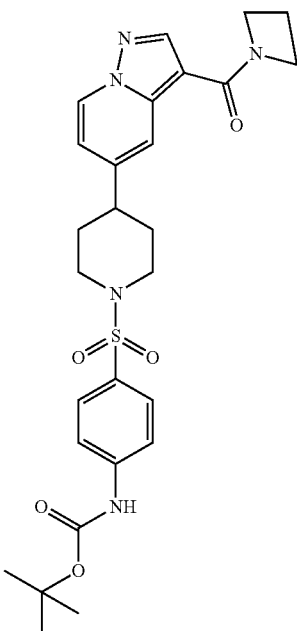 [SMILES: CC(C)(C)OC(=O)Nc1ccc(S(=O)(=O)N2CCC(c3ccn4ncc(C(=O)N5CCC5)c4c3)CC2)cc1]
7HQ
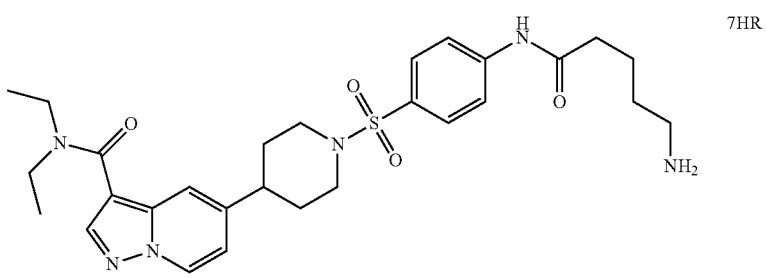
7HR
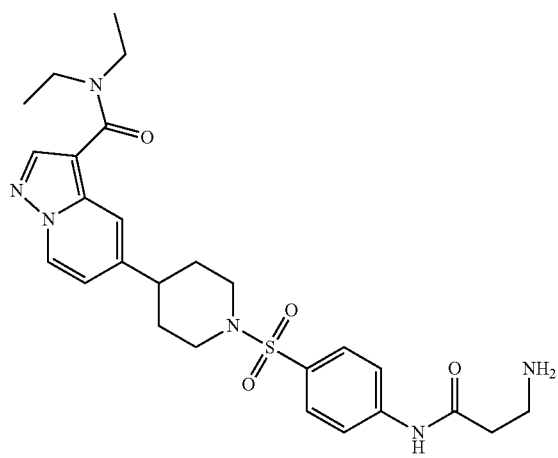 [SMILES: CCN(CC)C(=O)c1cnn2ccc(C3CCN(S(=O)(=O)c4ccc(NC(=O)CCN)cc4)CC3)cc12]
7HS
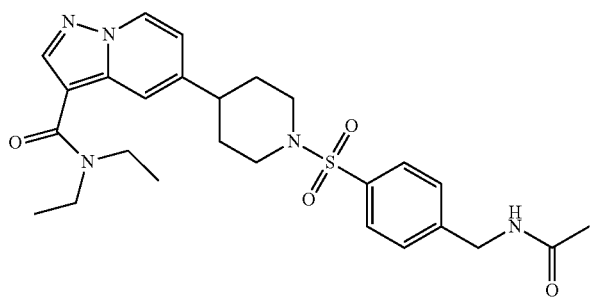 [SMILES: CCN(CC)C(=O)c1cnn2ccc(C3CCN(S(=O)(=O)c4ccc(CNC(C)=O)cc4)CC3)cc12]
7HT TABLE C-continued
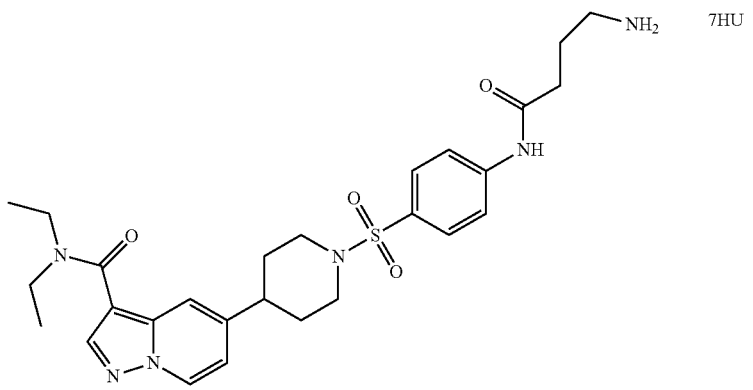
7HU
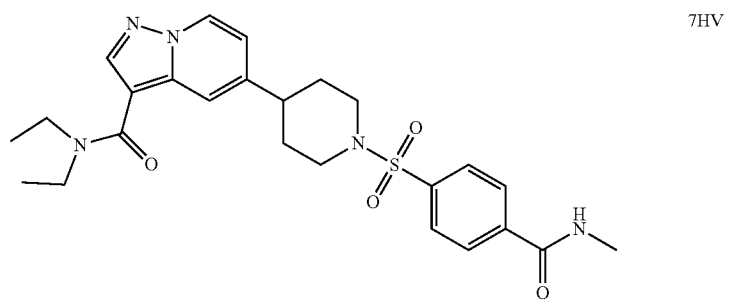
7HV
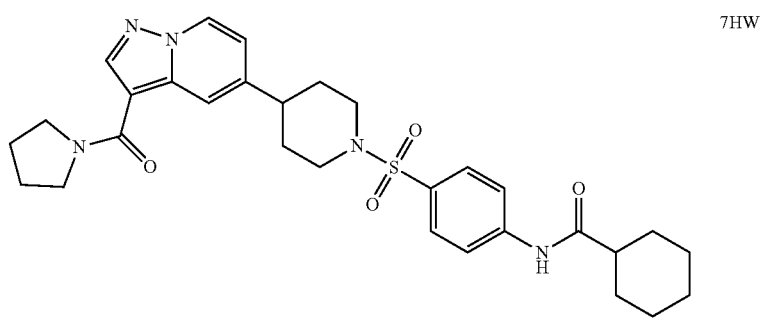
7HW
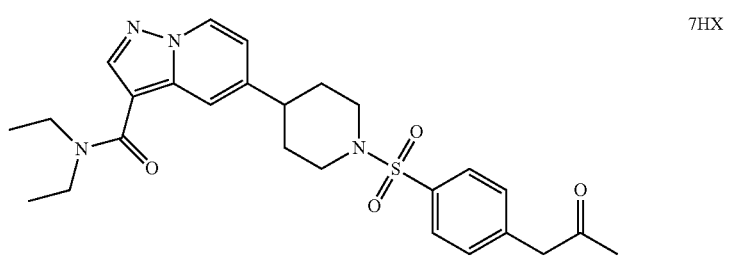
7HX TABLE C-continued
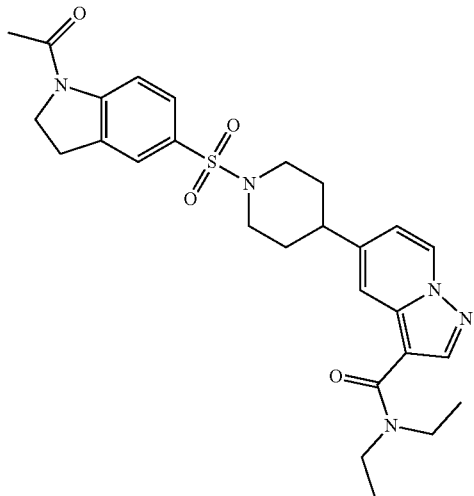 [SMILES: CCN(CC)C(=O)c1cnn2ccc(C3CCN(S(=O)(=O)c4ccc5c(c4)CCN5C(C)=O)CC3)cc12]
7HY
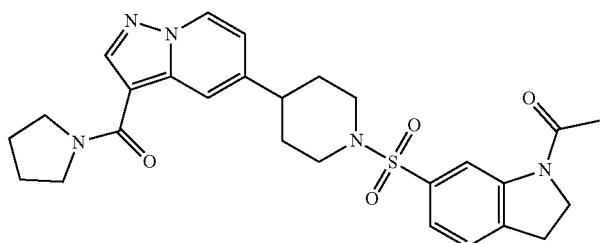
7HZ
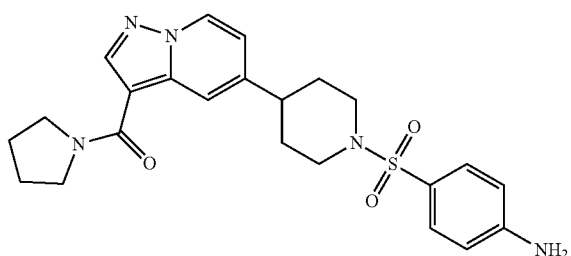
7IA
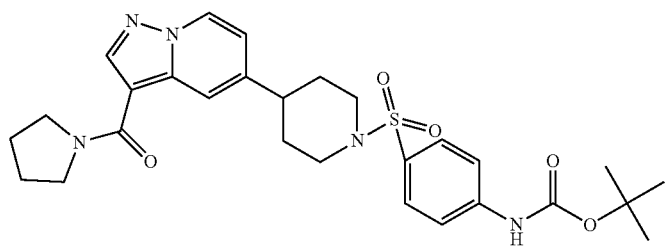 [SMILES: CC(C)(C)OC(=O)Nc1ccc(S(=O)(=O)N2CCC(c3ccn4ncc(C(=O)N5CCCC5)c4c3)CC2)cc1]
7IB
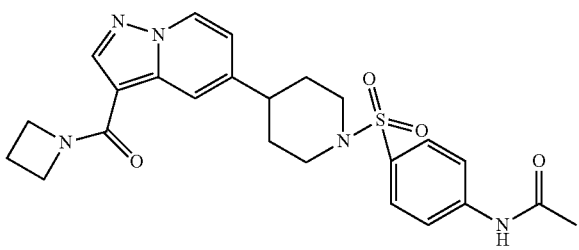 [SMILES: CC(=O)Nc1ccc(S(=O)(=O)N2CCC(c3ccn4ncc(C(=O)N5CCC5)c4c3)CC2)cc1]
7IC TABLE C-continued
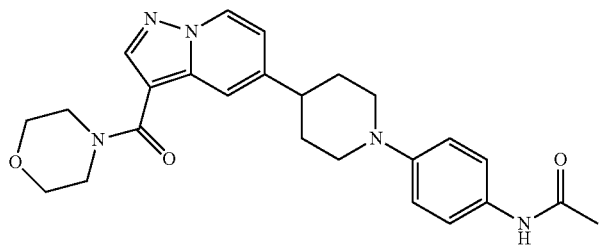 [SMILES: CC(=O)Nc1ccc(N2CCC(c3ccn4ncc(C(=O)N5CCOCC5)c4c3)CC2)cc1]
7ID
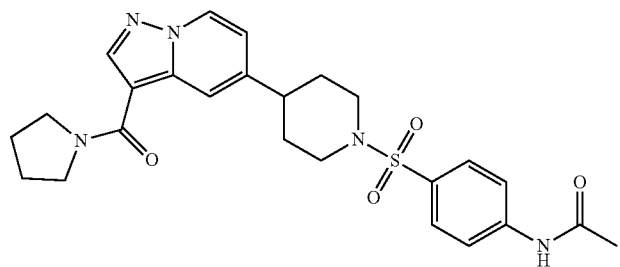 [SMILES: CC(=O)Nc1ccc(S(=O)(=O)N2CCC(c3ccn4ncc(C(=O)N5CCCC5)c4c3)CC2)cc1]
7IE
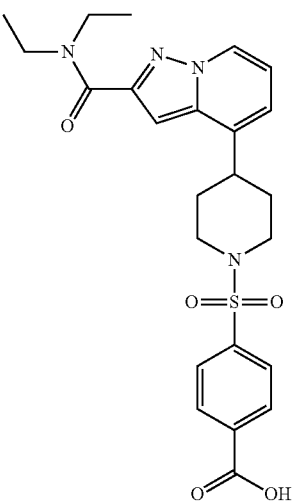 [SMILES: CCN(CC)C(=O)c1cc2c(C3CCN(S(=O)(=O)c4ccc(C(=O)O)cc4)CC3)cccn2n1]
7IF
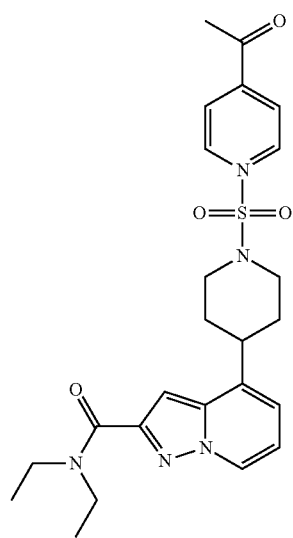
7IG

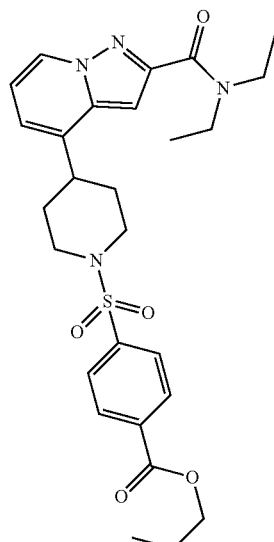

7IH

In some embodiments, the compounds disclosed herein include an aryl sulfonyl group, which participates in hydrogen bonding interactions with Tyr1019 on NACK, as well as additional hydrogen bond donor and acceptor atoms that participate in favorable water interactions. The compounds disclosed herein also include an alkyl amide, the nitrogen of which forms a hydrogen bond with Lys1022, and the alkyl groups of which participate in hydrophobic interactions deep within the binding pocket of NACK. It was found that an increase in carbon atoms on the alkyl chains of the alkyl amide improve interaction of the compound with the binding pocket, and particularly so for cyclic moieties (e.g., when $R^3$ and $R^4$ together with the nitrogen to which they are attached form a ring). Without being bound to any particular theory, straight chain alkyl moieties can increase steric hindrance and entropy. The compounds disclosed herein also include an azaindole moiety, which participates in hinge interactions with His1095.

Synthesis of the NACK Inhibitors

The compounds of the disclosure can be synthesized by any method known to one skilled in the art. Scheme 1, below, depicts one method for synthesizing the compounds of the disclosure. For example, 4-(piperidine-4-yl)pyridine (1) can be protected (e.g., with BOC) to result in 2, which can reacted with, for example, mesitylenesulfonylhydroxylamine ("MSH") to form an aminopyridinium salt. The aminopyridinium salt can undergo a 3+2 cycloaddition with a desired propiolate to form a desired methyl-pyrazolo[1,5-a]pyridine-carboxylate (3). The methyl carboxylate 3 can undergo hydrolysis (e.g., with LiOH) to result in carboxylic acid (4), which can be reacted with a desired amine using standard coupling chemistry to form a desired amide (5). The amide can then be deprotected (6) and reacted with a desired sulfonyl chloride to result in an inhibitor of the disclosure (7).

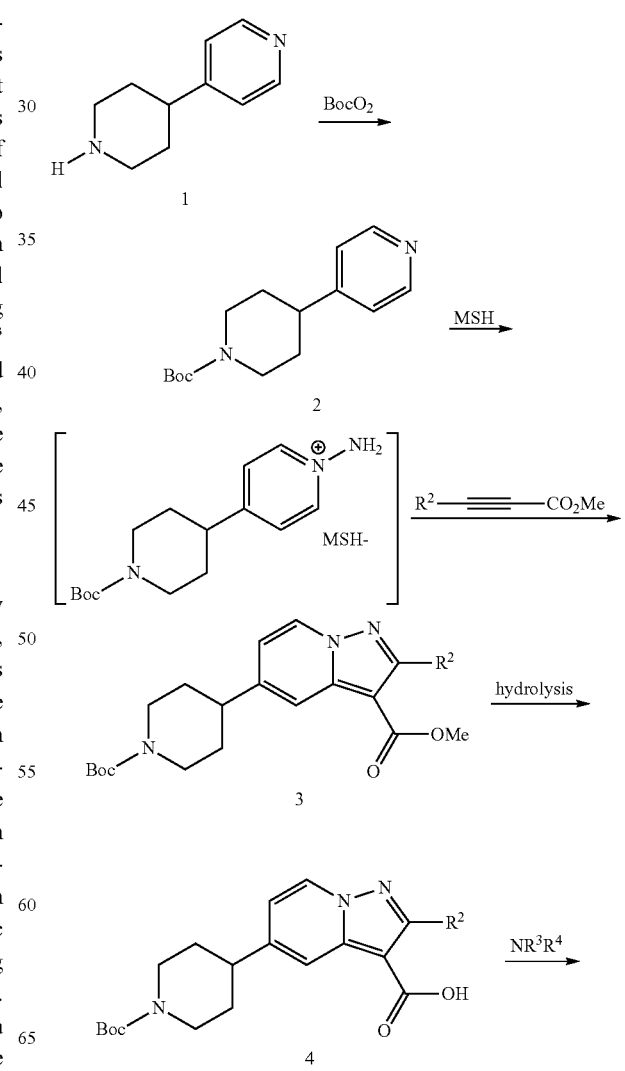

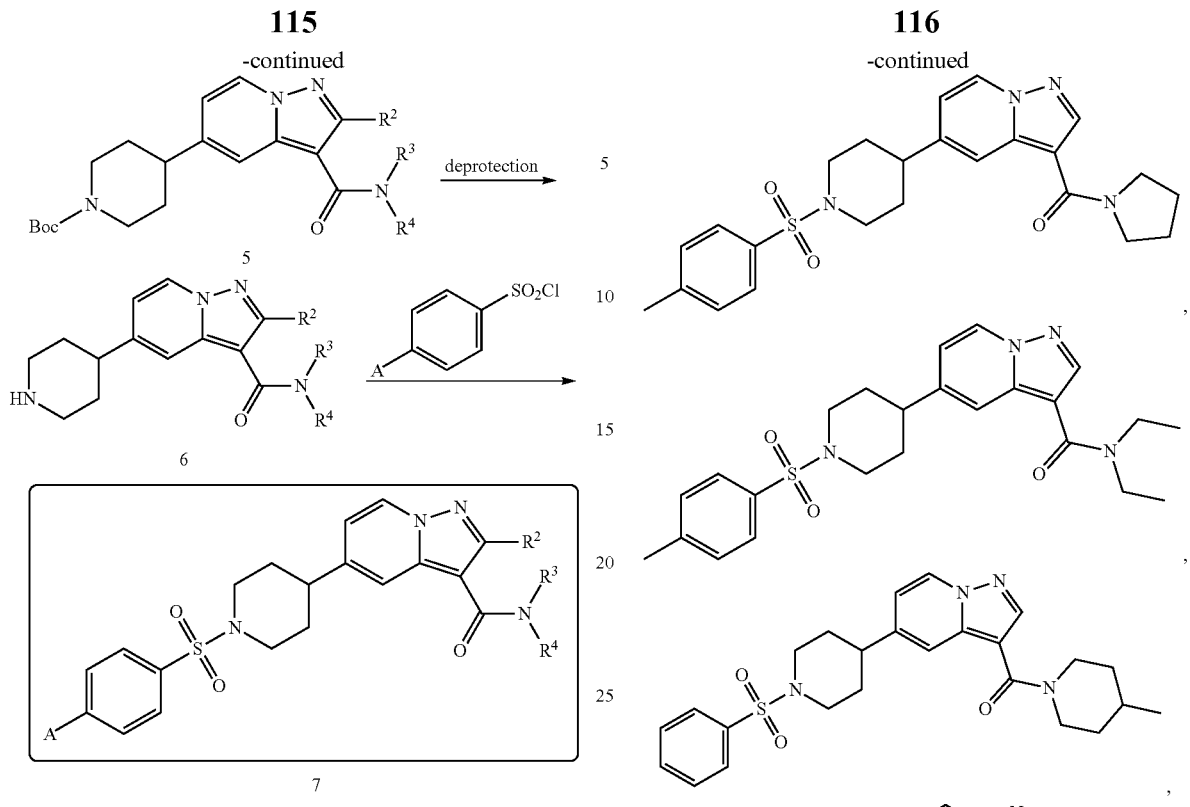

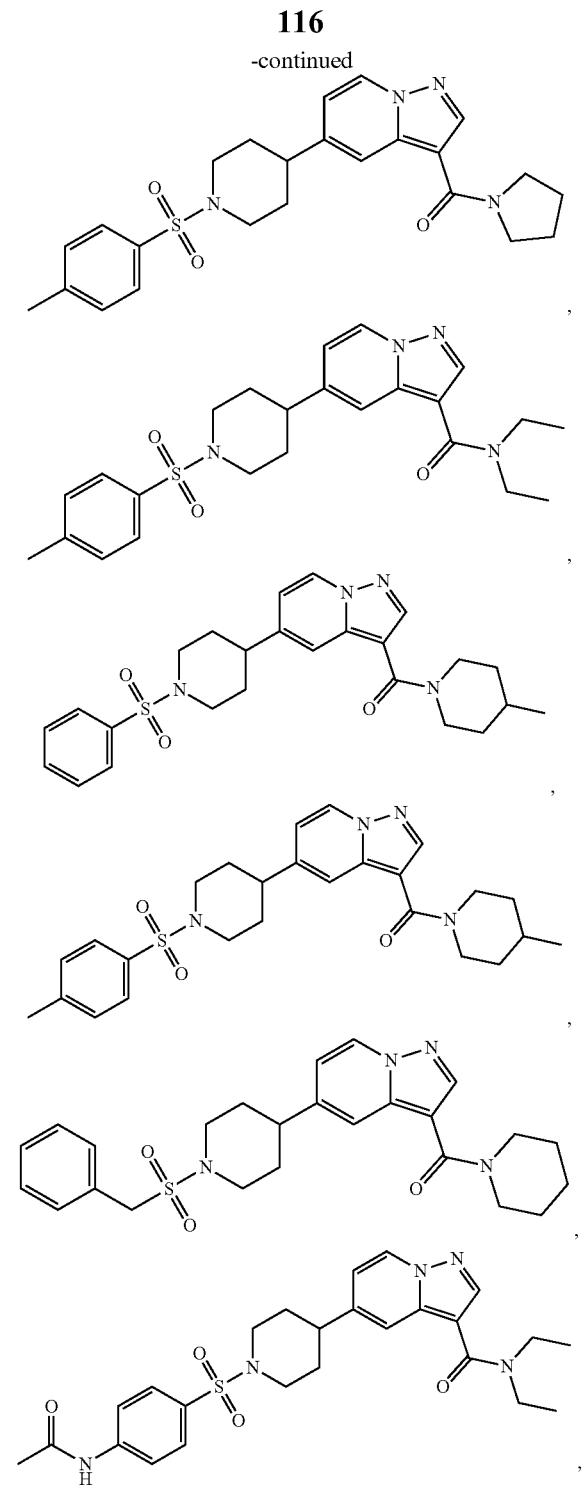

Additional synthetic procedures for preparing the compounds disclosed herein can be found in the Examples section.

Methods of Using the NACK Inhibitors

The compounds of the disclosure can inhibit Notch activation complex kinase ("NACK") by disrupting recruitment of NACK to the Notch transcription complex ("NTC") in a cell, which is useful in preventing or treating diseases associated with deregulation of the Notch transcriptional activation complex.

The Notch pathway is restricted to small populations of progenitor and stem cells of regenerating tissues, such as the colon and brain. However, in many human cancers, the Notch pathway becomes reactivated, and this deregulation of the Notch pathway underlies many aspects of cancer physiology, depending on cell type and context.

Therefore, one aspect of the disclosure relates to a method of inhibiting the Notch activation kinase complex ("NACK") in a cell, comprising contacting the cell with one or more compounds as disclosed herein (e.g., a compound of Formula (I), a compound of Formula (Ia), a compound listed in Table A, Table B, Table C,

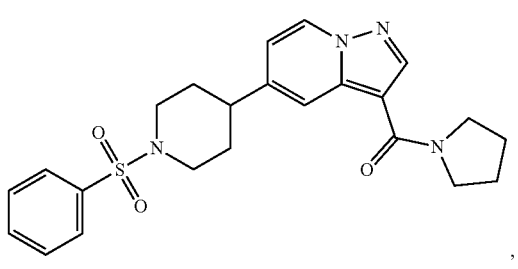

and pharmaceutically acceptable salts of any of the foregoing) in an amount effective to inhibit NACK.

In particular, provided herein is a method of inhibiting NACK recruitment to the Notch transcriptional complex ("NTC") in a cell by contacting the cell with one or more compounds disclosed herein in an amount effective to inhibit NACK recruitment to the NTC.

The compounds disclosed herein can inhibit NACK in a cell by contacting the cell in vitro or in vivo. In some embodiments, the contacting occurs in vitro. In other embodiments, the contacting occurs in vivo. The compounds can contact NACK in vivo by administering the compound to a subject or patient in need of regulation of NACK. Put another way, in various embodiments, the invention includes administering one or more compounds of the disclosure to a subject or patient, such as a human, in need thereof. In some of these embodiments, the patient suffers from a disease associated with deregulation of the Notch transcriptional activation complex (e.g., Tetralogy of Fallot ("TOF"), Alagille syndrome, multiple sclerosis, or cancer).

Another aspect of the disclosure relates to a method of treating a disease associated with deregulation of the Notch transcriptional activation complex in a patient, comprising administering to the patient a therapeutically effective amount of one or more compounds disclosed herein.

In some embodiments, the disease associated with deregulation of the Notch transcriptional activation complex is Tetralogy of Fallot ("TOF"), or Alagille syndrome. In some cases, the disease associated with deregulation of the Notch transcriptional activation complex is cancer. In various embodiments, the cancer is selected from the group consisting of T-cell acute lymphoblastic leukemia ("T-ALL"), B-cell acute lymphoblastic leukemia ("B-ALL"), breast cancer, medulloblastoma, colorectal cancer, non-small cell lung carcinoma ("NSCLC"), melanoma, cerebral autosomal-dominant ateriopathy with sub-cortical infarcts and leukoencephalophathy ("CADASIL"), chronic lymphocytic leukemia ("CLL"), hepatocellular carcinoma ("HOC"), myelomonocytic leukemia ("CMML"), pancreatic ductal adenocarcinoma ("PDAC"), head and neck squamous cell carcinoma ("HNSCC"), renal cell adenocarcinoma, fibrosarcoma, and combinations thereof. In some embodiments, the disease associated with deregulation of the Notch transcriptional activation complex is multiple sclerosis ("MS").

Use of a compound, or pharmaceutically acceptable salt thereof, as disclosed herein (e.g., a compound of Formula (I), a compound of Formula (Ia), a compound listed in Table A, Table B, Table C,

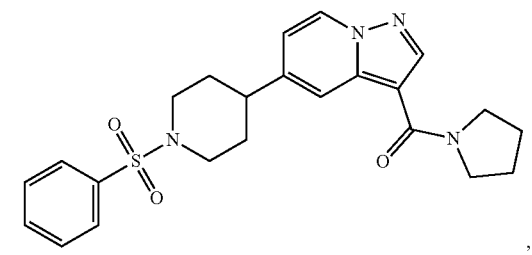

,

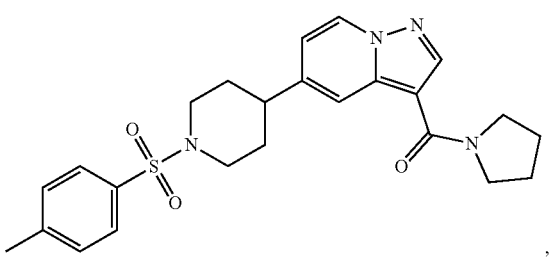

,

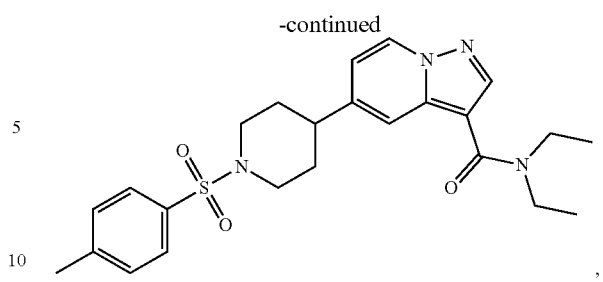

,

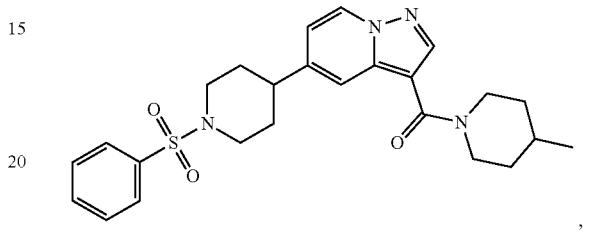

,

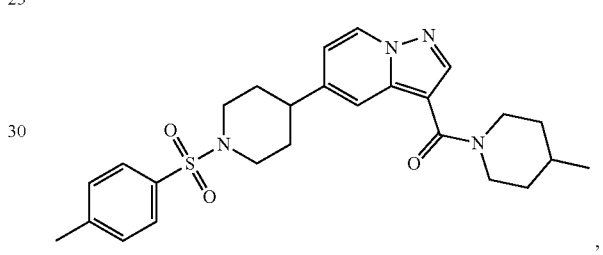

,

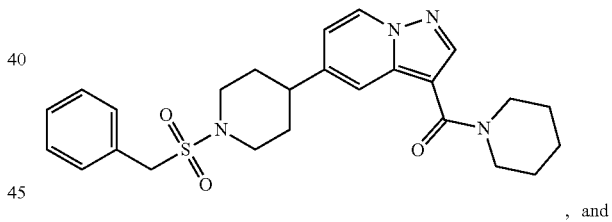

, and

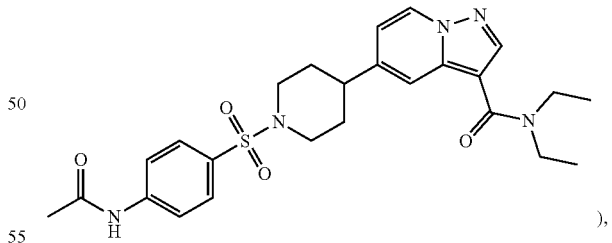

), to treat a condition resulting from deregulation of the Notch transcriptional activation complex in a patient, as well as use of the compound in the preparation of a medicament for treating the condition, also are contemplated.

Another aspect of the disclosure provides a method of inhibiting kinase activity, ATPase activity, or both in a cell, comprising contacting the cell with one or more compounds as disclosed herein (e.g., a compound of Formula (I), a compound of Formula (Ia), a compound listed in Table A, Table B, Table C,

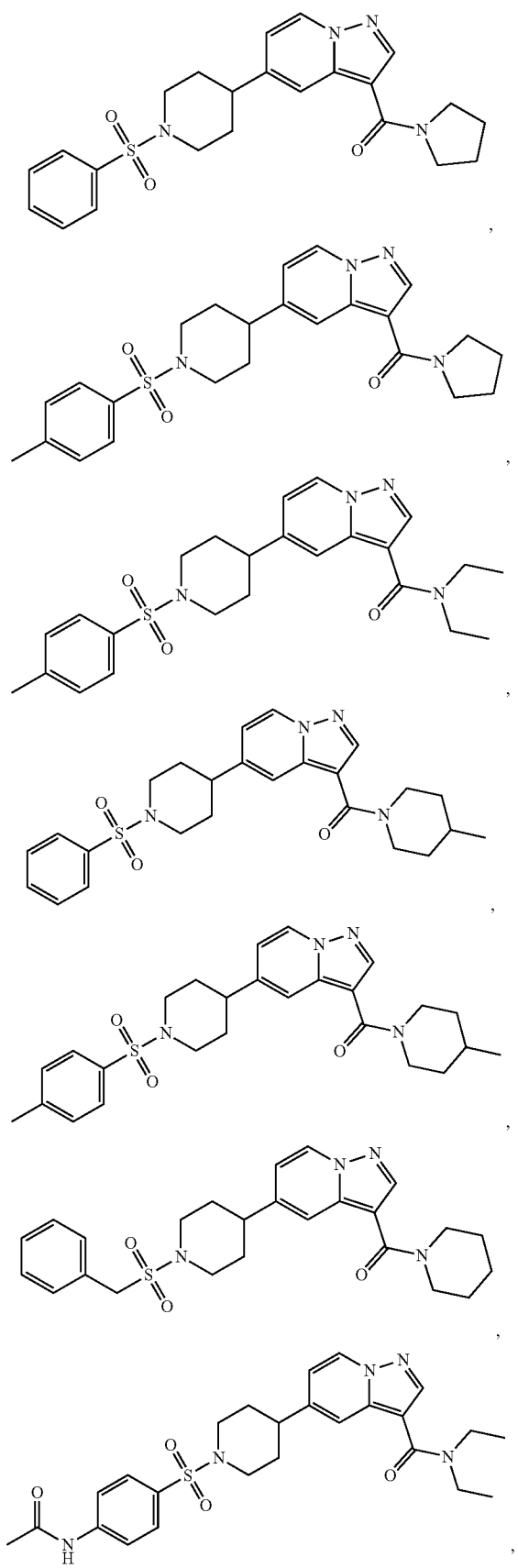

and pharmaceutically acceptable salts of any of the foregoing), in an amount effective to inhibit kinase and/or ATPase activity.

Elevated NACK Expression in Esophageal Adenocarcinoma ("EAC")

NACK plays an important role in activating Notch transcription and regulating the Notch-mediated tumorigenesis and development. See Weaver et al., Cancer Research 74, 4741-4751 (2014). Further, Notch drives stemness and tumorgenicity of esophageal adenocarcinoma ("EAC"). See Wang et al., Cancer Research 74, 6364-6374 (2014).

Figure 1B:
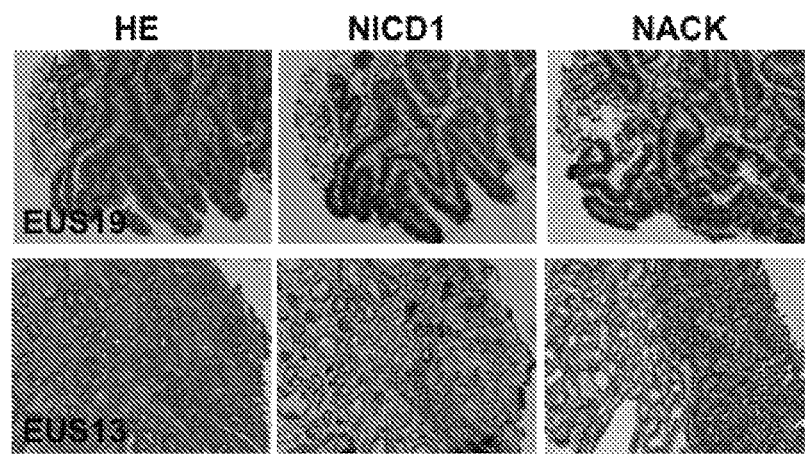
FIG. 1B shows that a high level of NACK and activated Notch1 expression are both observed in chemo-naïve esophageal adenocarcinoma samples from endoscopic ultrasound ("EUS") biopsies.
Figure 1C:
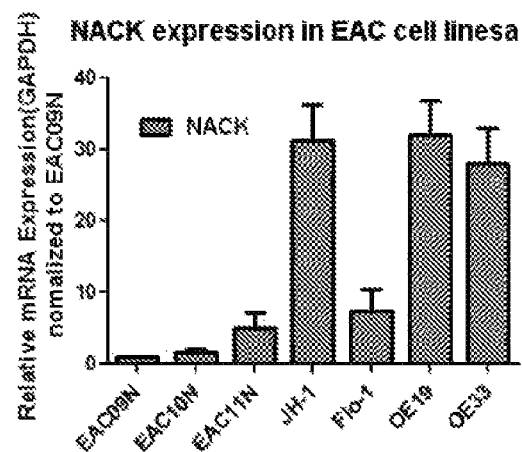
FIG. 1C shows the expression of NACK in EAC cell lines (OE33, OE19, Flo-1 and JH-1) by qPCR.

To evaluate the expression level of NACK in EAC, clinical samples derived from surgically resected primary esophageal adenocarcinoma were analyzed. As illustrated in FIG. 1A, the mRNA levels of NACK and Notch1 are elevated in tumor samples compared to their corresponding normal tissues. Consistently, high levels of NACK were observed in chemo-naïve esophageal adenocarcinoma samples from endoscopic ultrasound ("EUS") biopsies, which also have elevated levels of activated Notch1 (FIG. 1B).

The expression of NACK in esophageal adenocarcinoma cell lines (OE33, OE19, Flo-1 and JH-1) by qPCR was also analyzed (FIG. 10). Increased NACK expression was also observed in these esophageal adenocarcinoma cells compared to immortalized cells derived from normal tissue. These results demonstrate that the expression level of NACK is elevated and linked with the expression of activated Notch1 in esophageal adenocarcinoma tumor and cells.

Figure 1D:
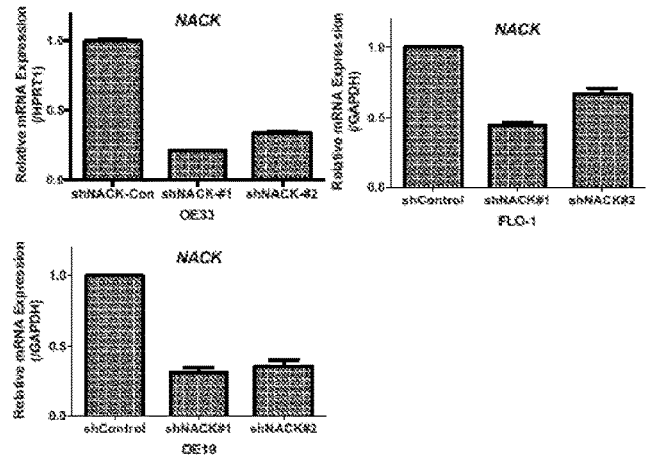
FIG. 1D shows that NACK knockdown was verified by Q-PCR.
Figure 1E:
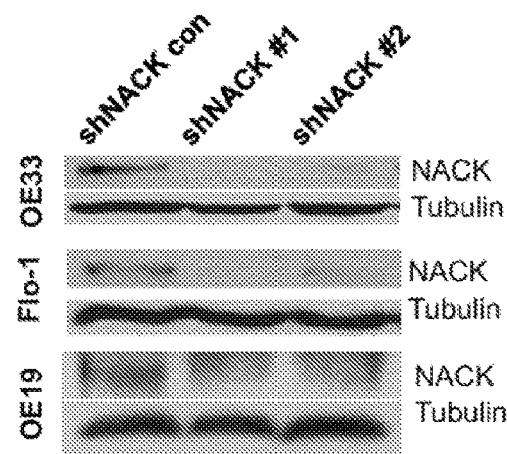
FIG. 1E shows that NACK knockdown was verified by Western blot.
Figure 1F:
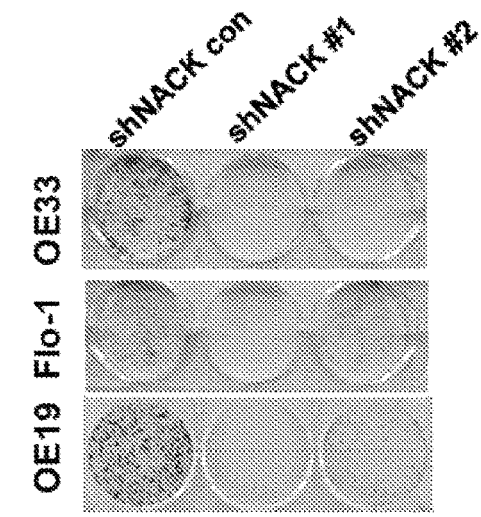
FIG. 1F shows that knockdown of NACK in EAC cells (OE33, OE19 and Flo-1) led to dramatic inhibition of the clonogenic potential of these cells.

To assess the importance of NACK in EAC, the viability of EAC cells was assessed by knocking down endogenous expression of NACK. Cell lines were infected with lentivirus expressing control shRNA or shRNA against NACK. Knockdown of NACK in esophageal adenocarcinoma cells (OE33, OE19 and Flo-1), as verified by qPCR and Western blot (FIGS. 1D and 1E), led to dramatic inhibition of the clonogenic potential of these cells (FIG. 1F). These data indicated that NACK is essential for the survival of EAC cells, which provide the rationale for targeting NACK as a therapeutic target.

Homology Modeling and Molecular Dynamic ("MD") Simulation of the Kinase Domain of NACK The NACK structure was constructed using homology modeling. The three-dimensional model of NACK was produced using the IntFOLD server, which adopted the multiple-template modeling method based on global and local sequence quality estimates and additional sequence-structure alignment methods. See McGuffin et al., Nucleic Acids Res 43, W169-73 (2015).

A good quality model was obtained based on the structure templates of protein kinases PKR (2A1A), STK16 (2BUJ), NEK1 (4APC) and CaMKII (2BDW). The three-dimensional model for NACK (full length) shows a largely disordered N-terminal domain (Met1-Gly974), an ordered kinase catalytic domain (Gly975-Trp1326), followed by a disordered C-terminal domain (Gly1327-Leu1402). The catalytic core of the protein kinase domain is composed of a β-sheet characterized N-lobe and an α-helix dominated C-lobe. In this regard, only the kinase domain model of NACK was employed for further molecular dynamic (MD) simulation.

To investigate the structural features of the NACK kinase domain, the NACK kinase domain model was compared to the crystallographic structure of PLK3 (PDB: 4B6L), which is a typical kinase. PLK3 is structurally similar to NACK, with an RMSD of 1.748 Å over 182 aligned residues, and 27.47% sequence identity calculated by YASARA (shown using PyMOL, FIGS. 2A and 2B). This model kinase domain structure of NACK is also similar to that of the atypical kinase CASK. The 3D structural superimposition using YASARA between the kinase domain of NACK and CASK (PDB: 3C01) has an RMSD of 1.69 Å over 176 aligned residues, with 21.59% sequence identity (shown using PyMOL, FIG. 2A). Superimposition of CASK with the NACK structure suggests that the adenine ring of 5'AMP can interact with the "hinge" residues of the NACK kinase domain. The hinge region contains several conserved residues that are essential for ATP binding and catalytic activity.

There are several key motifs in typical kinase domain structures that are needed for ATP binding, hydrolysis, and transfer. The HRD motif, containing a catalytic residue, functions to cleave the gamma-phosphate group and transfer it to the substrate. The VAIK motif is used to position the alpha and beta phosphate of ATP. The DFG motif contains the $Mg^{2+}$ binding site, which is required for ATP hydrolysis. NACK has several major protein kinase features such as the HRD motif, which includes a conserved aspartate (ASP1143) that is directly involved in catalytic activity (FIG. 2A). Moreover, the VAIK motif, with the alteration of the YAVK motif in NACK adopts a β-sheet secondary structure (FIG. 2A) is very similar to the corresponding regions of PLK3 and CASK (FAVK motif). In the loop between the N- and C-lobes, Arg1091 and Val1093 form a hinge that is structurally similar to that formed between Glu92 and Met94 in CASK. However, NACK lacks the conserved DFG motif that is involved in metal binding (FIG. 2A). As for CASK, it may still function as active kinase without metal binding site.

Figure 2C:
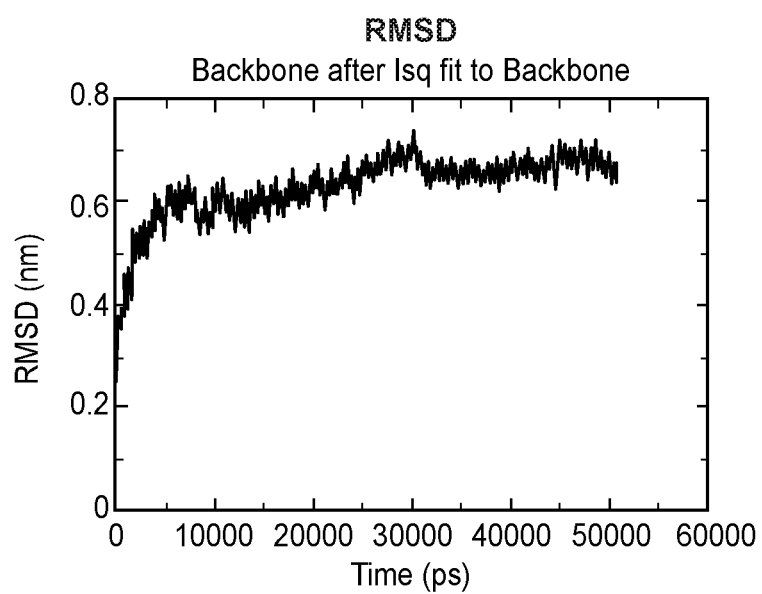
FIG. 2C depicts a plot showing the RMSD levels off to ~0.1 nm, indicating that the structure is very stable.
Figure 2D:
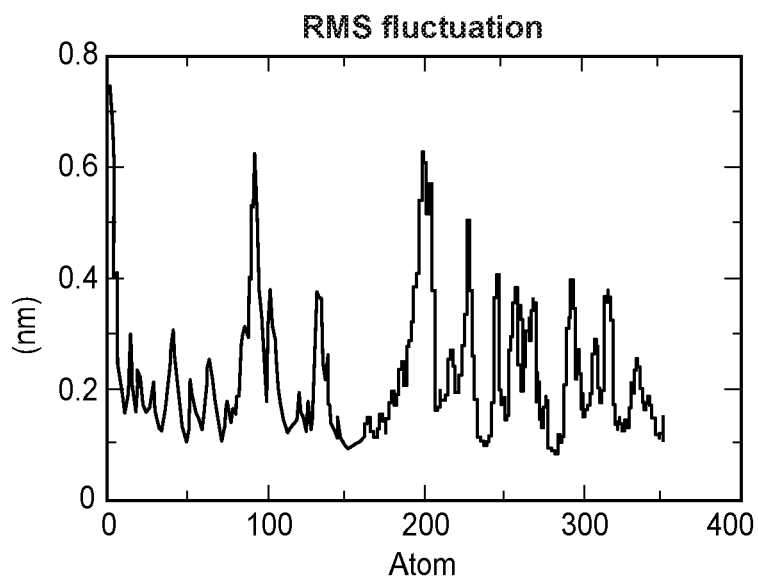
FIG. 2D is an RMSF showing the dynamic regions of NACK (Cys1049-Asp1084 and Cys1154-Leu1205).
Figure 2E:
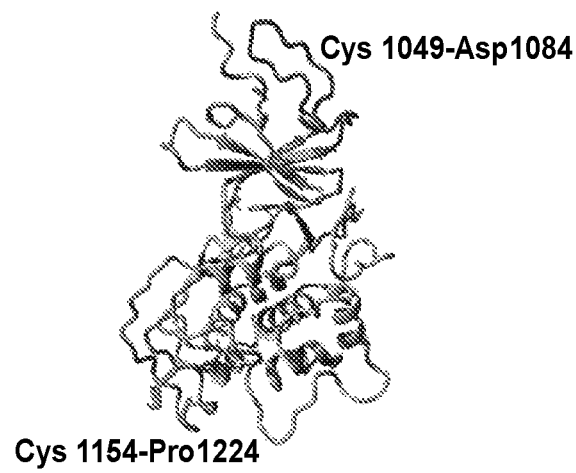
FIG. 2E depicts the most representative structure of NACK.

Following the homology modeling of NACK structure, a 50 ns all-atom MD simulation was performed in explicit water solvent to evaluate the stability of the NACK kinase domain model. Throughout the simulation, the Root Mean Square Deviation (RMSD) values increased up to 0.6 nm at 5 ns and remained around 0.7 nm as the time evolved (FIG. 2C). Moreover, the Root Mean Square Fluctuation (RMSF) was calculated to evaluate the flexibility of NACK kinase domain structure (FIG. 2D). Two regions appear to be the most flexible, which were Cys1049-Asp1084 and Cys1154-Leu1205 (shown in FIG. 2E respectively). The Cys1049-Aps1084 region forms a flexible loop between strands of the beta sheet in the N-lobe of NACK kinase domain, and Cys1154-Leu1205 constitutes the kinase insert domain.

MD Simulation Between NACK and ATP Reveals a Putative ATP Binding Pocket

Figure 3A:
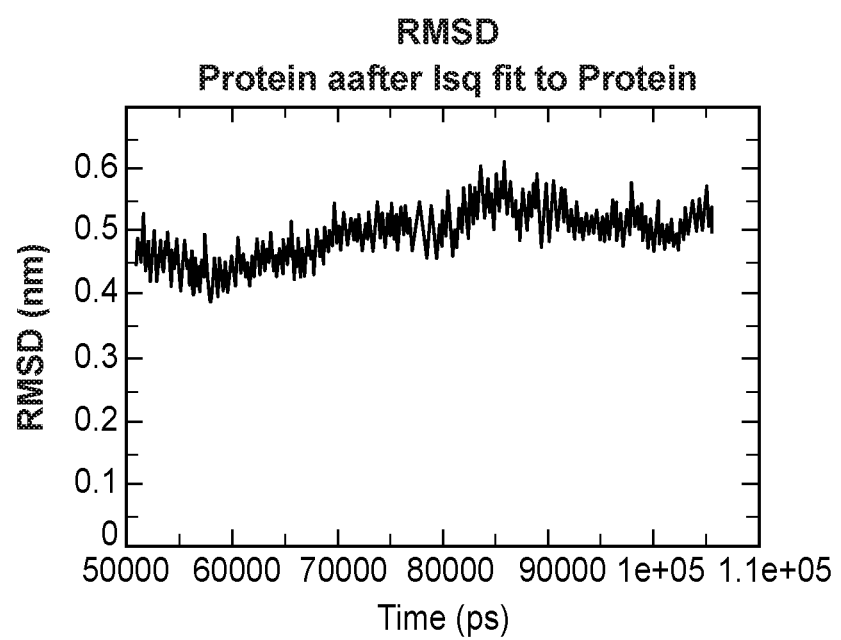
FIG. 3A is a RMSD plot demonstrating that during the simulation the structure is very stable.
Figure 3B:
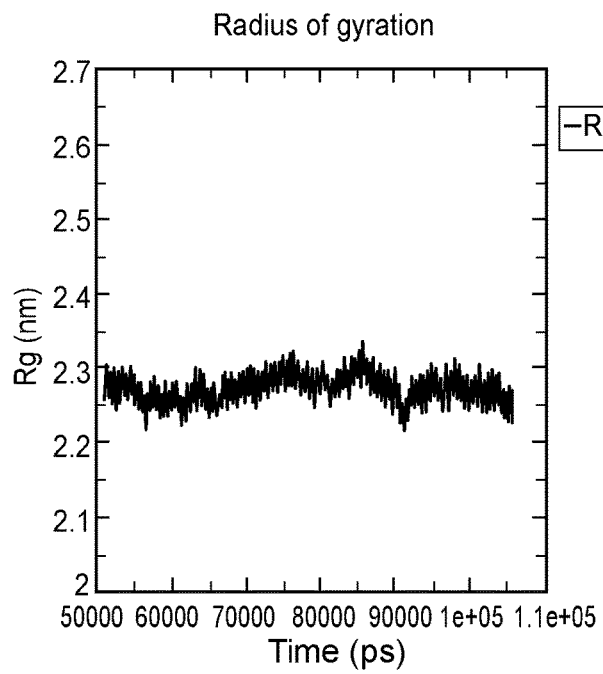
FIG. 3B shows that for the last 50 ns run, the radius of gyration of NACK maintains a relatively steady value of Rg.

In order to identify the catalytic pocket of NACK, a MD simulation between NACK and the ATP ligand was conducted. The most representative structure of NACK derived from the initial MD study served as the starting conformation for the NACK-ATP interaction simulation. The ATP molecule was pre-positioned in the kinase domain of NACK according to the proposed interactions (see Taylor, S. S. Bioessays 7, 24-9 (1987), with phosphate groups making interaction with Lys1022 and adenine head making contact with His1095 at hinge region of the kinase domain. A 100 ns MD simulation was conducted. During the second 50 ns the binding model stabilized with RMSD between 4 and 5.5 Å (FIG. 3A). The stability of the MD simulation was further validated by the Radius of Gyration (Rg). Rg is the distance of the atoms of the structure from its center of gravity during the simulation time. Rg reached plateau averaging around 2.3 nm, which further demonstrated that the simulation reached equilibrium (FIG. 3B).

Figure 3C:
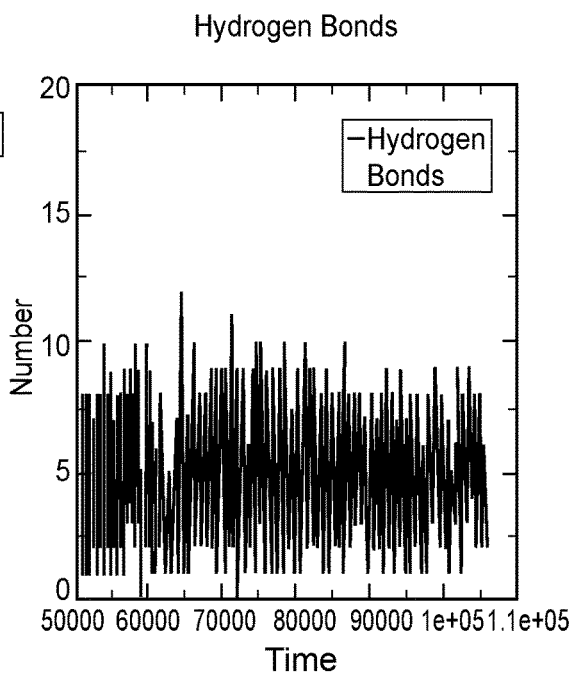
FIG. 3C is a plot showing that around 5 hydrogen bonds were formed between NACK and ATP during 50 to 100 ns simulation.
Figure 3D:
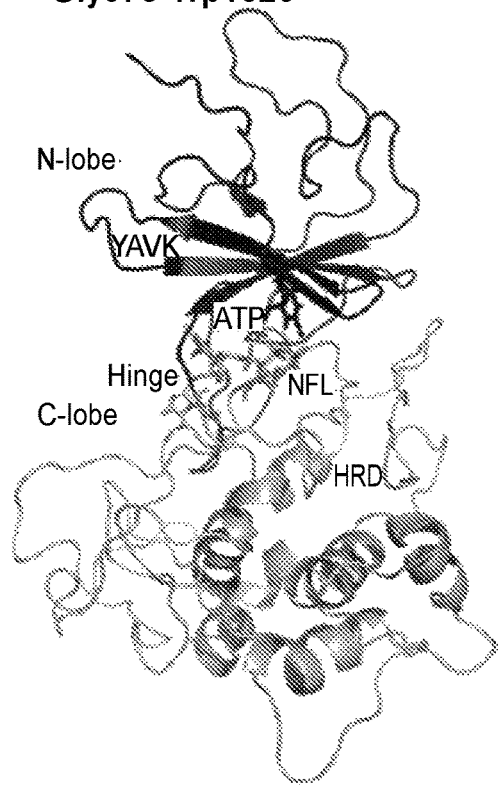
FIG. 3D depicts the most representative structure of NACK and ATP during the last 50 ns simulation.
Figure 3D:
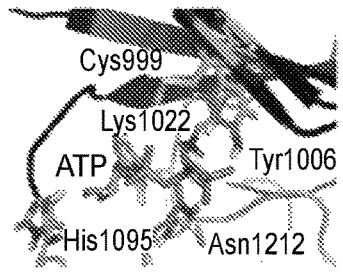

The molecular interactions between NACK and ATP were evaluated by calculating the number of hydrogen bonds. Five hydrogen bonds were consistently present between ATP and NACK in the last 50 ns of simulation (FIG. 3C). As for typical kinases, ATP was found to make seven to eight hydrogen bonds with residues at the active site. See Kuriyan, J., Konforti, B. & Wemmer, D. The molecules of life: Physical and chemical principles (Garland Science, 2012). The most representative structure of NACK with ATP molecule is shown in FIG. 3D. Several residues in the kinase domain of NACK were found to make important contacts with ATP (FIG. 3E). Notably, the salt bridge between Lys1022 and the beta phosphate group of ATP remained intact during the simulation. A hydrogen bond was found between the backbone hydrogen of His1095 and alpha phosphate oxygen ATP, whereas His1095 was in the position to make contact with adenine ring of ATP at the starting point of simulation. Residues Asn1212, Cys999 and Tyr1006 also formed hydrogen bonds with the phosphate groups of ATP. Asp1048 was found to make contact with adenine ring of ATP through a hydrogen bond (FIG. 3E). These results suggested that ATP could make stable contacts at the active site of NACK.

NACK Binds to the Notch Transcription Complex in an ATP-Dependent Manner

Previously, it had been demonstrated that NACK can be coprecipitated concomitantly with N1 ICD and Maml1 in a CSL-dependent manner from 293T cells transfected with N1 ICD, Maml1 and NACK in the CSL DNA affinity precipitation (CSL-DAP) assay. See Weaver, K. L. et al. Cancer Research 74, 4741-4751 (2014). To validate the model, residues Lys1002, Cys979, Tyr986 and His1076 were mutated in mouse NACK, which were found to make important interactions between NACK and ATP in the MD simulation (FIGS. 3D and 3E). The binding between ATP and mutated NACK was evaluated by the CSL-DAP experiment. NACK mutants (NACK-Lys1002, NACK-Cys979) showed decreased NACK binding to N1 ICD and Maml1 in a CSL-dependent manner, suggesting their importance for ATP binding (FIG. 4A). While the NACK-His1076 mutant does not alter the NACK recruitment as His residue interacted with ATP through backbone.

Figure 4D:
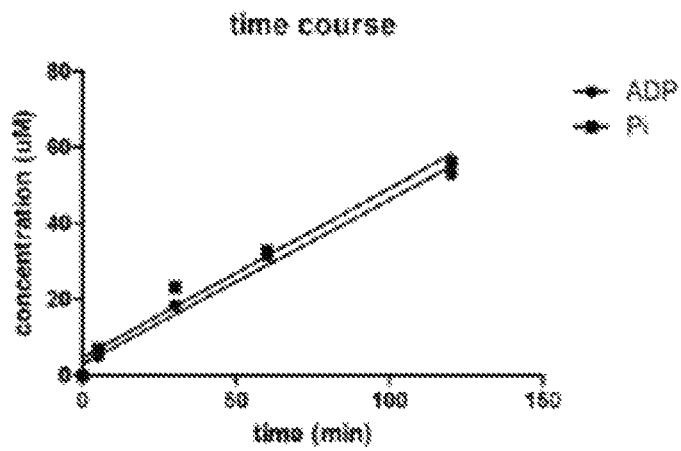
FIG. 4D shows that equal amounts of ADP and Pi were detected by ADP-Glo in vitro kinase assay and colorimetric phosphate assay after incubating NACK with ATP.
Figure 4E:
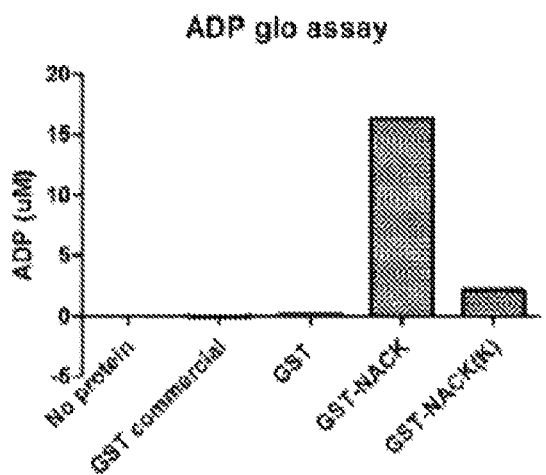
FIG. 4E shows that NACK "kinase-dead" mutant K1002A failed to hydrolyze ATP to ADP in the ADP-Glo assay.

To further explore the effect of ATP on NACK binding to the Notch transcription complex, a CSL-DAP assay was conducted by adding ATP or GTP to the cell lysate. Compared to the control, NACK recruitment was dramatically increased (FIG. 4B). In contrast, NACK was not observed in the condition of non-hydrolysable ATP or GTP (AMPPNP or GTP-gS) (FIG. 4B), suggesting that ATP or GTP hydrolysis is required for the recruitment of NACK to the Notch transcription complex. Moreover, the binding between NACK and ATP was confirmed by measuring the binding between NACK and ATP analog AMP-PNP using surface plasmon resonance (SPR). The binding constant was determined to be approximately 1.5 uM (FIG. 4C). Therefore, it has been demonstrated that NACK can hydrolyze ATP to ADP and Pi (FIG. 4D). In contrast, NACK "kinase-dead" mutant K1002A failed to hydrolyze ATP to ADP in the ADP-Glo assay (FIG. 4E). Taken together, these results suggested that NACK functions in an ATP dependent manner to bind to the Notch transcription complex and to activate Notch-mediated transcription.

NACK Inhibitors Selectively Inhibit the Viability of Notch/NACK Dependent Cell Line To establish a criterion for Notch/NACK-dependence, cell lines were classified into two groups based on their sensitivity to DAPT (a GSI) and NACK knockdown. In this scenario, it was reasoned that inhibition of cell growth and Notch target genes by either DAPT or NACK knockdown indicates specific inhibition of Notch/NACK activity. Therefore, cell lines in which cell growth and Notch target gene transcription were affected by either DAPT treatment or NACK knockdown were classified as Notch/NACK dependent cell lines. On the other hand, those in which cell growth and transcription did not significantly change upon DAPT treatment or NACK knockdown were defined as Notch/NACK independent cell lines.

Figure 5A:
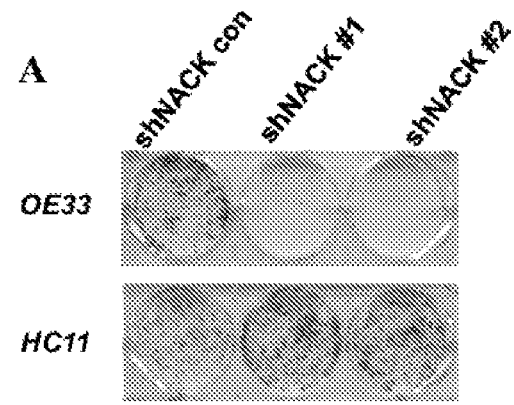
FIG. 5A shows that knockdown of NACK affects the viability of OE33 cell line, but not HC11.
Figure 5B:
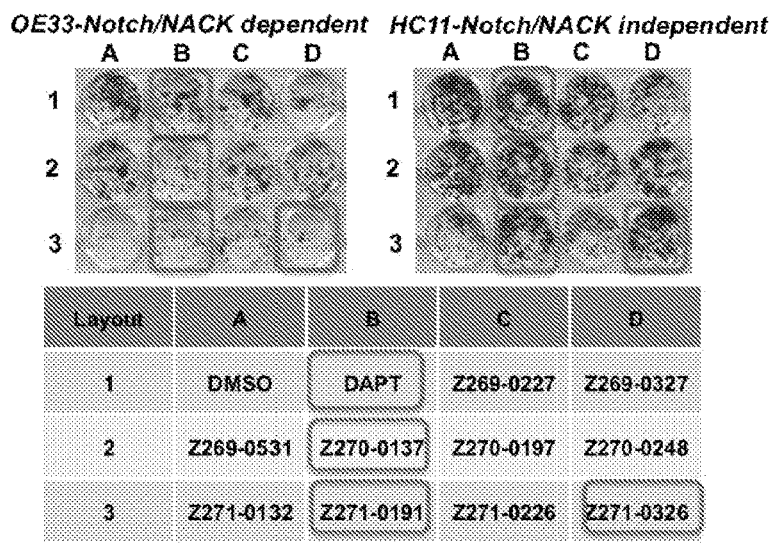
FIG. 5B shows that the compounds described herein selectively inhibit the viability of Notch/NACK dependent cell line.
Figure 5C:
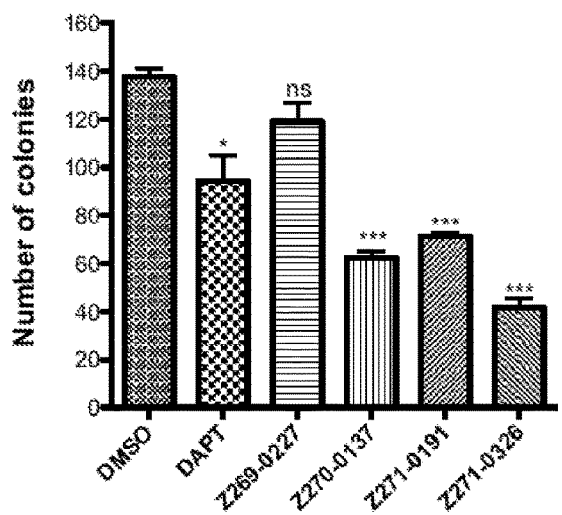
FIG. 5C show a summary of the colony formation assay.

A cell based colony formation assay was used in these experiments. Normal mouse mammary epithelia HC11 cells have little or no endogenous NACK expression, and NACK knockdown had no effect on the growth of HC11 cells (FIG. 5A, lower panel). On the other hand, knockdown of NACK in esophageal adenocarcinoma cell line OE33 showed significant inhibition of colony formation. Knockdown of NACK was confirmed by western blot and qPCR (FIGS. 1D and 1E). Furthermore, OE33 cell lines were responsive to gamma secretase inhibitor (GSI) DAPT treatment with a reduction in the colony formation compared to the mock treated cells, whereas DAPT treatment did not alter the viability of HC11 cells (FIG. 5B). Therefore, compounds that affect OE33 colony formation but not HC11 were desired. In order to screen the compounds, cells were treated with test compounds every other day. As shown in FIGS. 5B and 5C, compounds Z270-0137, Z271-0191, and Z271-0326 (depicted below) displayed remarkable potency and selectivity, which can effectively inhibit OE33 colony formation but not HC11 cell. These results suggested that a competitive inhibitor of NACK would affect the viability of Notch/NACK dependent cell lines, while have little or no impact on Notch/NACK-independent cells.

NACK Inhibitors can Selectively Inhibit NACK Recruitment to the Notch Transcription Complex Previously, NACK and Notch were observed at the Hes1 promoter by ChIP assay, demonstrating that Notch and NACK can be co-localized at CSL sites on chromatin and supporting the model that NACK is a component of the Notch transcriptional regulatory complex. See Weaver, K. L. et al. Cancer Research 74, 4741-4751 (2014). Moreover, it was demonstrated that ATP binding and hydrolysis is required to drive NACK binding to Notch, CSL and Maml (FIG. 4B).

Figure 6A:
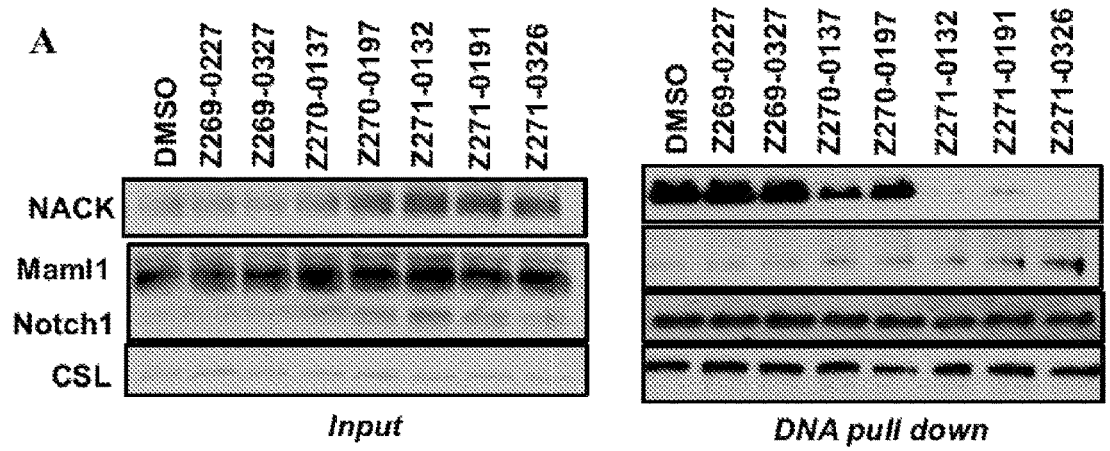
FIG. 6A shows that the NACK inhibitors described herein can selectively inhibit NACK recruitment to the Notch transcription complex.

To determine whether the inhibitors that were selective in the colony assay could inhibit NACK recruitment to the Notch transcription complex, compounds were tested by the CSL-DAP assay. Inhibitors that can block ATP from binding to NACK were sought, resulting in attenuation of NACK binding to N1ICD, Maml1 and CSL. Z271-0326, Z271-0191 and Z271-0132 (depicted below) were found to dramatically inhibit NACK binding to the NOTCH transcription complex compared to the control group (FIG. 6A).

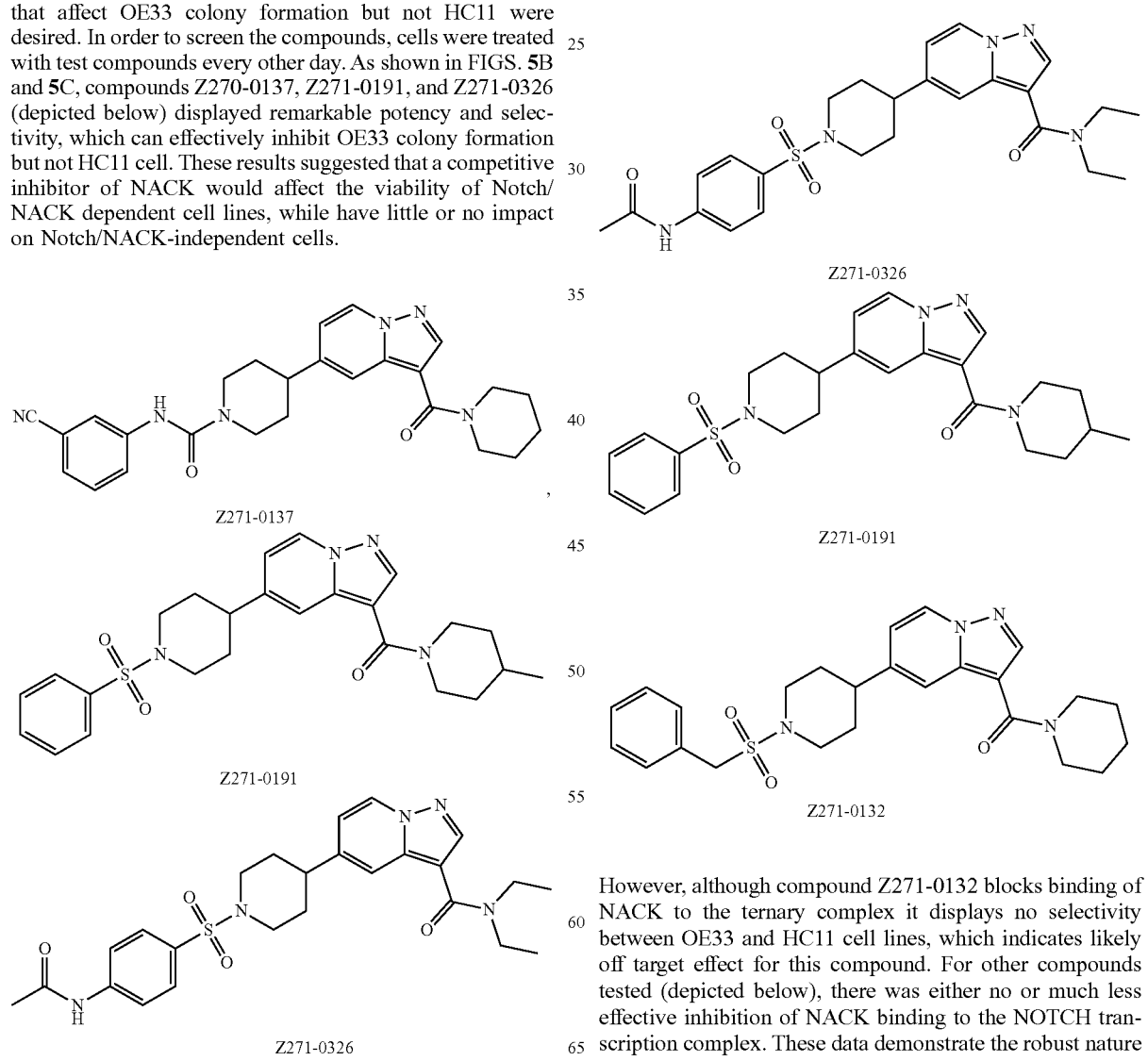

Z271-0326

Z271-0137

Z271-0191

Z271-0191

Z271-0132

Z271-0326

However, although compound Z271-0132 blocks binding of NACK to the ternary complex it displays no selectivity between OE33 and HC11 cell lines, which indicates likely off target effect for this compound. For other compounds tested (depicted below), there was either no or much less effective inhibition of NACK binding to the NOTCH transcription complex. These data demonstrate the robust nature of this secondary screen to inform on SAR at the biochemical level.

Z269-0227
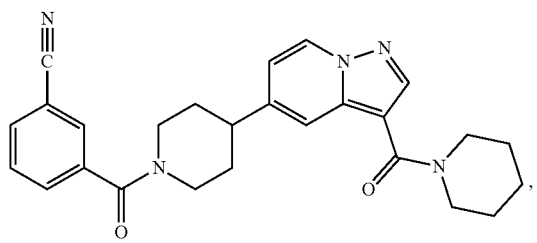

Z269-0441
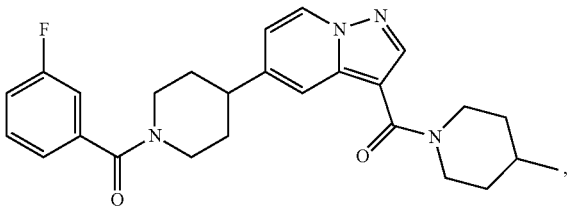

Z270-0137
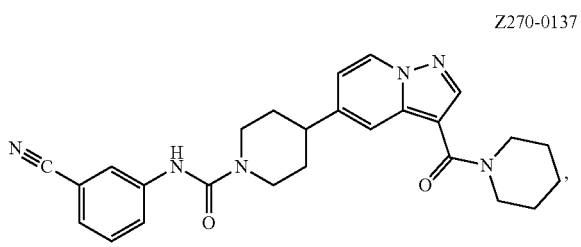

Z269-0516
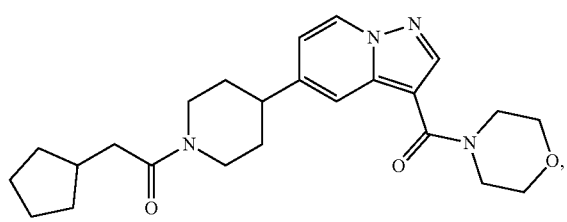

Z069-0327
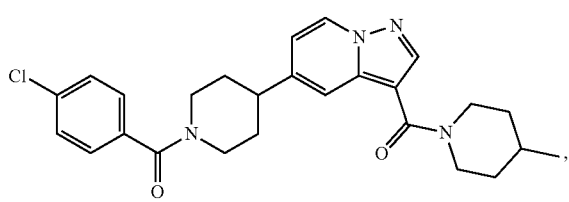

Z271-0226
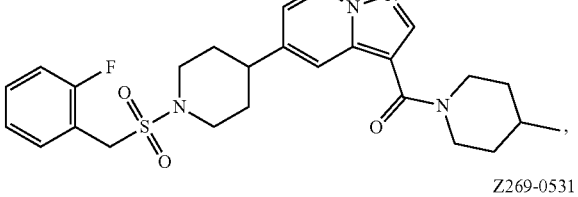

Z270-0197
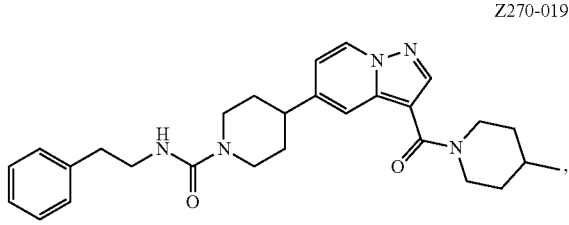

Z269-0531
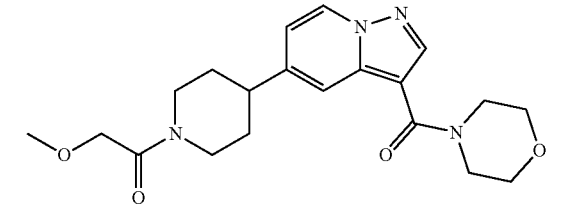

Z269-0386
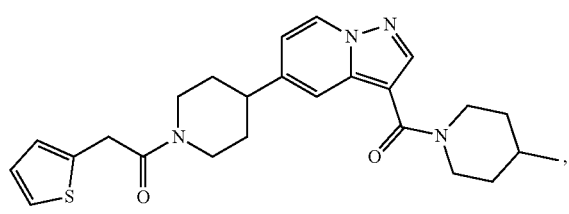

Z270-0248
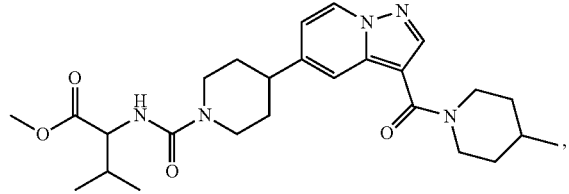

Z269-0437
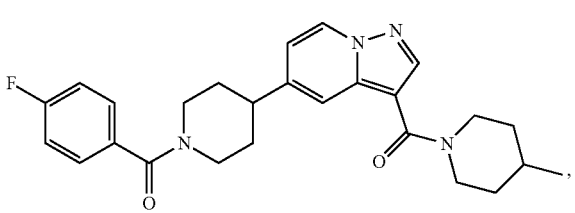

Compounds Inhibit Notch-Directed Transcriptional Activation

Figure 6B:
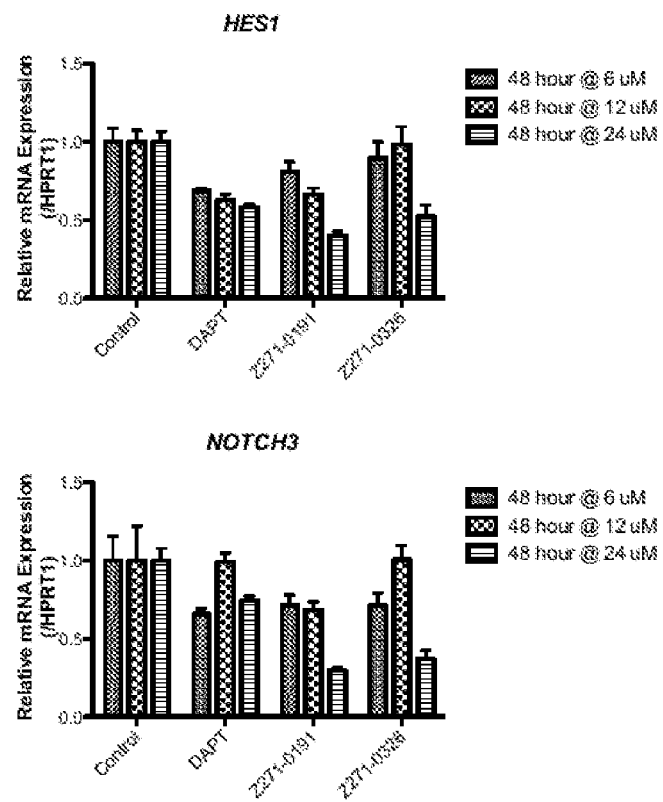
FIG. 6B shows that the NACK inhibitors described herein cause down regulation of Notch transcription activity.
Figure 6C:
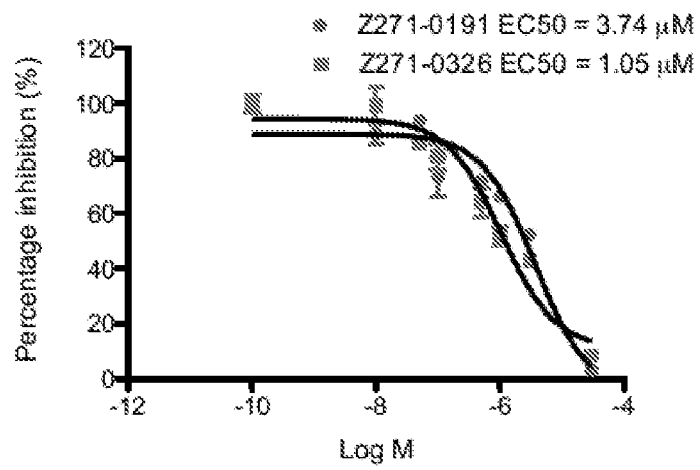
FIG. 6C shows the $EC_{50}$ of Z271-0326 and Z271-0191 estimated by colony formation titration assay.

To further explore the effects of NACK inhibitors on transcription of Notch target genes, it was demonstrated that treatment of OE33 with Z271-0191 and Z271-0326 decrease the mRNA levels of Notch target genes Hes1 and Notch3 (FIG. 6B). This result demonstrates that the inhibitors effectively attenuate the activity of NACK, which further down-regulated Notch mediated transcriptional activity. Based on colony formation titration assay, $EC_{50}$ of Z271-0326 and Z271-0191 were estimated to be 1.05 and 3.74 µM, respectively (FIG. 6C).

Secondary Sphere Formation is Effectively Attenuated by Inhibitors

Figure 7A:
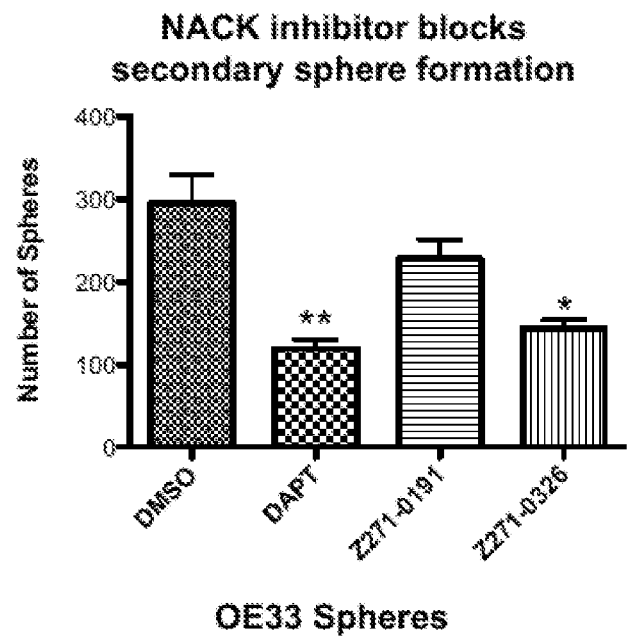
FIG. 7A shows that the NACK inhibitors described herein can attenuate the secondary sphere formation in OE33 cell line.
Figure 7B:
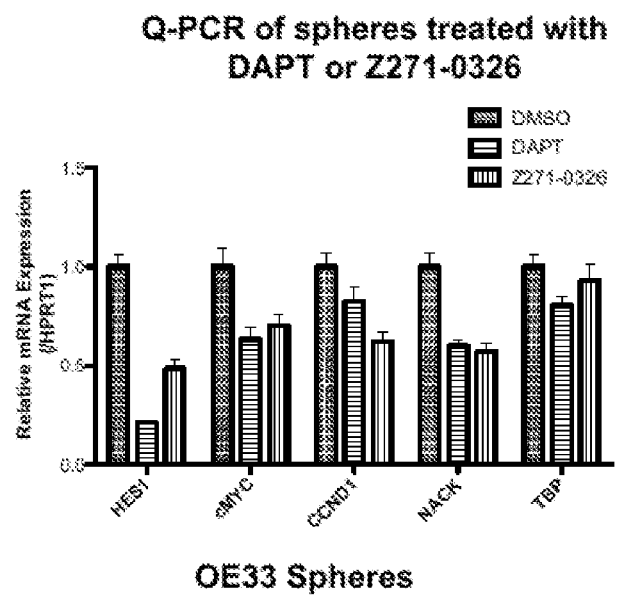
FIG. 7B. shows that treatment of OE33 spheres with Z271-0326 affects Notch target genes transcription.

Two compounds were tested by conducting tumor sphere assays. Compared to the vehicle group, the treatment of OE33 with Z271-0326 showed decrease in the ability of cell spheres to form secondary spheres, which works comparable with the DAPT group. While compound Z271-0191, it is less effective compared to Z271-0326 (FIG. 7A). Treatment of OE33 spheres with Z271-0326 also affected Notch target genes HES1, MYC, CCND1 and NACK transcription (FIG. 7B).

Figure 7C:
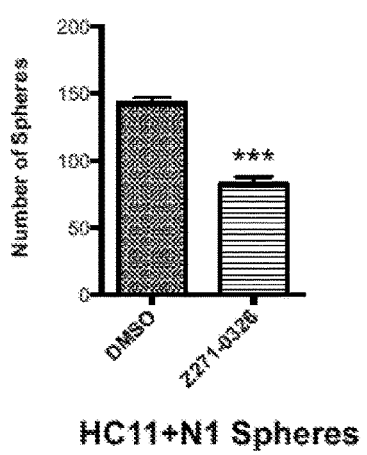
FIG. 7C shows that a NACK inhibitor can attenuate the secondary sphere formation in HC11/N1ICD.
Figure 7D:
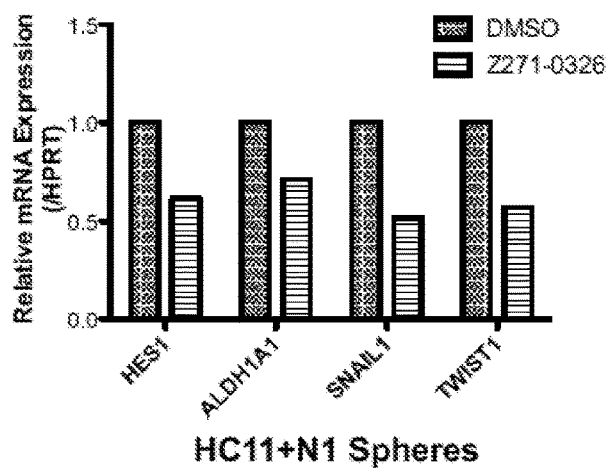
FIG. 7D shows that treatment of HC11/N1ICD spheres with Z271-0326 causes a decrease in HES1 gene expression as well as several other stem-cell marker genes. The figures show that HC11 cells are insensitive to inhibition of Notch/NACK. HC11 cells cannot form spheres themselves, but are transformed by Notch efficiently to form spheres and are tumorigenic in mice. The Notch-transformed HC11 cells are sensitive to NACK inhibition.

To further explore the effect of NACK inhibitors targeting Notch pathway, ectopic expression of Notch in HC11 mammary epithelial cells was constructed, as HC11 cells have little to no endogenous Notch activity. Moreover, HC11 cells are insensitive to either DAPT or Z271-0326 treatment as shown in previous colony formation assay (FIG. 5B). See Weaver et al., Cancer Research 74, 4741-4751 (2014). Compared to the control, HC11/N1ICD cells showed elevated Notch target gene transcription. Z271-0326 treatment inhibits the ability of HC11/N1ICD spheres to form secondary spheres (FIG. 7C). Furthermore, treatment of HC11/N1ICD spheres with Z271-0326 also causes a decrease in HES1 gene expression as well as several other stem-cell marker genes (ALDH1A1, SNAIL1 and TWIST1) (FIG. 7D). Therefore, transformation of HC11 cells by Notch now renders these cells dependent on Notch activity and sensitive to inhibition of NACK by Z271-0326.

NACK Inhibitors Block the NOTCH-NACK Complex Binding at the HES1 Promoter

Figure 8A:
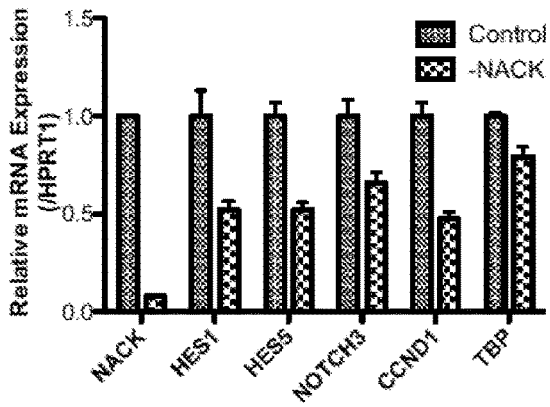
FIG. 8A shows Q-PCR and western blot results of NACK knock down in OE33 stable cell lines harboring doxycycline (DOX) inducible small hairpin RNA (shRNA) constructs.
Figure 8A:
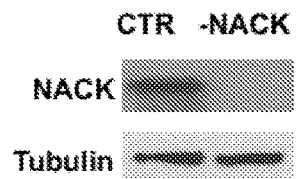
Figure 8B:
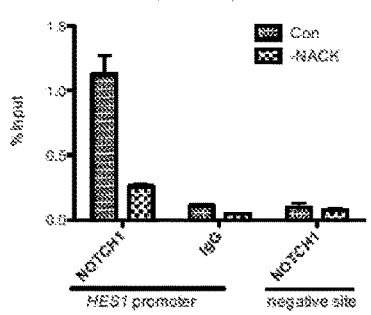
FIG. 8B depicts ChIP experiments to measure Notch1, NACK and activated Pol II occupancies on the HES1 promoter following NACK depletion in clone 1A3.
Figure 8B:
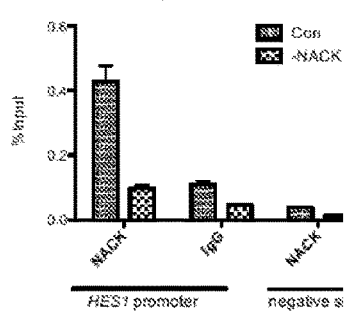
Figure 8B:
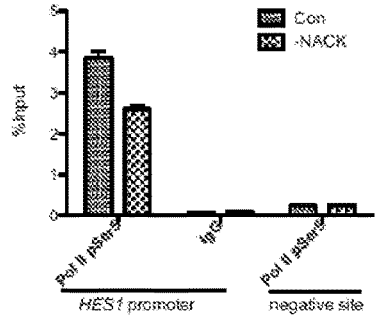

To study the molecular mechanism by which NACK coactivates Notch transcriptional activation of Notch target genes, OE33 stable cell lines were generated harboring doxycycline (DOX) inducible small hairpin RNA (shRNA) constructs. RT-qPCR analysis was performed in a cell clone 1A3 expressing tet-inducible shRNA against NACK, and DOX was added to the culture medium for 72 hrs to deplete the NACK mRNA and protein levels (FIG. 8A). RT-qPCR experiments were performed to determine the effects of NACK depletion on Notch target gene expression. TBP (TATA-binding protein), which is not a Notch target gene, was used as a negative control. Expression was normalized to HPRT1. NACK depletion reduces the expression of Notch target genes HES1, HES5, NOTCH3 and CCND1 (FIG. 8A). These results indicate that NACK inhibition blocks Notch transactivation of target genes. To further determine the mechanism of action of NACK on Notch target genes, ChIP experiments were performed to measure Notch1, NACK and activated Pol II occupancy on the HES1 promoter following NACK depletion in clone 1A3. To measure activated Pol II, antibody against Pol II pSer5 was used as a marker for active Pol II in transcription initiation. NACK depletion resulted in a profound decrease in Notch1, NACK and Pol II pSer5 ChIP signals (FIG. 8B). These results indicate that NACK inhibition by shRNA decreases Notch binding to the HES1 promoter and blocks transcription initiation.

Figure 8C:
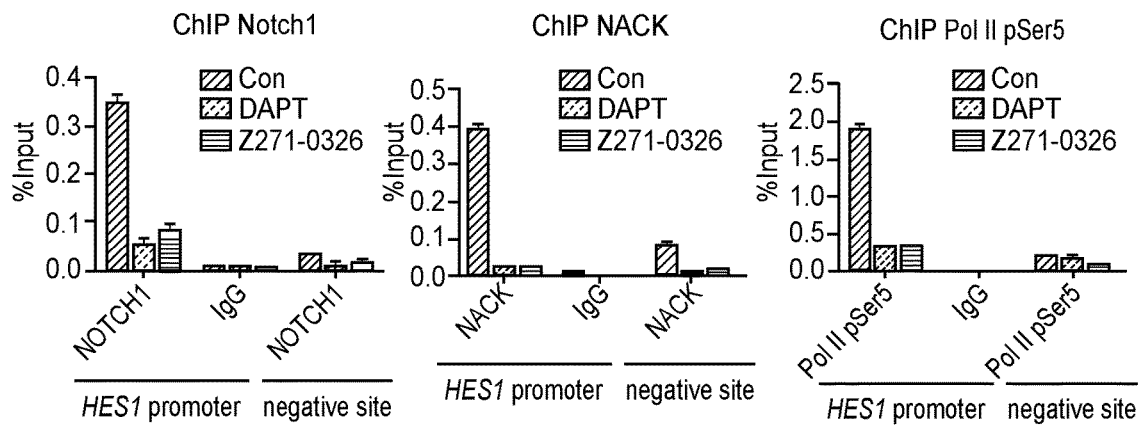
FIG. 8C depicts ChIP experiments to measure Notch1, NACK and activated Pol II occupancies on the HES1 promoter after drug treatment in OE33 cell line.

NACK inhibition by shRNA was found to attenuate Notch activity. Experiments were performed to determine whether NACK inhibitors can inhibit Notch transcription activity of the HES1 promoter, as HES1 expression is regulated by N1 ICD, MAML1 and CSL transcription complex. See Nam, Y. et al., Cell 124, 973-83 (2006). To explore this, chromatin immunoprecipitation (ChIP) experiments were performed by assaying the protein level of N1 ICD and NACK at the HES1 promoter. Treatment of OE33 cells with GSI DAPT or Z271-0326 both abrogated the binding of N1 ICD and NACK to the HES1 promoter (FIG. 8C), which supports that NACK inhibitor can attenuate Notch activity at the HES1 promoter. Furthermore, NACK inhibitor Z271-0326 not only blocks Notch components binding to the HES1 promoter, but also decreases the RNA polymerase initiation complex (Pol II pSer5) formation at the HES1 promoter (FIG. 8C). Without being bound by any theory, these data indicate that Z271-0326 blocks NACK binding to NOTCH target HES1 promoter, possibly causing decreased resident time of the Notch activation complex at Notch target promoters.

Figure 9A:
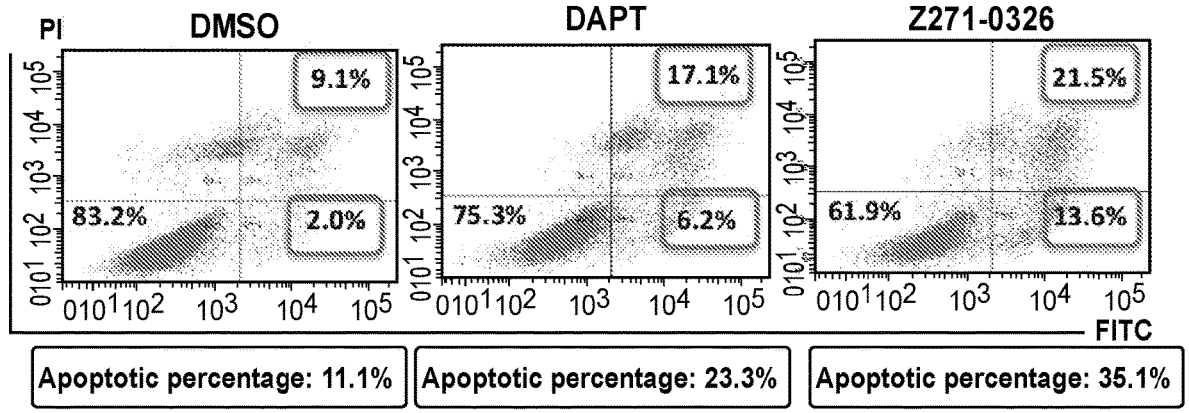
FIG. 9A shows that Z271-0326 induces cell apoptosis in OE33 cell line.
Figure 9B:
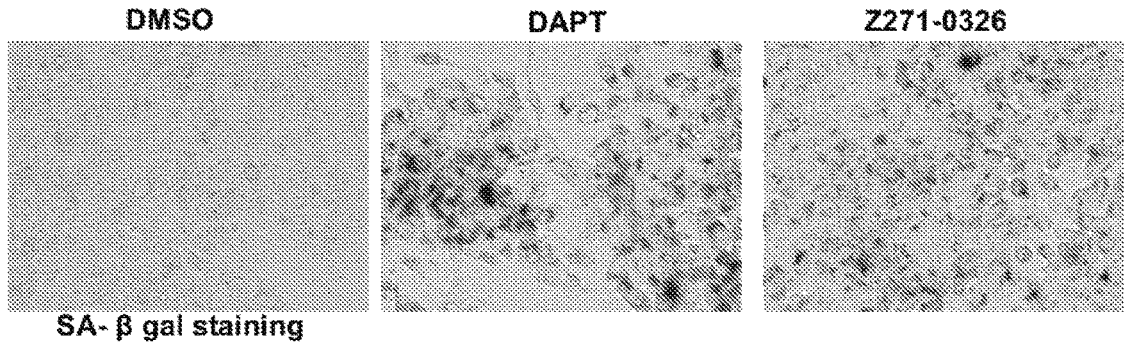
FIG. 9B shows that the senescence β-galactosidase staining was measured after treatment of the OE33 cells with either the drugs or DMSO (vehicle) for 3 weeks.

Notch Pathway Inhibition is Associated with Induction of Apoptosis and Senescence in EAC Cell Lines To investigate how Z271-0326 inhibits cell growth in EAC cell lines, the effect of Z271-0326 treatment was evaluated on apoptosis. OE33 cells were treated either with the GSI DAPT or Z271-0326, and their effects on apoptosis were analyzed at various time points after treatment. On day 7 of treatment, DAPT and Z271-0326 treatments result in a twofold and threefold increase in the percent of cells undergoing apoptosis, respectively, compared to the control. This result indicated that Notch pathway inhibition leads to apoptotic cell death, in OE33 cells (FIG. 9A). Similar to DAPT treatment, prolonged Z271-0326 treatment for 3 weeks of live cells of OE33 resulted in the induction of cellular senescence, as measured by senescence-associated β-galactosidase activity (FIG. 9B). These data indicate that inhibition of NACK activity induces apoptosis and cellular senescence to a similar extent as the GSI DAPT.

Characterization of the Interaction Between NACK and the Inhibitors Through SPR

The interaction between inhibitor Z271-0326 and target NACK was characterized using surface plasmon resonance (SPR). For this purpose, GST tagged NACK was captured by a GST antibody that was previously immobilized onto the surface of the chip through standard amide coupling. The dissociation constants associated with binding of the compounds to NACK was determined using the equilibrium approach, which consists of plotting the equilibrium response (Req) as a function of concentration of the compound and fitting the data to a 1:1 binding model. The dissociation constant associated with Z271-0326 binding to NACK ($K_D$=0.89±0.07 μM) is comparable to the affinity observed for AMP-PNP, a non-hydrolysable ATP analog ($K_D$=1.5±0.5 μM), (FIG. 10A).

Figure 10D:
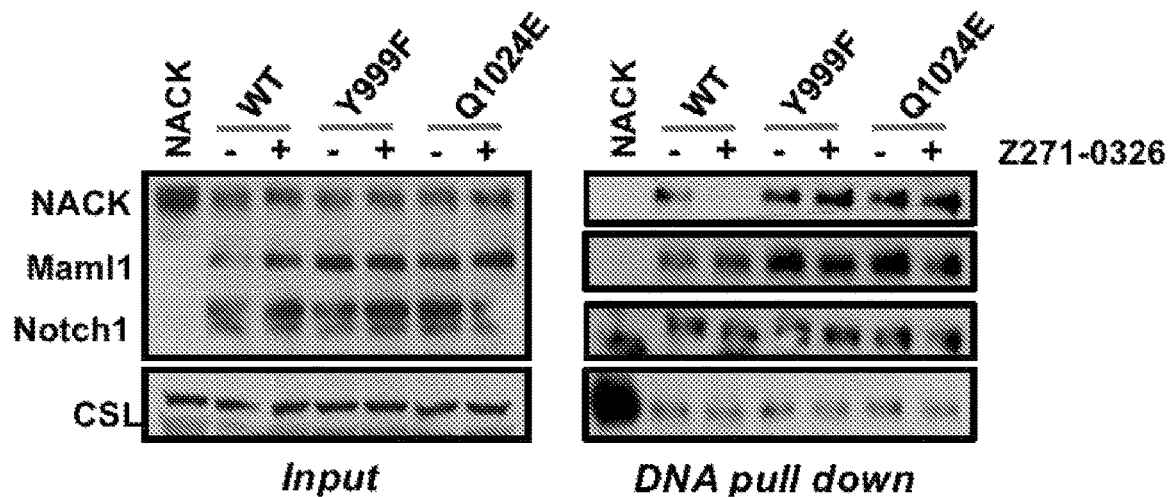
FIG. 10D. shows that NACK (Y999F or Q1024E) mutations in mouse NACK failed to abolish NACK binding to the Notch complex in the condition of adding Z271-0326.

The initial docking results revealed several interactions between NACK and Z271-0326 (FIGS. 10B and 10C). At the active site of NACK, residues Lys1022, His1095, Gln1046 and Tyr1019 were found to form important hydrogen bonds with Z271-0326. In order to validate the importance of these residues, residues Q1024 and Y999 were mutated in mouse NACK. The binding between ATP and mutated NACK was evaluated by the CSL-DAP assay with or without Z271-0326. Z271-0326 was found to block recruitment of NACK to the Notch ternary complex when WT NACK is used (FIG. 10D). However, Y999F NACK and Q1024E NACK were insensitive to inhibition by Z271-026 as indicated by NACK binding to the Notch complex in the presence or absence of Z271-0326.

Figure 11A:
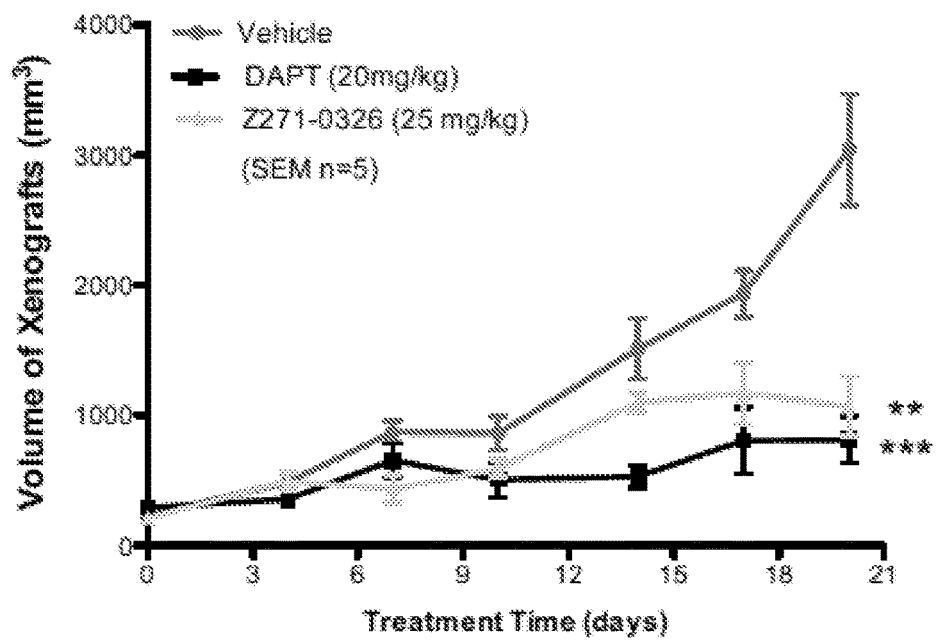
FIG. 11A shows the tumor growth of EAC47 PDX after treatment with either vehicle (DMSO), DAPT or Z271-0326 for 20 days.
Figure 11B:
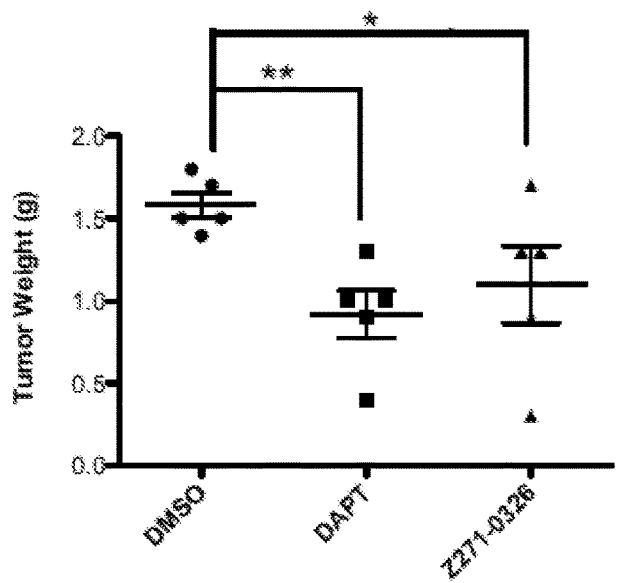
FIG. 11B shows the tumor weights collected at end point.
Figure 11C:
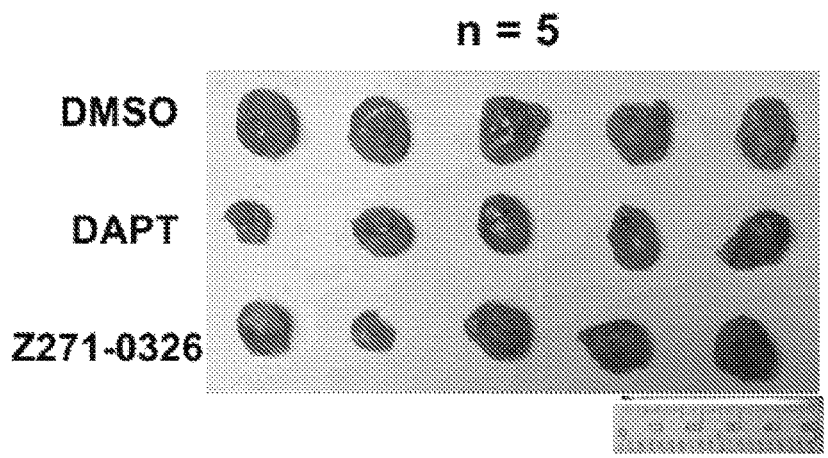
FIG. 11C shows the tumors collected at the end point.
Figure 11D:
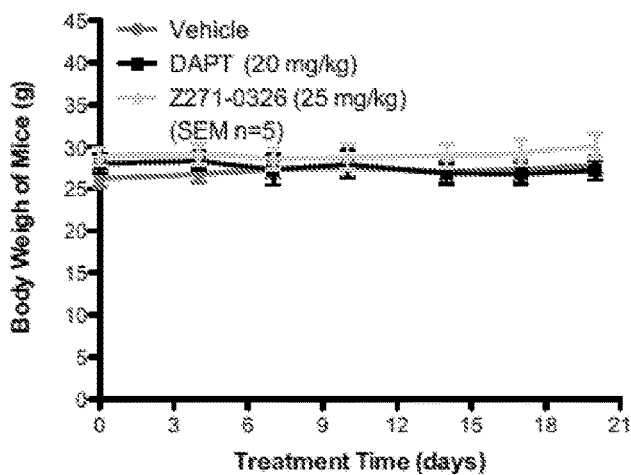
FIG. 11D shows the body weights of EAC47 PDX during treatment.
Figure 13A:
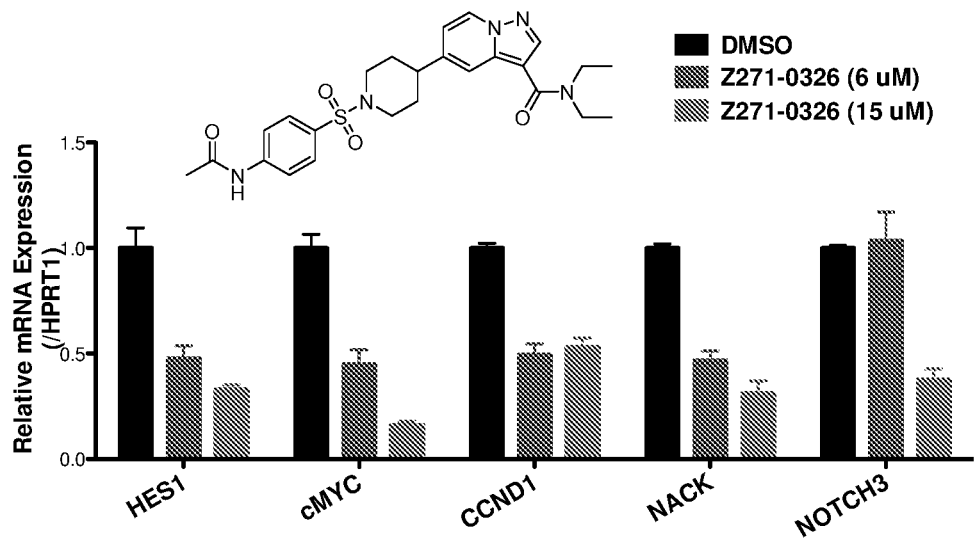
FIG. 13 shows the q-PCR profile of the NACK inhibitor analogs (7W, 7H, 7M). As compared to NACK inhibitor Z271-0326 (FIG. 13A), compound 7W does not show any effect in down regulating Notch target genes (FIG. 13B). Compound 7H performed the best in down regulating Notch target genes, even better than Z271-0326 as seen in qPCR results (FIG. 13C). Compound 7M can also down regulate Notch target genes, but not as good as compound 7H (FIG. 13D).
Figure 13B:
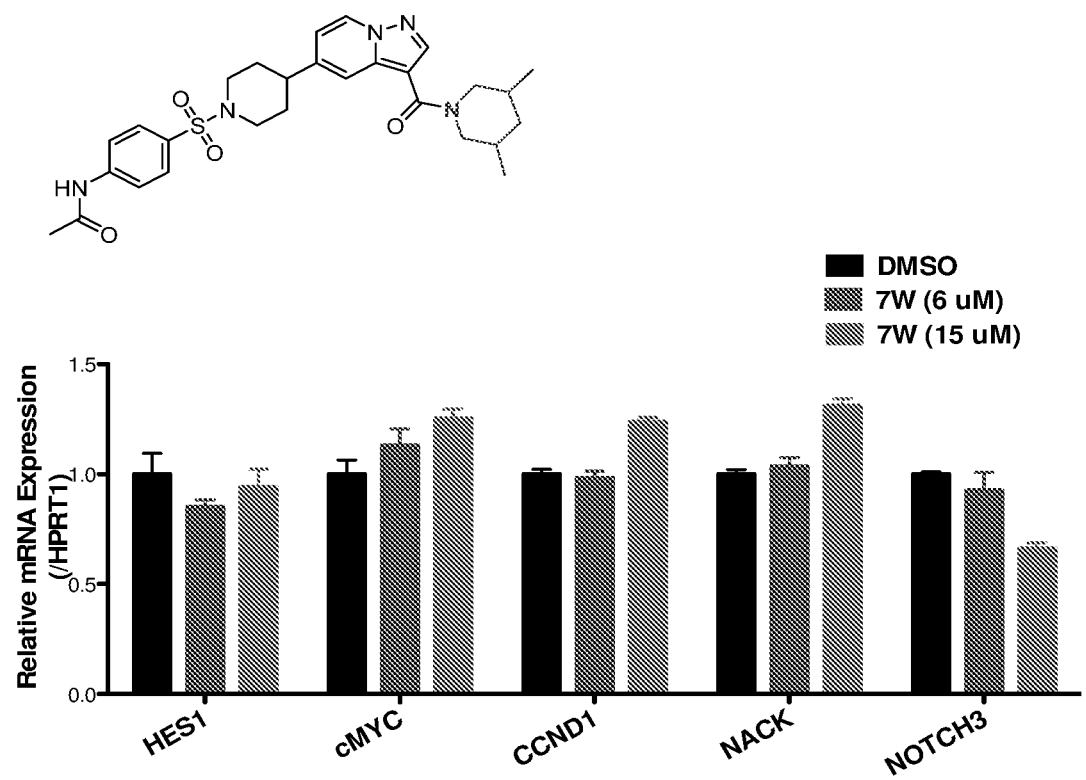
Figure 13C:
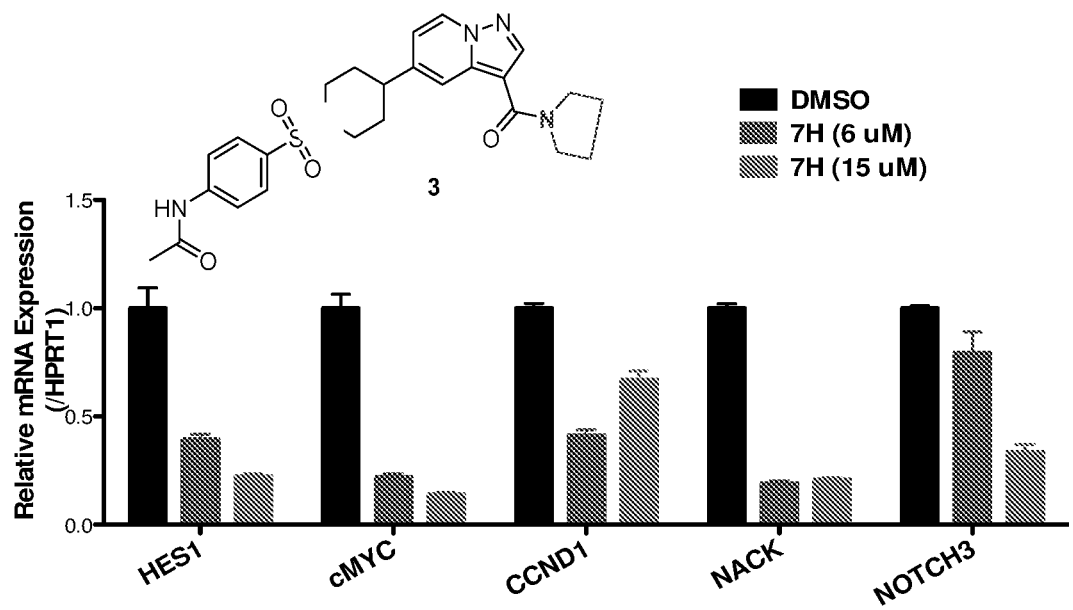
Figure 13D:
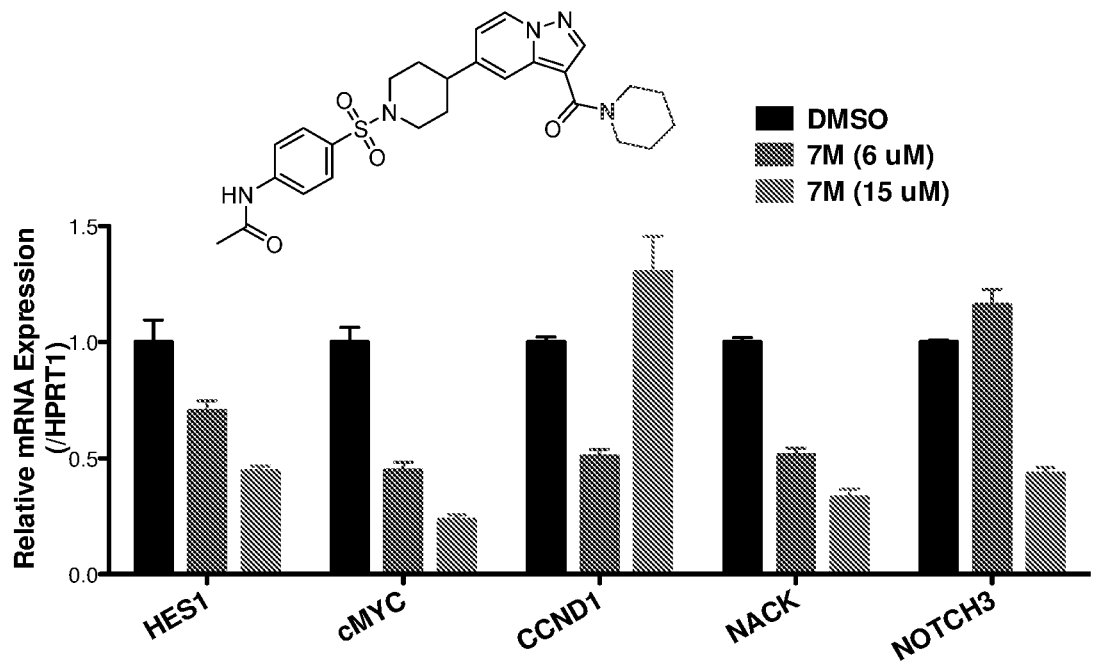

NACK Inhibitors can Suppress Tumor Growth in Esophageal Adenocarcinoma (EAC) PDX Models A well-established xenograft model was employed to assess the effect of Z271-0326 on tumor formation in animal model using PDX. Compared to cell line-based xenografts, PDX models better represent the diversity of human cancer and are more representative of the original tumor. See Wang, Z. et al. Cancer Research 74, 6364-6374 (2014). Two EAC PDX models were constructed (EAC47 and EAC36) from patient tumor samples. Mice harboring established tumors (approx. 200 mm$^3$) were treated with either DAPT (20 mg/kg) or Z271-0326 (25 mg/kg) daily via intraperitoneal injections. Growth of these tumors was significantly attenuated by Z271-0326 treated mice to a comparable level as DAPT compared to the vehicle treated group (FIGS. 11A, 11B and 11C). Moreover, body weights of the treated groups were not statistically different from the vehicle treated group (FIG. 11D). A decrease in proliferation index was also observed in Z271-0326 treated group as compared to the control group, measured via Ki67 staining (FIG. 11E). These results indicate that Z271-0326 can inhibit growth of Notch dependent esophageal adenocarcinoma tumor.

Plasma Pharmacokinetics of Z271-0326

The plasma pharmacokinetic profile of Z271-0326 was investigated following a single intravenous and intraperitoneal dose administration in male C57 BL/6 mice (FIG. 12). Following a single intravenous administration of Z271-0326 at 5 mg/kg, to male C57BL/6 mice, compound exhibited moderate systemic plasma clearance (30 mL/min/kg, normal liver blood flow in mice is 90 mL/min/kg) with terminal elimination half-life of 0.23 hr. The Vss was similar to the normal volume of total body water (0.7 L/kg). The Vss is a pharmacokinetic parameter, which represents the volume distribution of a drug in the body tissue. After a single intraperitoneal administration of Z271-0326 to male C57 BL/6 mice at 25 mg/kg dose, plasma concentrations were quantifiable up to 4 hr with Tmax of 0.25 hr. This dose was MTD for the 4-week efficacy studies shown in preliminary data. Following a single intraperitoneal administration of Z271-0326 to male C57 BL/6 mice at 100 mg/kg dose, plasma concentrations were quantifiable up to 24 hr with Tmax of 1.00 hr.

Effect of NACK Inhibitor on Cell Viability

Figure 14A:
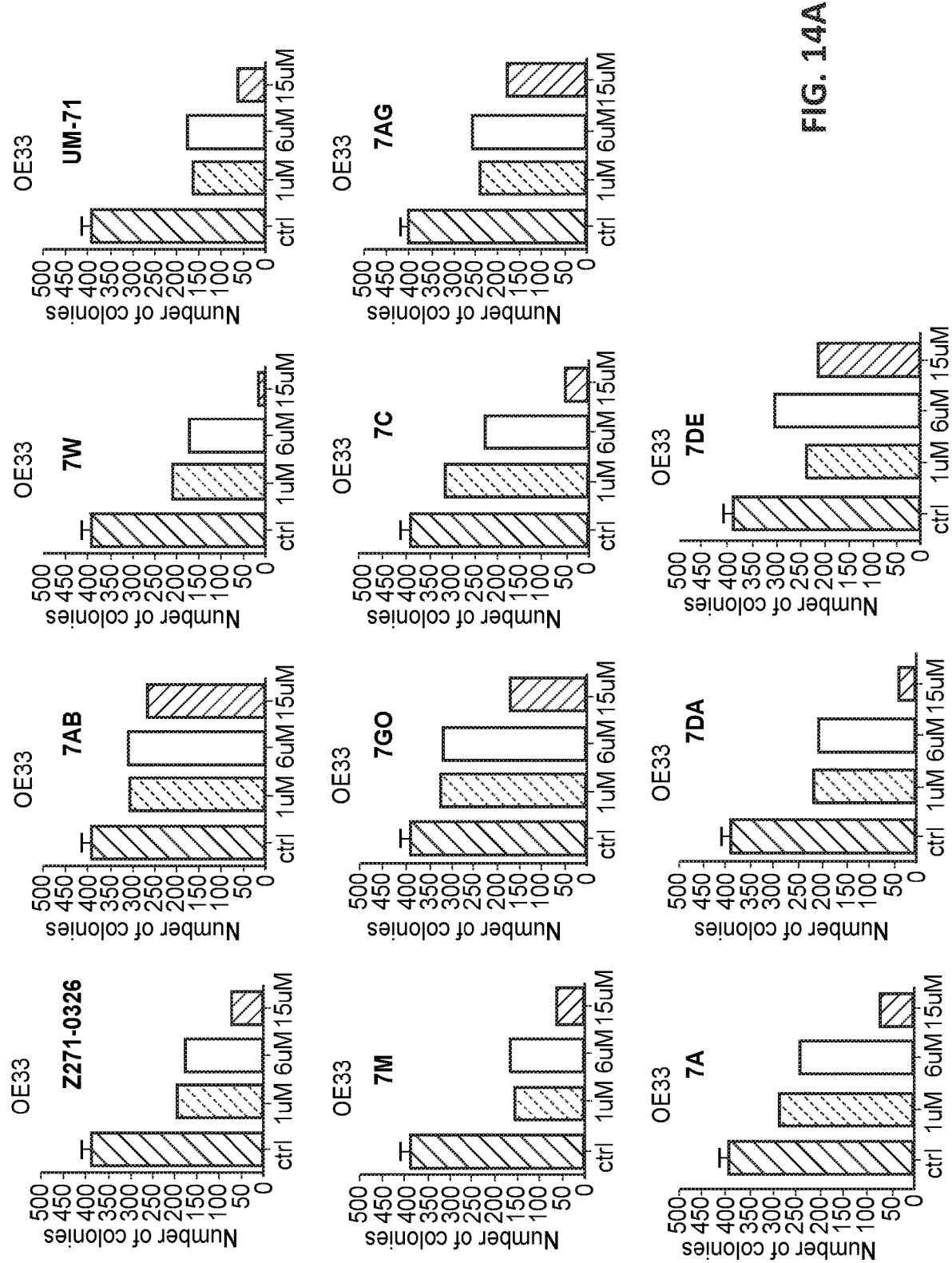
FIG. 14A and FIG. 14B show the inhibition of OE33 cells by compounds disclosed herein as number of colonies (FIG. 14A) or colonies with respect to a control (FIG. 14B).
Figure 14B:
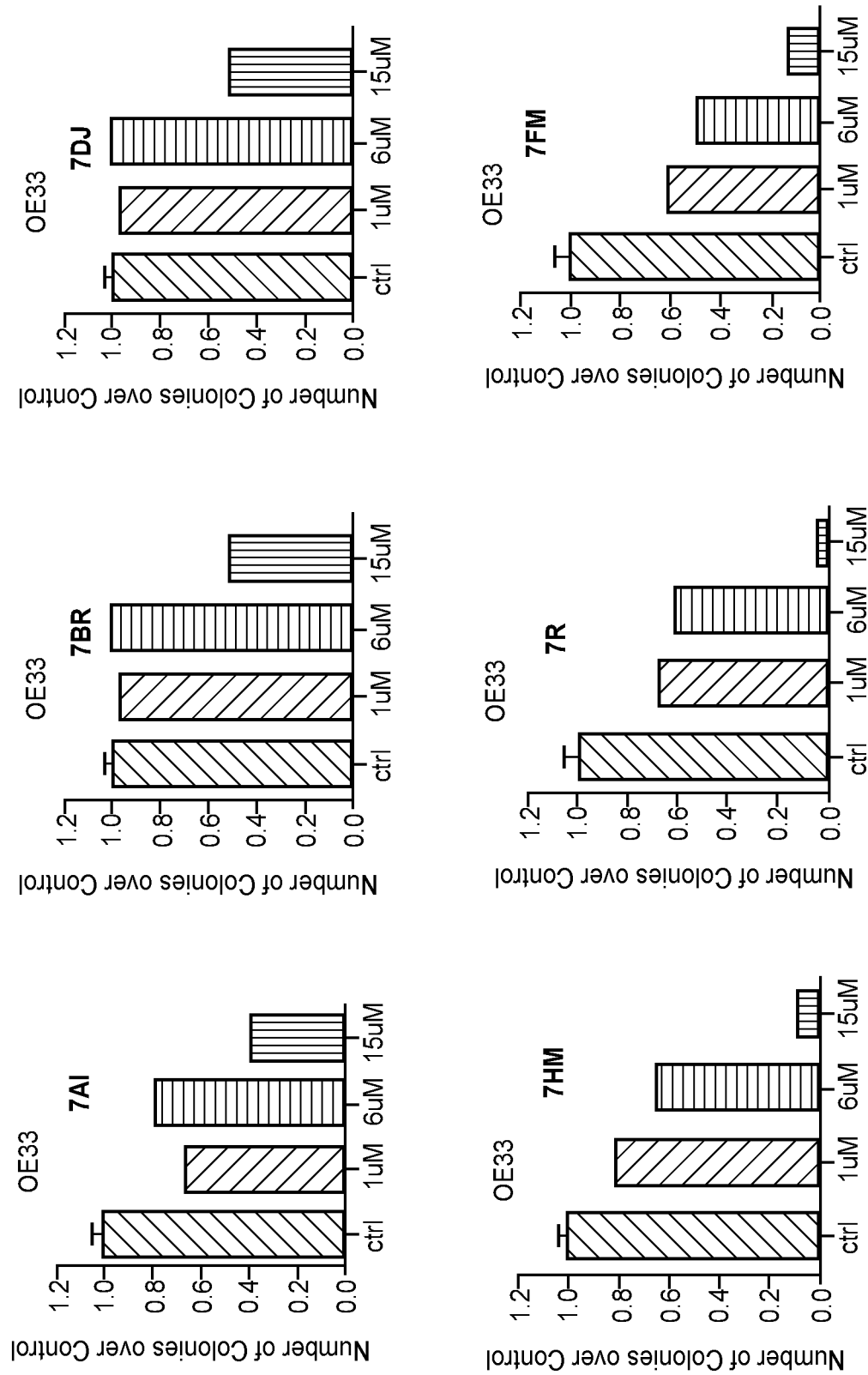
Figure 15:
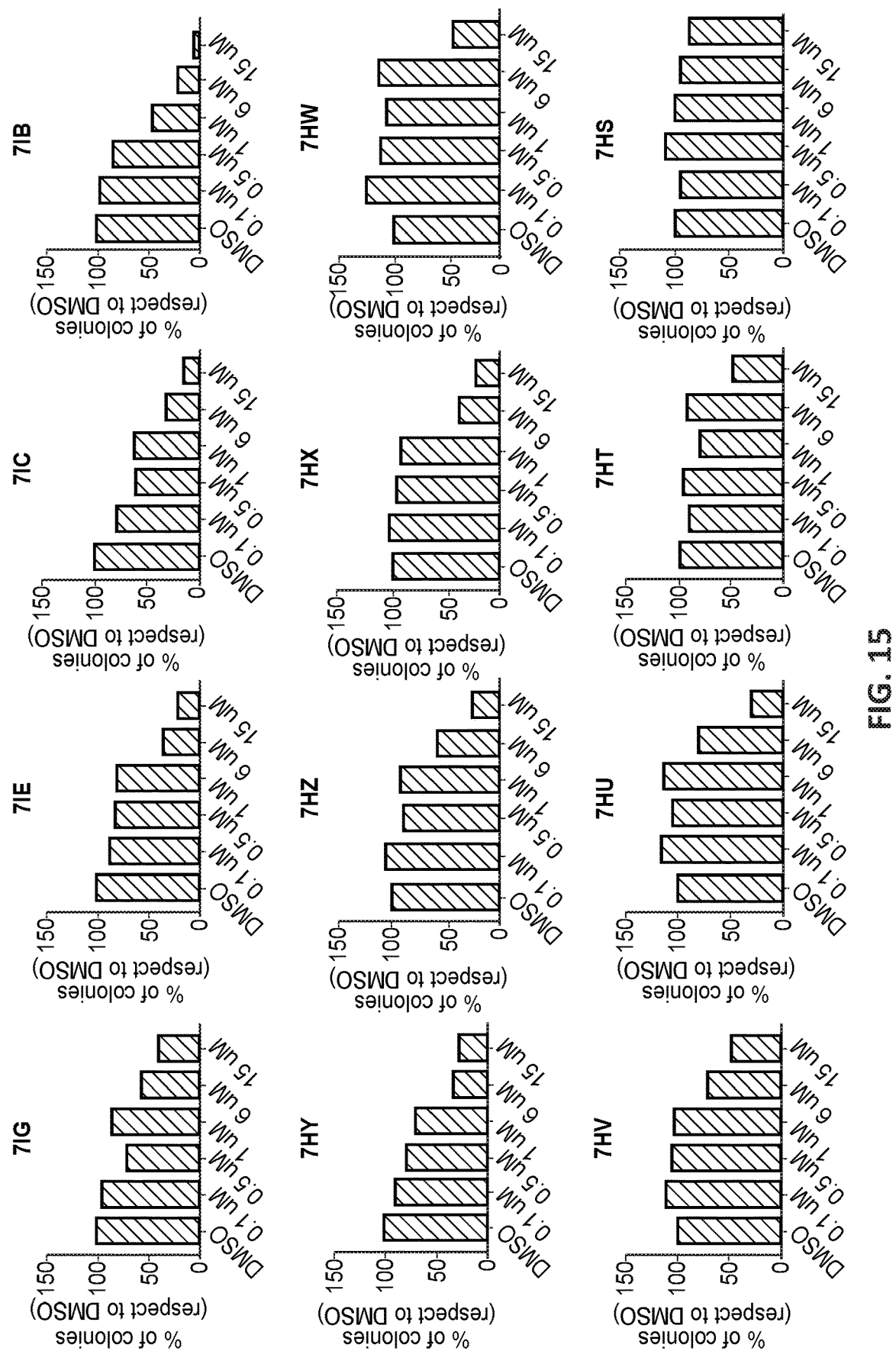
FIG. 15 shows the inhibition of OE33 cells by compounds disclosed herein with respect to number of colonies treated with DMSO.

To assess the effect of NACK inhibitor on Notch target gene transcription, Notch/NACK-dependent cell lines were treated with NACK inhibitors. The cells were also treated with DAPT as a positive control. DMSO treated cells served as a vehicle control for comparison. Gene expression was normalized to HPRT, and TBP served as a negative control to validate normalization. As shown in FIG. 14A, FIG. 14B, and FIG. 15 the compounds disclosed herein can effectively inhibit the number of colonies of OE33 cells.

Effect of NACK Inhibitor on Cell Viability

Figure 16:
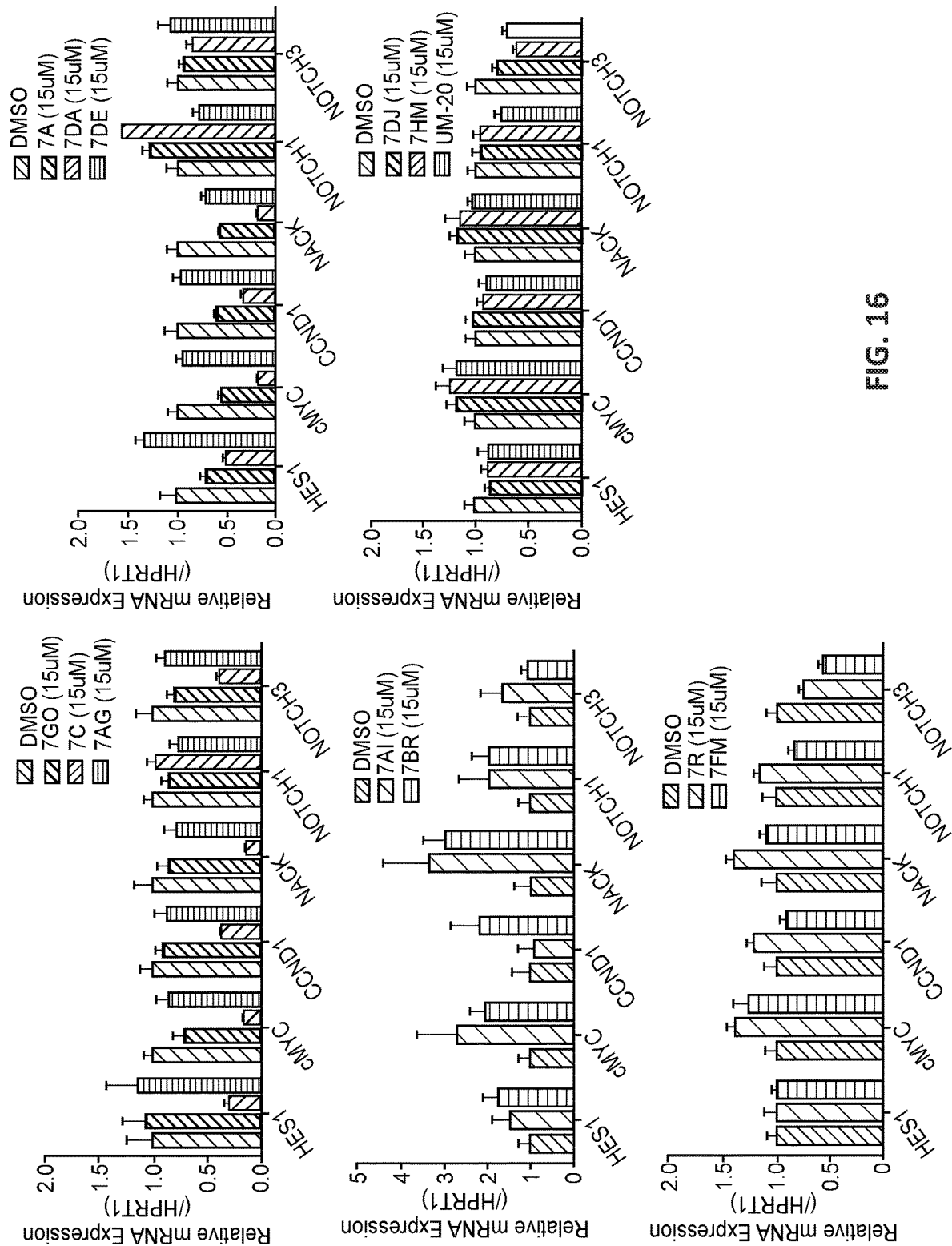
FIG. 16 shows the Q-PCR profile of NACK inhibitor analogs for the expression of several genes.
Figure 17A:
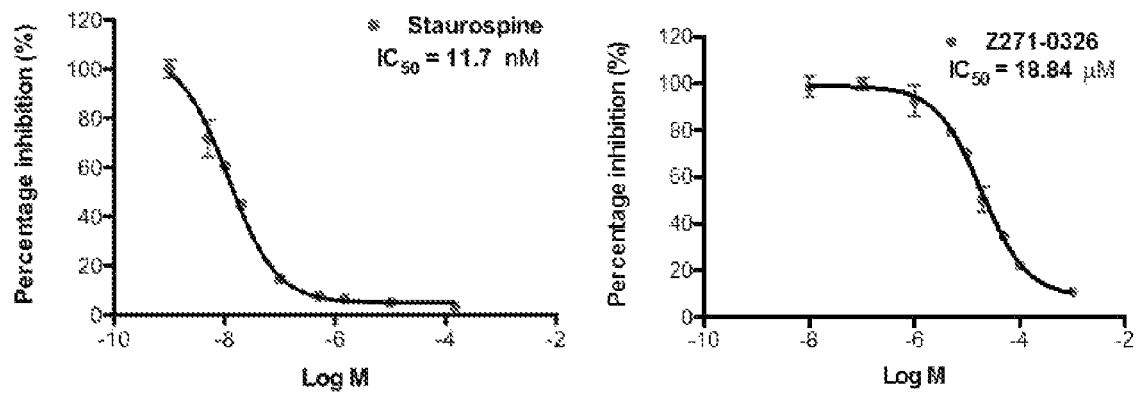
FIG. 17A-17C show ADP-GLO Kinase assay results using Z271-0326 or inhibitors of the corresponding kinases: MAP4K5 assay (FIG. 17A), LCK kinase assay (FIG. 17B), and TNIK kinase assay (FIG. 17C).
Figure 17B:
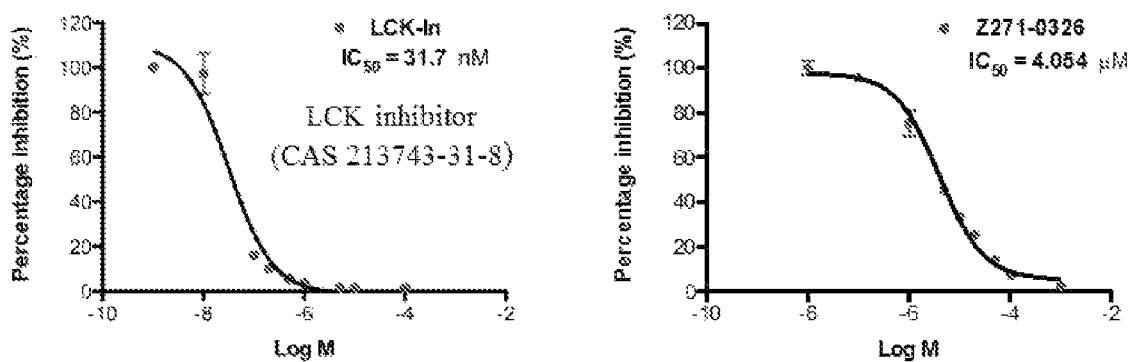
Figure 17C:
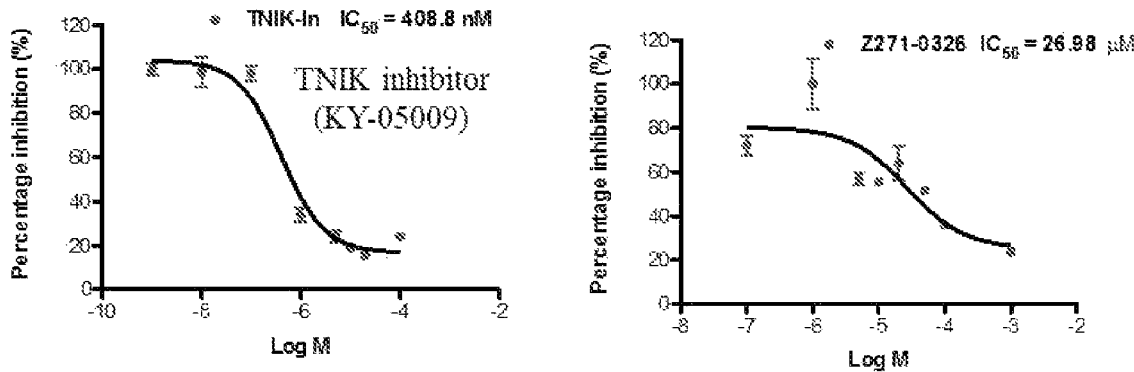
Figure 18:
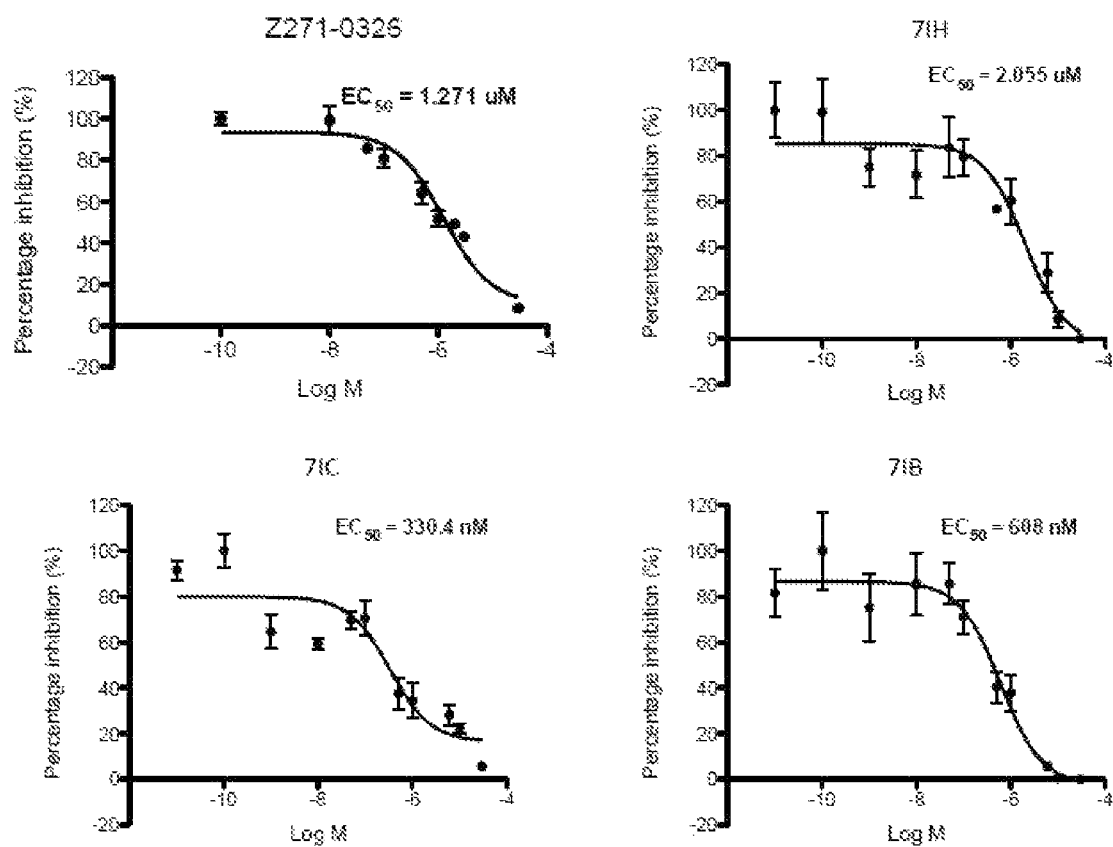
FIG. 18 shows the $EC_{50}$ values of several compounds disclosed herein as estimated by a colony formation titration assay in an OE33 cell line.

To assess the effect of NACK inhibitor on Notch target gene transcription, Notch/NACK-dependent cell lines were treated with NACK inhibitors. The cells were also treated with DAPT as a positive control. DMSO treated cells served as a vehicle control for comparison. Gene expression was normalized to HPRT, and TBP served as a negative control to validate normalization. As shown in FIG. 16, the NACK analogues 7C and 7DA downregulate oncogenes cMYC, CCND1, and HES1 with respect to DMSO and Z271-0326 (described previously). Effect of NACK Inhibitor on Cell Viability To assess the validity of the kinase profile screen results, Z271-0326 was screened in LCK, MAP4K5, and TNIK kinase assay. As shown in FIG. 17, Z271-0326 only meaningfully inhibits LCK out of the three kinases mentioned above Effect of NACK Inhibitor on Cell Viability As shown in FIG. 18, the $EC_{50}$ of Z271-0326 is 1.27 µM, and the analogues 71C and 71B have improved activity with $EC_{50}$s at 330 nM and 608 nM respectively.

LCK Kinase Assay

Figure 19:
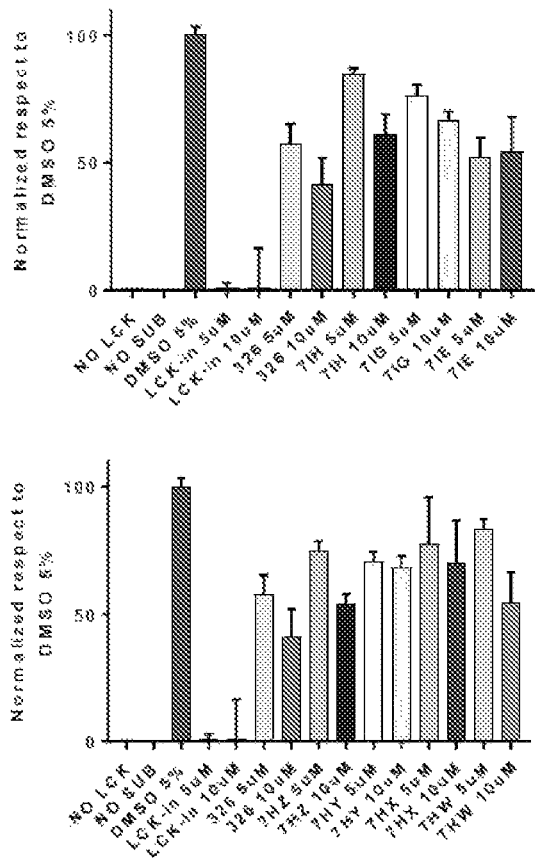
FIG. 19 shows the results of an LCK kinase assay using Z271-0326, a specific kinase inhibitor, and compounds disclosed herein at 10 µM, normalized with respect to DMSO.
Figure 19:
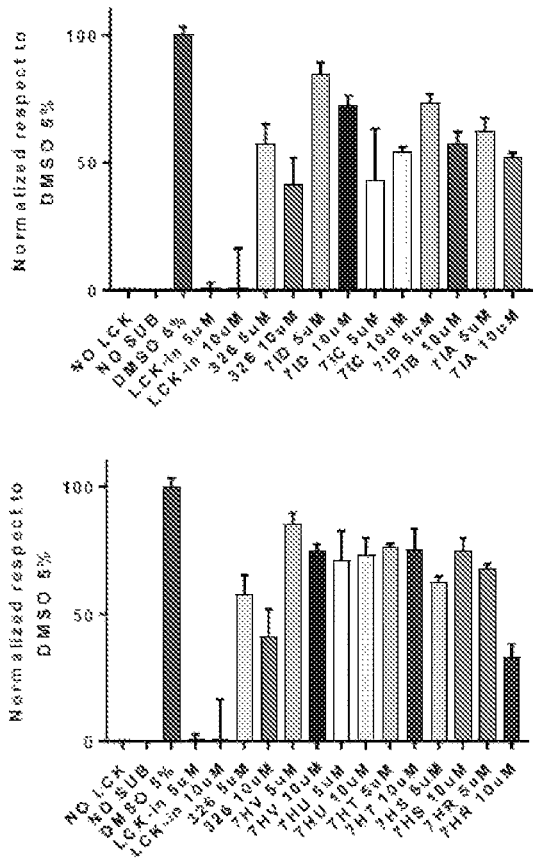
Figure 19:
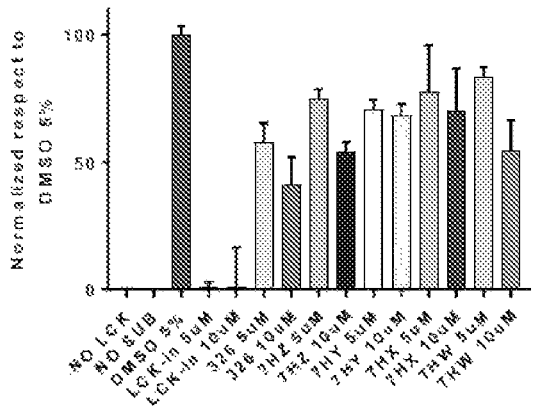
Figure 19:
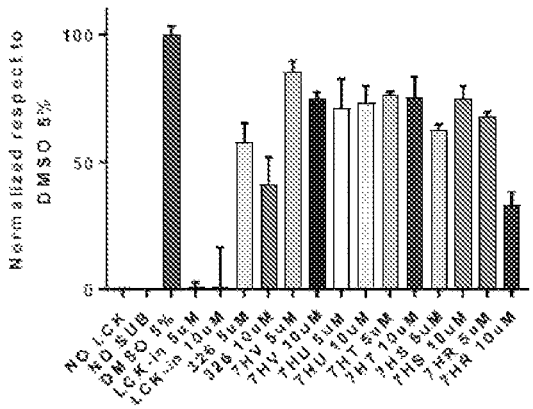

To continue to drive analogue selectivity for NACK, an LCK kinase assay was utilized as a counter screen. As shown in FIG. 19, the compounds described herein show a decreased affinity for LCK over Z271-0326.

Further guidance for using the compounds of the disclosure can be found in the Examples section, below.

Pharmaceutical Formulations

Also provided herein are pharmaceutical formulations that include the compounds of the disclosure, and one or more pharmaceutically acceptable excipients.

The compounds of the disclosure can be administered to a subject or patient in a therapeutically effective amount. The compounds can be administered alone or as part of a pharmaceutically acceptable composition or formulation. In addition, the compounds can be administered all at once, as for example, by a bolus injection, multiple times, e.g. by a series of tablets, or delivered substantially uniformly over a period of time, as for example, using transdermal delivery. It is also noted that the dose of the compound can be varied over time.

The compounds disclosed herein and other pharmaceutically active compounds, if desired, can be administered to a subject or patient by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. eneteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compounds of the disclosure can be administered to a subject or patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the subject or patient, the severity of the condition or disease being treated, and the pharmacological activity of the compound being administered. The determination of dosage ranges and optimal dosages for a particular subject or patient is within the ordinary skill in the art.

In jurisdictions that forbid the patenting of methods that are practiced on the human body, the meaning of "administering" of a composition to a human subject or patient shall be restricted to prescribing a controlled substance that a human subject or patient will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Examples

The following examples are provided for illustration and are not intended to limit the scope of the invention.

Cell Lines

OE19 and OE33, human esophageal adenocarcinoma cell lines, were obtained from the European Collection of Cell Culture. 293T and HC11 cell lines were obtained from ATCC. All cell lines were propagated in growth media as specified by the provider.

Chromatin Immunoprecipitation ("ChIP") Analysis

Notch/NACK-dependent cells were treated with either DAPT as a positive control, DMSO (vehicle) as a negative control, or compounds for screening for 24 hours. After treatment, cells were cross-linked and sonicated to yield chromatin fragments of approximately 500 bp, as previously described (See Weaver et al., Cancer Research 74, 4741-4751 (2014)). Lysates were immunoprecipitated with either α-Notch1 (Bethyl Laboratories, Montgomery, Tex.; A301-894A), α-Maml1 (Cell Signaling, 12166s), α-NACK (Bethyl Laboratories, A302-675A), or α-PolII pSer5 (Abcam, ab5131) antibodies. DNA immunoprecipitates were cleaned using the PCR purification Kit (Qiagen). DNA were detected by Syber green qPCR using HES1 specific oligonucleotide primers (forward: 5'CGTGTCTCCTCCTCC-CATT3' (SEQ ID NO: 2); reverse: 5'GGGGGAT-TCCGCTGTTAT3' (SEQ ID NO:3)).

RT-qPCR Analysis.

Reverse transcription and qPCR analysis were performed as described previously (See Weaver et al., Cancer Research 74, 4741-4751 (2014)). Gene expression was normalized to the TATA-binding protein ("TBP") gene. As a control, hypoxanthine phosphoribosyltransferase 1 ("HPRT") gene expression was also monitored.

Colony Assay

Colony formation assay was utilized to determine the effect of small molecule inhibitors on cell proliferation. In general, different cell lines (NACK dependent or independent) will be seeded in 6-well plates at a density of 2000 cells per well and allowed to attach overnight. Inhibitor treatment commenced 24 hours post seeding, and the media containing inhibitor was changed every 48 hours thereafter. After 168 hours, colonies were be stained with Crystal Violet (Millipore) and counted.

CSL-DNA Affinity Precipitation (CSL-DAP) Assay

To determine the specificity of hit-to-lead compounds targeting NACK activity, it was evaluated whether iNACK can block NACK binding to the Notch complex by conducting CSL-DNA affinity precipitation (CSL-DAP) assay. Compounds, which showed selective inhibition on NACK/Notch dependent cells lines, were further assessed in this assay. In the CSL-DAP assay, 293T cells were co-transfected with N1$^{ICD}$ Maml1 and NACK. Transfections were performed using LipoJet transfection reagent (SL100468, SignaGen Laboratories) according to the manufacturer recommended protocol. After two days of transfection, cells were treated with compounds for 2 hours prior collecting the cell lysate. Cell lysates were incubated with DNA streptavidin beads. Proteins that bound to the beads were analyzed by Western blot.

Western Blot

Western blot was performed as described previously (See Weaver et al., Cancer Research 74, 4741-4751 (2014)). Primary antibodies were α-NACK (1:1,000; against aa209-287 of NACK and affinity purified), α-CSL (1:1,000; generated against full-length CSL and affinity purified), α-Maml1 (1:5,000; Cell Signaling Technology), α-cleaved-Notch1 (1:1,000; Cell Signaling Technology).

Tumor Sphere Formation Assay

In order to assess the effect of hit to lead compounds on the proliferation of stem cell like population of Notch/

NACK dependent cells, the primary tumor spheres were treated with NACK inhibitor and allow the cells to be propagated as secondary cultures. To obtain tumor spheres, cells were cultured in DMEM/F12 with 2% B-27 serum-free supplement (17604-044; Invitrogen), 20 ng/mL epidermal growth factor (EGF; PHG0311L; Invitrogen), and 20 ng/mL basic fibroblastic growth factor (bFGF; PHG0266; Invitrogen) for 14 days. Resulting tumor spheres were examined and counted under the microscope. Furthermore, the tumor spheres were collected for further RT-qPCR analysis to test the effect of hit to lead compounds on the stem like target genes.

Determination of Affinity of Lead Inhibitors to Target Protein

A GST capture kit (GE Healthcare) were utilized to covalently immobilize an anti-GST antibody, provided in the kit, to the sensor chip surface (CM5 chip, GE Healthcare) by following the manufacturer's instructions. Capture were performed by injecting GST-NACK (1 μg/μL) over the immobilized anti-GST antibody in Hepes buffer (10 mM Hepes, pH 7.5, 150 mM NaCl, 3 mM EDTA, 0.0005% NP-40) for 7 min at 10 μL/min. A reference flow cell was prepared by capturing GST following the procedure described above. The GST capture resulted in a stable baseline. Experiments were performed on a Biacore T200 instrument (GE Healthcare) at 25° C. Small molecule inhibitors binding to NACK were performed in 50 mM Tris buffer, pH 7.5, containing 150 mM NaCl, 10 mM $MgCl_2$ and 5% DMSO (running buffer). The SPR signal arising from the sample was corrected for its respective control containing DMSO. Data visualization and analysis was performed using Biacore T200 software (GE Healthcare) and Origin 8.0 (OriginLab).

Plasma Pharmacokinetics of Z271-0326

The plasma pharmacokinetic profile of Z271-0326 was investigated following a single intravenous and intraperitoneal dose administration in male C57 BL/6 mice.

Efficacy in Mouse Models and Analysis of Biomarkers In Vivo

PDX models were employed to determine the effect of lead candidates on tumor growth. When the tumor size reaches 200 mm$^3$, the corresponding groups were either treated with vehicle (DMSO) or lead compound by IP injection daily.

ADP-Glo Kinase Assay

ADP-Glo kinase assay was performed using ADP-Glo™ Kinase Assay (Promega, V6930) according to the manufacture recommended protocol.

Cell Apoptosis and Cell Senescence Assays

To investigate how Z271-0326 inhibits cell growth in EAC cell lines, the effect of Z271-0326 treatment was evaluated on apoptosis. OE33 was treated either with the GSI DAPT or Z271-0326 every other day, and their effects on apoptosis were analyzed. On day 7 of treatment, cell apoptosis was analyzed using FITC Annexin V/Dead Cell Apoptosis Kit with FIFC annexin V and PI for flow cytometry (Invitrogen, V13242).

After prolonged Z271-0326 or DAPT treatment for 3 weeks of live cells of OE33, cells were measured by senescence-associated β-galactosidase activity according to the manufacture recommended protocol (Senescence β-Galactosidase Staining Kit, Cell Signaling, #9860).

SYNTHETIC EXAMPLES

Example 1. Synthesis of 5-(1-((4-acetamidophenyl)sulfonyl)piperidin-4-yl)-N,N-diethylpyrazolo[1,5-a]pyridine-3-carboxamide (Z271-0326)

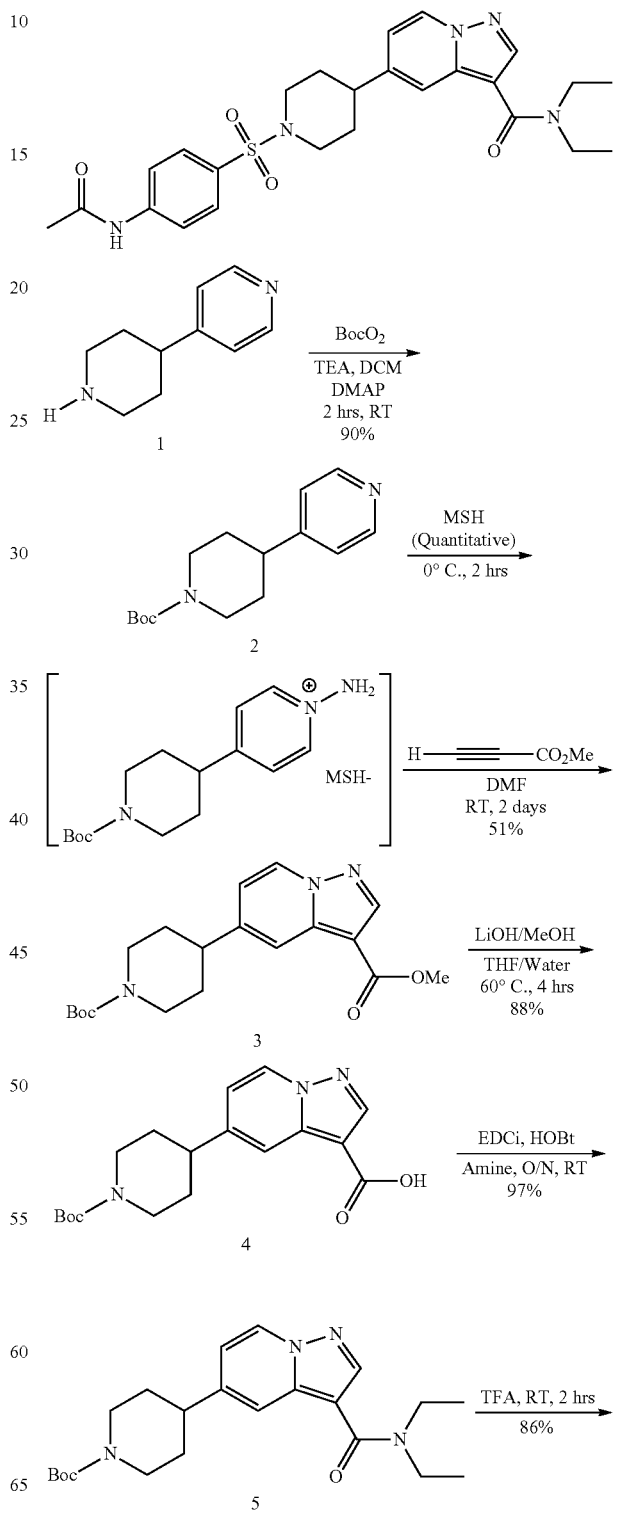

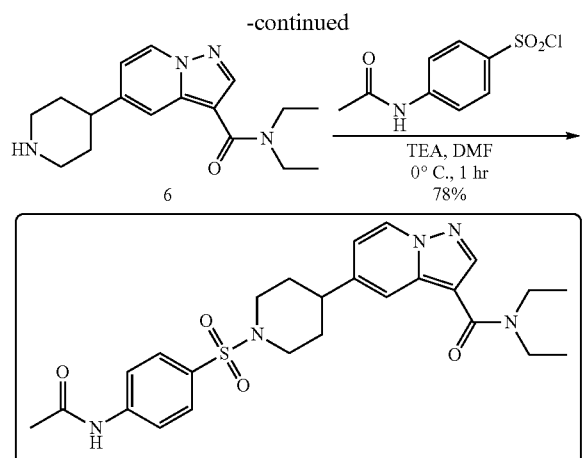

Preparation of Boc-4-pyridin-4-yl-piperidine (2)

Boc anhydride (1.52 g, 6.96 mmol) was added to a flame dried and argon purged round-bottom flask and dissolved in DCM (11 mL). DMAP (7.33 mg, 0.06 mmol), 4-pyridin-4-yl-piperidine (1.00 g, 6.33 mmol), followed by TEA (1.05 mL) was added in that order and the reaction was allowed to stir at room temperature for 2 hours. At this point, all starting material had been converted as seen on TLC. Reaction was washed with water twice, and once again with brine, dried with sodium sulfate and concentrated in vacuo. Product was purified via flash chromatography using a 50/50 EtOAc/Hexane gradient. Yield was 90%, 1.50 g, yellow oil. $^1$H NMR (400 MHz, Chloroform-d) δ 8.52 (dd, J=4.3, 1.9 Hz, 2H), 7.16-7.09 (m, 2H), 4.26 (s, 2H), 2.80 (t, J=12.5 Hz, 2H), 2.69-2.59 (m, 1H), 1.83 (d, J=13.1 Hz, 2H), 1.68-1.53 (m, 2H), 1.48 (s, 9H). m/z: 263.2 [M+H].

Preparation of
N-Boc-O-(mesitylsulfonyl)hydroxylamine
(N-Boc-MSH)

2-Mesitylenesufonylchloride (2.00 g, 9.17 mmol) was added to a flame dried and argon purged round-bottom flask and dissolved in ether (18 mL), followed by the addition of N-Boc-hydroxylamine (1.47 g, 11.00 mmol). The flask was cooled to 0° C., and then TEA was added dropwise (1.3 mL). The reaction stirred for 2 hours at 0° C., at which all starting material had been converted as seen by TLC. The TEA-Cl, white solid, was filtered, and washed with ether. The filtrate was concentrated in vacuo, and purified via flash chromatography in 25/75 EtOAc/hexane gradient. Yield was quantitative, 2.16 g, white solid. $^1$H NMR (400 MHz, Chloroform-d) δ 7.77 (1H, s), 6.98 (2H, s), 2.66 (6H, s), 2.31 (3H, s), 1.30 (9H, s). $^{13}$C NMR: (100 MHz, CDCl$_3$) δ 154.5, 144.7, 142.2, 131.9, 128.7, 84.1, 27.9, 23.4, 21.4. m/z: 315.0 [M+H].

Preparation of O-mesitylenesulfonylhydroxylamine
(MSH)

TFA (2.1 mL) was added to a flame dried and argon purged round-bottom flask and cooled to 0° C. N-Boc-O-(mesitylsulfonyl)hydroxylamine (500 mg, 2.1 mmol) was added in 2 portions, and the reaction stirred at 0 C for two hours. After which, all starting material had been converted, as seen by TLC. Ice and cold water was added to the reaction to precipitate MSH. The MSH was filtered, washed with cold water, and dried under high-vacuum overnight to remove excess TFA and water. No further purification was necessary. Compound is a white solid, with a quantitative yield of 422 mg. $^1$H NMR: (400 MHz, Chloroform-d) δ 7.00 (s, 2H), 4.80 (s, 3H), 2.65 (s, 6H), 2.33 (s, 3H). $^{13}$C NMR: (100 MHz, CDCl3): δ 21.1, 22.7, 128.9, 131.7, 141.0, 143.9.

General Procedure for (3)

Boc-4-pyridin-4-yl-piperidine was dissolved in DMF (3.8 mL) and added to a flame dried and argon purged round-bottom flask. MSH was added in two portions (535 mg, 2.5 mmol) and the reaction stirred at RT for two hours. After which, methyl prop-2-ynoate was added (170 μL, 1.9 mmol) followed by K$_2$CO$_3$ (264 mg, 1.91 mmol). The reaction stirred for 2 days at RT, and was then diluted with water and extracted three times with DCM. Compound was purified via flash chromatography and eluted with a 1:1 mixture of EtOAc and hexanes. Fractions were concentrated in-vacuo and dried under high-vac overnight.

Preparation of tert-butyl 4-[3-(methoxycarbonyl)pyrazolo[1,5-a]pyridin-5-yl]piperidine-1-carboxylate (3A): Yield: 53%, light orange solid. $^1$H NMR: (400 MHz, Acetonitrile-d$_3$) δ 8.51 (s, 1H), 8.30 (s, 1H), 7.92 (s, 1H), 6.98 (d, J=7.2 Hz, 1H), 4.21 (d, J=13.3 Hz, 2H), 3.86 (s, 3H), 2.85 (m, J=14.8, 13.1 Hz, 3H), 1.87 (d, J=14.0 Hz, 3H), 1.65-1.53 (m, 3H), 1.48-1.42 (s, 9H). $^{13}$C NMR (101 MHz, Chloroform-d) δ 164.06, 154.88, 146.28, 145.29, 141.21, 129.20, 115.69, 113.92, 103.16, 79.86, 51.35, 42.47, 28.60. m/z: 360.19 [M+H].

Preparation of tert-butyl 4-[3-(ethoxycarbonyl)-2-(trifluoromethyl)pyrazolo[1,5-a]pyridin-5-yl]piperidine-1-carboxylate (3B): 40% yield, light yellow solid. $^1$H NMR (400 MHz, Chloroform-d) δ 8.47 (dd, J=7.5, 3.2 Hz, 1H), 8.10 (s, 1H), 6.97 (d, J=2.1 Hz, 0H), 4.49-4.36 (m, 2H), 2.93-2.68 (m, 3H), 1.91 (d, J=13.1 Hz, 2H), 1.69 (t, J=12.6 Hz, 2H), 1.61-1.55 (m, 3H), 1.51 (s, 4H), 1.43 (dq, J=6.7, 3.3 Hz, 2H).

Preparation of tert-butyl4-[3-(methoxycarbonyl)-2-methylpyrazolo[1,5-a]pyridin-5-yl]piperidine-1-carboxylate (3C): 34% yield, light yellow solid, $^1$H NMR (400 MHz, Chloroform-d) δ 8.34 (d, J=7.0 Hz, 0H), 7.89 (s, 0H), 6.76 (d, J=7.1 Hz, 0H), 4.13 (qd, J=7.2, 2.2 Hz, 1H), 3.93 (s, 1H), 1.89 (d, J=13.1 Hz, 1H), 1.72-1.65 (m, 1H), 1.50 (s, 4H). $^{13}$C NMR (101 MHz, Chloroform-d) δ 164.81, 156.10, 154.81, 145.99, 142.47, 128.42, 115.56, 113.24, 100.69, 79.78, 51.06, 42.44, 28.55, 14.51. m/z: 374.21 [M+H].

General Procedure for (4)

tert-butyl 4-[3-(methoxycarbonyl)pyrazolo[1,5-a]pyridin-5-yl]piperidine-1-carboxylate (204 mg, 0.56 mmol) was dissolved in a 2:1:2 solvent mixture of THF: MeOH: Water (2.25 mL, 1.5 mL, 2.25 mL) and added to an argon filled round-bottom flask, equipped with a reflux condenser. LiOH was added (13 mg, 0.56 mmol) and the reaction was heated to 60° C. and stirred at this temperature for 4 hours. After which, all starting material had been converted, as seen by TLC. DCM was added to the reaction, and then washed with 1 M HCl x 2, followed by water. Aqueous extracts were combined and extracted once more with DCM. The organic extracts were combined and washed with brine, followed by drying with Na2SO4 and then concentrated in vacuo. Crude product was purified via flash chromatography with a 70:30 solvent mixture of EtOAc/Hexanes.

Preparation of 5-{1-[(tert-butoxy)carbonyl]piperidin-4-yl}pyrazolo[1,5-a]pyridine-3-carboxylic acid (4A): 88% yield, white solid. $^1$H NMR (400 MHz, Chloroform-d) δ 8.39 (dd, J=7.4, 2.8 Hz, 1H), 8.02 (d, J=3.0 Hz, 1H), 7.96 (s, 1H), 6.75 (d, J=7.4 Hz, 1H), 4.27 (s, 2H), 3.66-3.50 (m, 3H), 2.78 (d, J=15.5 Hz, 1H), 2.74-2.68 (m, OH), 1.87 (d, J=13.1 Hz, 2H), 1.67 (s, 1H), 1.48 (s, 3H). $^{13}$C NMR (101 MHz, Chloroform-d) δ 169.27, 155.20, 146.47, 141.95, 129.71, 116.28, 114.53, 102.99, 80.24, 42.84, 32.82, 28.93. m/z: 344.05 [M+H].

Preparation of 5-{1-[(tert-butoxy)carbonyl]piperidin-4-yl}-2-methylpyrazolo[1,5-a]pyridine-3-carboxylic acid (4B): 78% yield, white solid. $^1$H NMR (400 MHz, Chloroform-d) δ 8.38 (d, J=9.8 Hz, 1H), 7.98 (s, 1H), 6.80 (d, J=7.1 Hz, 1H), 4.30 (s, 1H), 2.92-2.76 (m, 3H), 2.71 (s, 3H), 1.90 (d, J=13.0 Hz, 2H), 1.69 (q, J=12.2, 11.6 Hz, 2H), 1.50 (s, 9H). $^{13}$C NMR (100 MHz, Chloroform-d) δ 169.40, 157.11, 154.85, 146.69, 143.07, 128.60, 115.95, 113.54, 100.05, 79.83, 77.31, 42.54, 28.57. m/z: 360.19 [M+H].

Preparation of 5-{1-[(tert-butoxy)carbonyl]piperidin-4-yl}-2-(trifluoromethyl)pyrazolo[1,5-a]pyridine-3-carboxylic acid (4C): Yield: 75%, white solid. $^1$H NMR (400 MHz, Chloroform-d) δ 8.51 (d, J=8.3 Hz, 1H), 8.15 (s, 1H), 7.01 (d, J=7.2 Hz, 1H), 4.33 (s, 1H), 2.85 (t, J=12.9 Hz, 3H), 1.92 (d, J=13.0 Hz, 2H), 1.70 (q, J=11.3 Hz, 2H), 1.50 (s, 9H). $^{13}$C NMR (101 MHz, CHLOROFORM-D) δ 168.74, 168.70, 154.57, 147.72, 129.03, 122.68 (q, J=3.8) Hz 116.71, 115.56, 79.72, 77.16, 77.16, 76.84, 76.52, 42.34, 32.10, 28.29. m/z: 436.15 [M+Na$^+$].

General Procedure for (5)

5-{1-[(tert-butoxy)carbonyl]piperidin-4-yl}pyrazolo[1,5-a]pyridine-3-carboxylic acid (75 mg, 0.22 mmol) was dissolved in DCM (2.2 mL) and added to an argon filled round-bottom flask. HOBt (60 mg, 0.44 mmol), EDCi (68 mg, 0.44 mmol), and diethylamine (34 µL, 0.33 mmol) were added to the flask in that order. The reaction was stirred at RT overnight after which all starting material had been converted, as seen by TLC. DCM was added to the reaction, and then washed with 1 M NaOH×2, followed by water. Aqueous extracts were combined and extracted once more with DCM. The organic extracts were combined and washed with brine, followed by drying with Na$_2$SO$_4$ and then concentrated in-vacuo. Crude product was purified via flash chromatography with a 60:40 solvent mixture of EtOAc/hexanes.

tert-butyl 4-[3-(diethylcarbamoyl)pyrazolo[1,5-a]pyridin-5-yl]piperidine-1-carboxylate (5A): 75% yield, white solid. $^1$H NMR (400 MHz, Acetonitrile-d$_3$) δ 8.45 (d, J=7.6 Hz, 1H), 8.04 (s, 1H), 7.80 (s, 1H), 6.89 (d, J=7.1 Hz, 1H), 4.26-4.11 (m, 2H), 3.64-3.45 (m, 4H), 2.81 (d, J=15.9 Hz, 3H), 1.56 (dd, J=12.6, 4.4 Hz, 3H), 1.45 (s, 9H), 1.23 (td, J=7.1, 2.7 Hz, 7H); $^{13}$C NMR (100 MHz, Chloroform-d) δ 164.45, 154.81, 144.41, 141.93, 141.13, 128.46, 116.44, 113.59, 106.14, 79.75, 42.38, 32.49, 28.60. m/z: 401.25 [M+H].

tert-butyl 4-[3-(diethylcarbamoyl)-2-(trifluoromethyl)pyrazolo[1,5-a]pyridin-5-yl]piperidine-1-carboxylate (5B): 89% yield, white solid. $^1$H NMR (400 MHz, Chloroform-d) δ 8.41 (d, J=8.5 Hz, 1H), 7.30 (s, 1H), 6.85 (d, J=7.3 Hz, 1H), 2.89-2.76 (m, 2H), 2.71 (t, J=12.4 Hz, 1H), 1.85 (d, J=13.0 Hz, 2H), 1.74-1.53 (m, 4H), 1.48 (s, 9H), 1.33-1.22 (m, 3H). $^{13}$C NMR (100 MHz, Chloroform-d) δ 162.41, 154.51, 144.24, 140.42 (d, J=37.5 Hz), 138.69, 128.47, 122.26, 119.57, 114.84, 113.83, 106.10, 79.62, 77.05, 41.93, 32.05, 28.26, 20.89. m/z: 469.24 [M+H].

tert-butyl 4-[3-(diethylcarbamoyl)-2-methylpyrazolo[1,5-a]pyridin-5-yl]piperidine-1-carboxylate (5C): 74% yield, yellow oil. $^1$H NMR (400 MHz, Chloroform-d) δ 8.28 (d, J=7.6 Hz, 1H), 7.20 (s, 1H), 6.61 (d, J=7.2 Hz, 1H), 4.11 (d, J=7.2 Hz, 1H), 3.49 (d, J=7.4 Hz, 3H), 2.80 (t, J=13.1 Hz, 1H), 2.66 (t, J=12.2 Hz, 1H), 2.46 (s, 3H), 1.84 (d, J=13.0 Hz, 2H), 1.60 (q, J=15.7, 13.9 Hz, 2H), 1.48 (s, 9H), 1.26 (d, J=7.5 Hz, 3H), 1.16 (d, J=7.4 Hz, 6H). $^{13}$C NMR (101 MHz, CHLOROFORM-D) δ 165.95, 154.83, 150.51, 143.38, 139.49, 128.03, 113.20, 112.04, 105.96, 79.75, 77.43, 60.48, 42.21, 32.45, 28.54, 21.14, 14.28, 14.00, 13.02. m/z: 437.25 [M+Na$^+$].

tert-butyl 4-[3-(methylcarbamoyl)pyrazolo[1,5-a]pyridin-5-yl]piperidine-1-carboxylate (5D): Yield: 95%, white solid; $^1$H NMR (400 MHz, Chloroform-d) δ 8.39 (d, J=7.1 Hz, 1H), 8.12 (d, J=9.2 Hz, 2H), 6.77 (d, J=7.2 Hz, 1H), 6.03 (s, 1H), 4.26 (d, J=13.4 Hz, 2H), 3.00 (s, 3H), 2.89-2.67 (m, 3H), 1.86 (d, J=13.1 Hz, 2H), 1.65 (q, J=13.2, 12.6 Hz, 2H), 1.48 (s, 9H). $^{13}$C NMR (101 MHz, CHLOROFORM-D) δ 164.57, 155.15, 145.44, 141.20, 140.98, 128.97, 116.53, 114.08, 106.66, 77.16, 42.69, 32.77, 28.90, 26.56. m/z: 359.10 [M+H].

tert-butyl 4-[3-(pyrrolidine-1-carbonyl)pyrazolo[1,5-a]pyridin-5-yl]piperidine-1-carboxylate (5G): 75% yield. $^1$H NMR (400 MHz, Chloroform-d) δ 8.41 (s, 1H), 8.15 (s, 2H), 6.78 (d, J=7.1 Hz, 1H), 4.26 (d, J=13.5 Hz, 1H), 3.74 (d, J=31.6 Hz, 4H), 2.88-2.63 (m, 4H), 1.99 (d, J=17.8 Hz, 4H), 1.86 (d, J=13.1 Hz, 2H), 1.64 (q, J=13.9, 13.5 Hz, 2H), 1.48 (s, 9H). 13C NMR (101 MHz, CHLOROFORM-D) δ 154.79, 144.89, 141.96, 141.91, 131.69, 128.37, 126.61, 124.87, 116.84, 113.90, 106.58, 100.00, 79.73, 77.43, 77.11, 76.79, 42.31, 32.42. m/z: 399.24 [M+H].

tert-butyl 4-[3-(piperidine-1-carbonyl)pyrazolo[1,5-a]pyridin-5-yl]piperidine-1-carboxylate (5J): $^1$H NMR (500 MHz, Chloroform-d) δ8.41 (d, J=7.5 Hz, 1H), 8.15 (s, 2H), 6.76 (dd, J=7.1, 1H), 4.30 (d, J=12.5 Hz, 2H), 3.85 (t, J=31.6 Hz, 4H), 3.18-3.02 (m, 3H), 2.01 (d J=13.0 Hz, 2H), 1.82-1.75 (m, 1H), 1.79-1.69 (m, 7H), 1.68-1.64 (m, 1H), 1.47 (s, 9H). 13C NMR (101 MHz, Chloroform-d) δ 155.63, 147.76, 142.66, 142.26, 131.37, 130.37, 125.73, 113.37, 79.77, 78.73, 77.43, 40.29, 38.32, 29.55, 26.33, 25.43, 24.26. m/z: 413.15 [M+H].

tert-butyl 4-(3-(4-methylpiperidine-1-carbonyl)pyrazolo[1,5-a]pyridin-5-yl)piperidine-1-carboxylate (5M): $^1$H NMR (400 MHz, Chloroform-d) δ 8.38 (d, J=8.6 Hz, 1H), 7.99 (s, 1H), 7.78 (s, 1H), 6.74 (d, J=7.6 Hz, 1H), 4.45 (d, J=12.9 Hz, 2H), 4.26 (s, 2H), 2.99 (d, J=13.2 Hz, 2H), 2.76 (dt, J=34.9, 12.7 Hz, 3H), 1.87 (d, J=13.1 Hz, 2H), 1.68 (dt, J=37.7, 13.0 Hz, 5H), 1.47 (s, 9H), 1.24 (p, J=13.4, 12.1 Hz, 2H), 0.99 (t, J=5.0 Hz, 3H). $^{13}$C NMR (101 MHz, CHLOROFORM-D) δ 164.46, 155.12, 144.63, 142.31, 141.64, 116.16, 113.81, 106.25, 80.07, 77.80, 77.48, 77.16, 42.64, 34.89, 32.77, 31.77, 29.02, 28.95, 28.87, 28.80, 22.25. m/z: 427.20 [M+H].

tert-butyl 4-(3-(3,5-dimethylpiperidine-1-carbonyl)pyrazolo[1,5-a]pyridin-5-yl)piperidine-1-carboxylate (5P): $^1$H NMR (400 MHz, Chloroform-d) δ 8.39 (d, J=7.1 Hz, 1H), 7.98 (s, 1H), 7.77 (s, 1H), 6.74 (d, J=7.2 Hz, 1H), 4.26 (s, 2H), 3.76 (d, J=12.2 Hz, 1H), 3.55-3.06 (m, OH), 2.86-2.66 (m, 3H), 2.00 (s, 1H), 1.87 (d, J=12.4 Hz, 3H), 1.79-1.56 (m, 5H), 1.49 (t, 1H), 1.47 (s, 9H), 0.93 (dd, J=16.8, 6.7 Hz, 6H). $^{13}$C NMR (101 MHz, CHLOROFORM-D) δ 163.85, 154.77, 144.31, 141.98, 141.32, 128.51, 128.49, 115.77, 113.51, 105.93, 79.72, 77.44, 77.13, 76.81, 42.66, 42.28, 39.72, 32.45, 32.43, 28.55, 19.14, 18.26, 14.29. m/z: 441.20 [M+H].

tert-butyl 4-(3-(benzylcarbamoyl)pyrazolo[1,5-a]pyridin-5-yl)piperidine-1-carboxylate (5S): $^1$H NMR (400 MHz, Chloroform-d) δ 8.40-8.36 (m, 1H), 8.16 (s, 1H), 8.09 (s, 1H), 7.34 (d, J=8.9 Hz, 4H), 7.29-7.24 (m, 1H), 6.77 (d, J=8.3 Hz, 1H), 6.26 (s, 1H), 4.64 (s, 2H), 4.25 (d, J=13.1 Hz, 1H), 2.76 (dt, J=24.1, 12.3 Hz, 1H), 1.86 (d, J=13.2 Hz, 2H), 1.65 (q, J=13.3, 12.3 Hz, 3H), 1.47 (s, 9H). $^{13}$C NMR (101 MHz, CHLOROFORM-D) δ 163.40, 154.81, 145.34, 141.09, 140.69, 138.74, 128.85, 128.71, 127.69, 127.64, 116.33, 113.88, 106.05, 79.79, 77.16, 43.47, 42.41, 36.77, 32.46, 28.60, 24.90, 23.52. m/z: 457.22 [M+Na$^+$].

tert-butyl 4-(3-(azepane-1-carbonyl)pyrazolo[1,5-a]pyridin-5-yl)piperidine-1-carboxylate (5V): $^1$H NMR (400 MHz, Chloroform-d) δ 8.39 (d, J=6.4 Hz, 1H), 8.04 (s, 1H), 7.97 (s, 1H), 6.75 (d, J=7.2 Hz, 1H), 4.26 (d, J=13.4 Hz, 2H), 3.73 (s, 4H), 2.76 (dt, J=26.0, 12.6 Hz, 3H), 1.86 (d, J=11.9 Hz, 6H), 1.65 (d, J=13.1 Hz, 6H), 1.47 (s, 9H). 13C NMR (101 MHz, CHLOROFORM-D) δ 164.99, 154.75, 144.36, 141.90, 141.54, 128.39, 116.46, 113.54, 106.28, 79.68, 77.43, 77.11, 76.80, 42.34, 32.45, 28.55. m/z: 449.25 [M+Na$^+$].

General Procedure for (6)

tert-butyl 4-[3-(diethylcarbamoyl)pyrazolo[1,5-a]pyridin-5-yl]piperidine-1-carboxylate (100 mg, 0.25 mmol) was dissolved in DCM (250 μL) and added to an argon purged round-bottom flask. TFA (2.5 mL) was added to the flask and stirred at RT for 1 hr. Reaction was diluted with DCM, and 1 M NaOH was added until aqueous solution was basic. The aqueous layer was extracted with DCM x 3. The organic extracts were combined and washed with brine, followed by drying with Na$_2$SO$_4$ and then concentrated in-vacuo. Crude product was purified via flash chromatography with a 10:90 solvent mixture of MeOH:DCM.

N,N-diethyl-5-(piperidin-4-yl)pyrazolo[1,5-a]pyridine-3-carboxamide (6A): 87% yield, 66 mg, white solid. $^1$H NMR (400 MHz, Chloroform-d) δ 8.38 (d, J=7.1 Hz, 1H), 8.01 (s, 1H), 7.93 (s, 1H), 6.78 (d, J=7.5 Hz, 1H), 3.59 (d, J=7.1 Hz, 4H), 3.23 (d, J=12.2 Hz, 2H), 2.74 (q, J=15.6, 14.1 Hz, 3H), 2.48 (s, 1H), 1.89 (d, J=12.9 Hz, 2H), 1.69 (q, J=12.5, 11.0 Hz, 2H), 1.34-1.25 (m, 7H). $^{13}$C NMR (101 MHz, CHLOROFORM-D) δ 164.84, 145.37, 142.16, 141.41, 128.74, 116.64, 113.85, 106.42, 77.79, 77.48, 77.44, 77.16, 46.98, 42.80, 33.64, 30.13, 14.27. m/z: 301.05 [M+H].

The following compounds were used in step 7 without further characterization: N,N-diethyl-2-methyl-5-(piperidin-4-yl)pyrazolo[1,5-a]pyridine-3-carboxamide (6B). N,N-diethyl-5-(piperidin-4-yl)-2-(trifluoromethyl)pyrazolo[1,5-a]pyridine-3-carboxamide (6C). N-methyl-5-(piperidin-4-yl)pyrazolo[1,5-a]pyridine-3-carboxamide (6D). N,2-dimethyl-5-(piperidin-4-yl)pyrazolo[1,5-a]pyridine-3-carboxamide (6E). N-methyl-5-(piperidin-4-yl)-2-(trifluoromethyl)pyrazolo[1,5-a]pyridine-3-carboxamide (6F). 5-(piperidin-4-yl)pyrazolo[1,5-a]pyridin-3-yl)(pyrrolidin-1-yl)methanone (6G). 2-methyl-5-(piperidin-4-yl)pyrazolo[1,5-a]pyridin-3-yl)(pyrrolidin-1-yl)methanone (6H). 5-(piperidin-4-yl)-2-(trifluoromethyl)pyrazolo[1,5-a]pyridin-3-yl)(pyrrolidin-1-yl)methanone (6I). piperidin-1-yl(5-(piperidin-4-yl)pyrazolo[1,5-a]pyridin-3-yl)methanone (6J). (2-methyl-5-(piperidin-4-yl)pyrazolo[1,5-a]pyridin-3-yl)(piperidin-1-yl)methanone (6K). piperidin-1-yl(5-(piperidin-4-yl)-2-(trifluoromethyl)pyrazolo[1,5-a]pyridin-3-yl)methanone (6L). azepan-1-yl(5-(piperidin-4-yl)pyrazolo[1,5-a]pyridin-3-yl)methanone (6M). azepan-1-yl(2-methyl-5-(piperidin-4-yl)pyrazolo[1,5-a]pyridin-3-yl)methanone (6N). azepan-1-yl(5-(piperidin-4-yl)-2-(trifluoromethyl)pyrazolo[1,5-a]pyridin-3-yl)methanone (6O). N-benzyl-5-(piperidin-4-yl)pyrazolo[1,5-a]pyridine-3-carboxamide (6P). N-benzyl-2-methyl-5-(piperidin-4-yl)pyrazolo[1,5-a]pyridine-3-carboxamide (6Q). N-benzyl-5-(piperidin-4-yl)-2-(trifluoromethyl)pyrazolo[1,5-a]pyridine-3-carboxamide (6R). (4-methylpiperidin-1-yl)(5-(piperidin-4-yl)pyrazolo[1,5-a]pyridin-3-yl)methanone (6S). (2-methyl-5-(piperidin-4-yl)pyrazolo[1,5-a]pyridin-3-yl)(4-methylpiperidin-1-yl)methanone (6T). (4-methylpiperidin-1-yl)(5-(piperidin-4-yl)-2-(trifluoromethyl)pyrazolo[1,5-a]pyridin-3-yl)methanone (6U). (3,5-dimethylpiperidin-1-yl)(5-(piperidin-4-yl)pyrazolo[1,5-a]pyridin-3-yl)methanone (6V). (3,5-dimethylpiperidin-1-yl)(2-methyl-5-(piperidin-4-yl)pyrazolo[1,5-a]pyridin-3-yl)methanone (6W). (3,5-dimethylpiperidin-1-yl)(5-(piperidin-4-yl)-2-(trifluoromethyl)pyrazolo[1,5-a]pyridin-3-yl)methanone (6X).

General Procedure for (7)

N,N-diethyl-5-(piperidin-4-yl)pyrazolo[1,5-a]pyridine-3-carboxamide (82 mg, 0.27 mmol) was dissolved in DCM (900 μL, 0.3 M) and added to a flame-dried, argon purged round-bottom flask. The flask was cooled to 0° C., and TEA (90 μL) was added, followed by 4-acetamidobenzenesulfonyl chloride and stirred at RT for 1 hr. The reaction was diluted with additional DCM and washed with water twice. The aqueous extracts were combined and extracted again with ethyl acetate. Organic extracts were combined and washed with brine, followed by drying with Na$_2$SO$_4$ and then concentrated in-vacuo. Crude product was purified via flash chromatography with a 10:90 solvent mixture of MeOH:DCM.

Z231-0326: 78% yield, white solid. $^1$H NMR: (400 MHz, Chloroform-d) δ 8.40 (d, J=7.1 Hz, 1H), 8.03 (s, 1H), 7.85-7.66 (m, 6H), 6.71 (d, J=7.0 Hz, 1H), 4.13 (dd, J=7.0, 1.1 Hz, 1H), 3.98 (d, J=11.7 Hz, 2H), 3.61 (q, J=7.1 Hz, 3H), 2.55-2.39 (m, 3H), 2.24 (s, 3H), 1.88 (d, J=13.0 Hz, 2H), 1.76 (d, J=13.7 Hz, 2H), 1.32 (t, J=7.2 Hz, 5H), 1.29 (dd, J=2.4, 1.2 Hz, 1H), 1.26 (s, 6H). 13C NMR (100 MHz, Chloroform-d) δ 164.22, 143.50, 141.47, 143.11, 140.86, 132.89, 129.53, 128.33, 128.29, 127.56, 116.37, 112.69, 105.99, 46.21, 41.19, 31.56, 21.41. m/z: 497.0 [M+H].

N,N-diethyl-5-[1-(4-methylbenzenesulfonyl)piperidin-4-yl]pyrazolo[1,5-a]pyridine-3-carboxamide (7A): 63% yield across two steps, white solid. $^1$H NMR (400 MHz, Chloroform-d) δ 8.38 (dd, J=7.3, 2.2 Hz, 1H), 8.01 (dd, J=3.8, 2.0 Hz, 1H), 7.90 (d, J=2.4 Hz, 1H), 7.67 (ddd, J=8.1, 3.8, 2.0 Hz, 2H), 7.38-7.30 (m, 2H), 6.69 (ddt, J=5.7, 3.9, 2.0 Hz, 1H), 3.93 (d, 2H), 3.57 (tt, J=9.3, 5.9 Hz, 4H), 2.51 (tt, J=11.7, 3.8 Hz, 1H), 2.44 (s, 3H), 2.34 (tq, J=8.8, 2.9 Hz, 2H), 1.96-1.78 (m, 4H), 1.33-1.22 (m, 6H). $^{13}$C NMR (100 MHz, Chloroform-d) δ 164.22, 143.50, 141.47, 143.11, 140.86, 132.89, 129.53, 128.33, 128.29, 127.56, 116.37, 112.69, 105.99, 46.21, 41.19, 31.56, 21.41. m/z: 455.21 [M+H].

methyl N-[4-({4-[3-(diethylcarbamoyl)pyrazolo[1,5-a]pyridin-5-yl]piperidin-1-yl}sulfonyl)phenyl]carbamate (7C): 44% yield across two steps, white solid. $^1$H NMR (400 MHz, Chloroform-d) δ 8.39 (d, J=7.2 Hz, 1H), 8.03 (s, 1H), 7.86 (s, 1H), 7.75 (d, J=8.2 Hz, 2H), 7.60 (d, J=8.5 Hz, 2H), 7.17 (s, 1H), 6.70 (d, J=9.1 Hz, 1H), 3.95 (d, J=11.7 Hz, 2H), 3.81 (d, 3H), 3.60 (q, J=7.1 Hz, 4H), 2.51 (t, J=12.0 Hz, 1H), 2.42 (t, J=11.3 Hz, 1H), 1.89 (d, J=13.1 Hz, 2H), 1.79 (q, J=12.1 Hz, 2H), 1.31 (t, J=7.1 Hz, 6H). $^{13}$C NMR (100 MHz, Chloroform-d) δ 164.76, 154.02, 143.83, 142.72, 142.13, 141.55, 130.98, 129.53, 128.98, 118.83, 116.92, 113.58, 106.58, 53.20, 46.89, 41.84, 32.00. m/z: 514.21 [M+H].

N-[4-({4-[3-(pyrrolidine-1-carbonyl)pyrazolo[1,5-a]pyridin-5-yl]piperidin-1-yl}sulfonyl)phenyl]acetamide (7H): 44% yield across two step, white solid. $^1$H NMR (400 MHz, Chloroform-d) δ 8.40 (dd, J=7.1, 0.9 Hz, 1H), 8.16 (s, 1H), 8.03 (s, 1H), 7.89 (s, 1H), 7.85-7.66 (m, 4H), 6.73 (dd, J=7.2, 2.1 Hz, 1H), 3.97 (d, J=12.0 Hz, 2H), 3.81-3.70 (m, 4H), 2.50 (q, J=14.0, 12.4 Hz, 3H), 2.21 (s, 3H), 2.04-1.95 (m, 4H), 1.85 (d, J=12.9 Hz, 2H), 1.79-1.66 (m, 2H). $^{13}$C NMR (101 MHz, CHLOROFORM-d) δ 164.27, 154.80, 144.39, 141.90, 141.18, 138.42, 128.51, 126.64, 124.83, 115.68, 113.49, 109.96, 105.72, 79.76, 77.43, 42.25, 32.40, 28.55, 26.33, 24.80. m/z: 496.10 [M+H].

N-[4-({4-[3-(piperidine-1-carbonyl)pyrazolo[1,5-a]pyridin-5-yl]piperidin-1-yl}sulfonyl)phenyl]acetamide (7M): 80% yield across two step, white solid. $^1$H NMR (400 MHz, Chloroform-d) δ 8.38 (dd, J=7.2, 0.9 Hz, 1H), 8.00 (s, 1H), 7.92-7.69 (m, 4H), 7.66 (s, 1H), 6.69 (dd, J=7.2, 2.0 Hz, 1H), 3.96 (d, J=11.8 Hz, 2H), 3.71 (t, J=5.4 Hz, 4H), 2.47 (ddd, J=23.6, 12.8, 9.5 Hz, 3H), 2.21 (s, 3H), 1.87 (d, J=13.1 Hz, 2H), 1.84-1.61 (m, 8H). $^{13}$C NMR (101 MHz, CHLOROFORM-D) δ 169.06, 164.21, 143.53, 142.56, 142.03, 141.12, 131.12, 128.97, 128.79, 119.74, 115.78, 113.26, 77.48, 77.16, 77.16, 76.84, 46.54, 41.39, 31.61, 26.38, 24.82, 24.74. m/z: 510.20 [M+H].

N-[4-({4-[3-(azepane-1-carbonyl)pyrazolo[1,5-a]pyridin-5-yl]piperidin-1-yl}sulfonyl)phenyl]acetamide (7R): 68% yield across two steps, white solid. $^1$H NMR (400 MHz, Chloroform-d) δ 7.93 (s, 1H), 7.83 (d, J=8.3 Hz, 1H), 7.48 (s, 1H), 7.17 (q, J=8.6 Hz, 5H), 6.15 (d, J=7.1 Hz, 1H), 3.37 (d, J=11.7 Hz, 2H), 3.17 (s, 4H), 1.96-1.80 (m, 3H), 1.60 (s, 3H), 1.30 (d, J=9.6 Hz, 6H), 1.21 (t, J=13.4 Hz, 3H), 1.08 (s, 4H). $^{13}$C NMR (101 MHz, CHLOROFORM-D) δ 168.83, 164.86, 143.32, 142.35, 141.36, 141.31, 130.69, 128.63, 128.38, 119.43, 116.05, 113.05, 105.97, 77.16, 50.66, 46.23, 41.11, 31.30, 24.39. m/z: 524.23 [M+H].

N-4-([4-{3-(3,5-dimethylpiperidine-1-carbonyl)pyrazolo[1,5-a]pyridin-5-yl]piperidin-1-yl}sulfonyl)phenyl]acetamide (7W): 78% yield across two steps, white solid. $^1$H NMR (400 MHz, Chloroform-d) δ 8.40 (dd, J=7.2, 1.1 Hz, 1H), 8.00 (dd, J=5.6, 1.0 Hz, 1H), 7.83-7.63 (m, 5H), 6.70 (d, J=7.3 Hz, 1H), 3.97 (d, J=12.1 Hz, 2H), 3.76 (d, J=9.4 Hz, 1H), 2.49 (dt, J=22.8, 11.7 Hz, 3H), 2.23 (s, 3H), 1.89 (d, J=11.9 Hz, 2H), 1.83-1.70 (m, 3H), 1.31-1.22 (m, 6H), 0.99-0.87 (m, 6H), 0.87-0.78 (m, 2H). $^{13}$C NMR (101 MHz, CHLOROFORM-D) δ 169.06, 164.82, 163.88, 143.53, 142.53, 142.01, 141.14, 128.93, 128.77, 119.68, 115.76, 113.26, 105.84, 77.44, 77.12, 76.81, 46.50, 42.58, 41.32, 31.57, 22.01, 24.69, 19.12, 18.25. m/z: 538.25 [M+H].

N-[4-({4-[3-(4-methylpiperidine-1-carbonyl)pyrazolo[1,5-a]pyridin-5-yl]piperidin-1-yl}sulfonyl)phenyl]acetamide (7AB): 65% yield across two steps, white solid. $^1$H NMR (400 MHz, Chloroform-d) δ 8.39 (d, J=9.3 Hz, 1H), 8.19 (s, 1H), 8.00 (s, 1H), 7.73 (s, 4H), 7.66 (s, 1H), 6.69 (d, J=7.3 Hz, 1H), 4.45 (d, J=13.1 Hz, 1H), 3.94 (d, J=11.7 Hz, 2H), 3.01 (d, J=12.9 Hz, 1H), 2.45 (dt, J=24.1, 12.0 Hz, 3H), 2.17 (s, 3H), 1.87 (d, J=13.2 Hz, 2H), 1.74 (p, J=12.0, 11.2 Hz, 6H), 1.23 (q, J=12.4, 11.2 Hz, 2H), 1.03-0.96 (m, 3H). $^{13}$C NMR (101 MHz, CHLOROFORM-D) δ 168.94, 164.13, 143.51, 142.46, 141.98, 141.14, 128.94, 128.74, 119.70, 115.79, 113.23, 105.85, 98.23, 46.49, 41.35, 34.52, 31.54, 31.38, 24.71, 21.84, 14.28. m/z: 526.21 [M+H].

N-{4-[(4-{3-[3-(hydroxymethyl)pyrrolidine-1-carbonyl]pyrazolo[1,5-a]pyridin-5-yl}piperidin-1-yl)sulfonyl]phenyl}acetamide (7AG): 40% yield, white solid. 1H NMR (400 MHz, Chloroform-d) δ 8.39 (dd, J=7.2, 2.1 Hz, 1H), 8.00 (d, J=2.2 Hz, 1H), 7.75 (td, J=8.2, 7.4, 3.2 Hz, 4H), 7.66 (s, 1H), 6.70 (dt, J=7.4, 2.2 Hz, 1H), 4.19-4.10 (m, 2H), 4.03 (s, 1H), 3.94 (d, J=11.9 Hz, 2H), 3.44 (t, J=11.3 Hz, 2H), 2.48 (dt, J=24.0, 12.1 Hz, 3H), 2.21 (dd, J=2.7, 1.6 Hz, 3H), 1.98 (d, J=12.5 Hz, 2H), 1.89 (d, J=13.1 Hz, 2H), 1.76 (q, J=12.4 Hz, 2H), 1.25 (q, J=2.7 Hz, 3H). $^{13}$C NMR (101 MHz, CHLOROFORM-D) δ 164.28, 154.77, 144.51, 141.97, 141.30, 128.58, 115.73, 113.56, 105.54, 98.05, 79.75, 77.42, 77.11, 76.79, 67.52, 42.31, 34.58, 32.44, 28.55, 14.28. m/z: 532.15 [M+H].

5-[1-(4-acetamidobenzenesulfonyl)piperidin-4-yl]-N,N-diethyl-2-methylpyrazolo[1,5-a]pyridine-3-carboxamide (7AI): 46% yield, white solid. $^1$H NMR (400 MHz, Chloroform-d) δ 8.82 (s, 1H), 8.28-8.22 (m, 1H), 7.66 (q, J=8.8 Hz, 4H), 6.54 (d, J=7.4 Hz, 1H), 3.89 (d, J=11.4 Hz, 2H), 2.43 (s, 4H), 2.34 (t, J=12.2 Hz, 3H), 2.13 (s, 3H), 1.89-1.67 (m, 8H), 1.15 (t, 7H). $^{13}$C NMR (101 MHz, Chloroform-d) δ 169.44, 166.06, 150.41, 142.78, 142.77, 139.28, 130.37, 128.82, 128.20, 119.55, 112.99, 112.05, 105.81, 50.80, 46.52, 41.14, 31.67, 24.50, 12.97. m/z: 512.23 [M+H].

5-[1-(4-acetamidobenzenesulfonyl)piperidin-4-yl]-N,N-diethyl-2-(trifluoromethyl)pyrazolo[1,5-a]pyridine-3-carboxamide (7BR): 65% yield across two steps, white solid. $^1$H NMR (400 MHz, Chloroform-d) δ 8.39 (d, J=10.8 Hz, 0H), 8.10 (s, 1H), 7.68 (s, 4H), 7.20 (s, 1H), 6.78 (d, J=8.1 Hz, 1H), 3.94 (d, J=11.8 Hz, 2H), 3.28 (s, 1H), 2.49 (t, J=12.2 Hz, 1H), 2.40 (t, J=11.8 Hz, 2H), 2.18 (s, 3H), 1.88 (d, J=12.9 Hz, 2H), 1.76 (t, J=12.6 Hz, 2H), 1.33-1.20 (m, 6H). $^{13}$C NMR (100 MHz, Chloroform-d) δ 169.02, 162.77, 143.79, 142.42, 140.57, 138.79, 130.87, 128.93 (d, J=4.9 Hz), 119.60, 115.01, 113.92, 106.31, 77.32, 46.39, 41.12, 31.50, 24.68, 14.19. m/z: 566.21 [M+H].

5-[1-(benzenesulfonyl)piperidin-4-yl]-N,N-diethylpyrazolo[1,5-a]pyridine-3-carboxamide (7DA): 57% yield across two steps, white solid. $^1$H NMR (400 MHz, Chloroform-d) δ 8.40 (dd, J=7.2, 0.9 Hz, 1H), 8.04 (s, 1H), 7.92 (dt, J=1.9, 0.9 Hz, 1H), 7.85-7.79 (m, 2H), 7.69-7.54 (m, 3H), 6.71 (dd, J=7.3, 2.0 Hz, 1H), 3.99 (dq, J=10.5, 2.7 Hz, 2H), 3.60 (q, J=7.2 Hz, 4H), 2.54 (tt, J=11.7, 4.0 Hz, 1H), 2.39 (td, J=11.9, 2.9 Hz, 2H), 2.00-1.79 (m, 4H), 1.31 (t, J=7.1 Hz, 6H). m/z: 441.19 [M+H].

N,N-diethyl-5-(1-methanesulfonylpiperidin-4-yl)pyrazolo[1,5-a]pyridine-3-carboxamide (7DE): 23% yield across two steps, white solid. 1H NMR (400 MHz, Chloroform-d) δ 8.42 (dd, J=7.2, 1.0 Hz, 1H), 8.04 (s, 1H), 7.99 (dq, J=2.0, 1.0 Hz, 1H), 6.77 (dd, J=7.2, 2.0 Hz, 1H), 3.96 (d, J=11.9 Hz, 2H), 3.60 (q, J=7.1 Hz, 4H), 2.84 (s, 3H), 2.81-2.70 (m, 3H), 2.01 (d, J=13.0 Hz, 2H), 1.94-1.82 (m, 2H), 1.31 (t, J=7.1 Hz, 6H). $^{13}$C NMR (101 MHz, Chloroform-d) δ 168.99, 142.64, 142.35, 138.37, 137.37, 126.42, 116.27, 96.58, 60.06, 41.62, 40.89, 39.76, 29.84, 22.50, 13.03. m/z: 379.17 [M+H].

N,N-diethyl-5-(1-phenylmethanesulfonylpiperidin-4-yl)pyrazolo[1,5-a]pyridine-3-carboxamide (7DJ): 23% yield across two steps. 1H NMR (400 MHz, Chloroform-d) δ 8.40 (s, 1H), 8.02 (s, 1H), 7.92 (s, 1H), 7.45-7.38 (m, 4H), 6.70 (d, J=7.0 Hz, 1H), 4.26 (s, 2H), 3.79 (d, J=12.4 Hz, 2H), 3.59 (d, J=7.2 Hz, 4H), 2.63 (dt, J=24.0, 12.0 Hz, 3H), 1.83 (d, J=13.1 Hz, 2H), 1.74-1.59 (m, 3H), 1.30 (t, 6H). $^{13}$C NMR (100 MHz, Chloroform-d) δ 164.31, 143.41, 141.77, 141.12, 130.79, 129.02, 128.94, 128.93, 128.60, 116.71, 112.97, 106.26, 57.39, 46.48, 41.77, 32.45. m/z: 455.21 [M+H].

N-benzyl-5-[1-(4-acetamidobenzenesulfonyl)piperidin-4-yl]pyrazolo[1,5-a]pyridine-3-carboxamide (7FM): 40% yield across two steps, white solid. $^1$H NMR (400 MHz, Chloroform-d) δ 8.40 (d, J=7.1 Hz, 1H), 8.10 (s, 1H), 8.04

(s, 1H), 7.94 (s, 1H), 7.75 (s, 3H), 7.37 (s, 4H), 7.26 (s, 2H), 6.74 (d, J=7.1 Hz, 1H), 6.23 (s, 1H), 4.71-4.61 (m, 2H), 3.96 (d, J=12.0 Hz, 2H), 2.58-2.40 (m, 3H), 2.19 (s, 3H), 1.87 (d, J=13.0 Hz, 2H), 1.76 (d, J=13.0 Hz, 2H). $^{13}$C NMR (101 MHz, CHLOROFORM-D) δ 168.69, 146.60, 142.34, 140.74, 129.00, 128.91, 127.89, 127.72, 119.74, 113.60, 99.66, 77.42, 77.11, 76.79, 46.46, 43.48, 41.51, 31.50, 24.86. m/z: 532.20 [M+H].

methyl N-[4-({4-[3-(methylcarbamoyl)pyrazolo[1,5-a]pyridin-5-yl]piperidin-1-yl}sulfonyl)phenyl]carbamate (7GQ): 87% yield across two steps, white solid. $^1$H NMR (400 MHz, Chloroform-d) δ 8.39 (d, J=7.1 Hz, 1H), 8.17-8.07 (m, 4H), 8.12 (d, J=9.2 Hz, 2H), 6.77 (d, J=7.2 Hz, 1H), 6.03 (s, 1H), 4.26 (d, J=13.4 Hz, 2H), 3.00 (s, 3H), 2.89-2.67 (m, 3H), 2.49 (s, 3H) 1.86 (d, J=13.1 Hz, 2H), 1.65 (q, J=13.2, 2H). $^{13}$C NMR (101 MHz, CHLOROFORM-D) δ 168.03, 164.57, 155.15, 145.44, 145.65, 144.67, 141.20, 140.98, 138.97, 137,98, 128.97, 116.53, 114.08, 106.66, 77.16, 42.69, 32.77, 28.90, 27.75, 26.56. m/z: 456.10 [M+H].

N,N-diethyl-5-[1-(4-fluorobenzenesulfonyl)piperidin-4-yl]pyrazolo[1,5-a]pyridine-3-carboxamide (7HL): 60% yield across two steps. $^1$H NMR (400 MHz, Chloroform-d) δ 8.67 (m, 1H), 8.45 (s, 1H), 8.00 (m, 2H), 7.59 (d, J=1.5 Hz, 1H), 7.41 (m, 3H), 3.48 (q, J=6.3 Hz, 4H), 2.57 (m, 1H), 2.46 (m, 5H), 2.20 (m, 2H), 2.02 (m, 2H), 1.56 (t, J=6.3 Hz, 6H). $^{13}$C NMR (101 MHz, CHLOROFORM-D) δ 164.33, 143.04, 141.81, 141.21, 140.22, 134.83, 134.50, 128.70, 128.26, 122.01, 116.73, 112.99, 106.40, 77.48, 77.16, 76.84, 60.54, 46.55, 41.35, 31.88, 21.19, 14.33. m/z: 459.19 [M+H].

N,N-diethyl-5-{1-[4-(trifluoromethyl)benzenesulfonyl]piperidin-4-yl}pyrazolo[1,5-a]pyridine-3-carboxamide (7HM): 41% yield across two steps, white solid. $^1$H NMR (400 MHz, Chloroform-d) δ 8.40 (d, J=9.4 Hz, 1H), 8.03 (s, 1H), 7.92 (s, 3H), 7.85 (s, 1H), 7.82 (s, 1H), 6.70 (d, J=7.0 Hz, 1H), 3.99 (d, J=11.6 Hz, 2H), 3.59 (d, J=7.1 Hz, 4H), 2.55 (t, J=12.0 Hz, 1H), 2.43 (t, J=11.5 Hz, 2H), 1.97 (d, J=12.9 Hz, 2H), 1.88 (d, J=13.4 Hz, 2H), 1.32-1.26 (m, 6H). $^{13}$C NMR (101 MHz, CHLOROFORM-D) δ 164.33, 143.04, 141.81, 141.21, 140.22, 134.83, 134.50, 128.70, 128.26, 126.49 (q, J=3.8 Hz), 122.01, 116.73, 112.99, 106.40, 77.48, 77.16, 76.84, 60.54, 46.55, 41.35, 31.88, 21.19, 14.33. m/z: 509.18 [M+H].

The following compounds were synthesized in a similar manner to compounds Z231-0326 and 7A-7HM above:

benzyl N-[4-({4-[3-(diethylcarbamoyl)pyrazolo[1,5-a]pyridin-5-yl]piperidin-1-yl}sulfonyl)phenyl]carbamate (7HN). m/z: 590.35 [M+H]

4-({14-[3-(azetidine-1-carbonyl)pyrazolo[1,5-a]pyridin-5-yl]piperidin-1-yl}sulfonyl)aniline (7HO). m/z: 440.30 [M+H]

5-[1-(4-aminobenzenesulfonyl)piperidin-4-yl]-N,N-diethylpyrazolo[1,5-a]pyridine-3-carboxamide (7HP). m/z: 456.20 [M+H] tert-butyl N-[4-({4-[3-(azetidine-1-carbonyl)pyrazolo[1,5-a]pyridin-5-yl]piperidin-1-yl}sulfonyl)phenyl]carbamate (7HQ). m/z: 540.30 [M+H]

5-{1-[4-(5-aminopentanamido)benzenesulfonyl]piperidin-4-yl}-N,N-diethylpyrazolo[1,5-a]pyridine-3-carboxamide (7HR). m/z: 555.30 [M+H]

5-{1-[4-(3-aminopropanamido)benzenesulfonyl]piperidin-4-yl}-N,N-diethylpyrazolo[1,5-a]pyridine-3-carboxamide (7HS). m/z: 525.25 [M+H]

5-{1-[4-(acetamidomethyl)benzenesulfonyl]piperidin-4-yl}-N,N-diethylpyrazolo[1,5-a]pyridine-3-carboxamide (7HT). m/z: 512.30 [M+H]

5-{1-[4-(4-aminobutanamido)benzenesulfonyl]piperidin-4-yl}-N,N-diethylpyrazolo[1,5-a]pyridine-3-carboxamide (7HU). m/z: 541.3 [M+H]

N,N-diethyl-5-{1-[4-(methylcarbamoyl)benzenesulfonyl]piperidin-4-yl}pyrazolo[1,5-a]pyridine-3-carboxamide (7HV). m/z: 498.25 [M+H]

N-[4-({4-[3-(pyrrolidine-1-carbonyl)pyrazolo[1,5-a]pyridin-5-yl]piperidin-1-yl}sulfonyl)phenyl]cyclohexanecarboxamide (7HW). m/z: 564.75 [M+H]

N,N-diethyl-5-{1-[4-(2-oxopropyl)benzenesulfonyl]piperidin-4-yl}pyrazolo[1,5-a]pyridine-3-carboxamide (7HX). m/z: 497.3 [M+H]

5-{1-[(1-acetyl-2,3-dihydro-1H-indol-511)sulfonyl]piperidin-4-yl}-N,N-diethylpyrazolo[1,5-a]pyridine-3-carboxamide (7HY). m/z: 524.25 [M+H]

1-[6-({4-[3-(pyrrolidine-1-carbonyl)pyrazolo[1,5-a]pyridin-5-yl]piperidin-1-yl}sulfonyl)-2,3-dihydro-1H-indol-1-yl]ethan-1-one (7HZ). m/z: 522.6 [M+H]

4-({4-[3-(pyrrolidine-1-carbonyl)pyrazolo[1,5-a]pyridin-5-yl]piperidin-1-yl}sulfonyl)aniline (7IA). m/z: 454.20 [M+H]

tert-butyl N-[4-({4-[3-(pyrrolidine-1-carbonyl)pyrazolo[1,5-a]pyridin-5-yl]piperidin-1-yl}sulfonyl)phenyl]carbamate (7IB). m/z: 554.30 [M+H]

N-[4-({4-[3-(azetidine-1-carbonyl)pyrazolo[1,5-a]pyridin-5-yl]piperidin-1-yl}sulfonyl)phenyl]acetamide (7IC). m/z: 482.20 [M+H]

N-(4-{4-[3-(morpholine-4-carbonyl)pyrazolo[1,5-a]pyridin-5-yl]piperidin-1-yl}phenyl)acetamide (7ID). m/z: 512.25 [M+H]

N-[4-({4-[3-(pyrrolidine-1-carbonyl)pyrazolo[1,5-a]pyridin-5-yl]piperidin-1-yl}sulfonyl)phenyl]acetamide (7IE). m/z: 496.25 [M+H]

4-({4-[2-(diethylcarbamoyl)pyrazolo[1,5-a]pyridin-4-yl]piperidin-1-yl}sulfonyl)benzoic acid (7IF). m/z: 499.20 [M+H]

4-[1-(4-acetylbenzenesulfonyl)piperidin-4-yl]-N,N-diethylpyrazolo[1,5-a]pyridine-2-carboxamide (7IG). m/z: 483.39 [M+H] propyl 4-({4-[2-(diethylcarbamoyl)pyrazolo[1,5-a]pyridin-4-yl]piperidin-1-yl}sulfonyl)benzoate (7IH). m/z: 527.20 [M+H]

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step not specifically disclosed.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference.

We claim:
1. A compound of Formula (Ia), or a pharmaceutically acceptable salt thereof:

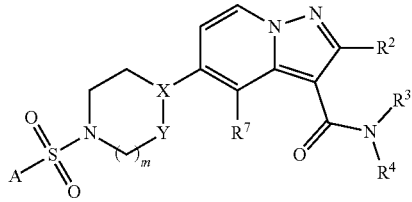
(Ia)

wherein:
A is $C_{1-4}$alkyl or

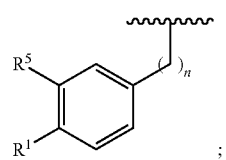;

X is CH or N;
Y is $CH_2$ or N, and when X is N, then Y is $CH_2$;
m is 0 or 1, and when m is 1 then Y is $CH_2$;
n is 0 or 1;
$R^1$ is H, $C_{1-6}$alkyleneC(=O)$R^6$, halo, cyano, aryloxy, amino, $C_{0-3}$alkylene-amido, carbamyl, S-thiocarbamyl, or ureido;
$R^2$ is H, halo, $C_{1-6}$alkyl, $C_{3-8}$cycloalkyl, or heteroaryl;
each $R^3$ and $R^4$ independently is H, $C_{1-6}$ alkyl, or $C_{1-3}$aralkyl, or $R^3$ and $R^4$ and the nitrogen to which they are attached join together to form a 3-6 membered ring optionally comprising 1 to 3 additional heteroatoms selected from N, 0, and S;
$R^5$ is H, or $R^1$ and $R^5$ together with the atoms to which they are attached form a 5- or 6-membered heterocyclic ring comprising 1 to 3 ring heteroatoms selected from N, O, and S;
$R^6$ is OH, $C_{1-6}$alkyl, or O$C_{1-6}$alkyl; and
$R^7$ is H, halo or amino;
with the proviso that the compound is not

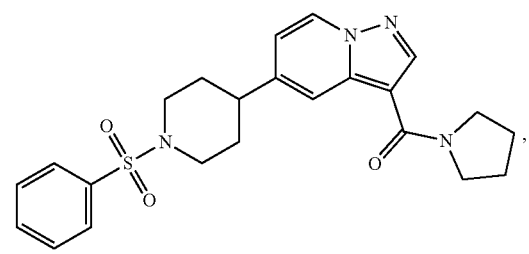

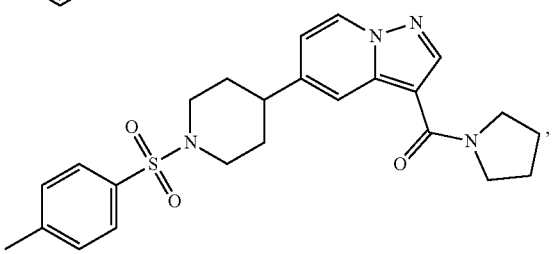

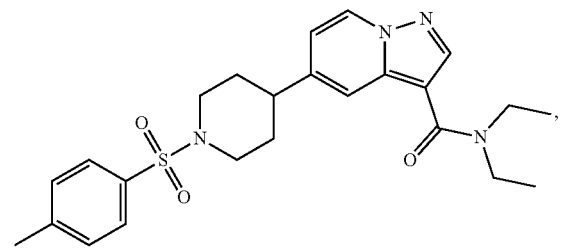

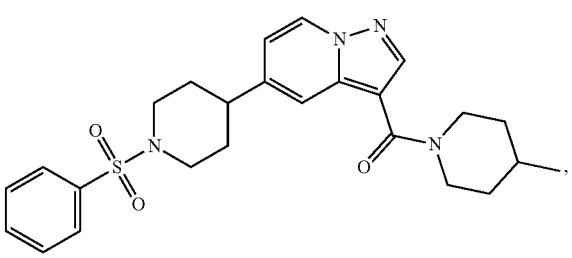

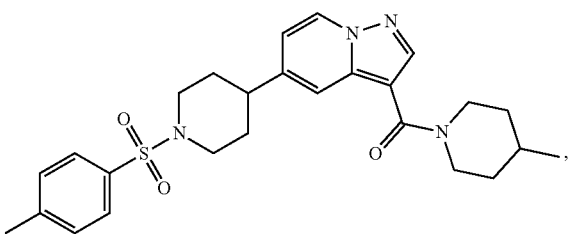

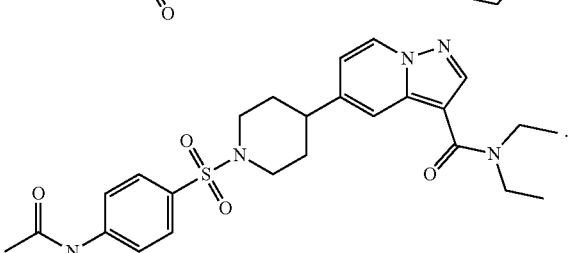, or

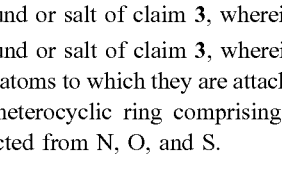.

2. The compound of claim 1, wherein A is methyl, ethyl, propyl, isopropyl, n-butyl, s-butyl, isobutyl, or t-butyl.

3. The compound or salt of claim 1, wherein A is

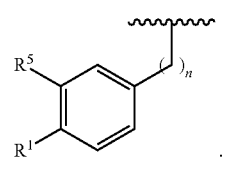.

4. The compound or salt of claim 3, wherein n is 0.

5. The compound or salt of claim 3, wherein $R^1$ and $R^5$ together with the atoms to which they are attached form a 5- or 6-membered heterocyclic ring comprising 1 to 3 ring heteroatoms selected from N, O, and S.

6. The compound of claim 5, wherein A is selected from the group consisting of
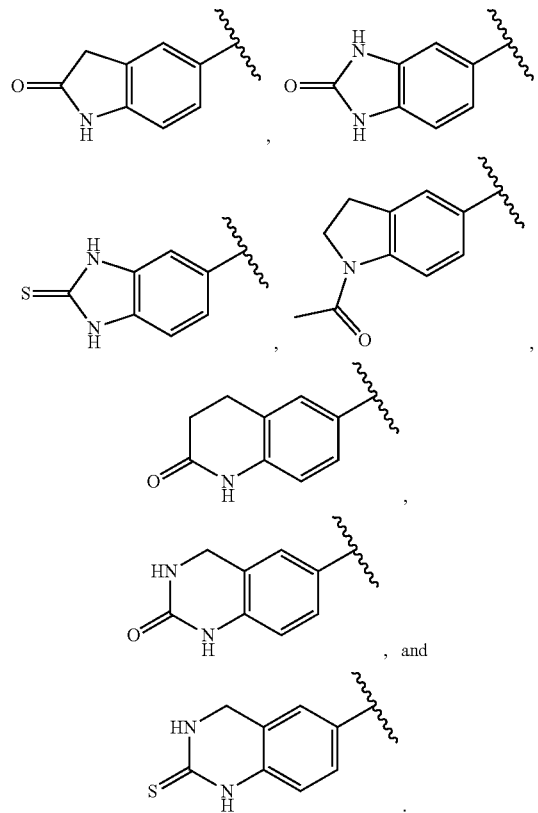
, and
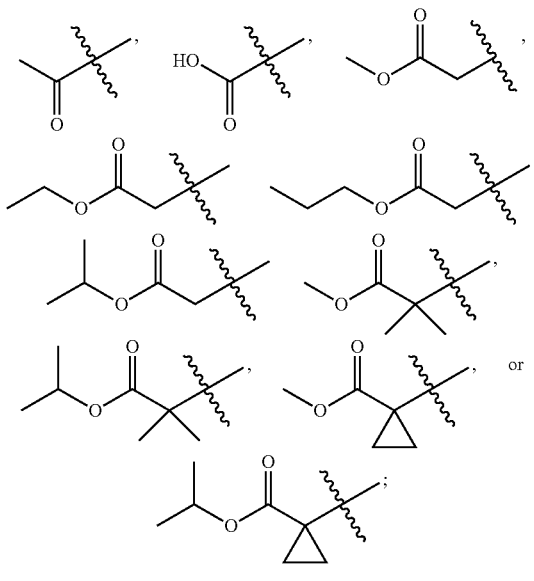
.
7. The compound or salt of claim 3, wherein $R^5$ is H.
8. The compound or salt of claim 7, wherein $R^1$ is:
(i) H;
(ii) methyl, ethyl, fluoromethyl, or trifluoromethyl;
(iii)
(iv) F;
(v) CN or —OPh;
(vi) $NH_2$, —$N(CH_3)_2$ or —$NH_2Ph$; or
(vii)
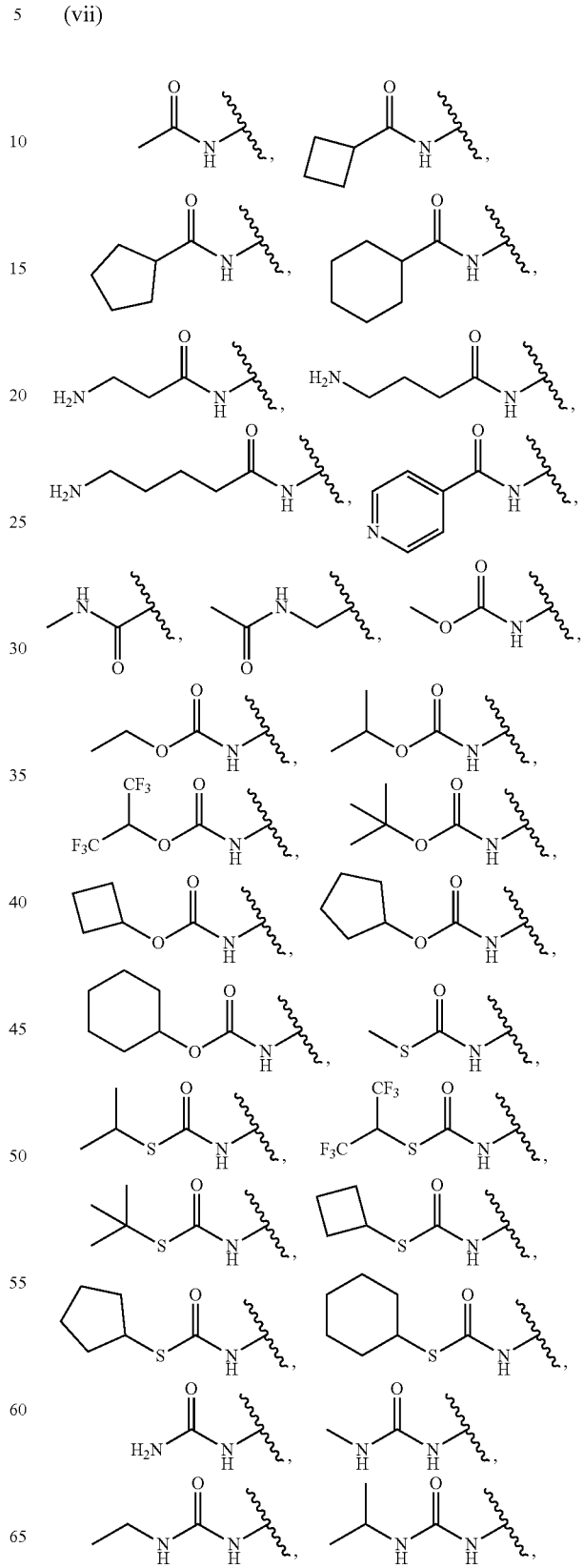

9. The compound or salt of claim 1, wherein A is selected from the group consisting of CH₃,

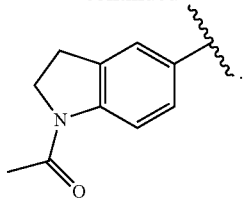

10. The compound or salt of claim 1, wherein m is 1.

11. The compound or salt of claim 1, wherein $R^2$ is:

H;

(ii) Br or Cl;

(iii) $CH_3$, $CF_3$, $CH_2OH$, or $CH_2OCH_3$;

(iv) cyclopropyl, cyclobutyl, cyclopentyl, or cyclohexyl; or (v) 3-furanyl.

12. The compound or salt of claim 1, wherein each of $R^3$ and $R^4$ independently is H, $C_{1-6}$ alkyl, or $C_{1-3}$ aralkyl.

13. The compound or salt of claim 12, wherein each of $R^3$ and $R^4$ independently is H, $CH_3$, $CH_2CH_3$, $^iBu$, or $CH_2Ph$.

14. The compound or salt of claim 1, wherein

is selected from the group consisting of:

(i)

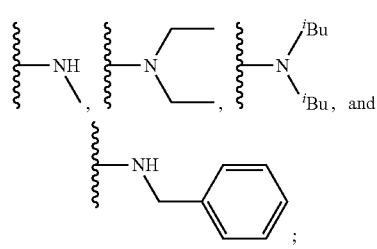

or (ii)

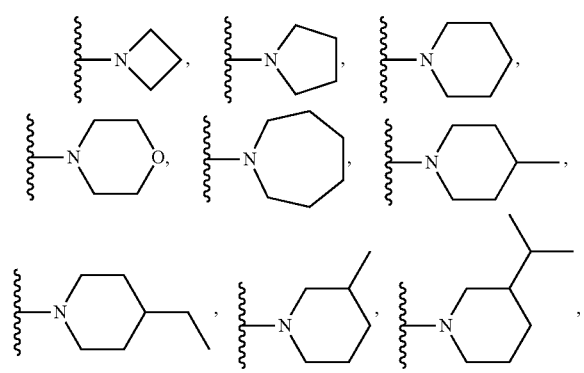

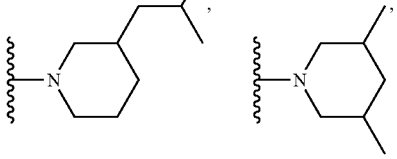

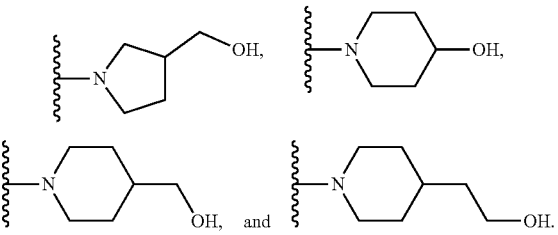

15. The compound or salt of claim 1, wherein $R^7$ is:

(i) H; or (ii) $NH_2$, Br, Cl, or F.

16. A compound listed in Table A, Table B, Table C, or a pharmaceutically acceptable salt thereof.

17. A pharmaceutical composition comprising a compound of claim 1 and a pharmaceutically acceptable excipient.

18. A method of inhibiting the Notch activation complex kinase ("NACK") in a cell, comprising contacting the cell with a compound of claim 1,

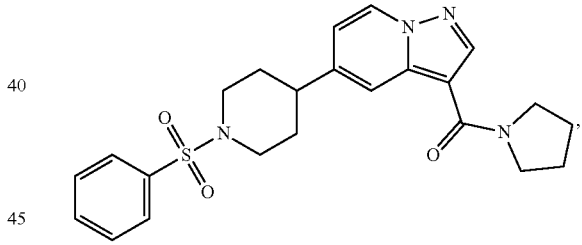

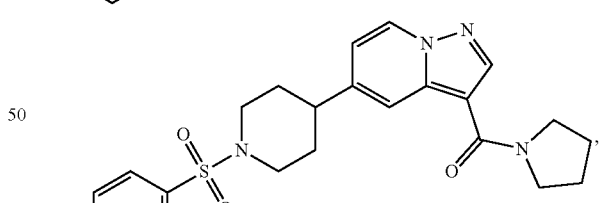

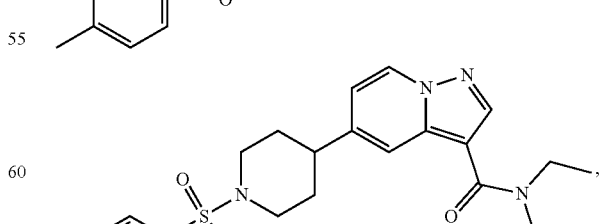

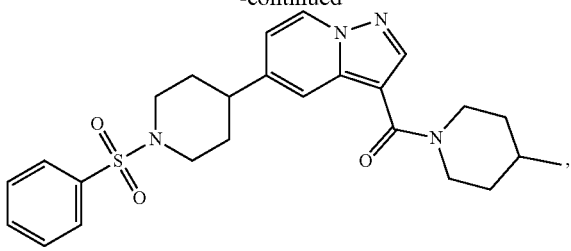

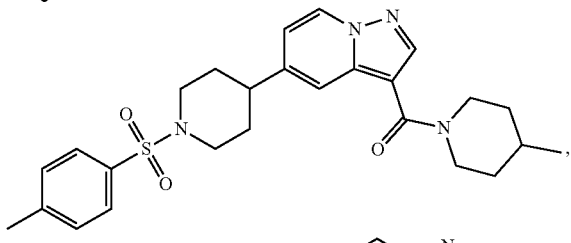

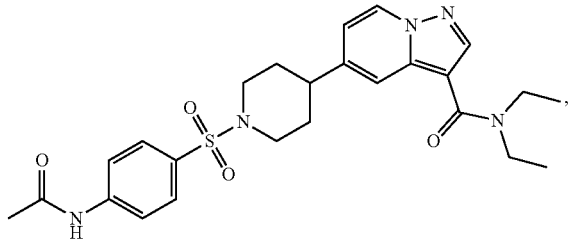

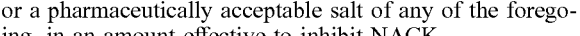
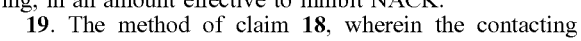

or a pharmaceutically acceptable salt of any of the foregoing, in an amount effective to inhibit NACK.

19. The method of claim 18, wherein the contacting comprises administering to a patient in need thereof, wherein the patient suffers from a disease associated with deregulation of the Notch transcriptional activation complex, and the disease is:
  (i) Tetralogy of Fallot ("TOF") or Alagille syndrome;
  (ii) cancer; or
  (iii) multiple sclerosis ("MS").

20. A method of inhibiting kinase activity, ATPase activity, or both in a cell, comprising contacting the cell with a compound of claim 1,

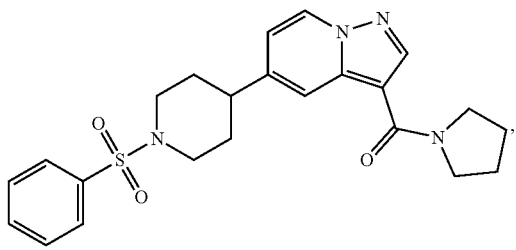

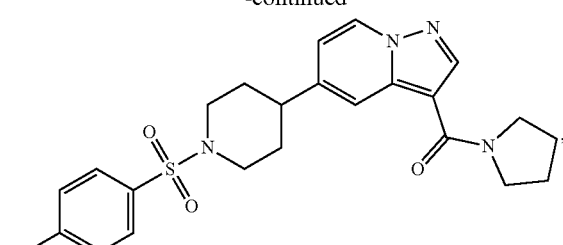

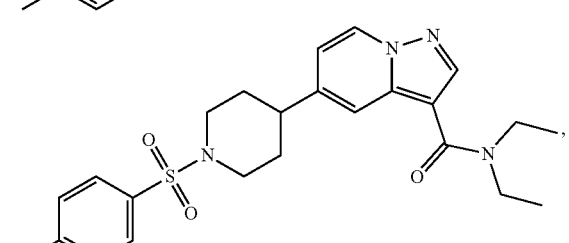

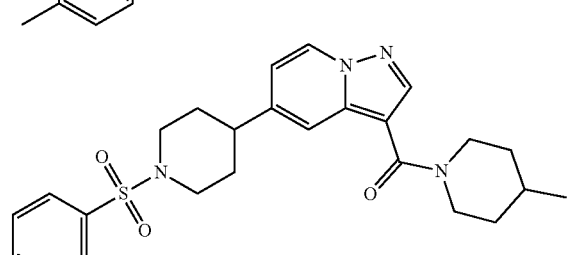

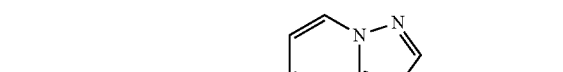

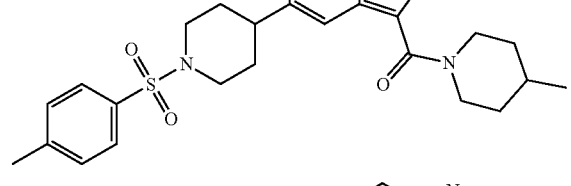

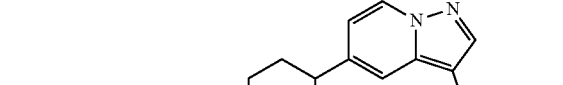
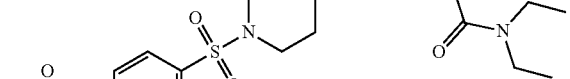

or a pharmaceutically acceptable salt of any of the foregoing in an amount effective to inhibit kinase activity, ATPase activity, or both in the cell.

* * * * *